(12) United States Patent
Griffioen et al.

(10) Patent No.: US 12,178,805 B2
(45) Date of Patent: *Dec. 31, 2024

(54) INHIBITORS OF PDE6DELTA FOR USE IN THE PREVENTION AND/OR TREATMENT OF EPILEPSY AND/OR NEURODEGENERATIVE DISORDERS

(71) Applicants: ReMYND N.V., Leuven (BE); Katholieke Universiteit Leuven, Leuven (BE)

(72) Inventors: Johan Gerard Griffioen, Kessel-Lo (BE); Katrien Princen, Heverlee (BE); Tom François L. Van Dooren, Koningshooikt (BE); Koen De Witte, Ukkel (BE)

(73) Assignees: ReMYND N.V., Leuven (BE); Katholieke Universiteit Leuven, Leuven (BE)

( * ) Notice: Subject to any disclaimer, the term of this patent is extended or adjusted under 35 U.S.C. 154(b) by 78 days.

This patent is subject to a terminal disclaimer.

(21) Appl. No.: 16/612,225

(22) PCT Filed: May 11, 2018

(86) PCT No.: PCT/EP2018/062195
§ 371 (c)(1),
(2) Date: Nov. 8, 2019

(87) PCT Pub. No.: WO2018/206757
PCT Pub. Date: Nov. 15, 2018

(65) Prior Publication Data
US 2020/0253934 A1 Aug. 13, 2020

(30) Foreign Application Priority Data
May 11, 2017 (EP) .................................. 17170610

(51) Int. Cl.
*A61K 31/422* (2006.01)
*A61K 45/06* (2006.01)
*A61P 25/08* (2006.01)
*A61P 25/28* (2006.01)

(52) U.S. Cl.
CPC ............ *A61K 31/422* (2013.01); *A61K 45/06* (2013.01); *A61P 25/08* (2018.01); *A61P 25/28* (2018.01)

(58) Field of Classification Search
CPC ......... A61K 31/422; A61P 25/28; A61P 25/08
See application file for complete search history.

(56) References Cited

U.S. PATENT DOCUMENTS

| | | |
|---|---|---|
| 4,997,834 A | 3/1991 | Muro et al. |
| 5,270,163 A | 12/1993 | Gold et al. |
| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |
| 7,323,490 B2 * | 1/2008 | Lockhart ................. A61P 19/08 514/427 |
| 8,618,138 B2 * | 12/2013 | Griffioen ............ A61K 31/4192 514/339 |
| 2005/0182125 A1 | 8/2005 | Lockhart et al. |
| 2020/0253934 A1 | 8/2020 | Griffioen et al. |

FOREIGN PATENT DOCUMENTS

| | | | |
|---|---|---|---|
| EP | 0370498 | 5/1990 | |
| EP | 0721331 | 12/2001 | |
| WO | WO 95/09615 | 4/1995 | |
| WO | WO 99/33792 | 7/1999 | |
| WO | WO 99/33793 | 7/1999 | |
| WO | WO 99/33795 | 7/1999 | |
| WO | WO 99/33815 | 7/1999 | |
| WO | WO 2006/110918 | 10/2006 | |
| WO | WO 2009/037244 | * 3/2009 | ........... C07D 231/06 |
| WO | WO 2010/142801 | 12/2010 | |
| WO | WO 2011/084642 | 7/2011 | |
| WO | WO 2014/210159 | 12/2014 | |

OTHER PUBLICATIONS

Hyman, A glimmer of light for neuropsychiatric disorders, 2008, Nature, vol. 455, p. 890-893 (Year: 2008).*
Khoshnoud et al., "Anticonvulsant activity of atorvastatin against seizure induced by pentylenetetrazole and maximal electroshock in mice" Trends in Pharmaceutical Sciences (2015) 1(1):44-47.
Martin-Gago et al., "Structure-based development of PDEδ inhibitors" Biol. Chem. (2017) 398(5-6):535-545.
Sherpard et al., "Identification of PDE6D as a Molecular Target of Anecortave Acetate via a Methotrexate-Anchored Yeast Three-Hybrid Screen" ACS Chem. Biol. (2013) 8:549-558.
Surguchov et al., "Pore-Forming Proteins as Mediators of Novel Epigenetic Mechanism of Epilepsy" Frontiers in Neurology (2017) 8(3):1-8.
Yuan et al., "Systematic review of atorvastatin for the treatment of Alzheimer's disease" Neural. Regn. Res. (2012) 7(17):1344-1351.
International Search Report and Written Opinion dated Sep. 11, 2018 for PCT Application No. PCT/EP2018/062195, filed May 11, 2018.
International Preliminary Report on Patentability mailed Nov. 21, 2019 for PCT Application No. PCT/EP2018/062195, filed May 11, 2018.
Devos et al. "Antisense Reduction of Tau in Adult Mice Protects against Seizures" The Journal of Neuroscience (2013) 33(31):12887-12897.
Holth et al. "Tau Loss Attenuates Neuronal Network Hyperexcitability in Mouse and *Drosophila* Genetic Models of Epilepsy" The Journal of Neuroscience, (2013) 33(4):1651-1659.
Schulze-Bonhage, A., "Perampanel for epilepsy with partial-onset seizures: a pharmacokinetic and pharmacodynamic evaluation" Expert Opinion on Drug Metabolism & Toxicology (2015) 11(8):1329-1337.

(Continued)

*Primary Examiner* — Alicia L Otton
(74) *Attorney, Agent, or Firm* — Knobbe Martens Olson & Bear LLP

(57) ABSTRACT

The present provides compounds and methods for preventing and/or treating epilepsy and/or neurodegenerative disorders. More particularly, the invention provides inhibitors of PDE6δ for use in the prevention and/or treatment of neurodegenerative disorders and/or epilepsy.

10 Claims, 12 Drawing Sheets

(56) References Cited

OTHER PUBLICATIONS

A. Swaminathan "Epilepsy In Neurodegenerative Disease: A Commentary" J. Exper. Neurol. (2020) 1(1):13-16.
Chidley et al., "A yeast-based screen reveals that sulfasalazine inhibits tetrahydrobiopterin biosynthesis" Nat Chem. Biol., (2011) 7(6):375-83.
"Definitive Rules for Nomenclature of Organic Chemistry" J. Am. Chem. Soc. (1960) 82(21):5545-5574.
Dewachter et al., "Aging Increased Amyloid Peptide and Caused Amyloid Plaques in Brain of Old APP/V717I Transgenic Mice by a Different Mechanism than Mutant Presenilin1" The Journal of Neuroscience, (2000) 20(17):6452-6458.
Dietrich et al., "Structural and functional changes during epileptogenesis in the mouse model of medial temporal lobe epilepsy" Conf Proc IEEE Eng Med Biol Soc., (Aug. 2016):4005-4008.
Ellington et al., "In vitro selection of RNA molecules that bind specific ligands" Nature (1990) 346:818-822.
Gröticke et al., "Behavioral alterations in a mouse model of temporal lobe epilepsy induced by intrahippocampal injection of kainate" Experimental Neurology (2008) 213(1):71-83.
Horwell, D.C. "The 'peptoid' approach to the design of non-peptide, small molecule agonists and antagonists of neuropeptides" Trends Biotechnol. (1995) 13(4):132-134.
Klein, "Aβ toxicity in Alzheimer's disease: globular oligomers (ADDLs) as new vaccine and drug targets" Neurochemistry International (2002) 41(5):345-352.
Kurreck, J., "Antisense technologies Improvement through novel chemical modifications" Eur. J. Biochem. (2003) 270:1628-1644.
Moechars et al., "Early Phenotypic Changes in Transgenic Mice That Overexpress Different Mutants of Amyloid Precursor Protein in Brain" J. Biol. Chem., (1999) 274(10):6483-6492.
Papke et al., "Identification of pyrazolopyridazinones as PDEδ inhibitors" Nature Communications (2016) 7:11360 in 9 pages.
Paquette, Leo A. "Principles of Modern Heterocyclic Chemistry" (W.A. Benjamin, New York, 1968), particularly Chapters 1, 3, 4, 6, 7, and 9 (Table of Contents only).
Racine, R. J., "Modification of seizure activity by electrical stimulation: Cortical areas" Electroencephalogr Clin Neurophysiol., (1975) 38(1):1-12.
Schlager et al., "Bicaudal D Family Adaptor Proteins Control the Velocity of Dynein-Based Movements" Cell Reports (2014) 8(5):1248-1256.
Tuerk et al., "Systematic evolution of ligands by exponential enrichment: RNA ligands to bacteriophage T4 DNA polymerase" Science (1990) 249(4968):505-510.
Zimmerman et al., "Small molecule inhibition of the KRAS-PDEδ interaction impairs oncogenic KRAS signalling" Nature (2013) 497(7451):638-642.
The Aptamer Handbook: Functional Oligonucleotides and Their Applications, by Klussmann, ed., Wiley-VCH 2006, ISBN 3527310592 (Table of Contents Only).
The Chemistry of Heterocyclic Compounds, A series of Monographs (John Wiley & Sons, New York, 1950 to present), in particular vols. 13, 14, 16, 19, and 20 (Table of Contents only).
Almarsson et al., "Crystal engineering of the composition of pharmaceutical phases. Do pharmaceutical co-crystals represent a new path to improved medicines?" Chem Commun., (2004) 17:1889-1896.
Britain, H.G. (ed.), Polymorphism in Pharmaceutical Solids (2nd Ed., 1995, Marcel Dekker, New York, New York).
Brunton (ed.), The Pharmacological Basis of Therapeutics (11th Ed, 1992, McGraw-Hill, Int. Ed.).

Demirel et al., "Total tau and Phosphorylated Tau Protein Serum Levels in Patients with Schizophrenia Compared with Controls" Psychiatr Q (2017) 88:921-928.
Di et al., "Abnormal tau induces cognitive impairment through two different mechanisms: synaptic dysfunction and neuronal loss" Nature Scientific Reports (2016) 6:20833.
Gomperts et al., "Tau PET imaging in the Lewy body diseases" JAMA Neurol (2016) 73(11):1334-1341.
Haggerty et al., "Hyperphosphorylated tau in an a-synuclein overexpressing transgenic model of Parkinson's disease" Eur J Neurosci (2011) 33(9):1598-1610.
Haleblian, J.K., "Characterization of Habits and Crystalline Modification of Solids and Their Pharmaceutical Applications" J Pharm Sci,, (1975) 64(8):1269-1288.
Hartshorne et al., Crystals and the Polarizing Microscope (4th Ed., 1970, Edward Arnold, Elsevier, New York), Summary Only.
Jakobsson et al., "CACNA1C polymorphism and altered phosphorylation of tau in bipolar disorder" The British Journal of Psychiatry (2016) 208:195-196.
Lavretsky et al., "Depression and Anxiety Symptoms Are Associated with Cerebral FDDNP-PET Binding in Middle-Aged and Older Non-Demented Adults" Am J Geriatr Psychiatry (2009) 17(6):493-502.
Murray et al., "Hyperphosphrylated Tau is Elevated in Alzheimer's Disease with Psychosis" J Alzheimers Dis (2014) 39(4):759-773.
Reichling et al., "Pain and Death: Neurodegenerative Disease Mechanisms in the Nociceptor" Ann Neurol (2011) 69:13-21.
Riku et al., "Extensive aggregation of a-synuclein and tau in juvenile-onset neuroaxonal dystrophy: an autopsied individual with a novel mutation in the PLA2G6 gene-splicing site" Acta Neuropathologica Communications (2013) 1:12.
Ryoo et al., "DYRK1A-mediated Hyperphosphorylation of Tau A Functional Link Between Down Syndrome and Alzheimer Disease" The Journal of British Chemistry (2007) 282(48):34850-34857.
Saito et al., "Widespread expression of a-synuclein and t immunoreactivity in Hallervorden—Spatz syndrome with protracted clinical course" Journal of the Neurological Sciences (2000) 177:48-59.
Sanchez et al., "Tau-Induced Pathology in Epilepsy and Dementia: Notions from Patients and Animal Models" International Journal of Molecular Sciences 2018, 19:1092.
Simic et al., "Tau Protein Hyperphosphorylation and Aggregation in Alzheimer's Disease and Other Taupathies, and Possible Neuroprotective Strategies" Biomolecules (2016) 6:6.
Skillback et al., "Diagnostic Performance of Cerebrospinal Fluid Total Tau and Phosphorylated Tau in Creutzfeldt-Jakob Disease Results From the Swedish Mortality Registry" JAMA Neurol (2014) 71(4):476-483.
Spittaels et al., "Prominent Axonopathy in the Brain and Spinal Cord of Transgenic Mice Overexpressing Four-Repeat Human tau Protein" AJP (1999) 155(6):2153-2165.
Stahl and Wermuth (eds), Handbook of Pharmaceutical Salts: Properties, Selection, and Use (Wiley-VCH, 2002).
Strong et al., "Alternations in Tau Metabolism in ALS and ALS-FTSD" Frontiers in Neurology (2020) 11:Article 598907.
Vuono et al., "The rule of tau in the pathological process and clinical expression of Huntington's disease" Brain (2015) 138:1907-1918.
Wallin et al., "Alzheimer's disease and cigarette smoke components: effects of nicotine, PAHs, and Cd(II), Cr(III), Pb(II), Pb (IV) ions on amyloid-b-peptide aggregation" Nature Scientific Reports (2017) 7:14423.
Zarranz et al., "Tau-Predominant-Associated Pathology in a Sporadic Late-Onset Hallervorden-Spatz Syndrome" Movement Disorders (2006) 21(1): 107-111.

* cited by examiner

A

B

Compound 6          Compound 2

INHIBITORS OF PDE6DELTA FOR USE IN THE PREVENTION AND/OR TREATMENT OF EPILEPSY AND/OR NEURODEGENERATIVE DISORDERS

CROSS REFERENCE TO RELATED APPLICATIONS

This application is a U.S. National Phase Application of PCT International Application No. PCT/EP2018/062195, filed on May 11, 2018, designating the United States of America and published in the English language, which claims priority to EP application Ser. No. 17/170,610.4, filed May 11, 2017. The disclosures of the above-referenced applications are hereby expressly incorporated by reference in their entireties.

TECHNICAL FIELD

The present invention is situated in the field of methods for preventing and/or treating epilepsy and/or neurodegenerative disorders. More particularly, the invention provides proteins, polypeptides, peptides, peptidomimetics, nucleic acids, small organic molecules and compounds for use in the prevention and/or treatment of neurodegenerative disorders and/or epilepsy.

BACKGROUND OF THE INVENTION

Epilepsy is a chronic disorder in which affected patients are predisposed to generate epileptic seizures which can vary from uncontrolled jerking movement to as subtle as a momentary loss of awareness. Epilepsy has a prevalence of about 1% and is independent of socio-economic status, age or gender. The underlying causes of epilepsy (epileptogenesis) are heterogeneous and include both genetic and non-genetic risk factor (such as stroke or infection). Although at present a host of therapeutic options exists for epilepsy, about 30% of the patient population is resistant to treatment, illustrating a large medical need. Moreover, current antiepileptic drugs (AEDs) have side effects such as impaired cognitive performance which has a large negative impact on the quality of life of treated patients. Finally, current treatments are merely symptomatic and do not delay or stop epileptogenesis or neuronal degeneration after a primary insult.

Although epileptic seizures are sometimes observed in patients suffering of neurodegenerative disease (in particular Alzheimer's disease) epilepsy in itself is is not considered a neurodegenerative disease. In fact epilepsy reflects a hyperactive state of neurons and of associated neuronal networks which leads to the observed symptomatology including uncontrolled movements. Consequentlty, current treatments are aimed at restraining neuronal activity to alleviate the symptoms but may as a consequence also lead to undesired side effects such as cognitive impairement.

Alzheimer's disease (AD), a chronic neurodegenerative disease, is the most common cause of dementia among elderly and one of the leading sources of morbidity and mortality in the aging population. In people with early-onset Alzheimer's, a genetic mutation is usually the cause. Late-onset Alzheimer's is caused by a combination of genetic, environmental, and lifestyle factors. Current treatment options for AD are limited and mainly focussed on delaying or ameliorating the symptoms, for instance by helping patients to maintain their mental function, and not on treating the disease. Therefore, there is a need for developing treatments addressing underlying disease processes.

Though comorbidity between epileptic seizures and Alzheimer's disease has been suggested, there is no clear causative link between both diseases. Both of these diseases are very common neurological diseases and thus cause significant health problems and represent an important cost on health care.

There is a need in the art for identifying and/or designing drugs for therapeutic treatments that target the underlying molecular mechanism of epilepsy and/or Alzheimer's disease.

SUMMARY

The present inventors have surprisingly found that PDE6δ plays a pivotal role in the pathology and thus in the treatment and prevention of Alzheimer's disease-. Further investigation revealed unexpectedly that other effects of PDE6δ play also a pivotal role in epilepsy. Accordingly, the present invention provides for the use of inhibitors of PDE6δ in the treatment and prevention of Alzheimer's disease and/or epilepsy.

Accordingly, provided herein is an inhibitor of PDE6δ for use in the prevention and/or treatment of epilepsy. In particular embodiments, the inhibitor of PDE6δ is not atorvastatin.

In particular embodiments, the inhibitor of PDE6δ for use in the prevention and/or treatment of epilepsy is a compound selected from the group consisting of pyrazolopyridazinones, pyrazolo-pyrimidinones, benzimidazoles, bis-benzimidazoles, 3-oxo-pregna-4,9-dienes, solvates, hydrates, salts or prodrugs thereof, or a compound of formula (AA1), (BB1) or (CC1) as described in PCT application WO2010/142801, stereoisomers, enantiomers, tautomers, solvates, hydrates, salts or prodrugs thereof.

In particular embodiments, the compound of formula (AA1) as described in PCT application WO2010/142801 is a compound selected from Table 1 as described in PCT application WO 2010/142801.

In particular embodiments, the compound of formula (AA1) as described in PCT application WO2010/142801 is a compound of formula (I) or a tautomer thereof,

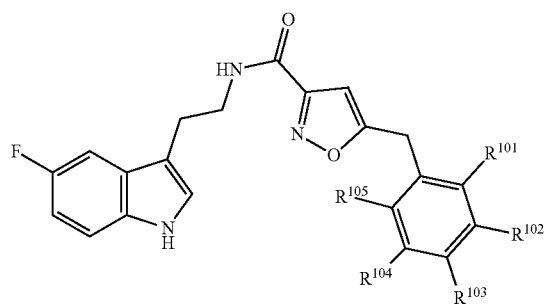

(I)

wherein,
$R^{101}$ is selected from the group consisting of hydrogen; F, Cl, and Br;
$R^{102}$ is selected from the group consisting of hydrogen, F, Cl, and Br;
$R^{103}$ is selected from the group consisting of hydrogen, F, Cl, and Br;

$R^{104}$ is selected from the group consisting of hydrogen, F, Cl, and Br;

$R^{105}$ is selected from the group consisting of hydrogen, F, Cl, and Br;

with the proviso that at least one of $R^{101}$, $R^{102}$, $R^{103}$, $R^{104}$ or $R^{105}$ is not hydrogen;

with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt (in particular a pharmaceutically acceptable salt) or a prodrug thereof.

In particular embodiments, the compound of formula (I) is a compound of any one of formula (II), (III), (IV), (V) or (VI)

(II)
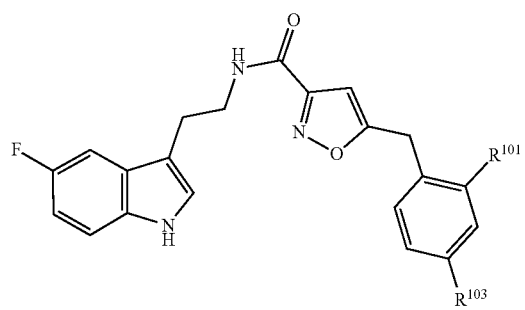

(III)
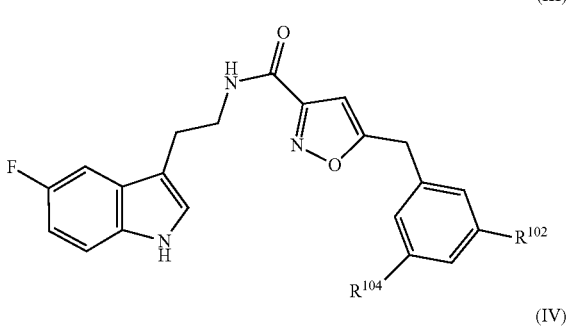

(IV)
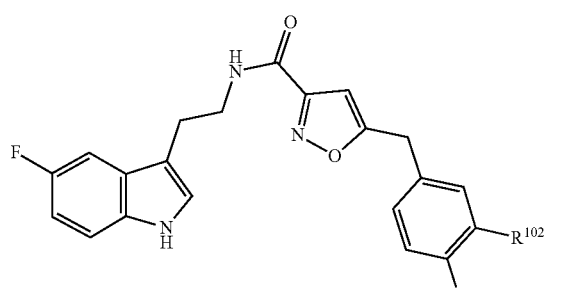

(V)
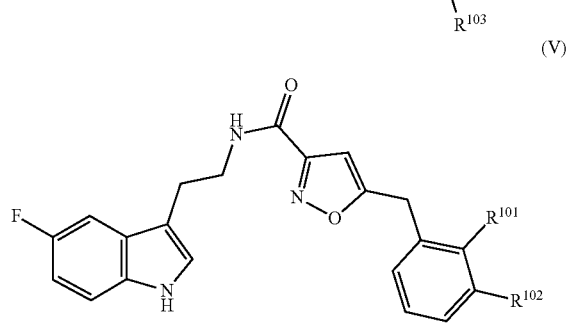

(VI)
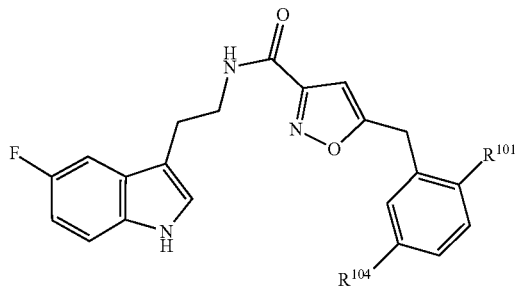

wherein $R^{101}$, $R^{102}$, $R^{103}$ and $R^{104}$ have the same meaning as defined above.

In particular embodiments, the compound of formula (I) is selected from the group consisting of:
5-[(2,4-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(4-fluorophenyl)methyl]isoxazole-3-carboxamide;
5-[(2,3-difluorophenyl)methyl]-N-[2-(5-fluoro-1H-indol-3-yl)ethyl]isoxazole-3-carboxamide;
5-[(2,5-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(2-fluorophenyl)methyl]isoxazole-3-carboxamide;
5-[(3,4-difluorophenyl)methyl]-N-[2-(5-fluoro-1H-indol-3-yl)ethyl]isoxazole-3-carboxamide; and
5-[(3,5-difluorophenyl)methyl]-N-[2-(5-fluoro-1H-indol-3-yl)ethyl]isoxazole-3-carboxamide.

Also provided herein is an inhibitor of PDE6δ for use in the prevention and/or treatment of a neurodegenerative disorder, wherein said inhibitor is not a compound of formula (AA1), (BB1) or (CC1) as described in PCT application WO 2010/142801.

In particular embodiments, the inhibitor of PDE6δ for use in the prevention and/or treatment of a neurodegenerative disorder is a compound selected from the group consisting of pyrazolopyridazinones, pyrazolo-pyrimidinones, benzimidazoles, bis-benzimidazoles or 3-oxo-pregna-4,9-dienes, solvates, hydrates, salts or prodrugs thereof.

Also provided herein is an inhibitor of PDE6δ for use in the prevention and/or treatment of a neurodegenerative disorder wherein said inhibitor is a compound of formula (I) or a tautomer thereof, (I)
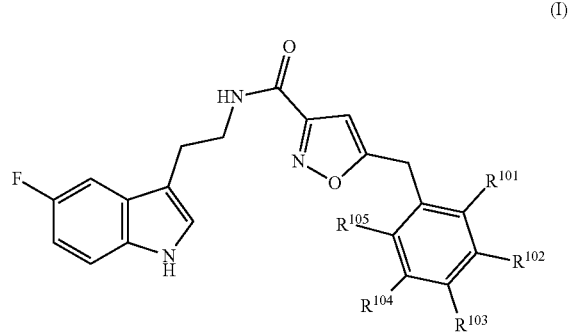

wherein,
$R^{101}$ is selected from the group consisting of hydrogen; F, Cl, and Br;

$R^{102}$ is selected from the group consisting of hydrogen, F, Cl, and Br;

$R^{103}$ is selected from the group consisting of hydrogen, F, Cl, and Br;

$R^{104}$ is selected from the group consisting of hydrogen, F, Cl, and Br;

$R^{105}$ is selected from the group consisting of hydrogen, F, Cl, and Br;

with the proviso that at least one of $R^{101}$, $R^{102}$, $R^{103}$, $R^{104}$ or $R^{105}$ is not hydrogen;

with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt (in particular a pharmaceutically acceptable salt) or a prodrug thereof.

In particular embodiments, the compound of formula (I) is a compound of any one of formula (II), (III), (IV), (V) or (VI)

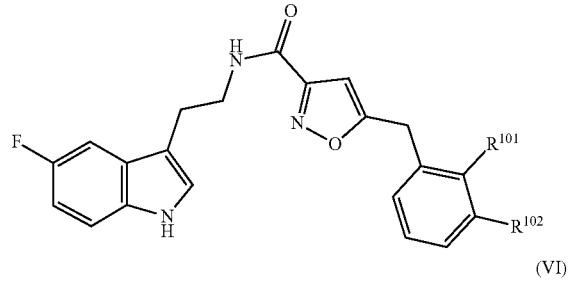

wherein $R^{101}$, $R^{102}$, $R^{103}$ and $R^{104}$ have the same meaning as defined above.

In particular embodiments, the compound of formula (I) is selected from the group consisting of:
5-[(2,4-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(4-fluorophenyl)methyl]isoxazole-3-carboxamide;
5-[(2,3-difluorophenyl)methyl]-N-[2-(5-fluoro-1H-indol-3-yl)ethyl]isoxazole-3-carboxamide;
5-[(2,5-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(2-fluorophenyl)methyl]isoxazole-3-carboxamide;
5-[(3,4-difluorophenyl)methyl]-N-[2-(5-fluoro-1H-indol-3-yl)ethyl]isoxazole-3-carboxamide; and
5-[(3,5-difluorophenyl)methyl]-N-[2-(5-fluoro-1H-indol-3-yl)ethyl]isoxazole-3-carboxamide.

In particular embodiments, the neurodegenerative disease is selected from Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis and Creutzfeld-Jacob's disease, preferably said neurodegenerative disease is Alzheimer's disease.

In particular embodiments, the inhibitor is contained within a pharmaceutical composition in a therapeutically effective amount.

BRIEF DESCRIPTION OF THE DRAWINGS

The following description of the figures of specific embodiments of the invention is merely exemplary in nature and is not intended to limit the present teachings, their application or uses.

(A) AT8 p-TAU, indicates the antibody recognising p-TAU phosphorylated on serine 202 and threonine 205, (B) AD2 p-TAU, indicates the antibody recognising p-TAU phosphorylated on serines 396 and 404, (C) phosphorylated TAU on T231, and (D) phosphorylated TAU on S262.

Figure 7:
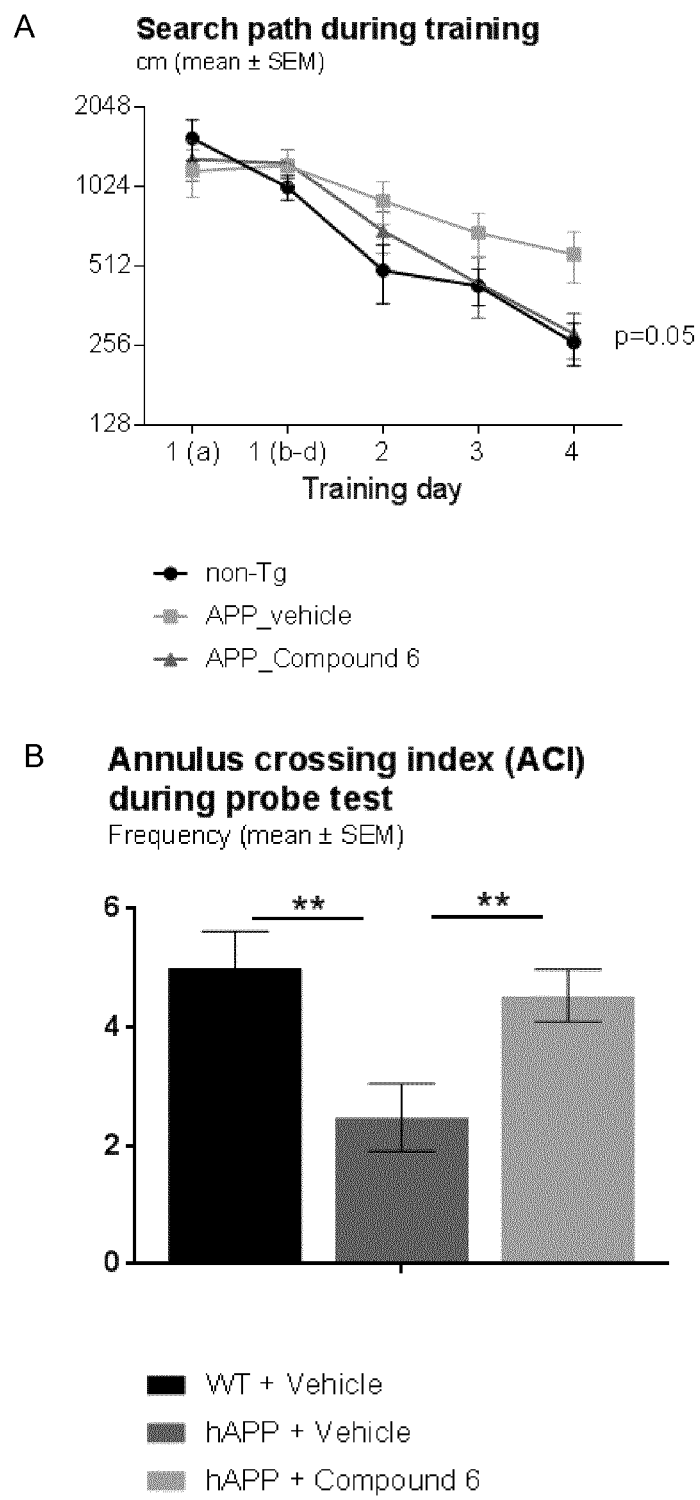

FIG. 7 shows the outcome of a Morris Water Maze test of transgenic APP mice treated with exemplary Compound 6. (A) shows the search path length during the training phase. P-value refers to the treatment of transgenic APP mice with exemplary Compound 6 versus vehicle. Section B shows the annulus crossing index (relative frequency of crossing an imaginary platform region) from the probe test. ** indicate p<0.01.

Figure 8:
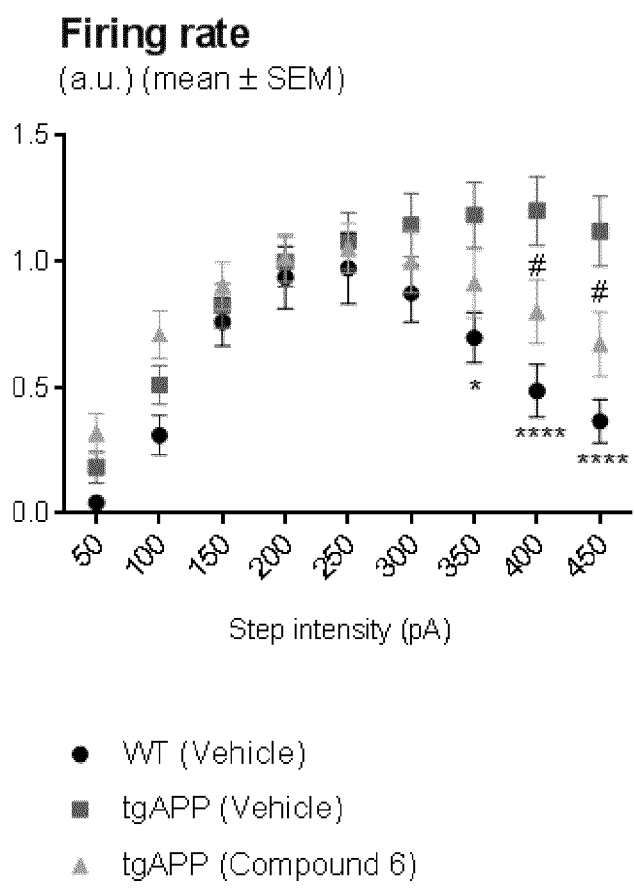

FIG. 8 represents a graph plotting neuronal firing rate of wild-type and tgAPP mice as a function of electrical stimulation (step intensity (pA)) for exemplary Compound 6. * and **** indicate p<0.05 and p<0.0001, respectively of wild type versus transgenic APP mice. # indicate p<0.05 of transgenic APP mice treated with vehicle versus Compound 6.

Figure 9:
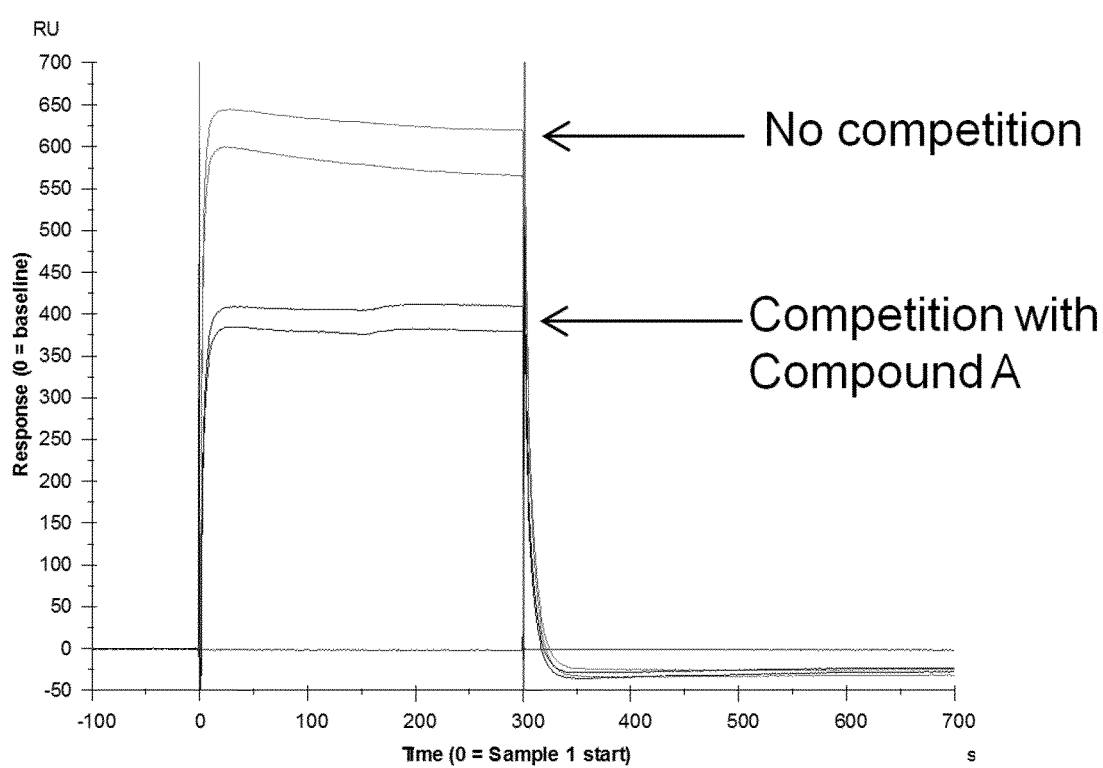
Figure 9:
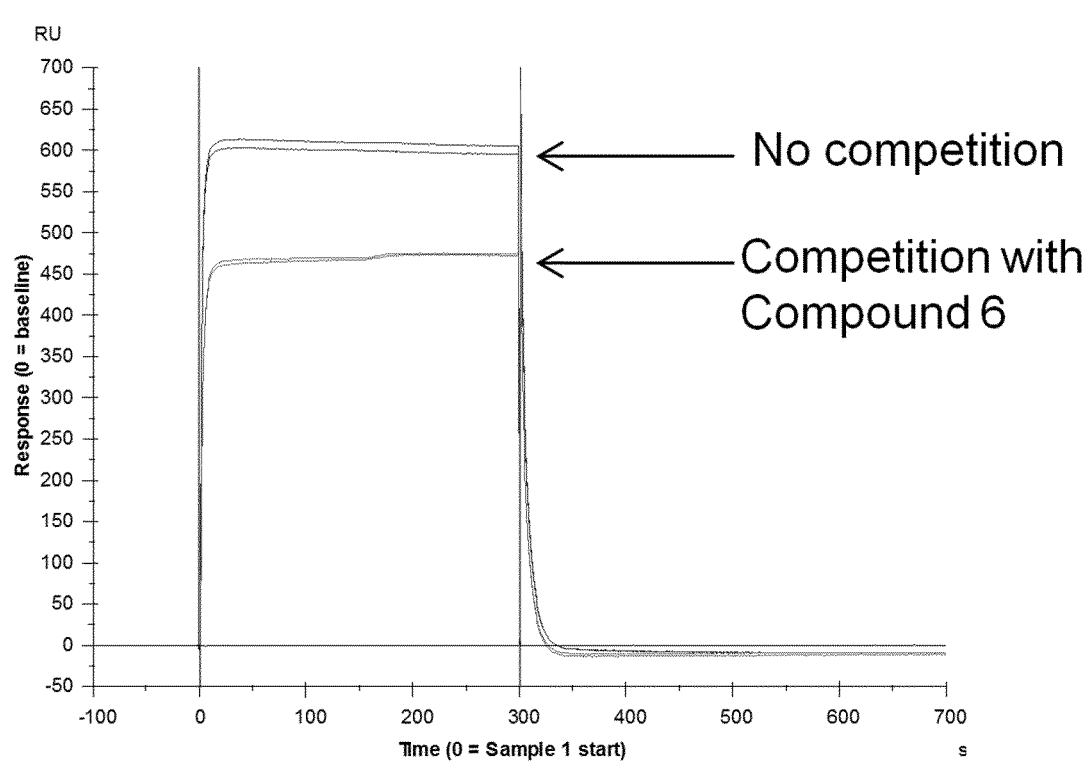
Figure 9:
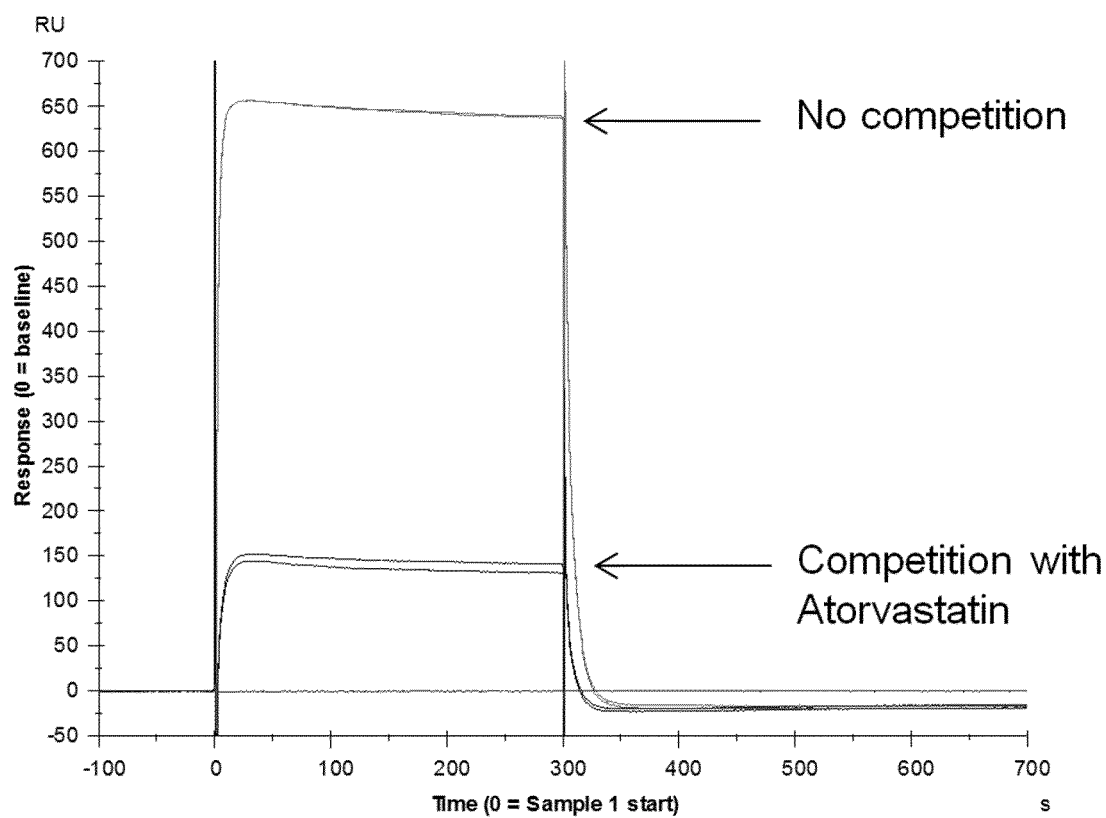

FIG. 9 shows (A-C) Surface Plasmon Resonance (SPR) analysis of immobilised MFC-42826 and recombinant PDE6δ. Competition of the MFC-42826-PDE6δ interaction with (A) Compound A, (B) exemplary Compound 6 and (C) atorvastatin.

Figure 10:
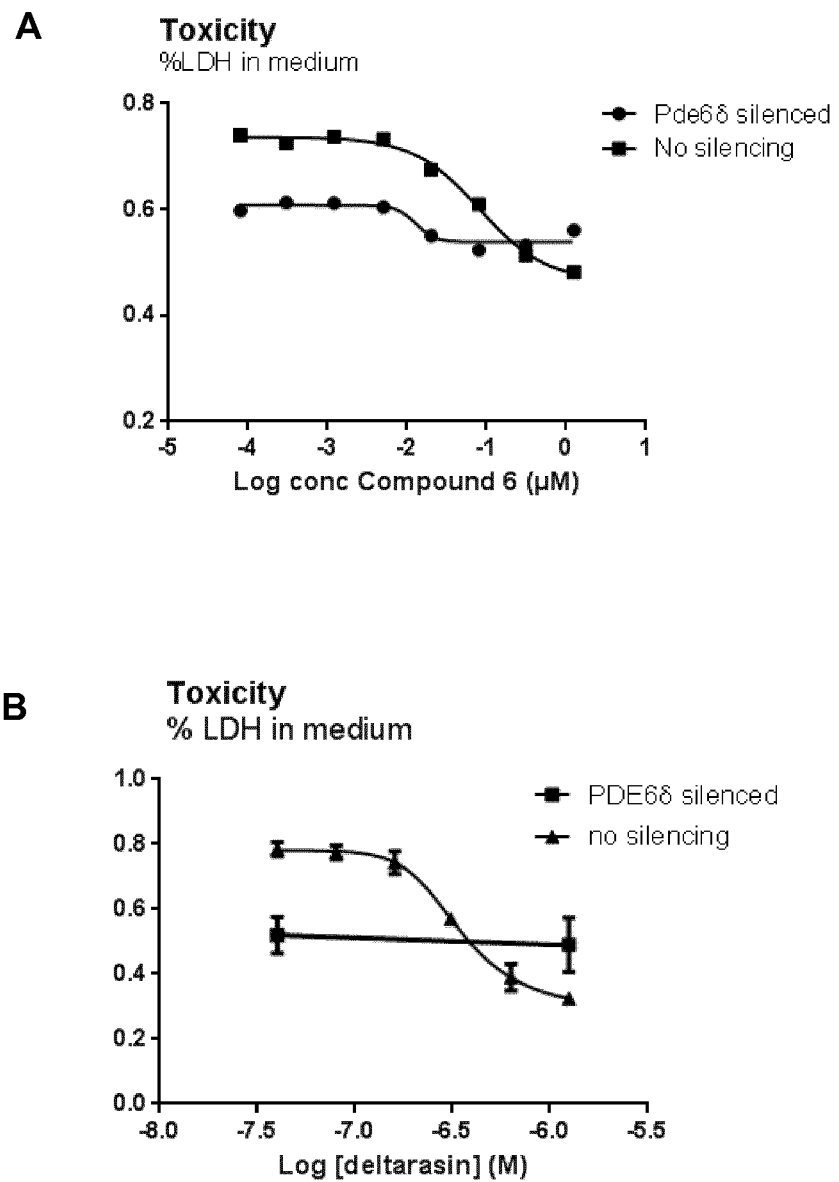

FIG. 10 shows the inhibition of TAU-toxicity by exemplary Compound 6 (A) or deltarasin (B) using the method described in example 16 in PDE6δ silenced cells and control (not silenced) cells.

Figure 11:
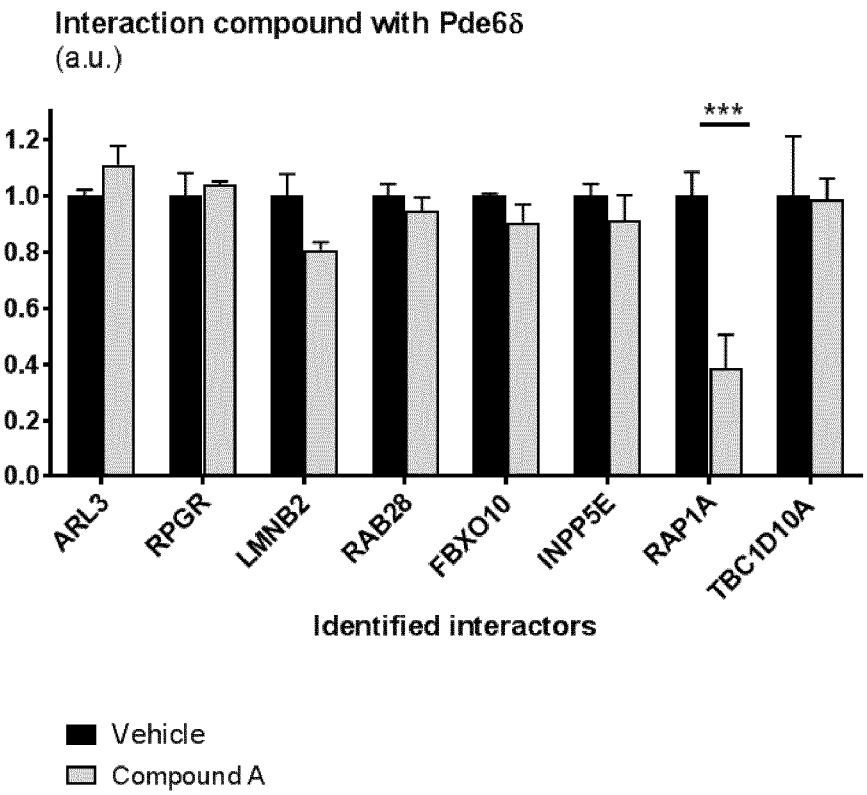

FIG. 11 shows the identification of PDE6S interactors with and without 1 hour incubation of 1 µM of Compound A. *** indicate p=<0.001 vehicle versus compound treated cells.

Figure 12:
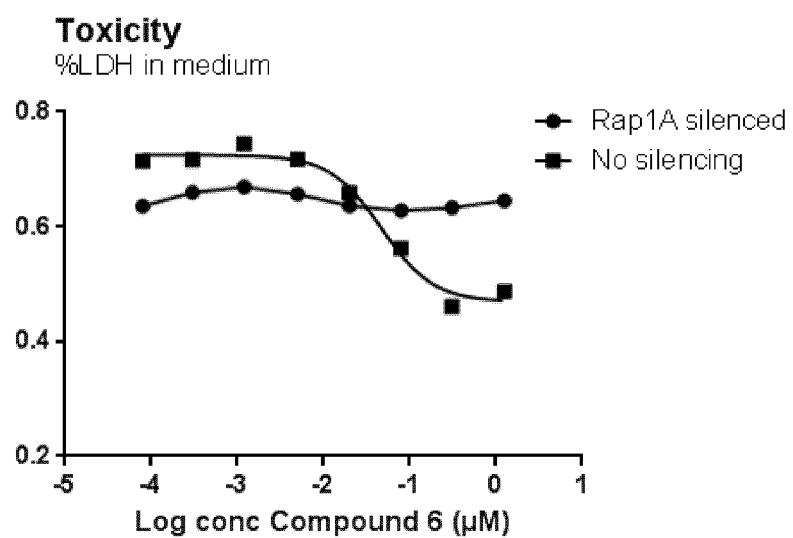

FIG. 12 shows the inhibition of TAU-toxicity by exemplary Compound 6 using the method described in example 18 in control (not silenced) and RAP1A silenced cells.

Figure 13:
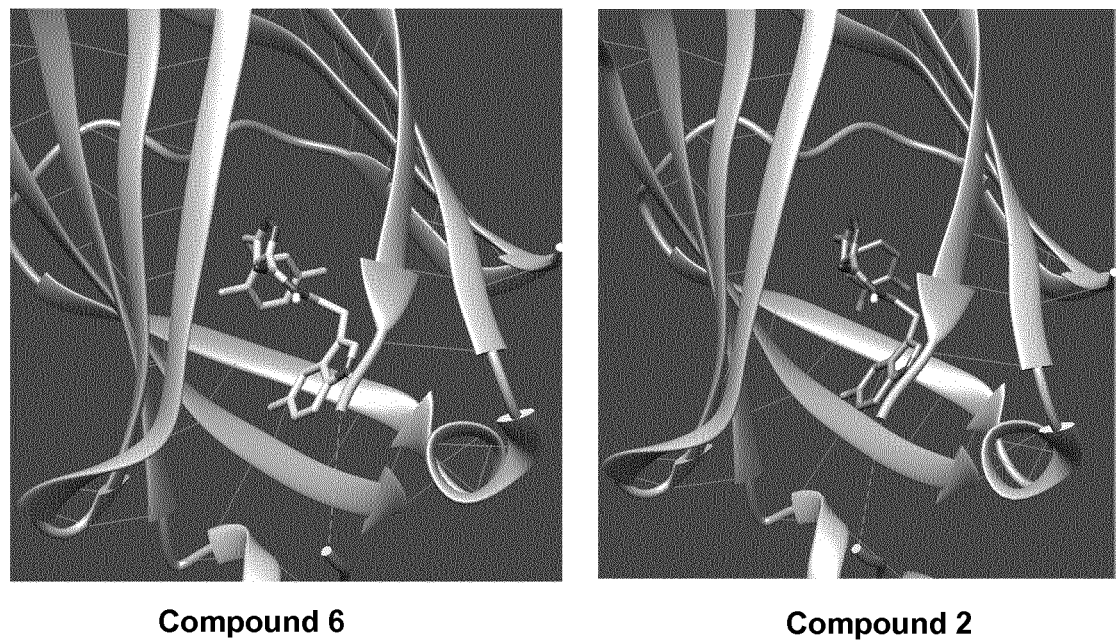

FIG. 13 shows the visualization of exemplary Compounds 2 and 6 docked in the prenyl binding site of PDE6δ.

Figure 14:
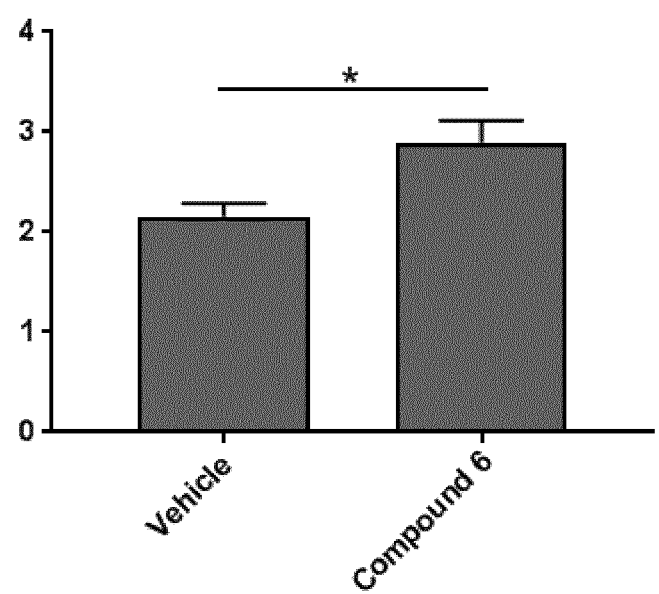

FIG. 14 shows the afterhyperpolarization (AHP) of single action potentials by somatic current clamp recordings using mouse brain slices incubated with vehicle or Compound 6. * indicates p<0.05.

DETAILED DESCRIPTION OF THE INVENTION

Before the present invention is described, it is to be understood that this invention is not limited to particular inhibitors of PDE6δ and uses thereof described, as such inhibitors of PDE6δ and uses thereof may, of course, vary. It is also to be understood that the terminology used herein is not intended to be limiting, since the scope of the present invention will be limited only by the appended claims.

When describing the inhibitors of PDE6δ and uses thereof of the invention, the terms used are to be construed in accordance with the following definitions, unless a context dictates otherwise.

As used in the specification and the appended claims, the singular forms "a", "an," and "the" include both singular and plural referents unless the context clearly dictates otherwise. By way of example, "a compound" means one compound or more than one compound.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims and statements, any of the embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

When describing the present invention, the terms used are to be construed in accordance with the following definitions, unless a context dictates otherwise.

The present inventors have identified PDE6δ as a target of disease pathophysiology for both epilepsy and neurodegenerative disorders, such as Alzheimer's disease (AD). In line herewith, present applicant has found that inhibitors of PDE6δ, preferably small organic molecules or compounds that can inhibit PDE6δ, more preferably small organic compounds or molecules that can bind the prenyl binding pocket of PDE6δ and thereby compete with (prenylated) (small) GTPases for binding to PDE6δ, can be used in the treatment of both epilepsy and neurodegenerative disorders.

Furthermore, present applicant provides novel compounds for use in the prevention or treatment of epilepsy and/or neurodegenerative diseases.

The identification of PDE6δ as a target for alzheimer's disease and epilepsy allows for the development of a new category of therapeutic compounds for these diseases.

Indeed, the present inventors have found by use of in-silico docking and calculation of the predicted Gibbs binding energy that compounds currently used in the treatment of epilepsy (e.g. Valproate, Levitercetam, Topiramate, Gabapentin, Perempanel, lacosamide, Vigobatrin) or Alzheimer's disease (e.g. Memantine, Galantamine, Rivastigmine) do not bind with high affinity to the PDE6δ prenyl binding pocket (Table 2).

TABLE 2

| Compound | Gibbs energy ΔG (kcal/mol)* |
|---|---|
| Known compounds used in the treatment of epilepsy | |
| Valproate | −4.6 |
| Levitercetam | −5.8 |
| Topiramate | −7.8 |
| Gabapentin | −5.8 |
| Perempanel | −9.0 |
| Lacosamide | −6.9 |
| Vigabatrin | −4.4 |
| Known compounds used in the treatment of Alzheimer's disease | |
| Memantine | −6.5 |
| Galantamine | −8.8 |
| Rivastigmine | −6.8 |

TABLE 2-continued

| Compound | Gibbs energy ΔG (kcal/mol)* |
|---|---|
| Compound known to bind the prenyl-binding pocket of PDE6δ (control) | |
| Deltarasin | −12.5 |

*a Gibbs energy value of less than −10 kcal/mol indicates high affinity binding

The term "PDE6δ", "PDE6delta", "PDE6δ", "PDEδ", "PDEdelta", "PrBP/δ", "phosphodiesterase 6 δ", "phosphodiesterase 6 delta", "phosphodiesterase δ" or "phosphodiesterase delta" as used herein, refers to the 17 kDa delta subunit of cGMP 3',5' phosphodiesterase delta subunit, which interacts with prenyl groups, more particularly with prenylated (e.g. geranylgeranylated or farnesylated), carboxymethylated C-terminal Cys residues and functions as chaperone/co-factor in the transport of a subset of prenylated proteins. By means of an example, the nucleic acid sequence of human PDE6δ is annotated under NCBI Genbank (http://www.ncbi.nlm.nih.gov/) accession number CR456980.1 and the amino acid sequence of human PDE6δ is annotated under NCBI Genbank (http://www.ncbi.nlm.nih.gov/) accession number CAG33261.1. An exemplary crystal structure of PDE6δ can be found under RCSB protein databank reference 4JV6 (http://www.rcsb.org/pdb/explore/explore.do?structureId=4JV6).

Unless otherwise apparent from the context, reference herein to PDE6δ may generally also encompass modified forms of PDE6δ, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "inhibitor" as used herein refers to any chemical (e.g., inorganic or organic), biochemical or biological substance, compound, molecule or macromolecule (e.g., biological macromolecule), a combination or mixture thereof, a sample of undetermined composition, or an extract made from biological materials such as bacteria, plants, fungi, or animal cells or tissues capable of inhibiting PDE6δ. Non-limiting examples of inhibitors include nucleic acids, oligonucleotides, ribozymes, polypeptides or proteins, peptides, peptidomimetics, antibodies and fragments and derivatives thereof, aptamers, photoaptamers, chemical substances, such as (small) organic molecules or compounds, lipids, carbohydrates, polysaccharides, etc., and any combinations thereof. The term "inhibit" as used herein is intended to be synonymous with terms such as "decrease", "reduce", "diminish", "interfere", "disrupt", or "disturb", and denotes a qualitative or quantitative decrease of expression and/or activity of PDE6δ. The term encompasses any extent of such interference. For example, the interference may encompass a decrease (in particular statistically significant decrease) of at least about 10%, e.g., of at least about 20%, of at least about 30%, e.g., of at least about 40%, of at least about 50%, e.g., of at least about 60%, of at least about 70%, e.g., of at least about 80%, of at least about 90%, e.g., of at least about 95%, such as of at least about 96%, 97%, 98%, 99% or even of 100%, compared to a reference situation without said interference.

The reference to the "activity" as used herein, is to be interpreted broadly and may generally encompass any one or more aspects of the biological activity of PDE6δ at any level (e.g., molecular, cellular and/or physiological), such as without limitation any one or more aspects of its biochemical activity, enzymatic activity, signalling activity, interaction activity, ligand activity, receptor activity or structural activity, e.g., within a cell, tissue, organ or an organism. By means of an example and not limitation, reference to the activity of PDE6δ may particularly denote the interaction activity of PDE6δ for one or more prenylated or non-prenylated (e.g. RCC1, Arf-like proteins Arl2 and Arl3) polypeptides, preferably prenylated polypeptides, even more preferably prenylated (small) GTPases. Non-limiting examples of prenylated polypeptides binding to or interacting with PDE6δ include PDEα, PDEβ, GRK1, GRK7, cTγ, Tγ, DmPDE5/6, Rab13, Rheb, Rho6, Rap1a, Rap1b, Rap2a, H-Ras, N-Ras, K-Ras, RhoA, RhoB or prostacyclin-R. The term "prenylation" as used herein, refers to a posttranslational modification consisting of the transfer of either a 15-carbon farnesyl isoprenoid or a 20-carbon geranyl-geranyl isoprenoid moiety to C-terminal cysteine residue(s) of a target protein. Preferably, the C-terminal cysteine residue(s) are located in a C-terminal CAAX box motif, wherein C is a cysteine, A is an aliphatic amino acid and X can be any amino acid. The C-terminal X of the CAAX box motif may determine the nature of the lipid chain, as leucine specifies geranylgeranylation and all other amino acid restudies result in farnesylation. The prenyl chain may be attached to the CAAX box cysteine via a thioether bond by cytosolic prenyl transferase.

Methods of measuring the decrease of activity of PDE6δ are known by the skilled person. For example, the interaction between a prenylated protein, such as a prenylated small GTPase, and PDE6δ may be assessed by fluorescence lifetime imaging microscopy as described in Papke et al. (Nature Communications, 2016). Furthermore, a decrease in the interaction activity of PDE6δ might result in a disruptance of the plasma membrane localisation of one or more small GTPase normally interacting with PDE6δ. As many small GTPases regulate cell growth, proliferation, cell morphology and/or nuclear and/or vesicle transport, disruptance of the plasma membrane localisation of a small GTPase may result in an altered signal transduction, cell proliferation, cytoskeletal organisation and/or intracellular membrane trafficking regulated by said small GTPase. Method for measuring signal transduction, cell proliferation, cytoskeletal organisation and intracellular membrane trafficking can be any method for measuring signal transduction, cell proliferation, cytoskeletal organisation and intracellular membrane trafficking known by the skilled person.

The term "interact", "bind", "specifically bind" or "specifically interact" as used throughout this specification means that an agent (e.g. the inhibitor as described herein) binds to or influences one or more desired molecules or analytes (e.g. PDE6δ) substantially to the exclusion of other molecules which are random or unrelated, and optionally substantially to the exclusion of other molecules that are structurally related. The term "bind", "interact", "specifically bind" or "specifically interact" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, than its affinity for a non-target molecule.

The binding or interaction between the inhibitor as described herein and PDE6δ may be covalent (i.e., mediated by one or more chemical bonds that involve the sharing of electron pairs between atoms) or, more typically, non-covalent (i.e., mediated by non-covalent forces, such as for example, hydrogen bridges, dipolar interactions, van der Waals interactions, and the like). The binding of an inhibitor to PDE6δ is characterized by its affinity and specificity for PDE6δ. In particular embodiments, the binding affinity is determined by in silico calculation, such as by in-silico docking and calculation of the predicted Gibbs binding energy. A Gibbs energy value of less than −10 kcal/mol indicates high affinity binding. Preferably, the inhibitor of present invention may bind to or interact with PDE6δ with affinity constant ($K_A$) of such binding $K_A \geq 1 \times 10^4$ M$^{-1}$, more preferably $K_A \geq 1 \times 10^5$ M$^{-1}$, yet more preferably $K_A \geq 1 \times 10^6$ M$^{-1}$, even more preferably $K_A \geq 1 \times 10^7$ M$^{-1}$, and still more preferably $K_A \geq 1 \times 10^5$ M$^{-1}$ or $K_A \geq 1 \times 10^9$ M$^{-1}$, wherein $K_A$= [A_T]/[A][T], A denotes the inhibitor, T denotes PDE6δ. Determination of $K_A$ can be carried out by methods known in the art, such as for example, using Surface Plasmon Resonance or equilibrium dialysis and Scatchard plot analysis. Specificity of the binding of a compound to PDE6δ can be determined by determining binding upon competition with a compound known to bind the prenyl-binding pocket of PDE6δ, by methods known in the art, such as for example, using Surface Plasmon Resonance. Specificity relates in this context to the specific or non-specific binding of a compound to the prenyl-binding pocket of PDE6δ.

As used herein, the terms "treating" or "treatment" refer to therapeutic treatment. The terms "treatment", "treating", and the like, as used herein also include amelioration or elimination of a developed disease or condition once it has been established or alleviation of the characteristic symptoms of such disease or condition. The terms "preventing" or "prevention" refer to prophylactic measures, wherein the object is to prevent or slow down (lessen) an undesired physiological change or disorder. As used herein these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. The terms "delaying" or "delay" may equally refer to postponing the onset of the disease or symptoms, as well as slowing down the progression of the disease or the symptoms.

"Subject" or "patient" are used interchangeably herein and refer to animals, preferably mammals, and specifically include human subjects and non-human mammals. Preferred subjects are humans. Particularly intended are subjects in need of treatment, meaning those subjects that would benefit from treatment of a given condition. Such subjects may include, without limitation, those that have been diagnosed with said disorder, those prone to contract or develop said disorder and/or those in whom said disorder is to be prevented.

Different types of inhibitors are envisaged in the context of the present invention. In particular embodiments, the inhibitor is capable of interacting with the gene RNA, preferably mRNA, encoding PDE6δ, or the agent is capable of interacting with the PDE6δ protein.

In particular embodiments, the interaction between the inhibitor as described in the present application and PDE6δ gene, RNA, preferably mRNA, or protein, preferably alters the activity or the level or both of said target. For example, the inhibitor as disclosed herein may be capable of interfering with the expression of PDE6δ by a cell, the transport of PDE6δ to the cytoplasm and/or the binding of proteins, preferably prenylated small GTPases, to PDE6δ.

In particular embodiments, the inhibitor of PDE6δ is selected from the group consisting of a protein, a polypeptide, a peptide, a peptidomimetic, a nucleic acid, a small organic molecule, and a compound or a combination of any two or more thereof. For example, an aptamer, a gene-editing system, an antisense agent, an RNAi agent, such as siRNA or shRNA or an antibody or functional fragment thereof. In certain preferred embodiments, the inhibitor for use according to the invention is a small organic molecule or compound.

The term "protein" as used herein generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, prenylation etc. The term further also includes protein variants or mutants which carry amino acid sequence variations vis-à-vis a corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The term "polypeptide" as used herein generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "peptide" as used herein preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "peptidomimetic" as used herein refers to a non-peptide agent that is a topological analogue of a corresponding peptide. Methods of rationally designing peptidomimetics of peptides are known in the art. For example, by means of a guidance, the rational design of three peptidomimetics based on the sulphated 8-mer peptide CCK26-33, and of two peptidomimetics based on the 11-mer peptide Substance P, and related peptidomimetic design principles, are described in Norwell 1995 (Trends Biotechnol 13: 132-134).

The term "nucleic acid" as used herein typically refers to a polymer (preferably a linear polymer) of any length composed essentially of nucleoside units. A nucleoside unit commonly includes a heterocyclic base and a sugar group. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Exemplary modified nucleobases include without limitation 5-substituted pyrimidines, 6-azapyrimidines and N-2, N-6 and O-6 substituted purines, including 2-aminopropyladenine, 5-propynyluracil and 5-propynylcytosine. In particular, 5-methylcytosine substitutions have been shown to increase nucleic acid duplex stability and may be preferred base substitutions in for example antisense agents, even more particularly when combined with 2'-O-methoxyethyl sugar modifications. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups (such as without limitation 2'-O-alkylated, e.g., 2'-O-methylated or 2'-O-ethylated sugars such as ribose; 2'-O-alkyloxyalkylated, e.g., 2'-O-methoxyethylated sugars such as ribose; or 2'-O,4'-C-alkylene-linked, e.g., 2'-O,4'-C-methylene-linked or 2'-O,4'-C-ethylene-linked sugars such as ribose; 2'-fluoro-arabinose, etc.). Nucleoside units may be linked to one another by any one of numerous known inter-nucleoside linkages, including inter alia phosphodiester linkages common in naturally-occurring nucleic acids, and further modified phosphate- or phosphonate-based linkages such as phosphorothioate, alkyl phosphorothioate such as methyl phosphorothioate, phosphorodithioate, alkylphosphonate such as methylphosphonate, alkylphosphonothioate, phosphotriester such as alkylphosphotriester, phosphoramidate, phosphoropiperazidate, phosphoromorpholidate, bridged phosphoramidate, bridged methylene phosphonate, bridged phosphorothioate; and further siloxane, carbonate, sulfamate, carboalkoxy, acetamidate, carbamate such as 3'-N-carbamate, morpholino, borano, thioether, 3'-thioacetal, and sulfone inter-nucleoside linkages. Preferably, inter-nucleoside linkages may be phosphate-based linkages including modified phosphate-based linkages, such as more preferably phosphodiester, phosphorothioate or phosphorodithioate linkages or combinations thereof. The term "nucleic acid" also encompasses any other nucleobase containing polymers such as nucleic acid mimetics, including, without limitation, peptide nucleic acids (PNA), peptide nucleic acids with phosphate groups (PHONA), locked nucleic acids (LNA), morpholino phosphorodiamidate-backbone nucleic acids (PMO), cyclohexene nucleic acids (CeNA), tricyclo-DNA (tcDNA), and nucleic acids having backbone sections with alkyl linkers or amino linkers (see, e.g., Kurreck 2003 (Eur J Biochem 270: 1628-1644)). "Alkyl" as used herein particularly encompasses lower hydrocarbon moieties, e.g., C1-C4 linear or branched, saturated or unsaturated hydrocarbon, such as methyl, ethyl, ethenyl, propyl, 1-propenyl, 2-propenyl, and isopropyl. Nucleic acids as intended herein may include naturally occurring nucleosides, modified nucleosides or mixtures thereof. A modified nucleoside may include a modified heterocyclic base, a modified sugar moiety, a modified inter-nucleoside linkage or a combination thereof. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature, can be recombinant, i.e., produced by recombinant DNA technology, and/or can be, partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear. Nucleic acids and particularly antisense oligonucleotides or RNAi agents may be herein denoted as comprising uracil (U) bases. It shall be appreciated that U may be optionally substituted by thymine (T) in (at least some) such nucleic acids and agents. For example, as 2'-O-methyl phosphorothioate antisense oligonucleotides are more 'RNA-like', U may be used and denoted in such molecules. With other antisense chemistries, such as peptide nucleic acids or morpholino backbones, T bases may be preferably denoted and used.

The term "aptamer" as used herein refers to single-stranded or double-stranded oligo-DNA, oligo-RNA or oligo-DNA/RNA or any analogue thereof that can specifically bind to a target molecule. Advantageously, aptamers can display fairly high specificity and affinity (e.g., $K_A$ in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term also encompasses photoaptamers, i.e., aptamers that contain one or more photoreactive functional groups that can covalently bind to or crosslink with a target molecule.

The term "small organic molecule", "small organic compound", "small molecule" or "small compound" as used herein encompasses organic compounds with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. Even more preferred small organic molecules have no more than five hydrogen bond donors, no more than 10 hydrogen bond acceptors, and/or an octanol-water partition coefficient log P not greater than five.

Examples of small molecule inhibitors of PDE6δ are elaborated upon herein below.

As used herein, the term "antibody" is used in its broadest sense and generally refers to any immunologic binding agent, such as a whole antibody, including without limitation a chimeric, humanized, human, recombinant, transgenic, grafted and single chain antibody, and the like, or any fusion proteins, conjugates, fragments, or derivatives thereof that contain one or more domains that selectively bind to an antigen of interest. The term antibody thereby includes a whole immunoglobulin molecule, a monoclonal antibody, a chimeric antibody, a humanized antibody, a human antibody, or an immunologically effective fragment of any of these. The term thus specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro, in cell culture, or in vivo. The term antibody as used herein also encompasses chimeric antibodies, fully human antibodies, humanized antibodies, primatized antibodies or intrabodies. Production of antibodies can be carried out by any processes known in the art.

In particular embodiments, the therapeutic or prophylactic agent according to the invention is a polyclonal antibody, a monoclonal antibody, a chimeric antibody, a humanized antibody, a primatized antibody, a human antibody, a Nanobody or mixtures thereof, as defined elsewhere in the specification.

In particular embodiments, the therapeutic or prophylactic agent as disclosed herein may be an intrabody, as defined elsewhere in the specification, specifically directed to PDE6δ, which may bind said PDE6δ intracellularly and thereby modulate, such as inhibit or increase, activity of PDE6δ, for instance, by preventing PDE6δ from binding small GTPases.

Targeted genome modification is a powerful tool for genetic manipulation of cells and organisms, including mammals. Genome modification or gene editing, including insertion, deletion or replacement of DNA in the genome, can be carried out using a variety of known gene editing systems. The term "gene editing system" or "genome editing system" as used herein refers to a tool to induce one or more nucleic acid modifications, such as DNA or RNA modifications, into a specific DNA or RNA sequence within a cell. Gene editing systems typically make use of an agent capable of inducing a nucleic acid modification. In certain embodiments, the agent capable of inducing a nucleic acid modification may be a (endo)nuclease or a variant thereof having altered or modified activity. (endo)Nucleases typically comprise programmable, sequence-specific DNA- or RNA-binding modules linked to a nonspecific DNA or RNA cleavage domain. In DNA, these nucleases create site-specific double-strand breaks at desired locations in the genome. The induced double-stranded breaks are repaired through non-homologous end-joining or homologous recombination, resulting in targeted mutations. In certain embodiments, said (endo)nuclease may be RNA-guided. In certain embodiments, said (endo)nuclease can be engineered nuclease such as a Clustered Regularly Interspaced Short Palindromic Repeats (CRISPR) associated (Cas) (endo)nuclease, such as Cas9, Cpf1, or C2c2, a (zinc finger nuclease (ZFN), a transcription factor-like effector nuclease (TALEN), a meganuclease, or modifications thereof. Methods for using TALEN technology, Zinc Finger technology and CRISPR/Cas technology are known by the skilled person.

In particular embodiments, the inhibitor of PDE6δ as disclosed herein is an antisense agent capable of binding to (annealing with) a sequence region in pre-mRNA or mRNA sequence of PDE6δ. Particularly intended may be such RNAi agents configured to target mRNA of PDE6δ.

The term "antisense" generally refers to an agent (e.g., an oligonucleotide as defined elsewhere in the specification) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein may typically be capable of annealing with (hybridising to) the respective target nucleic acid sequences at high stringency conditions, and capable of hybridising specifically to the target under physiological conditions.

The terms "complementary" or "complementarity" as used herein with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The sequence of an antisense agent need not be 100% complementary to that of its target sequence to bind or hybridise specifically with the latter as defined elsewhere in the specification. An antisense agent may be said to be specifically hybridisable when binding of the agent to a target nucleic acid molecule interferes with the normal function of the target nucleic acid such as to attain an intended outcome (e.g., loss of utility), and there is a sufficient degree of complementarity to avoid non-specific binding of the antisense agent to non-target sequences under conditions in which specific binding is desired, i.e., under physiological conditions in the case of in vivo assays or therapeutic treatment, and in the case of in vitro assays, under conditions in which the assays are performed. Thus, "specifically hybridisable" and "complementary" may indicate a sufficient degree of complementarity or precise pairing such that stable and specific binding occurs between an antisense agent and a nucleic acid target. Preferably, to ensure specificity of antisense agents towards the desired target over unrelated molecules, the sequence of said antisense agents may be at least about 80% identical, preferably at least about 90% identical, more preferably at least about 95% identical, such as, e.g., about 96%, about 97%, about 98%, about 99% and up to 100% identical to the respective target sequence.

The term "RNA interference agent" or "RNAi agent" refers to ribonucleic acid sequences, modified ribonucleic acid sequences, or DNA sequences encoding said ribonucleic acid sequences, which cause RNA interference and thus decrease expression of the target gene.

An RNAi (RNA interference) agent typically comprises, consists essentially of or consists of a double-stranded portion or region (notwithstanding the optional and potentially preferred presence of single-stranded overhangs) of annealed complementary strands, one of which has a sequence corresponding to a target nucleotide sequence (hence, to at least a portion of an mRNA) of the target gene to be down-regulated. The other strand of the RNAi agent is complementary to said target nucleotide sequence. Non-limiting examples of RNAi agents are shRNAs, siRNAs, miRNAs, and DNA-RNA hybrids.

Whereas the sequence of an RNAi agent need not be completely identical to a target sequence to be down-regulated, the number of mismatches between a target sequence and a nucleotide sequence of the RNAi agent is preferably no more than 1 in 5 bases, or 1 in 10 bases, or 1 in 20 bases, or 1 in 50 bases. Preferably, to ensure specificity of RNAi agents towards the desired target over unrelated molecules, the sequence of said RNAi agents may be at least about 80% identical, preferably at least about 90% identical, more preferably at least about 95% identical, such as, e.g., about 96%, about 97%, about 98%, about 99% and up to 100% identical to the respective target sequence.

Production of antisense agents and RNAi agents can be carried out by any processes known in the art, such as inter alia partly or entirely by chemical synthesis.

The inhibitor of PDE6δ as disclosed herein may be an expressible molecule such as an antibody or a fragment or derivative thereof, a protein or polypeptide, a peptide, a nucleic acid, an antisense agent or an RNAi agent, it shall be understood that the inhibitor itself may be introduced to a subject or may be introduced by means of a recombinant nucleic acid comprising a sequence encoding the inhibitor operably linked to one or more regulatory sequences allowing for expression of said sequence encoding the inhibitor (e.g., gene therapy or cell therapy).

Hence, the inhibitor of PDE6δ may comprise a recombinant nucleic acid comprising a sequence encoding one or more desired proteins, polypeptides, peptides, antisense agents or RNAi agents, operably linked to one or more regulatory sequences allowing for expression of said sequence or sequences encoding the proteins, polypeptides, peptides, antisense agents or RNAi agents, e.g., in vitro, in a host cell, host organ and/or host organism (expression constructs). Such recombinant nucleic acid may be comprised in a suitable vector.

By "encoding" is meant that a nucleic acid sequence or part(s) thereof corresponds, by virtue of the genetic code of an organism in question to a particular amino acid sequence, e.g., the amino acid sequence of one or more desired proteins or polypeptides, or to another nucleic acid sequence in a template-transcription product (e.g. RNA or RNA analogue) relationship.

Preferably, a nucleic acid encoding one or more proteins, polypeptides or peptides may comprise one or more open reading frames (ORF) encoding said one or more proteins, polypeptides or peptides. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a protein, polypeptide or peptide. Hence, the term may be synonymous with "coding sequence" as used in the art.

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence.

The precise nature of regulatory sequences or elements required for expression may vary between expression environments, but typically include a promoter and a transcription terminator, and optionally an enhancer.

Reference to a "promoter" or "enhancer" is to be taken in its broadest context and includes transcriptional regulatory sequences required for accurate transcription initiation and where applicable accurate spatial and/or temporal control of gene expression or its response to, e.g., internal or external (e.g., exogenous) stimuli. More particularly, "promoter" may depict a region on a nucleic acid molecule, preferably DNA molecule, to which an RNA polymerase binds and initiates transcription. A promoter is preferably, but not necessarily, positioned upstream, i.e., 5', of the sequence the transcription of which it controls. Typically, in prokaryotes a promoter region may contain both the promoter per se and sequences which, when transcribed into RNA, will signal the initiation of protein synthesis (e.g., Shine-Dalgarno sequence).

In embodiments, promoters contemplated herein may be constitutive or inducible.

The terms "terminator" or "transcription terminator" refer generally to a sequence element at the end of a transcriptional unit which signals termination of transcription. For example, a terminator is usually positioned downstream of, i.e., 3' of ORF(s) encoding a polypeptide of interest. For instance, where a recombinant nucleic acid contains two or more ORFs, e.g., successively ordered and forming together a multi-cistronic transcription unit, a transcription terminator may be advantageously positioned 3' to the most downstream ORF.

The term "vector" generally refers to a nucleic acid molecule, typically DNA, to which nucleic acid segments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, viral vectors, etc., as appropriate. Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise suitable regulatory sequences.

As noted elsewhere, in particular embodiments, the inhibitor of PDE6δ is a protein, polypeptide or peptide. Such may be suitably obtained through expression by host cells or host organisms, transformed with an expression construct encoding and configured for expression of said protein, polypeptide or peptide in said host cells or host organisms, followed by purification of the protein, polypeptide or peptide.

The terms "host cell" and "host organism" may suitably refer to cells or organisms encompassing both prokaryotes, such as bacteria, and eukaryotes, such as yeast, fungi, protozoan, plants and animals. Contemplated as host cells are inter alia unicellular organisms, such as bacteria (e.g., *E. coli, Salmonella tymphimurium, Serratia marcescens*, or *Bacillus subtilis*), yeast (e.g., *Saccharomyces cerevisiae* or *Pichia pastoris*), (cultured) plant cells (e.g., from *Arabidopsis thaliana* or *Nicotiana tobaccum*) and (cultured) animal cells (e.g., vertebrate animal cells, mammalian cells, primate cells, human cells or insect cells). Contemplated as host organisms are inter alia multi-cellular organisms, such as plants and animals, preferably animals, more preferably warm-blooded animals, even more preferably vertebrate animals, still more preferably mammals, yet more preferably primates; particularly contemplated are such animals and animal categories which are non-human.

Such protein, polypeptide or peptide may be suitably isolated. The term "isolated" with reference to a particular component (such as for instance a nucleic acid, protein, polypeptide or peptide) generally denotes that such component exists in separation from—for example, has been separated from or prepared and/or maintained in separation from—one or more other components of its natural environment. For instance, an isolated human or animal protein or complex may exist in separation from a human or animal body where it naturally occurs. The term "isolated" as used herein may preferably also encompass the qualifier "purified" as defined elsewhere in the specification Further, there are several well-known methods of introducing nucleic acids (e.g., antisense and RNAi agents) into animal cells, any of which may be used herein. At the simplest, the nucleic acid can be directly injected into the target cell/target tissue. Other methods include fusion of the recipient cell with bacterial protoplasts containing the nucleic acid, the use of compositions like calcium chloride, rubidium chloride, lithium chloride, calcium phosphate, DEAE dextran, cationic lipids or liposomes or methods like receptor-mediated endocytosis, biolistic particle bombardment ("gene gun" method), infection with viral vectors (i.e. derived from lentivirus, adeno-associated virus, adenovirus, retrovirus or antiviruses), electroporation, and the like. Other techniques or methods which are suitable for delivering nucleic acid molecules to target cells include the continuous delivery of an NA molecule from poly (lactic-Co-Glycolic Acid) polymeric microspheres or the direct injection of protected (stabilized) NA molecule(s) into micropumps delivering the product. Another possibility is the use of implantable drug-releasing biodegradable micropsheres. Also envisaged is encapsulation of NA in various types of liposomes (immunoliposomes, PEGylated (immuno) liposomes), cationic lipids and polymers, nanoparticules or dendrimers, poly (lactic-Co-Glycolic Acid) polymeric microspheres, implantable drug-releasing biodegradable microspheres, etc; and co-injection of NA with protective agent like the nuclease inhibitor aurintricarboxylic acid. It shall be clear that also a combination of different above-mentioned delivery modes or methods may be used.

Reference to inhibitors of PDE6δ also includes without limitation naturally-occurring binding and/or regulatory partners of PDE6δ. Inhibitors of PDE6δ can be readily identified by standard protein-protein interaction (PPI) detection methods, such as co-immunoprecipitation, phage display, chemical cross-linking, or yeast two hybrid screens.

Exemplary methods for screening compounds, proteins or other molecules capable of inhibiting PDE6δ include methods for screening for compounds which bind to the prenyl-binding pocket of PDE6δ. Such a screening method may comprise the steps of:

performing in-silico docking of compounds compared to a control in the PDE6δ prenyl binding site with affinity; and testing the binding of compounds to PDE6δ using Surface Plasmon Resonance. In these assays, competition with a compound known to bind the prenyl-binding pocket of PDE6δ (such as Atorvastatin or deltarasin), can be tested to ensure specificity.

The compounds or molecules used in the screening methods envisaged herein can include random libraries or libraries of compounds designed to interact with PDE6δ, based on its structure as well as generated through immunization of a mammal. As the present inventors have identified a correlation between PDE6δ-inhibition and activity in a TAU toxicity assay for a number of compounds it can be envisaged to prescreen compounds or molecules based on their activity in a TAU toxicity assay.

In particular embodiments, the inhibitor as described herein may be contained within a pharmaceutical composition in a therapeutically effective amount, wherein said pharmaceutical composition optionally comprises a pharmaceutically acceptable carrier. Such pharmaceutical formulations or compositions may be comprised in a kit of parts.

The term "effective amount" as used herein may refer to a prophylactically effective amount, which is an amount of an active compound or pharmaceutical agent, more particularly a prophylactic agent, that inhibits or delays in a subject the onset of a disorder as being sought by a researcher, veterinarian, medical doctor or other clinician, or may refer to a therapeutically effective amount, which is an amount of active compound or pharmaceutical agent, more particularly a therapeutic agent, that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the agents as taught herein.

Pharmaceutical compositions of the invention may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous, intramuscular, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions of the invention can be, for example, systemic, local, tissue-specific, etc., depending of the specific needs of a given application of the invention.

The term "pharmaceutically acceptable" as used herein is consistent with the art and means compatible with the other ingredients of a pharmaceutical composition and not deleterious to the recipient thereof.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being preferred. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

For example, for parenteral administration, pharmaceutical compositions may be advantageously formulated as solutions, suspensions or emulsions with suitable solvents, diluents, solubilisers or emulsifiers, etc. Suitable solvents are, without limitation, water, physiological saline solution or alcohols, e.g. ethanol, propanol, glycerol, in addition also sugar solutions such as glucose, invert sugar, sucrose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. The inhibitors of the invention can also be lyophilised and the lyophilisates obtained used, for example, for the production of injection or infusion preparations. For example, one illustrative example of a carrier for intravenous use includes a mixture of 10% USP ethanol, 40% USP propylene glycol or polyethylene glycol 600 and the balance USP Water for Injection (WFI). Other illustrative carriers for intravenous use include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Where aqueous formulations are preferred, such may comprise one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipahnitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:active substance molar ratio in an aqueous formulation will be from about 10:1 to about 1:10, more typically from about 5:1 to about 1:5, however any effective amount of surfactant may be used in an aqueous formulation to best suit the specific objectives of interest.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquidify and/or dissolve in the rectal cavity to release the drug.

Suitable carriers for microcapsules, implants or rods are, for example, copolymers of glycolic acid and lactic acid.

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

The dosage or amount of the inhibitors as described herein, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the inhibitors used, on whether the therapy is acute or chronic or prophylactic, or on whether other active compounds are administered in addition to the inhibitor(s) of the invention.

The present inventors have found that certain known compounds are in fact inhibitors of PDE6δ and thus useful in the context of the present invention. More particularly, the present inventors have found that the compounds as described in PCT application WO2010/142801 are able to inhibit PDE6δ. And suggest that said compounds bind to PDE6δ and disrupt the interaction activity of PDE6δ with prenylated small GTPases, such as RAP1.

It is evident that known PDE6δ inhibitors can also be used in the context of the present invention. Accordingly, compounds envisaged within the context of the present invention include pyrazolopyridazinones, pyrazolo-pyrimidinones, benzimidazoles, bis-benzimidazoles and 3-oxo-pregna-4,9-dienes.

A first aspect relates to the use of inhibitors of PDE6δ for in the treatment of epilepsy and PDE6δ inhibitors for use in the treatment of epilepsy. Indeed, it has been found that the effect of inhibition of PDE6δ is comparable to inhibition of Ca' influx through voltage-gated calcium channels (VGCC), which has been found relevant in the activity of compounds which are active in models of epilepsy (such as isradepine).

In particular embodiments, the inhibitor of PDE6δ for use in the treatment of epilepsy as described herein inhibits the binding of PDE6δ to one or more GTPases, wherein said GTPase is preferably a small GTPase, more preferably RAP1, even more preferably RAP1a. In particular embodiments, the inhibitor of PDE6δ for use in the treatment of epilepsy inhibits the binding of PDE6δ to a prenylated region of a GTPase.

The term "epilepsy" as used herein, refers to a group of disorders characterized by epileptic seizures, which are episodes that can vary from brief and nearly undetectable to long periods of vigorous shaking. Non-limiting examples of epilepsy include refractory epilepsy, West syndrome, Doose syndrome, benign rolandic epilepsy, Rasmussens's syndrome, Lennox-Gastaut syndrome, West syndrome, Sturge-Weber syndrome, juvenile myoclonic epilepsy, childhood absence epilepsy, idiopathic localization-related epilepsies, temporal lobe epilepsy, partial seizures, simple partial seizures, tonic seizures, tonic-clonic seizures, clonic seizures, myoclonic seisures, absence seizures and atonic seizures. In the context of epilepsy, treatment of the disease involves amelioration of one or more symptoms. In particular embodiments, treatment may also involve prevention of worsening of one or more symptoms of the disease. In particular embodiments, the methods may also be envisaged for use on a subject prone to develop epilepsy.

Epilepsy affects subjects of all ages thus, the age of the patient is not critical. As the present inventors have identified the relevance of PDE6δ in the pathology of epilepsy, the use of the inhibitors of PDE6δ is envisaged for the prevention and/or treatment of epilepsy in a subject, independent of the subject's age or sex. In particular embodiments, the subject is less than 65 years old. In particular embodiments, the subject is less than 50 years old. In particular embodiments, the patient does not suffer from another neurological condition, more particular does not suffer from a neurodegenerative diseases. In further particular embodiment, the patient is not diagnosed with Alzheimer's disease, preferably not diagnosed with moderate or advanced Alzheimer's disease.

The nature of the compound envisaged for the prevention and/or treatment of epilepsy is not critical. Accordingly, any compound which is an inhibitor of PDE6δ is considered to be useful for the prevention and/or treatment of epilepsy. It will be understood however, that the scope of the present application is not intended to encompass compounds or molecules known for the prevention and/or treatment of epilepsy. Accordingly, in certain embodiments, the compound for use in the prevention and/or treatment of epilepsy as described herein is not Atorvastatin.

In certain embodiments, the compound for use in the prevention and/or treatment of epilepsy as described herein may be a compound selected from the group consisting of pyrazolopyridazinone, pyrazolo-pyrimidinone, bis-benzimidazole, 3-oxo-pregna-4,9-diene, solvates, hydrates, salts or prodrugs thereof or a compound as described in PCT application WO2010/142801, or stereoisomers, enantiomers, tautomers, solvates, hydrates, salts or prodrugs thereof.

In certain embodiments, the pyrazolo-pyrimidinones for use in the prevention and/or treatment of epilepsy as described herein is PF-3717842 or PF-4540124.

In certain embodiments, the bis-benzimidazole for use in the prevention and/or treatment of epilepsy as described herein is Deltarasin.

In certain embodiments, the 3-oxo-pregna-4,9-diene for use in the prevention and/or treatment of epilepsy as described herein is Anecortave acetate.

In embodiments, the compound for use in the prevention and/or treatment of epilepsy as described herein is a compound which falls within the scope of formula (AA1), (BB1) or (CC1) as disclosed in PCT application WO2010/142801, including stereoisomers, enantiomers, tautomers, solvates, hydrates, salts or prodrugs thereof.

As will be understood, in line with the above, the application encompasses methods of prevention and/or treatment of a subject suffering from or prone to develop epilepsy, comprising administering an effective amount of the inhibitor as described herein, or a pharmaceutical composition comprising the inhibitor as described herein to a subject in need thereof. Similarly, the application also relates to the use of the inhibitor as described herein for the manufacture of a medicament for the prevention and/or treatment of epilepsy.

As described earlier, the present applicants have identified PDE6δ as a common target of disease pathophysiology in epilepsy and neurodegenerative disorders, such as Alzheimer's disease (AD).

Accordingly, a further aspect relates to inhibitors of PDE6δ for use in the prevention and/or treatment of a neurodegenerative disorder.

The term "neurodegenerative disorders" as used herein, unless otherwise stated, refers to tauopathy and α-synucleopathy, and thereby includes, but is not limited to Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy. The term "Tauopathy" as used herein, unless otherwise stated, refers to a disease characterised by dysfunctioning of the TAU protein, for instance manifested by insoluble aggregates or polymers of said protein. Such diseases include, but are not limited to, Alzheimer's disease, Pick's disease, corticobasal degeneration, progressive supranuclear palsy, frontotemporal dementia and parkinsonism (linked to chromosome 17, FTDP-17). The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Also here, the nature of the compound envisaged for the treatment of a neurodegenerative disorder and more particular AD is not critical. Accordingly, any compound which is an inhibitor of PDE6δ is considered to be useful for the prevention and/or treatment of a neurodegenerative disorder and more particular AD. Accordingly, in particular embodiments, the inhibitor for use in the prevention and/or treatment of a neurodegenerative disorder as described herein, is selected from the group consisting of a protein, a polypeptide, a peptide, a peptidomimetic, a nucleic acid, a small organic molecule, and a compound or a combination of any two or more thereof. For example, an aptamer, a gene-editing system, an antisense agent, an RNAi agent, such as siRNA or shRNA or an antibody or functional fragment thereof.

In certain preferred embodiments, the inhibitor for use according to the invention is a small organic molecule or compound. The preferred small organic molecules or compounds for use in the treatment of a neurodegenerative disorder as described herein are elaborated upon elsewhere herein.

In certain embodiments, the compound for use in the prevention and/or treatment of a neurodegenerative disorder as described herein may be a compound selected from the group consisting of pyrazolopyridazinones, pyrazolo-pyrimidinones, benzimidazoles, bis-benzimidazoles and 3-oxo-pregna-4,9-dienes, solvates, hydrates, salts or prodrugs thereof.

In certain embodiments, the pyrazolo-pyrimidinones for use in the prevention and/or treatment of a neurodegenerative disorder as described herein is PF-3717842 or PF-4540124.

In certain embodiments, the bis-benzimidazole for use in the prevention and/or treatment of a neurodegenerative disorder as described herein is Deltarasin.

In certain embodiments, the 3-oxo-pregna-4,9-diene for use in the prevention and/or treatment of a neurodegenerative disorder as described herein is Anecortave acetate.

It will be understood however, that the scope of the present application is not intended to encompass compounds or molecules known for the prevention and/or treatment of neurodegenerative disorders such as AD. Accordingly, in certain embodiments said inhibitor is not Atorvastatin. In certain embodiments said inhibitor is not a compound as described in PCT application WO2010/142801, more particularly not a compound of formula (AA1), (BB1) or (CC1) as described in PCT application WO2010/142801 or a stereoisomer, enantiomer, tautomer, solvate, hydrate, salt or prodrug thereof.

In particular embodiments, the neurodegenerative disorder is selected from Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis and Creutzfeld-Jacob's disease.

In particular embodiments, the neurodegenerative disorder is characterized by Ca' dyshomeostasis.

In particular embodiments, the neurodegenerative disorder is Alzheimer's disease.

The term "Alzheimer's disease" as used herein, also called Alzheimer disease, Senile Dementia of the Alzheimer Type (SDAT) or simply Alzheimer's refers to a chronic progressive nervous disease characterised by neurodegeneration with as most important (early) symptom being memory loss. As the disease advances, symptoms include confusion, irritability and aggression, mood swings, language breakdown, long-term memory loss, and the general withdrawal of the sufferer as their senses decline.

A further aspect relates to inhibitors of PDE6δ for use in the prevention and/or treatment of pain disorders, preferably wherein the pain disorder is selected from the group consisting of acute pain, persistent pain, chronic pain, inflammatory pain and neuropathic pain, anxiety disorders, preferably wherein the anxiety disorder is selected from the group consisting of panic attack, agoraphobia or specific phobias, obsessive-compulsive disorders, post-traumatic stress disorder, acute stress disorder, generalized anxiety disorder, eating disorder, substance-induced anxiety disorder, and nonspecified anxiety disorder, depression, bipolar disorder, psychosis, drug withdrawal, tobacco withdrawal, memory loss, dementia, schizophrenia, and panic and/or for preventing, treating and/or alleviating complications and/or symptoms associated therewith.

It will be understood that in line with the above, the application encompasses methods of prevention and/or treatment of neurodegenerative disorders, comprising administering an effective amount of the inhibitor as described herein, or a pharmaceutical composition comprising the inhibitor as described herein to a subject in need thereof, as well as methods of prevention and/or treatment of pain disorders, anxiety disorders, depression, bipolar disorder, psychosis, drug withdrawal, tobacco withdrawal, memory loss, dementia, schizophrenia, panic, comprising administering an effective amount of the inhibitor as described herein, or a pharmaceutical composition comprising the inhibitor as described herein to a subject in need thereof.

Also envisaged within the context of the present invention is the in vitro use of an inhibitor of PDE6δ for ensuring, one or more effects associated with PDE6δ inhibition described herein, such as inhibition of tau toxicity, more particularly reducing TAU aggregation, TAU hyper-phosphorylation and/or reducing voltage-gated calcium channel (VGCC) activity, increasing afterhyperpolarization of action potentials, preventing the solubilization of said small GTPase preventing $Ca^{2+}$ dyshomeostasis and/or for restoring $Ca^{2+}$ homeostasis; for decreasing neurotransmitter release and/or preventing $Ca^{2+}$ dyshomeostasis and/or neuronal hyperactivity.

In particular embodiments, the above uses are envisaged in vitro, or for the generation of an animal model.

A further aspect of the invention relates to the use of PDE6δ, and more particularly the use of compounds specifically binding to PDE6δ, such as, but not limited to PDE6δ inhibitors, for determining the susceptibility of a patient to the treatment with a PDE6δ-inhibitor. Indeed, it will be understood that based on the present finding that inhibitors of PDE6δ can be used in the treatment of AD and other neurodegenerative diseases and epilepsy, the use of PDE6δ in determining the susceptibility to PDE6δ treatment is also envisaged.

A further aspect of the invention relates to the use of PDE6δ in the diagnosis of Alzheimer and other neurodegenerative diseases or epilepsy or the likeliness of developing these diseases. Indeed, based on the ability of inhibition of PDE6δ to reduce symptoms of neurodegenerative diseases or epilepsy, increased or inappropriate signaling through PDE6δ can indicative of the development or likeliness of development of these diseases. Accordingly such methods involve the step of determining increased or inappropriate signaling through PDE6δ in a patient or a sample of said patient.

Described herein below are compounds, such as those described in WO 2010/142801 which, as detailed above, have been by the present inventors to be inhibitors of PDE6δ and are, based on the present teaching, useful in the prevention and/or treatment of epilepsy.

Also described herein below is a further aspect of the invention relating to novel inhibitors of PDE6δ for use in the prevention and/or treatment of a neurodegenerative disease and/or epilepsy as described above and methods of treatment and prevention of these conditions involving these novel compounds.

The compounds will be described based on the following terminology. When referring to a chemical group "L" depicted in a chemical structure, the terminology "L is independently selected from being not present" and other possibilities as used herein refers to the situation that the two groups which are linked by L are directly coupled to each other via a single bond. As used herein the term "not being present" and "single bond" are synonyms and used interchangeably. As an example, if the invention refers to a compound comprising the following formula

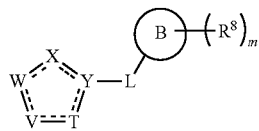

wherein L is independently selected from being not present; —O—; —NH—; —NR$^{10}$—; C$_{1-6}$alkylene; C$_{1-6}$alkenylene: and C$_{1-6}$alkenylene: then this comprises compounds with the following structure

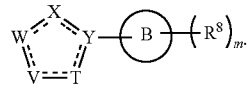

The terminology "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkylene, heteroalkenylene, heteroalkynylene, cycloheteroalkyl, cycloheteroalkenyl, cycloheteroalkynyl, heteroaryl, arylheteroalkyl(ene), heteroarylalkyl(ene), heteroarylheteroalkyl(ene), arylheteroalkenyl(ene), heteroarylalkenyl(ene), heteroarylheteroalkenyl (ene), heteroarylheteroalkenyl(ene), arylheteroalkynyl(ene), heteroarylalkynyl(ene), heteroarylheteroalkynyl(ene), among others. In other words, this term means that CH$_3$ can be replaced by —NH$_2$; —CH$_2$— by NH—, —O— or —S—; a CH= by N=; and ≡CH by ≡N. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, CH$_3$—O—CH$_2$—, CH$_3$—S—CH$_2$—, CH$_3$—CH$_2$—O—CH$_2$—, CH$_3$—NH—, (CH$_3$)$_2$—N—, (CH$_3$)$_2$—CH$_2$—NH—CH$_2$—CH$_2$—, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-CH$_2$—S—CH$_2$—, aryl-CH$_2$—O—CH$_2$—, aryl-NH—CH$_2$— among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a C=O, C=S, N=O, N=S, S=O or S(O)$_2$" as used herein, refers to a group where two or more hydrogen atoms on a carbon atom or heteroatom of said group are taken together to form C=O, C=S, N=O, N=S, S=O or S(O)$_2$. In other words, the expression means that a carbon atom or heteroatom of said group can be oxidized to form a C=O, C=S, N=O, N=S, S=O or S(O)$_2$. As an example, the terminology refers to "an alkyl wherein optionally two or more hydrogen atoms on a carbon atom or heteroatom of said alkyl can be taken together to form a C=O, C=S, N=O, N=S, S=O or S(O)$_2$", includes among other examples CH$_3$—C(O)—CH$_2$—, CH$_3$—C(O)—, CH$_3$—C(S)—CH$_2$— and (CH$_3$)$_2$—CH$_2$—C(O)—CH$_2$—CH$_2$—. As another example, as used herein and unless otherwise stated, the expression "two or more hydrogen atoms on a carbon atom or heteroatom of said heterocycle can be taken together to form a C=O, C=S, N=O, N=S, S=O or S(O)$_2$" means that a carbon atom or heteroatom of the ring can be oxidized to form a C=O, C=S, N=O, N=S, S=O or S(O)$_2$.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a C=O, C=S, N=O, N=S, S=O or S(O)$_2$" can combine the two aspects described herein above and includes, if the group referred to is alkyl, among other examples CH$_3$—

COO—, $CH_3$—COO—$CH_2$—, $CH_3$—NH—CO—, $CH_3$—NH—CO—$CH_2$—, $CH_3$—NH—CS—$CH_2$—, $CH_3$—NH—CS—NH—$CH_2$—, $CH_3$—NH—$S(O)_2$— and $CH_3$—NH—$S(O)_2$—NH—$CH_2$—.

The term "leaving group" as used herein means a chemical group which is susceptible to be displaced by a nucleophile or cleaved off or hydrolysed in basic or acidic conditions. In a particular embodiment, a leaving group is selected from a halogen atom (e.g., Cl, Br, I) or a sulfonate (e.g., mesylate, tosylate, triflate).

The term "alkyl" as used herein means $C_1$-$C_{18}$ normal, secondary, or tertiary, linear or cyclic, branched or straight hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons as further defined herein above.

The term "linear alkyl" as used herein means $C_1$-$C_{18}$ normal, secondary, or tertiary, linear, branched or straight, hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

The term "alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$), cyclopentenyl (—$C_5H_7$), cyclohexenyl (—$C_6H_9$) and 5-hexenyl (—$CH_2CH_2CH_2CH_2$CH=$CH_2$). The double bond may be in the cis or trans configuration. In a particular embodiment, the term alkenyl refers to $C_{1-12}$ hydrocarbons, yet more in particular to $C_{1-6}$ hydrocarbons as further defined herein above.

The term "linear alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$) and 5-hexenyl (—$CH_2CH_2CH_2CH_2$CH=$CH_2$). The double bond may be in the cis or trans configuration.

The term "cycloalkenyl" as used herein refers to $C_2$-$C_{18}$ normal, secondary or tertiary, cyclic hydrocarbon with at least one site (usually 1 to 3, preferably 1) of unsaturation, namely a carbon-carbon, sp2 double bond. Examples include, but are not limited to: cyclopentenyl (—$C_5H_7$) and cyclohexenyl (—$C_6H_9$). The double bond may be in the cis or trans configuration.

The term "alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH). In a particular embodiment, the term alkenyl refers to $C_{1-12}$ hydrocarbons, yet more in particular to $C_{1-6}$ hydrocarbons as further defined herein above.

The term "linear alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH).

The term "cycloalkynyl" as used herein refers to $C_2$-$C_{18}$ normal, secondary, tertiary, cyclic hydrocarbon with at least one site (usually 1 to 3, preferably 1) of unsaturation, namely a carbon-carbon, sp triple bond. Examples include, but are not limited to: cyclohex-1-yne and ethylene-cyclohex-1-yne.

The terms "alkylene" as used herein each refer to a saturated, branched or straight chain hydrocarbon radical of 1-18 carbon atoms (more in particular 1-12 or 1-6 carbon atoms), and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8α-hexahydroacenaphthylenyl, 1,2-dihydroacenaphthylenyl, and the like.

"Arylalkylene" as used herein refers to an alkyl radical in which one of the hydrogen atoms bonded to a carbon atom, typically a terminal or sp3 carbon atom, is replaced with an aryl radical. Typical arylalkylene groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkylene group comprises 6 to 20 carbon atoms, e.g. the alkylene moiety of the arylalkylene group is 1 to 6 carbon atoms and the aryl moiety is 5 to 14 carbon atoms.

"Arylalkenylene" as used herein refers to an alkenylene radical in which one of the hydrogen atoms bonded to a carbon atom, is replaced with an aryl radical. The arylalkenylene group comprises 6 to 20 carbon atoms, e.g. the alkenylene moiety of the arylalkenylene group is 1 to 6 carbon atoms and the aryl moiety is 5 to 14 carbon atoms.

"Arylalkynylene" as used herein refers to an alkynyl radical in which one of the hydrogen atoms bonded to a carbon atom, is replaced with an aryl radical. The arylalkynylene group comprises 6 to 20 carbon atoms, e.g. the alkynylene moiety of the arylalkynylene group is 1 to 6 carbon atoms and the aryl moiety is 5 to 14 carbon atoms.

The term "heterocycle" as used herein means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

"Heterocycle-alkylene" as used herein refers to an alkyl radical in which one of the hydrogen atoms bonded to a carbon atom, typically a terminal or sp3 carbon atom, is replaced with a heterocycle radical. An example of a heterocycle-alkylene group is 2-pyridyl-methylene. The heterocycle-alkylene group comprises 6 to 20 carbon atoms, e.g. the alkylene moiety of the heterocycle-alkyl group is 1 to 6 carbon atoms and the heterocycle moiety is 5 to 14 carbon atoms.

"Heterocycle-alkenylene" as used herein refers to an alkenyl radical in which one of the hydrogen atoms bonded to a carbon atom, is replaced with an heterocycle radical. The heterocycle-alkenylene group comprises 6 to 20 carbon atoms, e.g. the alkenylene moiety of the heterocycle-alkenylene group is 1 to 6 carbon atoms and the heterocycle moiety is 5 to 14 carbon atoms.

"Heterocycle-alkynylene" as used herein refers to an alkynylene radical in which one of the hydrogen atoms bonded to a carbon atom, is replaced with a heterocycle radical. The heterocycle-alkynylene group comprises 6 to 20 carbon atoms, e.g. the alkynylene moiety of the heterocycle-alkynylene group is 1 to 6 carbon atoms and the heterocycle moiety is 5 to 14 carbon atoms.

"Heteroaryl" means an aromatic ring system including at least one N, O, S, or P. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Heteroaryl-alkylene" as used herein refers to an alkyl radical in which one of the hydrogen atoms bonded to a carbon atom, typically a terminal or sp3 carbon atom, is replaced with a heterocycle radical. An example of a heteroaryl-alkylene group is 2-pyridyl-methylene. The heteroaryl-alkylene group comprises 6 to 20 carbon atoms, e.g. the alkylene moiety of the heteroaryl-alkylene group is 1 to 6 carbon atoms and the heteroaryl moiety is 5 to 14 carbon atoms.

"Heteroaryl-alkenylene" as used herein refers to an alkenyl radical in which one of the hydrogen atoms bonded to a carbon atom, is replaced with an heteroaryl radical. The heteroaryl-alkenylene group comprises 6 to 20 carbon atoms, e.g. the alkenylene moiety of the heteroaryl-alkenylene group is 1 to 6 carbon atoms and the heteroaryl moiety is 5 to 14 carbon atoms.

"Heteroaryl-alkynylene" as used herein refers to an alkynyl radical in which one of the hydrogen atoms bonded to a carbon atom, is replaced with a heteroaryl radical. The heteroaryl-alkynylene group comprises 6 to 20 carbon atoms, e.g. the alkynylene moiety of the heteroaryl-alkynylene group is 1 to 6 carbon atoms and the heteroaryl moiety is 5 to 14 carbon atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or B-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cycloalkoxy", "aryloxy", "arylalkyloxy", "oxyheterocycle ring", "thio-alkyl", "thio-cycloalkyl", "arylthio", "arylalkylthio" and "thioheterocycle" refer to substituents wherein an alkyl radical, respectively a cycloalkyl, aryl, arylalkyl or heterocycle radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine, chlorine, bromine and iodine.

Whenever the term "substituted" is used in the present invention, and unless otherwise stated, it is meant to indicate that one or more hydrogens on the atom, or group indicated in the expression using "substituted" is replaced with one or more group each independently selected from halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein R$^{10}$, R$^{11}$, R$^{12}$, R$^{13}$ have the same meaning as that defined herein.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "stereoisomer" refers to all possible different isomeric as well as conformational forms which the compounds of structural formula herein may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound as described herein, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

Preferred statements (features) and embodiments of the compounds and processes as described herein are now set forth. Each statements and embodiments of the invention so defined may be combined with any other statement and/or embodiments unless clearly indicated to the contrary. In particular, any feature indicated as being preferred or advantageous may be combined with any other feature or features indicated as being preferred or advantageous.

Numbered statements for these aspects of the invention are:

1. An inhibitor of PDE6δ for use in the prevention and/or treatment of epilepsy, wherein said inhibitor is compound of formula (AA1) or a stereoisomer, enantiomer, tautomer, solvate, hydrate, salt or prodrug thereof,

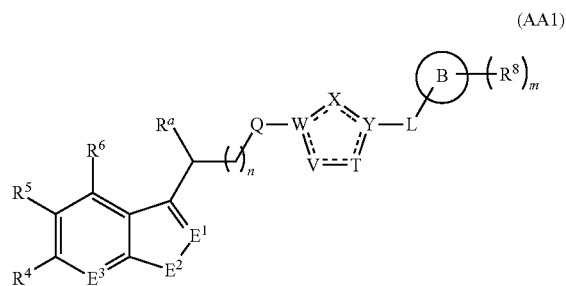

(AA1)

wherein,
each dotted line individually represents an optional double bond, wherein maximally two dotted lines selected from the five dotted lines are a double bond;
E$^1$ is independently selected from CR$^1$; and N;
E$^2$ is independently selected from NR$^2$; and O;
E$^3$ is independently selected from CR$^3$; and N;
Q is independently selected from NR$^b$—C(O); and C(O)NH;
R$^a$ is hydrogen or can be taken together with R$^b$ to form a substituted or unsubstituted 4, 5, 6, 7 or 8 membered ring containing one N atom;
R$^b$ is hydrogen or can be taken together with R$^a$ to form a substituted or unsubstituted 4, 5, 6, 7 or 8 membered ring containing one N atom;
each R$^1$, R$^3$, R$^4$, and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{16}$; —NR$^{16}$S(O)$_2$R$^{16}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl (ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;
R$^2$ is selected from hydrogen; alkyl; alkenyl; and alkynyl;
R$^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH;

—COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
- and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

n is selected from 0; 1 or 2;
L is independently selected from being not present; —O—; —NH—; —NR$^{10}$—; C$_{1-6}$alkylene; C$_{1-6}$alkenylene; or C$_{1-6}$alkynylene;
- wherein each of said C$_{1-6}$alkylene, C$_{1-6}$alkenylene or C$_{1-6}$alkynylene optionally includes one or more heteroatoms, said heteroatoms being selected from the heteroatoms consisting of O, S and N, and wherein each of said C$_{1-6}$alkylene, C$_{1-6}$alkenylene or C$_{1-6}$alkynylene, can be unsubstituted or substituted;
- and wherein a carbon atom or heteroatom of said C$_{1-6}$alkylene, C$_{1-6}$alkenylene or C$_{1-6}$alkynylene, can be oxidized to form a C=O, C=S, N=O, N=S, S=O or S(O)$_2$;

B represents a cyclic structure selected from cycloalkyl; cycloalkenyl; cycloalkynyl; aryl; and heterocycle;
m is selected from 0; 1; 2; 3; 4 and 5;
R$^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; or —C(O)R$^{11}$;
- wherein said alkyl, alkenyl and alkynyl optionally includes one or more heteroatoms, said heteroatoms being selected from the atoms O, S and N;
- and wherein said alkyl, alkenyl and alkynyl can be unsubstituted or substituted with Z;
- and wherein a carbon atom or heteroatom of said alkyl, alkenyl and alkynyl, can be oxidized to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; or —C(O)R$^{11}$;

each Z$^1$ is independently selected from hydrogen; alkyl; and Z;
each R$^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
- and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{101}$ is independently selected from hydrogen and R$^{10}$;
each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
- and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
- and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
- and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;
- and wherein R$^{12}$ and R$^{13}$ can be taken together in order to form a (5-, 6-, or 7-membered) heterocycle which can be unsubstituted or substituted;

and each of X, Y, T, W and V is independently selected from CZ$^1$H—; —OZ$^1$—; —C—; —N—; NR$^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa)
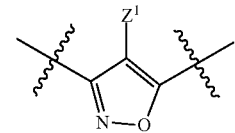
(Ia)
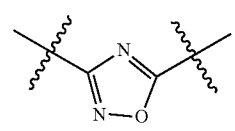
(IIa)
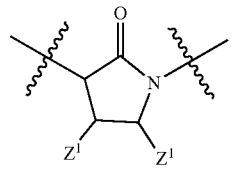
(IIIa)
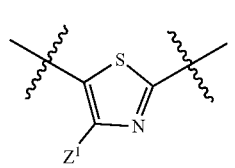
(IVa)
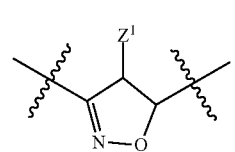
(Va)
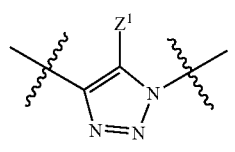
(VIa)
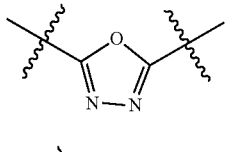
(VIIa)
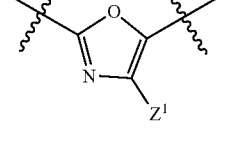
(VIIIa)
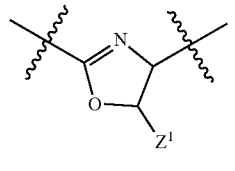
(IXa)
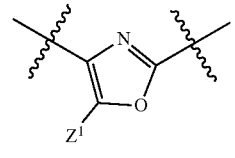
(Xa)
-continued
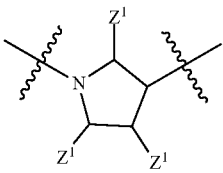
(XIa)
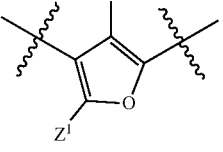
(XIIa)
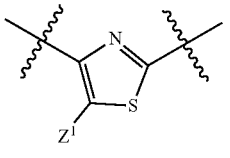
(XIIIa)
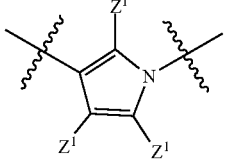
(XIVa)
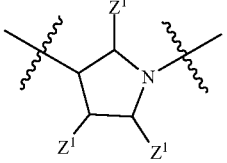
(XVa)
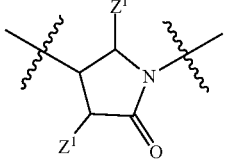
(XVIa)
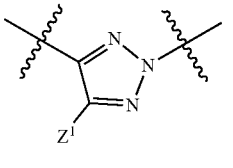
(XVIIa)
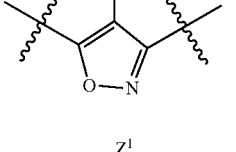
(XVIIIa)
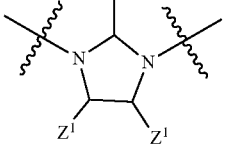
(XIXa)

-continued

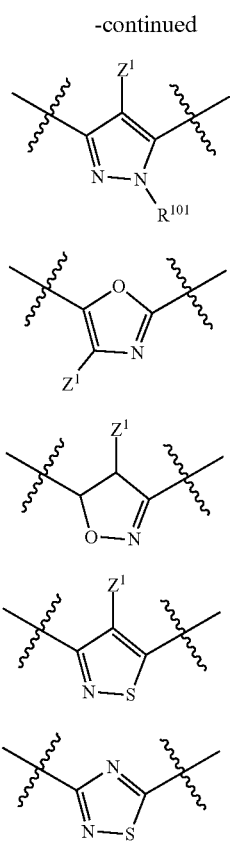

(XXa)

(XXIa)

(XXIIa)

(XXIIIa)

(XXIVa)

wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

2. The inhibitor for use according to statement 1, wherein L of said compound is selected from —O—; —NH—; —NR$^{10}$—; $C_{1-3}$alkylene; $C_{1-3}$alkenylene; $C_{1-3}$alkynylene; yet more in particular L is selected from —O—; —NH—; —NR$^{10}$—; $C_{1-2}$ alkylene; $C_{1-2}$ alkenylene; $C_{1-2}$alkynylene; still more in particular L is selected from —O—; —NH—; —NR$^{10}$—; and —CH$_2$—; yet still more in particular L is —CH$_2$—.

3. The inhibitor for use according to statements 1 or 2, wherein R$^5$ of said compound is halogen.

4. The inhibitor for use according to any one of statements 1 to 3 wherein
each dotted line individually represents an optional double bond, wherein maximally two dotted lines selected from the five dotted lines are a double bond;
E$^1$ is independently selected from CR$^1$; and N;
E$^2$ is independently selected from NR$^2$; and O;
E$^3$ is independently selected from CR$^3$; and N;
Q is independently selected from NR$^b$—C(O); C(O); and C(O)NH;
R$^a$ is hydrogen or can be taken together with Rb to form a substituted or unsubstituted 4, 5, 6, 7 or 8 membered ring containing one N atom;
R$^b$ is hydrogen or can be taken together with R$^a$ to form a substituted or unsubstituted 4, 5, 6, 7 or 8 membered ring containing one N atom;
each R$^1$, R$^3$, R$^4$, and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{16}$; —NHC(O)NR$^{12}$R$^{13}$; —NR$^{10}$C(O)R$^{16}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;
R$^2$ is selected from hydrogen; alkyl; alkenyl; and alkynyl;
R$^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;
n is selected from 0; 1 or 2;
B represents a cyclic structure selected from cycloalkyl; cycloalkenyl; cycloalkynyl; aryl; and heterocycle;
m is selected from 0; 1; 2; 3; 4 and 5;
R$^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

wherein L is independently selected from —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=S, N=O, N=S, S=O or $S(O)_2$;

and each of X, Y, T, W and V is independently selected from $CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa) as described herein.

5. The inhibitor for use according to any one of statements 1 to 4, wherein L is a straight unbranched linking chain of atoms linking B with the five membered ring, whereby said straight linking chain of atoms is maximally three, more specifically two, yet more specifically one atom long, whereby said atoms are selected from C, O and N.

6. The inhibitor for use according to any one of statements 1 to 5, wherein L is selected from —O—; —NH—; —$NR^{10}$—; $C_{1-3}$alkylene; $C_{1-3}$alkenylene; $C_{1-3}$alkynylene; yet more in particular L is selected from —O—; —NH—; —$NR^{10}$—; $C_{1-2}$ alkylene; $C_{1-2}$ alkenylene; $C_{1-2}$alkynylene; still more in particular L is selected from —O—; —NH—; —$NR^{10}$—; and —$CH_2$—; yet still more in particular L is —$CH_2$—.

7. The inhibitor for use according to any one of statements 1 to 6, wherein L is a single bond or is not present for a selection of compounds whereby X, Y, T, W and V form with the dotted lines formulae described herein, such as for formula (III).

8. The inhibitor for use according to any one of statements 1 to 7, wherein when each of X, Y, T, W and V form with the dotted lines a cycle of formula (VI), the $Z^1$ substituent in such formula (VI) is selected from hydrogen.

9. The inhibitor for use according to any one of statements 1 to 4, wherein each of X, Y, T, W and V is independently selected from $CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (Va), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa), more in particular having one of the structural formula (Ia), (IIa), (Va), (XVIIIa), (XXIIa), (XXIIIa) or (XXIVa) as described herein.

10. The inhibitor for use according to any one of statements 1 to 9, wherein each $R^1$, $R^3$, $R^4$, and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$;

trifluoromethyl; trifluoromethoxy; nitro; —NHC(O)R$^{10}$; —NHS(O)$_2$R$^{10}$; —NHC(O)NR$^{12}$R$^{13}$—, —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; and alkynyl; more in particular, each R$^1$, R$^3$, R$^4$, and R$^6$ is independently selected from hydrogen; halogen; —OH; —OR$^{10}$; —SH; —SR$^{10}$; trifluoromethyl; trifluoromethoxy; nitro; alkyl; alkenyl; and alkynyl.

11. The inhibitor for use according to any one of statements 1 to 10, wherein R$^1$ is hydrogen or alkyl, more in particular is hydrogen.

12. The inhibitor for use according to any one of statements 1 to 11, wherein R$^2$ is hydrogen or alkyl, yet more in particular is hydrogen.

13. The inhibitor for use according to any one of statements 1 to 12, wherein R$^3$ is hydrogen.

14. The inhibitor for use according to any one of statements 1 to 13, wherein R$^4$ is hydrogen. In another particular embodiment, R$^6$ is hydrogen.

15. The inhibitor for use according to any one of statements 1 to 14, wherein R$^3$, R$^4$ and R$^6$ are hydrogen.

16. The inhibitor for use according to any one of statements 1 to 15, wherein R$^1$ and R$^2$ are each hydrogen when X, Y, T, W and V form the cycle of formulae (VI), (XVI) or (XX).

17. The inhibitor for use according to any one of statements 1 to 16, wherein R$^8$ is selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein said alkyl, alkenyl and alkynyl optionally includes one or more heteroatoms, said heteroatoms being selected from the atoms O, S and N; and wherein said alkyl, alkenyl and alkynyl can be unsubstituted or substituted with Z; and wherein a carbon atom or heteroatom of said alkyl, alkenyl and alkynyl, can be oxidized to form a C=S, N=O, N=S, S=O or S(O)$_2$.

18. The inhibitor for use according to any one of statements 1 to 17, wherein R$^8$ is selected from hydrogen; halogen; alkyl; alkenyl; alkynyl; —OH; —OR$^{10}$; —SH; —SR$^{10}$; trifluoromethyl; trifluoromethoxy; —NR$^{12}$R$^{13}$; -cyano; preferably R$^8$ is selected from hydrogen; halogen; linear alkyl; linear alkenyl; linear alkynyl; —OH; —OR$^{10}$; —SH; —SR$^{10}$; trifluoromethyl; trifluoromethoxy; —NR$^{12}$R$^{13}$; -cyano; more preferably, R$^8$ is halogen; most preferably R$^8$ is fluor.

19. The inhibitor for use according to any one of statements 1 to 18, wherein R$^8$ is not 2-methylenetetrahydrofuranyl and R$^2$ is hydrogen when X, Y, T, W and V form the cycle of formula (VI).

20. The inhibitor for use according to any one of statements 1 to 19, wherein m is 2.

21. The inhibitor for use according to any one of statements 1 to 20, wherein compounds of formula (AA1) comprise maximally three monocyclic or cyclic fused ring systems selected from aryl or heterocycle.

22. The inhibitor for use according to any one of statements 1 to 21, wherein the compounds of formula (AA1) comprise maximally ring systems, whereby said three ring systems consist of:
indole;
the five-membered ring comprising X, Y, T, W and V; and
B.

23. The inhibitor for use according to any one of statements 1 to 22, wherein each of X, Y, T, W and V is independently selected from CZ$^1$H—; —CZ$^1$—; —C—; —N—; NR$^{101}$; —O—; —S—; or —CO—; and form one of the cycles having one of the structural formula selected from (Ia), (IIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa): wherein
Z$^1$ is independently selected from hydrogen, alkyl and Z;
Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;
each R$^{10}$ is independently selected from alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;
each R$^{101}$ is independently selected from hydrogen and R$^{10}$;
each R$^{11}$ is independently selected from hydroxyl; alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;
each R$^{12}$ and R$^{13}$ is independently selected from hydrogen; alkyl; alkenyl; alkynyl; wherein said alkyl, alkenyl, alkynyl, optionally include one or more heteroatoms in the alkyl, alkenyl or alkynyl moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$.

24. The inhibitor for use according to any one of statements 1 to 23, wherein each of X, Y, T, W and V is independently selected from CZ$^1$H—; —OZ$^1$—; —C—; —N—; NR$^{101}$; —O—; —S—; or —CO—; and form one of the cycles having one of the structural formula selected from (Ia), (IIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa): wherein
Z$^1$ is independently selected from hydrogen; alkyl; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;
each R$^{10}$ is independently selected from alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;
each R$^{101}$ is independently selected from hydrogen and R$^{10}$;

each $R^{11}$ is independently selected from hydroxyl; alkyl; alkenyl; alkynyl; wherein said alkyl, alkenyl, alkynyl optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$;

each $R^{12}$ and $R^{13}$ is independently selected from hydrogen; alkyl; alkenyl; alkynyl; wherein said alkyl, alkenyl, alkynyl, optionally include one or more heteroatoms in the alkyl, alkenyl or alkynyl moiety, said heteroatom selected from O, S and N; and wherein a carbon atom or heteroatom of said alkyl, alkenyl, alkynyl can be oxidized to form a C=O, C=S, N=O, N=S, S=O or S(O)$_2$.

25. The inhibitor for use according to any one of statements 1 to 24, wherein each of X, Y, T, W and V is independently selected from CH$_2$—; —CH—; —C—; —N—; NH; —O—; —S—; or —CO— and form with the dotted lines one of the cycles having one of the structural formula (Ia'), (IIa'), (IIIa'), (Va'), (VIIa'), (VIIIa'), (Ixa'), (Xa'), (Xia'), (XIIa'), (XIIIa'), (XIVa'), (XVa'), (XVIa'), (XVIIa'), (XVIIIa'), (XIXa'), (XXa'), (XXIa'), (XXIIa'), (XXIIIa') or (XXIVa'):

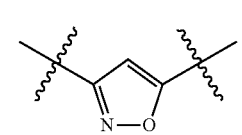

(Ia')

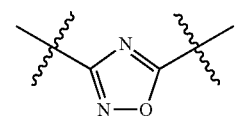

(IIa')

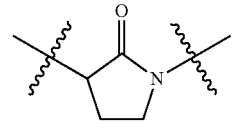

(IIIa')

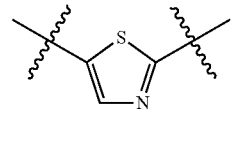

(IVa')

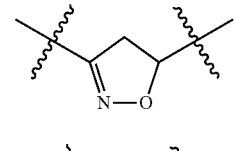

(Va')

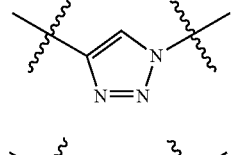

(VIa')

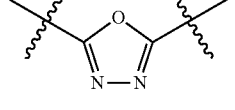

(VIIa')

-continued

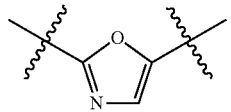

(VIIIa')

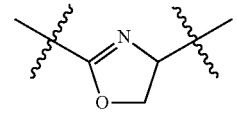

(IXa')

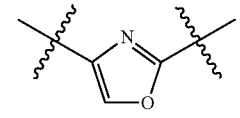

(Xa')

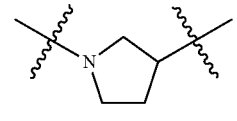

(XIa')

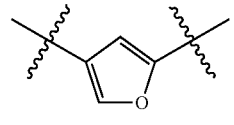

(XIIa')

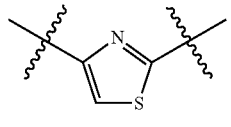

(XIIIa')

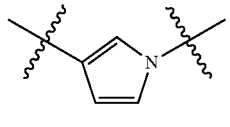

(XIVa')

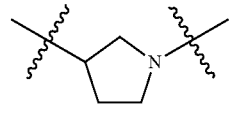

(XVa')

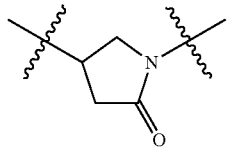

(XVIa')

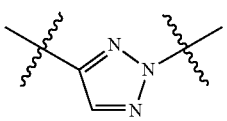

(XVIIa')

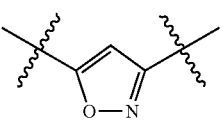

(XVIIIa')

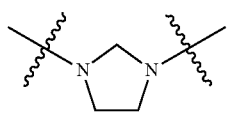

(XIXa')

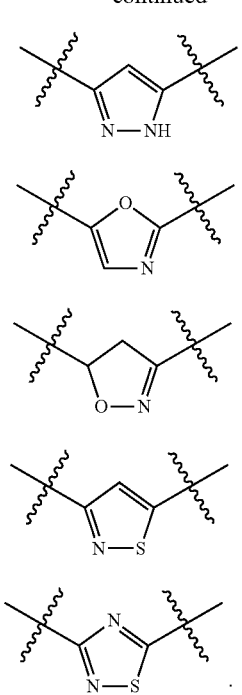

(XXa')

(XXIa')

(XXIIa')

(XXIIIa')

(XXIVa')

26. The inhibitor for use according to any one of statements 1 to 25, wherein
each dotted line individually represents an optional double bond, wherein maximally two dotted lines selected from the five dotted lines are a double bond;
$E^1$ is independently selected from $CR^1$; and N;
$E^2$ is independently selected from $NR^2$; and O;
$E^3$ is independently selected from $CR^3$; and N;
Q is independently selected from $NR^b$—C(O); C(O); and C(O)NH;
$R^a$ is hydrogen or can be taken together with Rb to form a substituted or unsubstituted 4, 5, 6, 7 or 8 membered ring containing one N atom;
$R^b$ is hydrogen or can be taken together with $R^a$ to form a substituted or unsubstituted 4, 5, 6, 7 or 8 membered ring containing one N atom;
each $R^1$, $R^3$, $R^4$, and $R^6$ is independently selected from hydrogen; halogen; —OH; —$OR^{10}$; —SH; —$SR^{10}$; —$S(O)_2R^{11}$; —$S(O)_2R^{11}$; —$SO_2NR^{12}R^{13}$; trifluoromethyl; trifluoromethoxy; nitro; —NHC(O)$R^{10}$; —NHS(O)$_2R^{16}$; —NHC(O)$NR^{12}R^{13}$; —$NR^{10}C(O)R^{16}$; —$NR^{10}S(O)_2R^{10}$; —$NR^{16}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
$R^2$ is selected from hydrogen; alkyl; alkenyl; and alkynyl;
$R^5$ is selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=o or $S(O)_2$;
n is selected from 0; 1 or 2;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
wherein said alkyl, alkenyl and alkynyl optionally includes one or more heteroatoms, said heteroatoms being selected from the atoms O, S and N;
and wherein said alkyl, alkenyl and alkynyl can be unsubstituted or substituted with Z;
and wherein a carbon atom or heteroatom of said alkyl, alkenyl and alkynyl, can be oxidized to form a C=O, C=S, N=O, N=S, S=O or $S(O)_2$;
each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
each $Z^1$ is independently selected from hydrogen; alkyl; and Z;
each $R^{10}$ is independently selected from alkyl; alkenyl; alkynyl; aryl; heterocycle;

arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

wherein L is independently selected from —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=S, N=O, N=S, S=O or $S(O)_2$;

and each of X, Y, T, W and V is independently selected from $CZ^1H$—; —$CZ^1$—; —C—; —N—; $NR^{101}$; —O—; —S—; or —CO—; and form with the dotted lines one of the cycles having one of the structural formula (Ia), (IIa), (IIIa), (IVa), (Va), (VIIa), (VIIIa), (IXa), (Xa), (XIa), (XIIa), (XIIIa), (XIVa), (XVa), (XVIIa), (XVIIIa), (XIXa), (XXIa), (XXIIa), (XXIIIa) or (XXIVa),

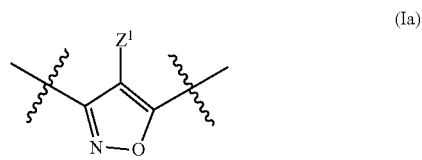

(Ia)

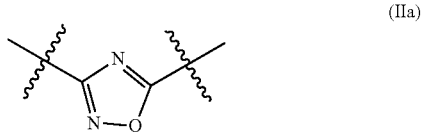

(IIa)

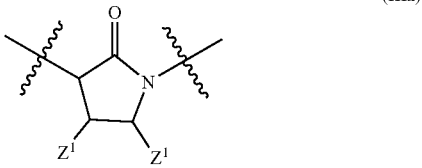

(IIIa)

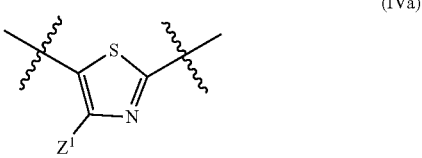

(IVa)

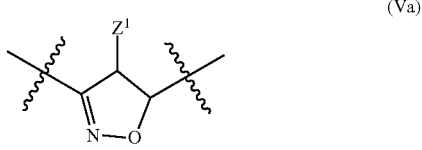

(Va)

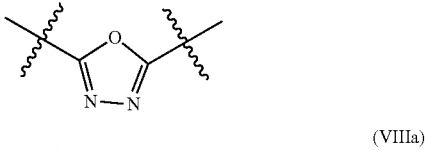

(VIIa)

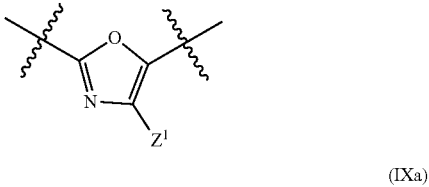

(VIIIa)

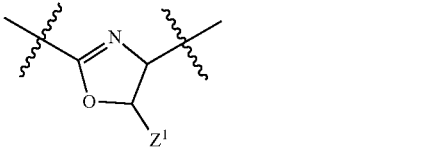

(IXa)

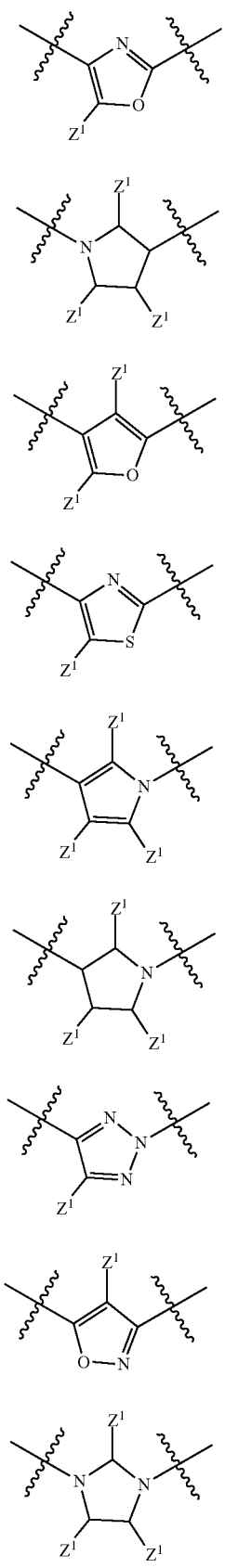

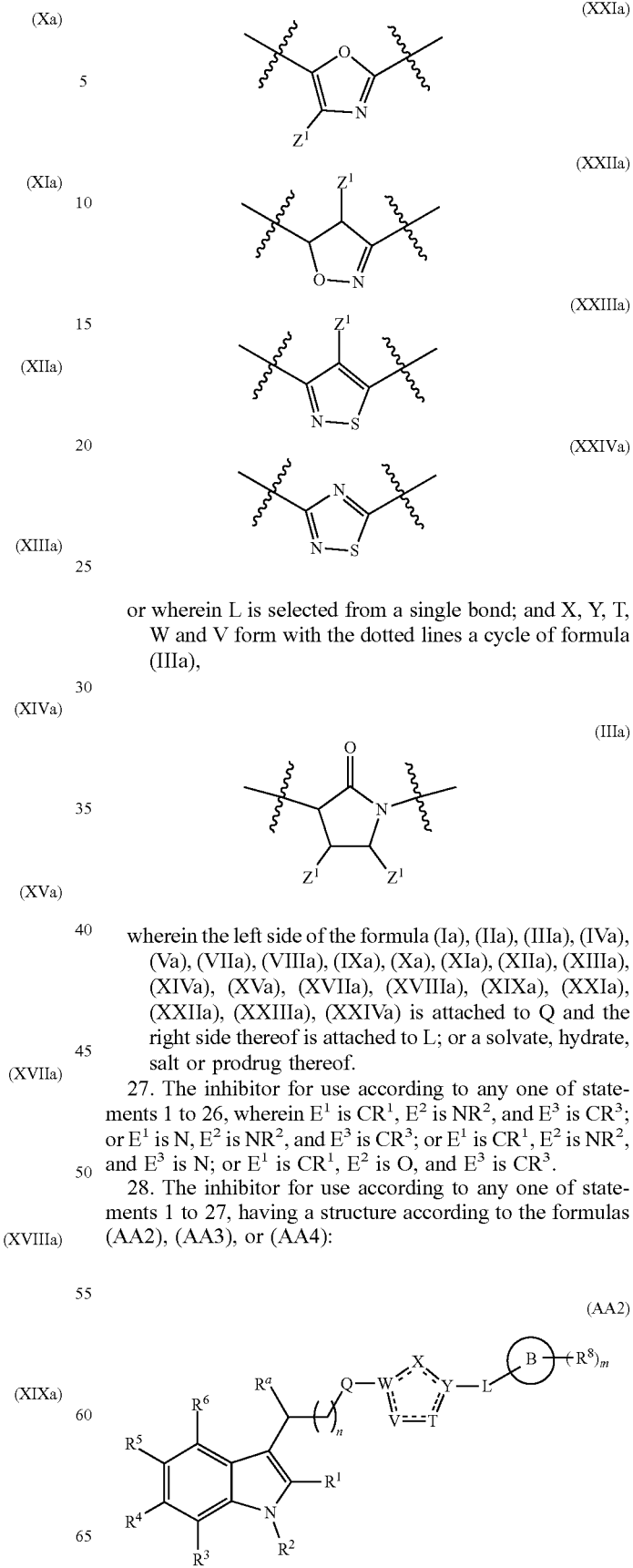

or wherein L is selected from a single bond; and X, Y, T, W and V form with the dotted lines a cycle of formula (IIIa), wherein the left side of the formula (Ia), (IIa), (IIIa), (IVa), (Va), (VIIa), (VIIIa), (IXa), (Xa), (XIa), (XIIa), (XIIIa), (XIVa), (XVa), (XVIIa), (XVIIIa), (XIXa), (XXIa), (XXIIa), (XXIIIa), (XXIVa) is attached to Q and the right side thereof is attached to L; or a solvate, hydrate, salt or prodrug thereof.

27. The inhibitor for use according to any one of statements 1 to 26, wherein $E^1$ is $CR^1$, $E^2$ is $NR^2$, and $E^3$ is $CR^3$; or $E^1$ is N, $E^2$ is $NR^2$, and $E^3$ is $CR^3$; or $E^1$ is $CR^1$, $E^2$ is $NR^2$, and $E^3$ is N; or $E^1$ is $CR^1$, $E^2$ is O, and $E^3$ is $CR^3$.

28. The inhibitor for use according to any one of statements 1 to 27, having a structure according to the formulas (AA2), (AA3), or (AA4):

-continued

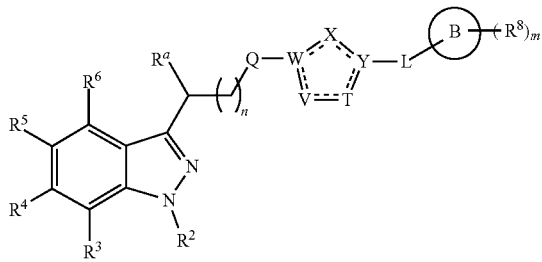

(AA3)

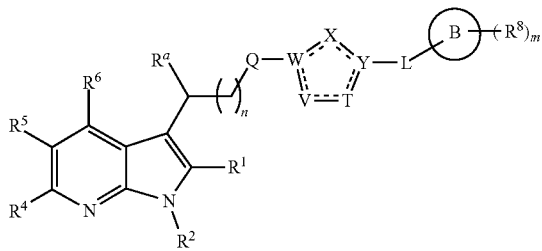

(AA4)

wherein R$^1$, R$^2$, R$^3$, R$^4$, R$^5$, R$^6$, R$^8$, R$^a$, Q, W, X, Y, V, T, L, B, m, n have the same meaning as that defined herein.

29. The inhibitor for use according to statement 28, wherein Q is NR$^b$—C(O).

30. The inhibitor for use according to any one of statements 1 to 29, wherein both R$^a$ and R$^b$ are hydrogen.

31. The inhibitor for use according to any one of statements 1 to 30, having structural formula (A1),

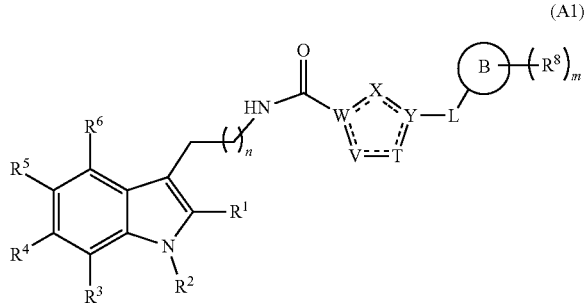

(A1)

wherein,
each dotted line individually represents an optional double bond, wherein maximally two dotted lines selected from the five dotted lines are a double bond;
each R$^1$, R$^3$, R$^4$, R$^5$ and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

R$^2$ is selected from hydrogen; alkyl; alkenyl; and alkynyl;
n is selected from 0; 1 or 2;
L is independently selected from being not present; —O—; —NH—; —NR$^{10}$—; C$_{1-6}$alkylene; C$_{1-6}$alkenylene; C$_{1-6}$alkynylene;
wherein each of said C$_{1-6}$alkylene, C$_{1-6}$alkenylene or C$_{1-6}$alkynylene optionally includes one or more heteroatoms, said heteroatoms being selected from the heteroatoms consisting of O, S and N, and wherein each of said C$_{1-6}$alkylene, C$_{1-6}$alkenylene or C$_{1-6}$alkynylene, can be unsubstituted or substituted;
and wherein two or more hydrogen atoms on a carbon atom or heteroatom of said C$_{1-6}$alkylene, C$_{1-6}$alkenylene or C$_{1-6}$alkynylene, can be taken together to form a C=O, C=S, N=O, N=S, S=O or S(O)$_2$; and
each of X, Y, T, W and V is independently selected from CZ$^1$H—; —CZ$^1$—; NR$^{101}$; —O—; —S—; or —CO—; to form with the dotted lines one of the cycles having one of the structural formula (Ia), (IIa), (IIIa), (IVa), (Va), (VIIa), (VIIIa), (IXa), (Xa), (XIa), (XIIa), (XIIIa), (XIVa), (XVa), (XVIIa), (XVIIIa), or (XIXa),
or wherein L is a single bond; and X, Y, T, W and V form with the dotted lines a cycle of formula (IIIa),
B represents a cyclic structure selected from cycloalkyl; cycloalkenyl; cycloalkynyl; aryl; and heterocycle;
m is selected from 0; 1; 2; 3; 4 and 5;
R$^8$ is independently selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{18}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;
wherein said alkyl, alkenyl and alkynyl optionally includes one or more heteroatoms, said heteroatoms being selected from the atoms O, S and N;
and wherein said alkyl, alkenyl and alkynyl can be unsubstituted or substituted with Z;
and wherein two or more hydrogen atoms on a carbon atom or heteroatom of said alkyl, alkenyl and alkynyl, can be taken together to form a C=O, C=S, N=O, N=S, S=O or S(O)$_2$;
each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{18}$; —NHS(O)$_2$R$^{10}$; —NHC(O)NR$^{12}$R$^{13}$; —NR$^{10}$C(O)R$^{18}$; —NR$^{10}$S(O)$_2$R$^{18}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

32. The inhibitor for use according to statement 31, wherein, each dotted line individually represents an optional double bond, wherein maximally two dotted lines selected from the five dotted lines are a double bond;

each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NR^{16}C(O)R^{16}$; —$NR^{16}S(O)_2R^{16}$; —$NR^{16}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

$R^2$ is selected from hydrogen; alkyl; alkenyl; and alkynyl;

n is selected from 0; 1 or 2;

L is independently selected from being not present; —O—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;

and wherein two or more hydrogen atoms on a carbon atom or heteroatom of said $C_{1-6}$alkylene, $C_{1-6}$alkenylene or $C_{1-6}$alkynylene, can be taken together to form a C=O, C=S, N=O, N=S, S=O or $S(O)_2$;

each of X, Y, T, W and V is independently selected from $CZ^1H$—; —$CZ^1$—; $NR^{101}$; —O—; —S—; or —CO—; to form with the dotted lines one of the cycles having one of the structural formula (Ia), (IIa), (IIIa), (IVa), (Va), (VIIa), (VIIIa), (IXa), (Xa), (XIa), (XIIa), (XIIIa), (XIVa), (XVa), (XVIIa), (XVIIIa), or (XIXa), or wherein L is a single bond; and X, Y, T, W and V form with the dotted lines a cycle of formula (IIIa), B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NR^{10}C(O)R^{18}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein two or more hydrogen atoms on a carbon atom or heteroatom of said alkyl, alkenyl and alkynyl, can be taken together to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NR$^{10}$C(O)R$^{18}$; —NR$^{10}$S(O)$_2$R$^{18}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$;

each Z$^1$ is independently selected from hydrogen and Z;

each R$^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or S(O)$_2$;

and wherein R$^{12}$ and R$^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

33. The inhibitor for use according to any one of statements 1 to 32, whereby V is N.

34. The inhibitor for use according to any one of statements 1 to 33, whereby T is O.

35. The inhibitor for use according to any one of statements 1 to 34, whereby V is N and T is O.

36. The inhibitor for use according to any one of statements 1 to 35, whereby W and Y are C.

37. The inhibitor for use according to any one of statements 1 to 36, wherein the dotted lines and X, Y, T, W and V are selected from CZ$^1$H—; —CZ$^1$—; —C—; —N—; NR$^{101}$; —O—; —S—; or —CO—; to form one of the following cycles:

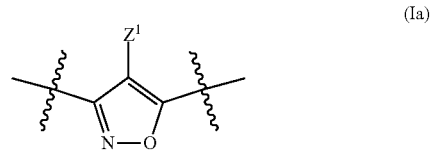
(Ia)

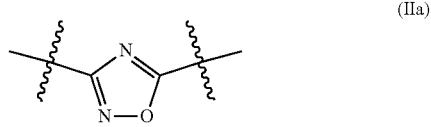
(IIa)

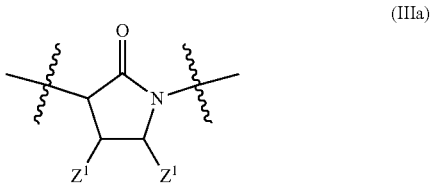
(IIIa)

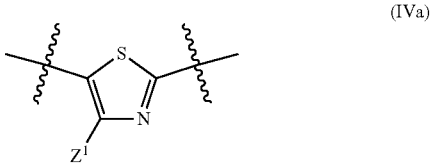
(IVa)

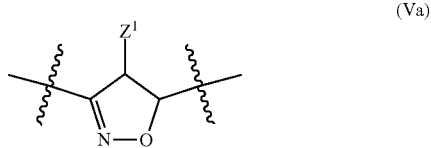
(Va)

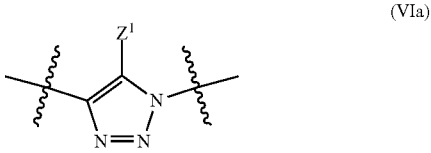
(VIa)

-continued
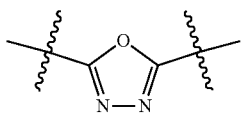
(VIIa)
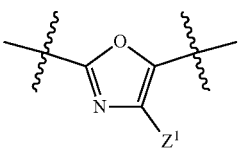
(VIIIa)
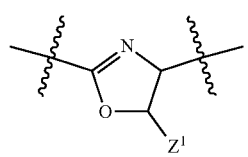
(IXa)
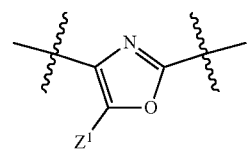
(Xa)
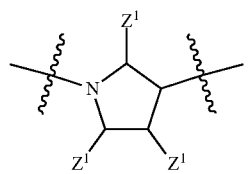
(XIa)
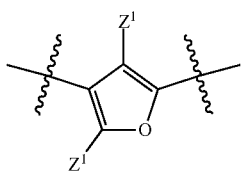
(XIIa)
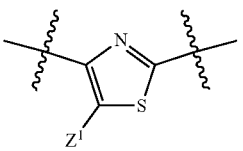
(XIIIa)
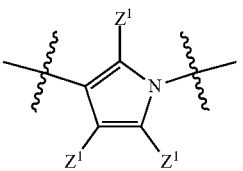
(XIVa)
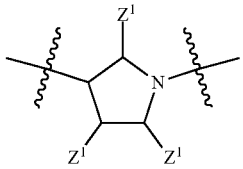
(XVa)
-continued
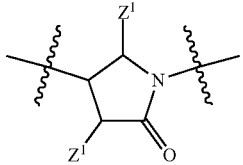
(XVIa)
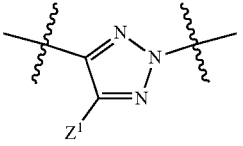
(XVIIa)
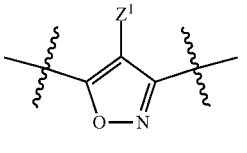
(XVIIIa)
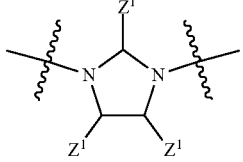
(XIXa)
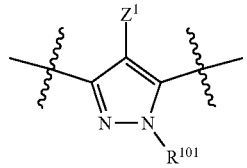
(XXa)
38. The compound according to any one of statements 1 to 37, wherein the dotted lines and X, Y, T, W and V are selected from $CZ^1H$—; —$CZ^1$—; $NR^{101}$; —O—; —S—; or —CO—; to form one of the following cycles:
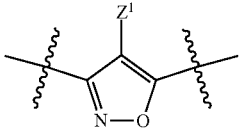
(Ia)
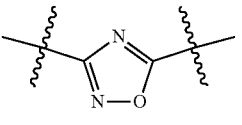
(IIa)
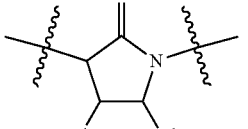
(IIIa)
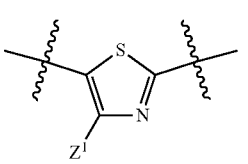
(IVa)

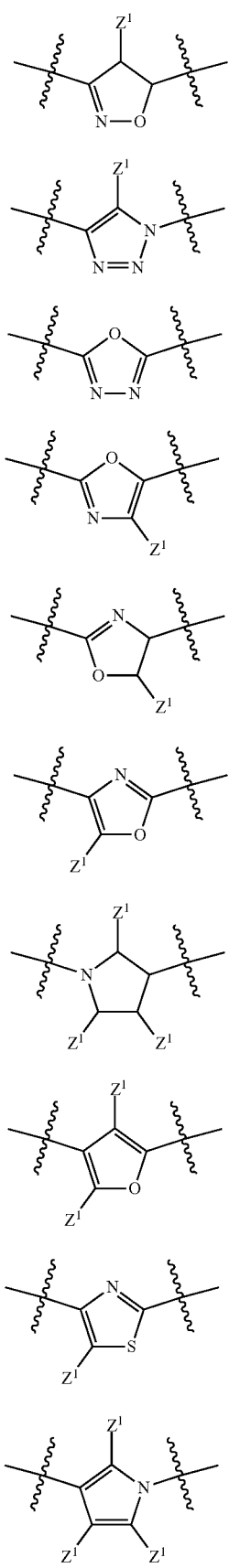
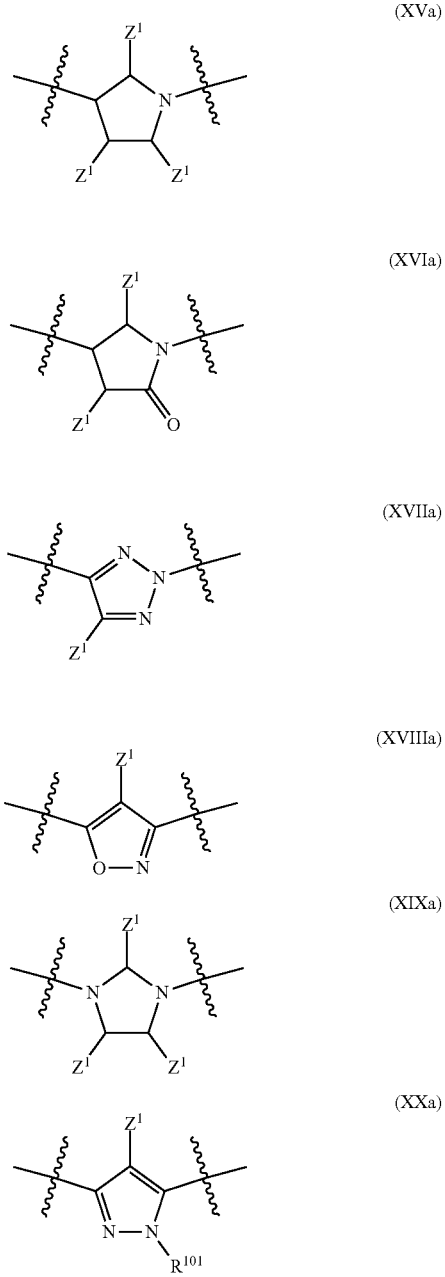
39. The inhibitor for use according to any one of statements 1 to 38, having a structure according to formula (A2), (A2'), (AB2) or (AB2');
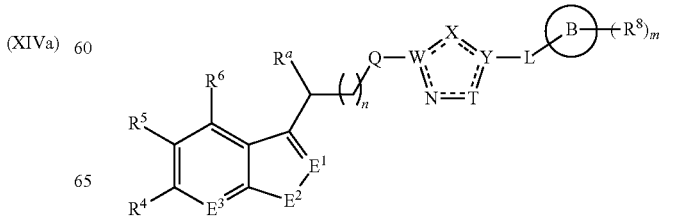
(AB2)

-continued

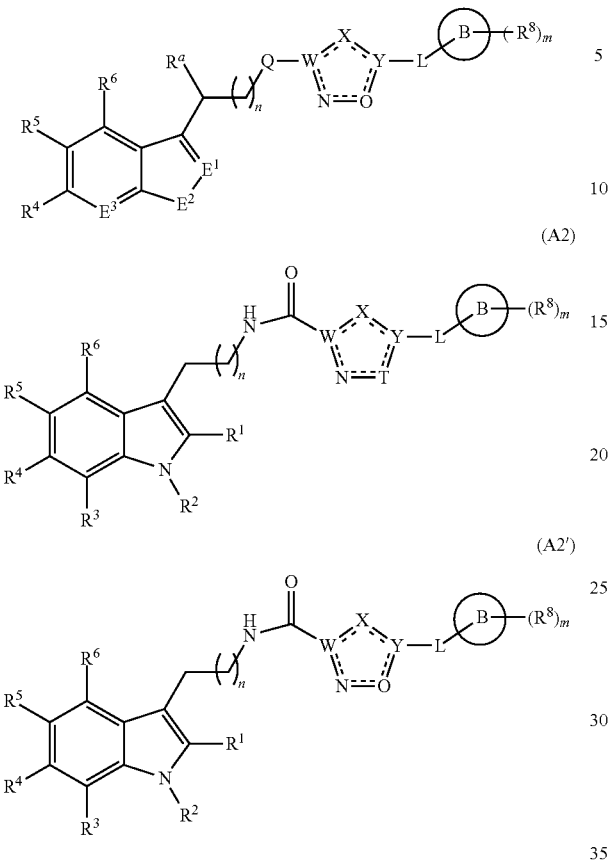

wherein $E^1$, $E^2$, $E^3$, $R^4$, $R^5$, $R^6$, $R^8$, $R^a$, Q, W, X, Y, L, B, m, n have the same meaning as defined herein or embodiments described herein.

40. The inhibitor for use according to statement 39, having a structure according to formula (A2'), wherein,
  each dotted line individually represents an optional double bond, wherein maximally two dotted lines selected from the five dotted lines are a double bond;
  each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
  and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

$R^2$ is selected from hydrogen; alkyl; alkenyl; and alkynyl;
n is selected from 0; 1 or 2;
each of X, Y and W is independently selected from $CZ^1H$—; —$CZ^1$=; =C—; =N—; $NR^{101}$; —O—; —S—; or —CO—; wherein at least one of X, Y or W is selected from $CZ^1H$— or —$CZ^1$= or C=; to form with the dotted lines one of the cycles having one of the structural formula (Ia), (IIa), (Va),
L is independently selected from —O—; —NH—; —$NR^{10}$—; $C_{1-6}$alkylene; $C_{1-6}$alkenylene; $C_{1-6}$alkynylene;
  wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
  and wherein two or more hydrogen atoms on a carbon atom or heteroatom of said $C_{1-6}$alkylene, $C_{1-6}$alkenylene or $C_{1-6}$alkynylene, can be taken together to form a C=O, C=S, N=O, N=S, S=O or $S(O)_2$;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
  wherein said alkyl, alkenyl and alkynyl optionally includes one or more heteroatoms, said heteroatoms being selected from the atoms O, S and N;
  and wherein said alkyl, alkenyl and alkynyl can be unsubstituted or substituted with Z;
  and wherein two or more hydrogen atoms on a carbon atom or heteroatom of said alkyl, alkenyl and alkynyl, can be taken together to form a C=O, C=S, N=O, N=S, S=O or $S(O)_2$;
each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
each $Z^1$ is independently selected from hydrogen; alkyl; and Z;
each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof,
provided that the compounds are not selected from:
3-Isoxazolecarboxamide, 5-cyclopropyl-N-[2-(1H-indol-3-yl)ethyl]-;
3-Isoxazolecarboxamide, 5-(2-furanyl)-N-[2-(1H-indol-3-yl)ethyl]-;
3-Isoxazolecarboxamide, 5-[(2,4-difluorophenoxy)methyl]-N-[2-(1H-indol-3-yl)ethyl]-;
3-Isoxazolecarboxamide, N-[2-(1H-indol-3-yl)ethyl]-5-(2-thienyl)-;
3-Isoxazolecarboxamide, N-[2-(1H-indol-3-yl)ethyl]-5-[[(6-methyl-3-pyridinyl)oxy]methyl]-;
3-Isoxazolecarboxamide, N-[2-(5-chloro-2,7-dimethyl-1H-indol-3-yl)ethyl]-5-(4-chlorophenyl)-;
3-Isoxazolecarboxamide, 5-(4-chlorophenyl)-N-[2-(5-methyl-1H-indol-3-yl)ethyl]-;
3-Isoxazolecarboxamide, N-[2-(1H-indol-3-yl)ethyl]-5-(4-morpholinylmethyl)-;
3-Isoxazolecarboxamide, N-[2-(1H-indol-3-yl)ethyl]-5-(1-pyrrolidinylmethyl)-;
3-Isoxazolecarboxamide, N-[2-(1H-indol-3-yl)ethyl]-5-phenyl-.

41. The inhibitor for use according to any one of statements 1 to 40, wherein the compound is not selected from:
3-Isoxazolecarboxamide, 5-cyclopropyl-N-[2-(1H-indol-3-yl)ethyl]-;
3-Isoxazolecarboxamide, 5-(2-furanyl)-N-[2-(1H-indol-3-yl)ethyl]-;
3-Isoxazolecarboxamide, 5-[(2,4-difluorophenoxy)methyl]-N-[2-(1H-indol-3-yl)ethyl]-;
3-Isoxazolecarboxamide, N-[2-(1H-indol-3-yl)ethyl]-5-(2-thienyl)-;
3-Isoxazolecarboxamide, N-[2-(1H-indol-3-yl)ethyl]-5-[[(6-methyl-3-pyridinyl)oxy]methyl]-;
3-Isoxazolecarboxamide, N-[2-(5-chloro-2,7-dimethyl-1H-indol-3-yl)ethyl]-5-(4-chlorophenyl)-;
3-Isoxazolecarboxamide, 5-(4-chlorophenyl)-N-[2-(5-methyl-1H-indol-3-yl)ethyl]-;
3-Isoxazolecarboxamide, N-[2-(1H-indol-3-yl)ethyl]-5-(4-morpholinylmethyl)-;
3-Isoxazolecarboxamide, N-[2-(1H-indol-3-yl)ethyl]-5-(1-pyrrolidinylmethyl)-;
3-Isoxazolecarboxamide, N-[2-(1H-indol-3-yl)ethyl]-5-phenyl-;
N-[2-(5-chloro-2-methyl-1H-indol-3-yl)ethyl]-1-(tetrahydro-2-furanylmethyl)-1H-1,2,3-triazole-4-carboxamide;
N-(2-(5-chloro-1H-indol-3-yl)ethyl)-1-(4-ethylphenyl)-2-oxopyrrolidine-3-carboxamide;
1-(4-ethylphenyl)-N-(2-(5-methyl-1H-indol-3-yl)ethyl)-2-oxopyrrolidine-3-carboxamide;
1-(4-chlorophenyl)-N-(2-(5-methyl-1H-indol-3-yl)ethyl)-2-oxo-3-pyrrolidine-carboxamide.

42. The inhibitor for use according to any one of statements 39 or 40 having a structure according to formula (A2'), wherein,
each dotted line individually represents an optional double bond, wherein maximally two dotted lines selected from the five dotted lines are a double bond;
each $R^1$, $R^3$, $R^4$, $R^5$ and $R^6$ is independently selected from hydrogen; halogen; —OH; —$OR^{16}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NR^{10}C(O)R^{10}$; —$NR^{16}S(O)_2R^{16}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

$R^2$ is selected from hydrogen; alkyl; alkenyl; and alkynyl;

n is selected from 0; 1 or 2;

each of X, Y and W is independently selected from $CZ^1H—$; $—CZ^1—$; $NR^{101}$; $—O—$; $—S—$; or $—CO—$; wherein at least one of X, Y or W is selected from $CZ^1H—$ or $—CZ^1—$; to form with the dotted lines one of the cycles having one of the structural formula (Ia), (IIa), (Va), L is independently selected from being not present; $—O—$; $—NR^{10}—$; $C_{1-6}$alkylene; $C_{1-6}$alkenylene; $C_{1-6}$alkynylene;
wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
and wherein two or more hydrogen atoms on a carbon atom or heteroatom of said $C_{1-6}$alkylene, $C_{1-6}$alkenylene or $C_{1-6}$alkynylene, can be taken together to form a C=O, C=S, N=O, N=S, S=O or $S(O)_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; $—OR^{18}$; —SH; $—SR^{10}$; $—S(O)R^{11}$; $—S(O)_2R^{11}$; $—SO_2NR^{12}R^{13}$; trifluoromethyl; trifluoromethoxy; nitro; $—NR^{10}C(O)R^{18}$; $—NR^{10}S(O)_2R^{10}$; $—NR^{10}C(O)NR^{12}R^{13}$; $—NR^{12}R^{13}$; -cyano; —COOH; $—COOR^{10}$; $—C(O)NR^{12}R^{13}$; $—C(O)R^{11}$;
wherein said alkyl, alkenyl and alkynyl optionally includes one or more heteroatoms, said heteroatoms being selected from the atoms O, S and N;
and wherein said alkyl, alkenyl and alkynyl can be unsubstituted or substituted with Z;
and wherein two or more hydrogen atoms on a carbon atom or heteroatom of said alkyl, alkenyl and alkynyl, can be taken together to form a C=O, C=S, N=O, N=S, S=O or $S(O)_2$;

each Z is independently selected from halogen; —OH; $—OR^{10}$; —SH; $—SR^{10}$; $—S(O)R^{11}$; $—S(O)_2R^{11}$; $—SO_2NR^{12}R^{13}$; trifluoromethyl; trifluoromethoxy; nitro; $—NR^{10}C(O)R^{18}$; $—NR^{10}S(O)_2R^{18}$; $—NR^{10}C(O)NR^{12}R^{13}$; $—NR^{12}R^{13}$; -cyano; —COOH; $—COOR^{10}$; $—C(O)NR^{12}R^{13}$; $—C(O)R^{11}$;

each $Z^1$ is independently selected from hydrogen and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein two or more hydrogen atoms on a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be taken together to form a C=O, C=S, N=O, N=S, S=O or $S(O)_2$;
and wherein $R^{12}$ and $R^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof, provided that the compounds are not selected from:

3-Isoxazolecarboxamide, 5-cyclopropyl-N-[2-(1H-indol-3-yl)ethyl]-;

3-Isoxazolecarboxamide, 5-(2-furanyl)-N-[2-(1H-indol-3-yl)ethyl]-;

3-Isoxazolecarboxamide, 5-[(2,4-difluorophenoxy)methyl]-N-[2-(1H-indol-3-yl)ethyl]-;

3-Isoxazolecarboxamide, N-[2-(1H-indol-3-yl)ethyl]-5-(2-thienyl)-;

3-Isoxazolecarboxamide, N-[2-(1H-indol-3-yl)ethyl]-5-[[(6-methyl-3-pyridinyl)oxy]methyl]-;

3-Isoxazolecarboxamide, N-[2-(5-chloro-2,7-dimethyl-1H-indol-3-yl)ethyl]-5-(4-chlorophenyl)-;

3-Isoxazolecarboxamide, 5-(4-chlorophenyl)-N-[2-(5-methyl-1H-indol-3-yl)ethyl]-;

3-Isoxazolecarboxamide, N-[2-(1H-indol-3-yl)ethyl]-5-(4-morpholinylmethyl)-;

3-Isoxazolecarboxamide, N-[2-(1H-indol-3-yl)ethyl]-5-(1-pyrrolidinylmethyl)-;

3-Isoxazolecarboxamide, N-[2-(1H-indol-3-yl)ethyl]-5-phenyl-.

In a particular embodiment, the compounds as described herein are not selected from:

3-Isoxazolecarboxamide, 5-cyclopropyl-N-[2-(1H-indol-3-yl)ethyl]-;

3-Isoxazolecarboxamide, 5-(2-furanyl)-N-[2-(1H-indol-3-yl)ethyl]-;

3-Isoxazolecarboxamide, 5-[(2,4-difluorophenoxy)methyl]-N-[2-(1H-indol-3-yl)ethyl]-;

3-Isoxazolecarboxamide, N-[2-(1H-indol-3-yl)ethyl]-5-(2-thienyl)-;

3-Isoxazolecarboxamide, N-[2-(1H-indol-3-yl)ethyl]-5-[[(6-methyl-3-pyridinyl)oxy]methyl]-;

3-Isoxazolecarboxamide, N-[2-(5-chloro-2,7-dimethyl-1H-indol-3-yl)ethyl]-5-(4-chlorophenyl)-;

3-Isoxazolecarboxamide, 5-(4-chlorophenyl)-N-[2-(5-methyl-1H-indol-3-yl)ethyl]-;

3-Isoxazolecarboxamide, N-[2-(1H-indol-3-yl)ethyl]-5-(4-morpholinylmethyl)-;

3-Isoxazolecarboxamide, N-[2-(1H-indol-3-yl)ethyl]-5-(1-pyrrolidinylmethyl)-;

3-Isoxazolecarboxamide, N-[2-(1H-indol-3-yl)ethyl]-5-phenyl-.

43. The inhibitor for use according to any one of statements 1 to 42 having a structure according to formula (A3), (A4), (A4') or (A4"),

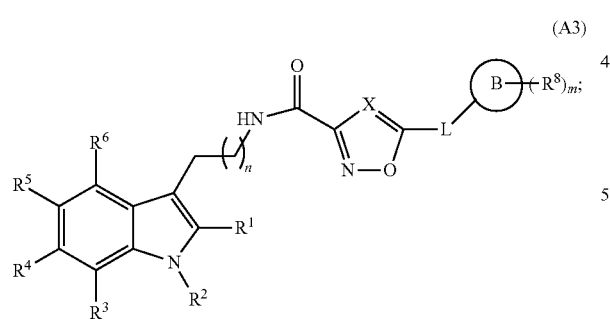
(A3)

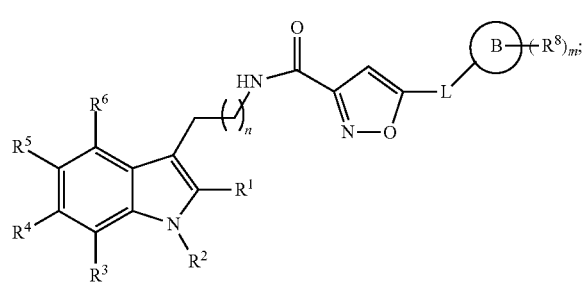
(A4)

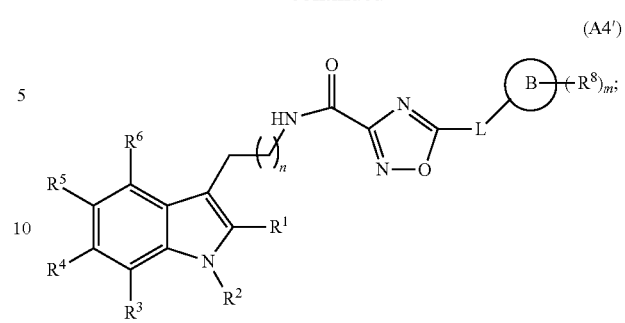
(A4')

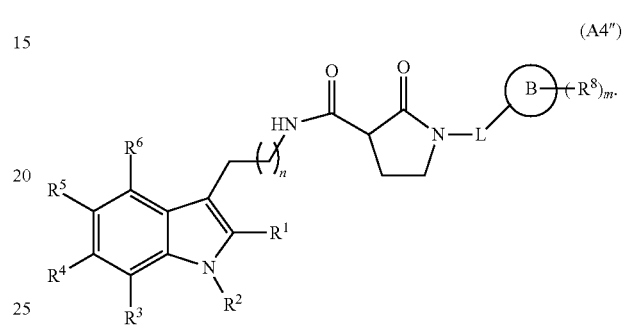
(A4")

44. The inhibitor for use according to any one of statements 1 to 43 having a structure according to formula (AB3), (AB4), (AB4') or (AB4"),

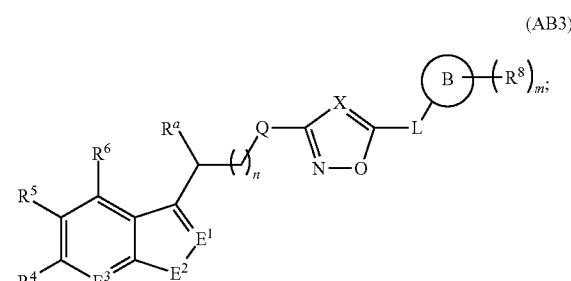
(AB3)

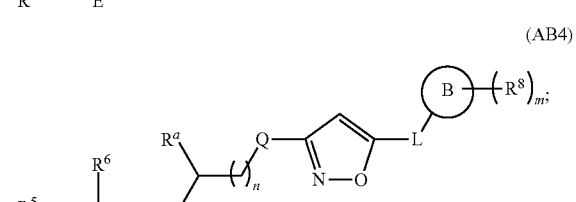
(AB4)

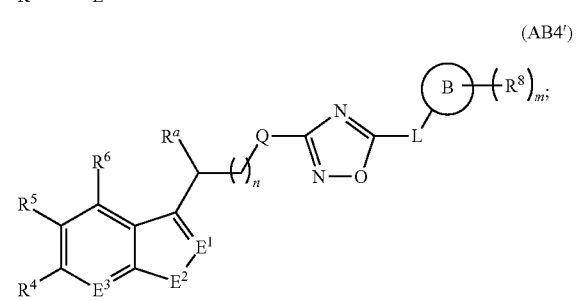
(AB4')

-continued (AB4″)

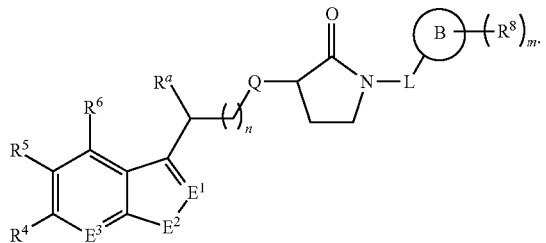

45. The inhibitor for use according to any one of statements 1 to 44, wherein n is 1.

46. The inhibitor for use according to any one of statements 1 to 45, whereby $R^2$ is H.

47. The inhibitor for use according to any one of statements 1 to 46, whereby $R^3$ is H.

48. The inhibitor for use according to any one of statements 1 to 47, wherein B is $C_{3-8}$cycloalkyl or $C_{6-10}$aryl and $R^8$ is selected from hydrogen, halogen, cyano, $C_{1-6}$alkoxy, trifluoromethyl; trifluoromethoxy.

49. The inhibitor for use according to any one of statements 1 to 48, whereby the cycle B is phenyl.

50. The inhibitor for use according to any one of statements 1 to 49, whereby L is selected from being not present; —O—; —NH—; —$NR^{10}$—; and $C_{1-6}$alkylene, yet more in particular, whereby L is selected from —O—; —NH—; —$NR^{10}$—; and $C_{1-6}$alkylene, and still more in particular, L is $C_{1-6}$alkylene, optionally substituted by one or more substituents each independently selected from halogen; $C_{1-6}$alkyl; halo$C_{1-6}$alkyl; halo$C_{1-6}$alkyloxy and still more in particular, whereby L is $CH_2$—.

51. The inhibitor for use according to any one of statements 1 to 50, whereby L is selected from being not present; —O—; —$NR^{10}$—; and $C_{1-6}$alkylene, yet more in particular, whereby L is selected from —O—; —$NR^{10}$—; and $C_{1-6}$alkylene, and still more in particular, L is $C_{1-6}$alkylene, optionally substituted by one or more substituents each independently selected from halogen; $C_{1-6}$alkyl, halo$C_{1-6}$alkyl; halo$C_{1-6}$alkyloxy and still more in particular, whereby L is $CH_2$—.

52. The inhibitor for use according to any one of statements 1 to 51, whereby $R^8$ is selected from hydrogen and halogen.

53. The inhibitor for use according to any one of statements 1 to 52, whereby $R^1$, $R^3$, $R^4$ and $R^6$ are hydrogen.

54. The inhibitor for use according to any one of statements 1 to 53 having a structure according to formula (A5), (A6), (A5'), (A5″), (A6') or (A6″):

(A5)

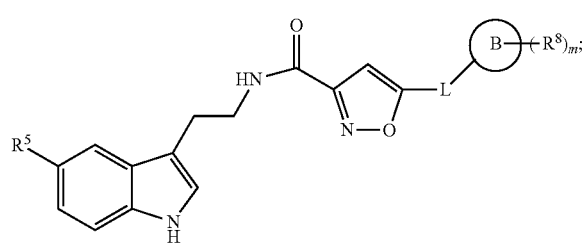

-continued (A6)

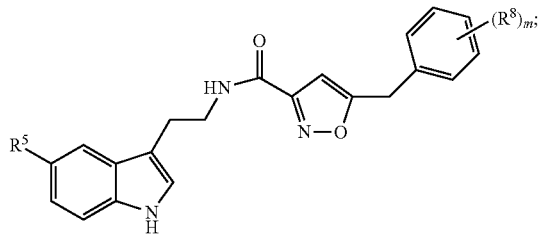

(A5')

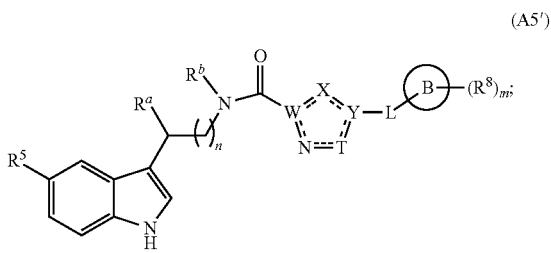

(A5″)

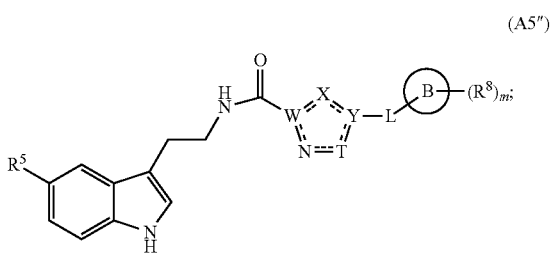

(A6')

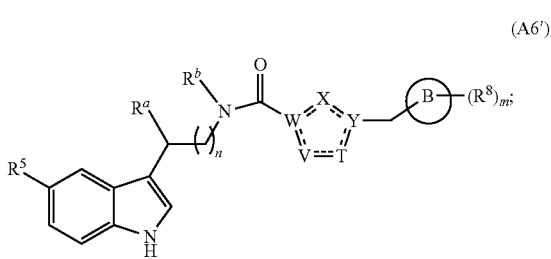

(A6″)

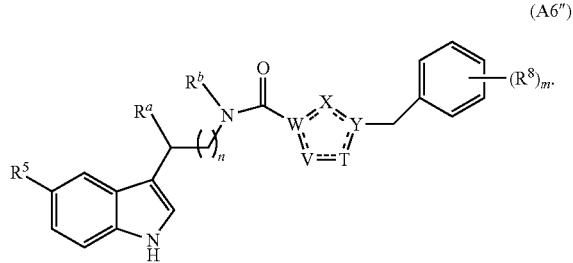

whereby all the remaining variables are as in formula (A1), (AA1) or other formula or all embodiments described herein.

55. The inhibitor for use according to any one of statements 1 to 54 having a structure according to formula (A7) or (A8)

(A7)

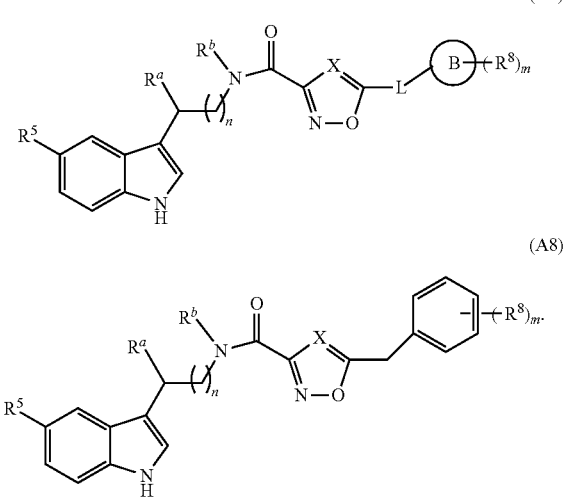

(A8)

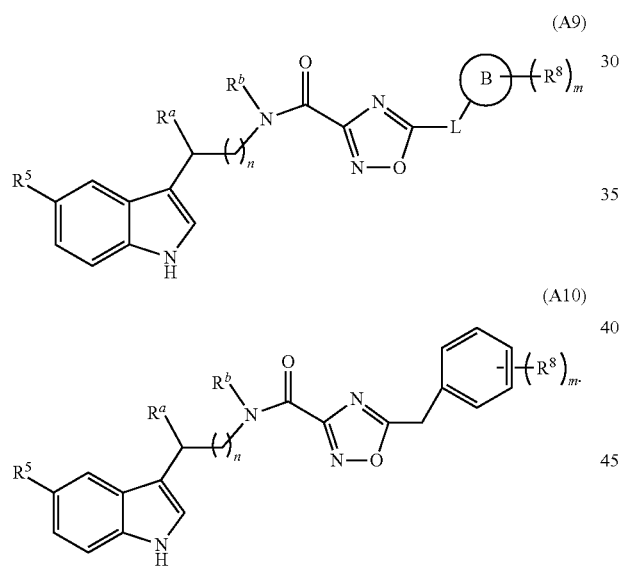

56. The inhibitor for use according to any one of statements 1 to 55 having a structure according to formula (A9) or (A10)

(A9)

(A10)

57. The inhibitor for use according to any one of statements 1 to 56 having a structure according to formula (A11) or (A12)

(A11)

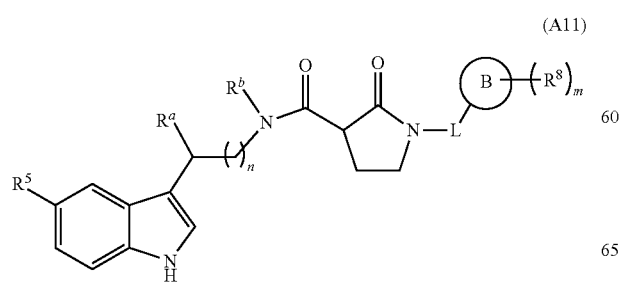

(A12)

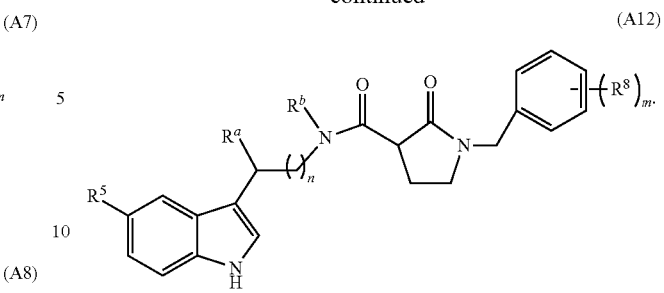

58. The inhibitor for use according to any one of statements 1 to 57 wherein,
each dotted line individually represents an optional double bond, wherein maximally two dotted lines selected from the five dotted lines are a double bond;
$E^1$ is independently selected from $CR^1$; and N; preferably $E^1$ is $CR^1$;
$E^2$ is independently selected from $NR^2$; and O; preferably $E^2$ is $NR^2$;
$E^3$ is independently selected from $CR^3$; and N; preferably $E^3$ is $CR^3$;
Q is independently selected from $NR^b$—C(O); or C(O)NH; preferably Q is selected $NR^b$—C(O);
$R^a$ is hydrogen or can be taken together with Rb to form a substituted or unsubstituted 4, 5, 6, 7 or 8 membered ring containing one N atom, for example a piperidine ring; preferably $R^a$ is hydrogen;
$R^b$ is hydrogen or can be taken together with $R^a$ to form a substituted or unsubstituted 4, 5, 6, 7 or 8 membered ring containing one N atom, for example a piperidine ring; preferably Rb is hydrogen;
$R^1$ is selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or $S(O)_2$; preferably $R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl, $C_{2-6}$alkenyl; $C_{2-6}$alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z; preferably R¹ is selected from hydrogen; halogen; —OH; —OR¹⁰; —SH; —SR¹⁰; trifluoromethyl; trifluoromethoxy; nitro; —NR¹²R¹³; -cyano; —COOH; —COOR¹⁰; $C_{1-6}$ alkyl; $C_{3-8}$cycloalkyl, $C_{6-10}$aryl; wherein said $C_{1-6}$alkyl, $C_{3-8}$cycloalkyl, or $C_{6-10}$aryl, can be unsubstituted or substituted with Z; preferably R¹ is selected from hydrogen; halogen; —OH; —OR¹⁰; trifluoromethyl; trifluoromethoxy; nitro; —NR¹²R¹³; -cyano; —COOH; —COOR¹⁰; $C_{1-6}$ alkyl; $C_{3-8}$cycloalkyl, $C_{6-10}$aryl; preferably R¹ is selected from hydrogen; halogen; —OH; $C_{1-6}$alkyloxy; trifluoromethyl; trifluoromethoxy; nitro; —NH₂; -cyano; —COOH; —COOC$_{1-6}$alkyl; $C_{1-6}$alkyl, $C_{3-8}$cycloalkyl; preferably R¹ is selected from hydrogen; halogen; $C_{1-6}$alkyl; preferably R¹ is hydrogen;

R³ is selected from hydrogen; halogen; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂; preferably R³ is selected from hydrogen; halogen; —OH; —OR¹⁰; —SH; —SR¹⁰; trifluoromethyl; trifluoromethoxy; nitro; —NR¹²R¹³; -cyano; —COOH; —COOR¹⁰; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl; $C_{2-6}$ alkenyl, $C_{2-6}$ alkynyl, $C_{6-10}$aryl, can be unsubstituted or substituted with Z; preferably R³ is selected from hydrogen; halogen; —OH; —OR¹⁰; —SH; —SR¹⁰; trifluoromethyl; trifluoromethoxy; nitro; —NR¹²R¹³; -cyano; —COOH; —COOR¹⁰; $C_{1-6}$alkyl; $C_{3-8}$cycloalkyl; $C_{6-10}$aryl; wherein said $C_{1-6}$alkyl, $C_{3-8}$cycloalkyl; or $C_{6-10}$aryl, can be unsubstituted or substituted with Z; preferably R³ is selected from hydrogen; halogen; —OH; —OR¹⁰; trifluoromethyl; trifluoromethoxy; nitro; —NR¹²R¹³; -cyano; —COOH; —COOR¹⁰; $C_{1-6}$alkyl; $C_{3-8}$cycloalkyl; $C_{6-10}$aryl; preferably R³ is selected from hydrogen; halogen; —OH; $C_{1-6}$ alkyloxy; trifluoromethyl; trifluoromethoxy; nitro; —NH₂; -cyano; —COOH; —COOC$_{1-6}$alkyl; $C_{1-6}$alkyl; $C_{3-8}$cycloalkyl; preferably R³ is selected from hydrogen; halogen; $C_{1-6}$alkyl; preferably R³ is hydrogen;

R⁴ is selected from hydrogen; halogen; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂; preferably R⁴ is selected from hydrogen; halogen; —OH; —OR¹⁰; —SH; —SR¹⁰; trifluoromethyl; trifluoromethoxy; nitro; —NR¹²R¹³; -cyano; —COOH; —COOR¹⁰; $C_{1-6}$alkyl; $C_{3-8}$cycloalkyl; $C_{2-6}$alkenyl; $C_{2-6}$alkynyl; $C_{6-10}$aryl; wherein said $C_{1-6}$alkyl, $C_{3-8}$cycloalkyl; $C_{2-6}$ alkenyl, $C_{2-6}$ alkynyl, $C_{6-10}$aryl, can be unsubstituted or substituted with Z; preferably R⁴ is selected from hydrogen; halogen; —OH; —OR¹⁰; —SH; —SR¹⁰; trifluoromethyl; trifluoromethoxy; nitro; —NR¹²R¹³; -cyano; —COOH; —COOR¹⁰; $C_{1-6}$alkyl; $C_{3-8}$cycloalkyl; $C_{6-10}$aryl; wherein said $C_{1-6}$alkyl, $C_{3-8}$cycloalkyl, or $C_{6-10}$aryl, can be unsubstituted or substituted with Z; preferably R⁴ is selected from hydrogen; halogen; —OH; —OR¹⁰; trifluoromethyl; trifluoromethoxy; nitro; —NR¹²R¹³; -cyano; —COOH; —COOR¹⁰; $C_{1-6}$alkyl; $C_{3-8}$cycloalkyl; $C_{6-10}$aryl; preferably R⁴ is selected from hydrogen; halogen; —OH; $C_{1-6}$alkyloxy; trifluoromethyl; trifluoromethoxy; nitro; —NH₂; -cyano; —COOH; —COOC$_{1-6}$alkyl; $C_{1-6}$alkyl; $C_{3-8}$cycloalkyl; preferably R⁴ is selected from hydrogen; halogen; $C_{1-6}$alkyl; preferably R⁴ is hydrogen;

R⁶ is selected from hydrogen; halogen; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; alkyl; alkenyl; alkynyl; aryl; heterocycle; arylalkylene; arylalkenylene; arylalkynylene; heterocycle-alkylene; heterocycle-alkenylene; heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$; preferably R$^6$ is selected from hydrogen; halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; C$_{1-6}$alkyl; C$_{3-8}$cycloalkyl; C$_{2-6}$alkenyl; C$_{2-6}$alkynyl; C$_{6-10}$aryl; wherein said C$_{1-6}$alkyl, C$_{3-8}$cycloalkyl; C$_{2-6}$alkenyl, C$_{2-6}$alkynyl, C$_{6-10}$aryl, can be unsubstituted or substituted with Z; preferably R$^6$ is selected from hydrogen; halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; C$_{1-6}$ alkyl; C$_{3-8}$cycloalkyl; C$_{6-10}$aryl; wherein said C$_{1-6}$alkyl, C$_{3-8}$cycloalkyl, or C$_{6-10}$aryl, can be unsubstituted or substituted with Z; preferably R$^6$ is selected from hydrogen; halogen; —OH; —OR$^{10}$; trifluoromethyl; trifluoromethoxy; nitro; —NR$^{12}$R$^{13}$; -cyano; —COOH; —COOR$^{10}$; C$_{1-6}$alkyl; C$_{3-8}$cycloalkyl; C$_{6-10}$aryl; preferably R$^6$ is selected from hydrogen; halogen; —OH; C$_{1-6}$alkyloxy; trifluoromethyl; trifluoromethoxy; nitro; —NH$_2$; -cyano; —COOH; —COOC$_{1-6}$alkyl; C$_{1-6}$ alkyl; C$_{3-8}$cycloalkyl; preferably R$^6$ is selected from hydrogen; halogen; C$_{1-6}$alkyl; preferably R$^6$ is hydrogen;

R$^2$ is selected from hydrogen; alkyl; alkenyl; and alkynyl; preferably R$^2$ is selected from hydrogen; C$_{1-6}$alkyl; C$_{3-8}$cycloalkyl; C$_{1-6}$alkenyl; and C$_{1-6}$alkynyl; preferably R$^2$ is selected from hydrogen, C$_{1-6}$alkyl, or C$_{3-8}$cycloalkyl; preferably R$^2$ is hydrogen;

R$^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$; preferably R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; C$_{1-6}$alkyl; C$_{3-8}$cycloalkyl; C$_{2-6}$alkenyl; C$_{2-6}$alkynyl; C$_{6-10}$aryl; wherein said C$_{1-6}$alkyl, C$_{3-8}$cycloalkyl; C$_{2-6}$alkenyl, C$_{2-6}$alkynyl, C$_{6-10}$aryl, can be unsubstituted or substituted with Z; preferably R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; C$_{1-6}$ alkyl; C$_{3-8}$ cycloalkyl; C$_{6-10}$aryl; wherein said C$_{1-6}$alkyl, C$_{3-8}$cycloalkyl, or C$_{6-10}$aryl, can be unsubstituted or substituted with Z; preferably R$^5$ is selected from halogen; —OH; —OR$^{10}$; trifluoromethyl; trifluoromethoxy; nitro; —NR$^{12}$R$^{13}$; -cyano; —COOH; —COOR$^{10}$; C$_{1-6}$alkyl; C$_{3-8}$cycloalkyl; C$_{6-10}$aryl; preferably R$^5$ is selected from halogen; —OH; C$_{1-6}$alkyloxy; trifluoromethyl; trifluoromethoxy; nitro; —NH$_2$; -cyano; —COOH; —COOC$_{1-6}$alkyl; C$_{1-6}$alkyl; C$_{3-8}$cycloalkyl; preferably R$^5$ is selected from halogen or C$_{1-6}$ alkyl; preferably R$^5$ is halogen; preferably R$^5$ is chloro or fluoro, preferably R$^5$ is chloro;

n is selected from 0; 1 or 2; preferably n is 1 or 2, preferably n is 1;

B represents a cyclic structure selected from cycloalkyl; cycloalkenyl; cycloalkynyl; aryl; or heterocycle; preferably B is selected from C$_{3-8}$cycloalkyl; C$_{5-8}$cycloalkenyl; C$_{6-10}$aryl; or heterocycle; preferably B is selected from C$_{3-8}$cycloalkyl; C$_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from C$_{3-6}$cycloalkyl; C$_{6-10}$aryl; or pyridyl, dihydropyridyl, piperidyl, thiazolyl, tetrahydrothiophenyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from C$_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;

m is selected from 0; 1; 2; 3; 4 and 5; preferably m is selected from 0, 1, 2, 3, preferably m is 0, 1, or 2;

$R^8$ is independently selected from hydrogen; halogen; aryl, alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; wherein said alkyl, alkenyl and alkynyl optionally includes one or more heteroatoms, said heteroatoms being selected from the atoms O, S and N; and wherein said alkyl, alkenyl and alkynyl can be unsubstituted or substituted with Z; and wherein a carbon atom or heteroatom of said alkyl, alkenyl and alkynyl, can be oxidized to form a C=O, C=S, N=O, N=S, S=O or $S(O)_2$; preferably $R^8$ is independently selected from hydrogen; halogen; $C_{1-6}$alkyl; $C_{3-8}$ cycloalkyl; $C_{2-6}$alkenyl; $C_{2-6}$ alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; wherein said $C_{1-6}$alkyl, $C_{3-8}$ cycloalkyl; $C_{2-6}$alkenyl and $C_{2-6}$alkynyl optionally includes one or more heteroatoms, said heteroatoms being selected from the atoms O, S and N; and wherein said $C_{1-6}$alkyl, $C_{3-8}$cycloalkyl; $C_{2-6}$ alkenyl and $C_{2-6}$ alkynyl can be unsubstituted or substituted with Z; preferably $R^8$ is independently selected from hydrogen; halogen; $C_{1-6}$alkyl; $C_{3-8}$cycloalkyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; wherein said $C_{1-6}$alkyl or $C_{3-8}$cycloalkyl, can be unsubstituted or substituted with Z; preferably $R^8$ is independently selected from hydrogen; halogen; $C_{1-6}$alkyl; —OH; —$OR^{10}$; —SH; —$SR^{10}$; —$S(O)_2R^{11}$; trifluoromethyl; trifluoromethoxy; nitro; —$NHC(O)R^{10}$; —$NR^{10}C(O)R^{10}$; —$NR^{12}R^{13}$; -cyano; —COOH; —$COOR^{10}$; —$C(O)NR^{12}R^{13}$; wherein said $C_{1-6}$alkyl can be unsubstituted or substituted with Z; preferably $R^8$ is independently selected from hydrogen; halogen; $C_{1-6}$alkyl; —OH; —$OR^{10}$; —SH; trifluoromethyl; trifluoromethoxy; nitro; —$NR^{12}R^{13}$; -cyano; —COOH; —$COOR^{10}$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; preferably each Z is independently selected from halogen; —OH; —$OR^{10}$; —SH; —$SR^{10}$; —$S(O)R^{11}$; —$S(O)_2R^{11}$; trifluoromethyl; trifluoromethoxy; nitro; —$NHC(O)R^{10}$; —$NR^{10}C(O)R^{10}$; —$NR^{12}R^{13}$; -cyano; —COOH; —$COOR^{10}$; preferably each Z is independently selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; preferably each Z is independently selected from halogen; —OH; —$OR^{10}$; trifluoromethyl; trifluoromethoxy; nitro; $NH_2$; -cyano; —COOH; or —$COO_{1-6}$ alkyl;

each $Z^1$ is independently selected from hydrogen; alkyl; or Z; preferably each $Z^1$ is independently selected from hydrogen, $C_{1-6}$alkyl, $C_{3-8}$ cycloalkyl or Z; preferably each $Z^1$ is independently selected from hydrogen, $C_{1-6}$alkyl, or Z; preferably each $Z^1$ is independently selected from hydrogen, or Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene; wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N; wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$; preferably each $R^{10}$ is independently selected from $C_{1-6}$alkyl; $C_{3-8}$cycloalkyl; $C_{2-6}$ alkenyl; $C_{2-6}$alkynyl; $C_{6-10}$aryl; heterocycle; $C_{6-10}$aryl$C_{1-6}$alkylene; $C_{6-10}$aryl$C_{2-6}$ alkenylene; $C_{6-10}$aryl$C_{2-6}$ alkynylene; heterocycle-$C_{1-6}$alkylene; heterocycle-$C_{2-6}$alkenylene or heterocycle-$C_{2-6}$alkynylene; wherein said $C_{1-6}$alkyl, $C_{3-6}$cycloalkyl; $C_{2-6}$ alkenyl, $C_{2-6}$ alkynyl, $C_{6-10}$aryl, heterocycle, $C_{6-10}$aryl$C_{1-6}$alkylene, $C_{6-10}$aryl$C_{2-6}$ alkenylene, $C_{6-10}$aryl$C_{2-6}$ alkynylene, heterocycle-$C_{1-6}$alkylene, heterocycle-$C_{2-6}C_{2-6}$alkenylene or heterocycle-$C_{2-6}$ alkynylene optionally include one or more heteroatoms in the $C_{1-6}$alkyl(ene), $C_{3-8}$cycloalkyl(ene), $C_{2-6}$alkenyl(ene) or $C_{2-6}$ alkynyl(ene) moiety, said heteroatom selected from O, S and N; wherein a carbon atom or heteroatom of said $C_{1-6}$alkyl, $C_{3-8}$cycloalkyl, $C_{2-6}$ alkenyl, $C_{2-6}$alkynyl, $C_{6-10}$aryl, heterocycle, $C_{6-10}$aryl$C_{1-6}$alkylene, $C_{6-10}$aryl$C_{2-6}$ alkenylene, $C_{6-10}$aryl$C_{2-6}$ alkynylene, heterocycle-$C_{1-6}$alkylene, heterocycle-$C_{2-6}$alkenylene or heterocycle-$C_{2-6}$alkynylene, can be oxidized to form a C=O, C=S, N=O, N=S, S=O or $S(O)_2$; preferably each $R^{10}$ is independently selected from $C_{1-6}$alkyl; $C_{3-8}$cycloalkyl; $C_{6-10}$aryl; heterocycle; $C_{6-10}$aryl$C_{1-6}$alkylene; heterocycle-$C_{1-6}$alkylene; preferably each $R^{10}$ is independently selected from $C_{1-6}$alkyl; $C_{3-8}$cycloalkyl; $C_{6-10}$aryl; or heterocycle; preferably each $R^{10}$ is independently selected from $C_{1-6}$alkyl; or $C_{6-10}$aryl; preferably each $R^{10}$ is $C_{1-6}$alkyl;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$; preferably R$^{11}$ is independently selected from hydroxyl; C$_{1-6}$alkyl, C$_{3-8}$cycloalkyl; C$_{2-6}$ alkenyl, C$_{2-6}$alkynyl, C$_{6-10}$aryl, heterocycle, C$_{6-10}$arylC$_{1-6}$alkylene, C$_{6-10}$arylC$_{2-6}$ alkenylene, C$_{6-10}$arylC$_{2-6}$ alkynylene, heterocycle-C$_{1-6}$alkylene, heterocycle-C$_{2-6}$C$_{2-6}$alkenylene or heterocycle-C$_{2-6}$alkynylene and wherein said C$_{1-6}$alkyl, C$_{3-8}$cycloalkyl; C$_{2-6}$ alkenyl, C$_{2-6}$alkynyl, C$_{6-10}$aryl, heterocycle, C$_{6-10}$arylC$_{1-6}$alkylene, C$_{6-10}$arylC$_{2-6}$alkenylene, C$_{6-10}$arylC$_{2-6}$alkynylene, heterocycle-C$_{1-6}$alkylene, heterocycle-C$_{2-6}$C$_{2-6}$ alkenylene or heterocycle-C$_{2-6}$ alkynylene optionally include one or more heteroatoms in the C$_{1-6}$alkyl(ene), C$_{3-8}$cycloalkyl(ene), C$_{2-6}$alkenyl(ene) or C$_{2-6}$alkynyl(ene) moiety, said heteroatom selected from O, S and N; and wherein a carbon atom or heteroatom of said C$_{1-6}$alkyl, C$_{3-8}$cycloalkyl; C$_{2-6}$ alkenyl, C$_{2-6}$ alkynyl, C$_{6-10}$aryl, heterocycle, C$_{6-10}$arylC$_{1-6}$alkylene, C$_{6-10}$arylC$_{2-6}$ alkenylene, C$_{6-10}$arylC$_{2-6}$alkynylene, heterocycle-C$_{1-6}$alkylene, heterocycle-C$_{2-6}$C$_{2-6}$ alkenylene or heterocycle-C$_{2-6}$alkynylene can be oxidized to form a C=O, C=S, N=O, N=S, S=O or S(O)$_2$; preferably R$^{11}$ is independently selected from hydroxyl; C$_{1-6}$alkyl, C$_{3-8}$cycloalkyl; C$_{6-10}$aryl, heterocycle, C$_{6-10}$arylC$_{1-6}$alkylene, heterocycle-C$_{1-6}$alkylene; preferably R$^{11}$ is independently selected from hydroxyl; C$_{1-6}$alkyl, C$_{3-8}$cycloalkyl; C$_{6-10}$aryl, heterocycle, preferably R$^{11}$ is independently selected from hydroxyl; C$_{1-6}$alkyl, or C$_{6-10}$aryl, preferably R$^{11}$ is independently selected from hydroxyl or C$_{1-6}$alkyl, each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene; and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N; and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$; and wherein R$^{12}$ and R$^{13}$ can be taken together in order to form a (5-, 6-, or 7-membered) heterocycle which can be unsubstituted or substituted; preferably each R$^{12}$ and R$^{13}$ is independently selected from hydrogen; C$_{1-6}$alkyl, C$_{3-8}$cycloalkyl; C$_{2-6}$ alkenyl, C$_{2-6}$alkynyl, C$_{6-10}$aryl, heterocycle, C$_{6-10}$arylC$_{1-6}$alkylene, C$_{6-10}$arylC$_{2-6}$alkenylene, C$_{6-10}$arylC$_{2-6}$alkynylene, heterocycle-C$_{1-6}$alkylene, heterocycle-C$_{2-6}$C$_{2-6}$alkenylene or heterocycle-C$_{2-6}$alkynylene; and wherein said C$_{1-6}$alkyl, C$_{3-8}$cycloalkyl; C$_{2-6}$alkenyl, C$_{2-6}$ alkynyl, C$_{6-10}$aryl, heterocycle, C$_{6-10}$arylC$_{1-6}$alkylene, C$_{6-10}$arylC$_{2-6}$alkenylene, C$_{6-10}$arylC$_{2-6}$alkynylene, heterocycle-C$_{1-6}$alkylene, heterocycle-C$_{2-6}$C$_{2-6}$alkenylene or heterocycle-C$_{2-6}$alkynylene optionally include one or more heteroatoms in the C$_{1-6}$alkyl(ene), C$_{3-8}$cycloalkyl(ene), C$_{2-6}$alkenyl(ene) or C$_{2-6}$alkynyl(ene) moiety, said heteroatom selected from O, S and N; and wherein a carbon atom or heteroatom of said C$_{1-6}$alkyl, C$_{3-8}$cycloalkyl; C$_{2-6}$ alkenyl, C$_{2-6}$ alkynyl, C$_{6-10}$aryl, heterocycle, C$_{6-10}$arylC$_{1-6}$alkylene, C$_{6-10}$arylC$_{2-6}$ alkenylene, C$_{6-10}$arylC$_{2-6}$ alkynylene, heterocycle-C$_{1-6}$alkylene, heterocycle-C$_{2-6}$C$_{2-6}$ alkenylene or heterocycle-C$_{2-6}$ alkynylene can be oxidized to form a C=O, C=S, N=O, N=S, S=O or S(O)$_2$; and wherein R$^{12}$ and R$^{13}$ can be taken together in order to form a (5-, 6-, or 7-membered) heterocycle which can be unsubstituted or substituted; preferably each R$^{12}$ and R$^{13}$ is independently selected from hydrogen; C$_{1-6}$alkyl, C$_{3-8}$cycloalkyl; C$_{6-10}$aryl, heterocycle, C$_{6-10}$arylC$_{1-6}$alkylene, heterocycle-C$_{1-6}$alkylene; preferably each R$^{12}$ and R$^{13}$ is independently selected from hydrogen; C$_{1-6}$alkyl, C$_{3-8}$cycloalkyl; C$_{6-10}$aryl, heterocycle, preferably each R$^{12}$ and R$^{13}$ is independently selected from hydrogen; C$_{1-6}$alkyl, C$_{3-6}$cycloalkyl, or C$_{6-10}$aryl, preferably each R$^{12}$ and R$^{13}$ is independently selected from hydrogen; or C$_{1-6}$alkyl, wherein L is independently selected from —O—; —NH—; —NR$^{10}$—; C$_{1-6}$alkylene; C$_{1-6}$alkenylene; C$_{1-6}$alkynylene; wherein each of said C$_{1-6}$alkylene, C$_{1-6}$alkenylene or C$_{1-6}$alkynylene optionally includes one or more heteroatoms, said heteroatoms being selected from the heteroatoms consisting of S and N, and wherein each of said C$_{1-6}$alkylene, C$_{1-6}$alkenylene or C$_{1-6}$alkynylene, can be unsubstituted or substituted; and wherein a carbon atom or heteroatom of said C$_{1-6}$alkylene, C$_{1-6}$alkenylene or C$_{1-6}$alkynylene, can be oxidized to form a C=S, N=O, N=S, S=O or S(O)$_2$; preferably L is independently selected from —O—; —NH—; —NR$^{10}$—; C$_{1-6}$alkylene; C$_{1-6}$alkenylene; C$_{1-6}$alkynylene; preferably L is independently selected from —O—; —NH—; —NR$^{10}$—; C$_{1-6}$alkylene; preferably L is independently selected from —O—; or C$_{1-6}$alkylene; preferably L is C$_{1-6}$alkylene;

and each of X, Y, T, W and V is independently selected from CZ$^1$H—; —CZ$^1$—; —C—; —N—; NR$^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa) preferably X, Y, T, W and V form with the dotted lines one of the cycles having one of the structural formula (Ia), (IIa), (IIIa), (IVa), (Va), (VIa), (VIIa), (VIIIa), (IXa), preferably X, Y, T, W and V form with the dotted lines one of the cycles having one of the structural formula (Ia), (IIa), (IIIa), (IVa), (Va), preferably X, Y, T, W and V form with the dotted lines one of the cycles having one of the structural formula (Ia) or (IIa) or (IIIa),

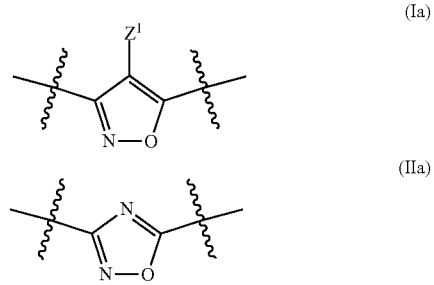

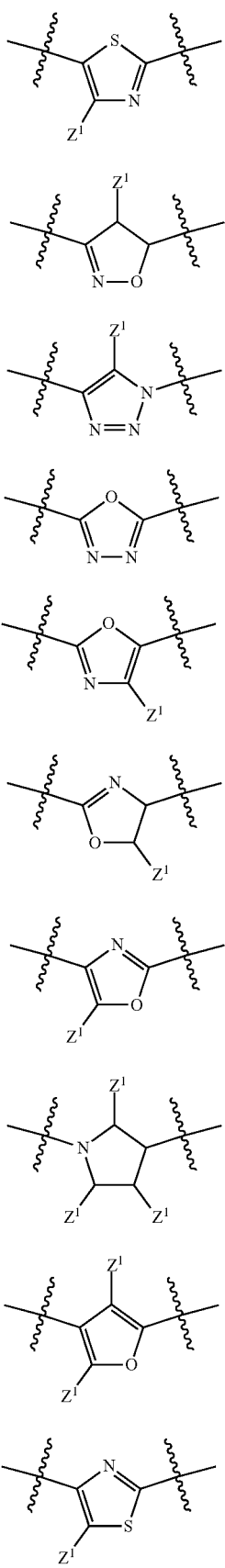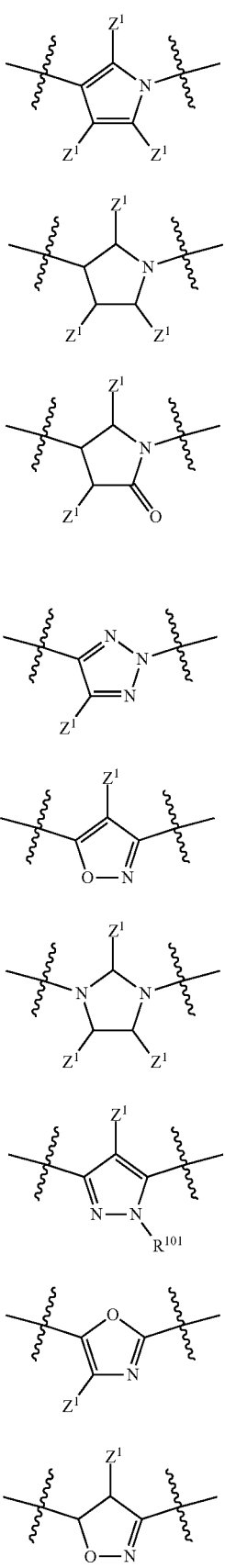

-continued (XXIIIa)

(XXIVa)

(IIIa)

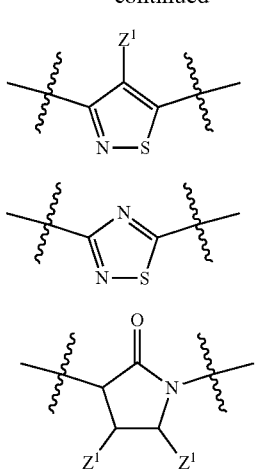

wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

59. The inhibitor for use according to any one of statements 1 to 58 wherein, $E^1$ is $CR^1$;
$E^2$ is $NR^2$;
$E^3$ is $CR^3$;
Q is selected $NR^b$—C(O);
$R^a$ is hydrogen;
$R^b$ is hydrogen;
$R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$ alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^3$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$ alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^4$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$alkenyl; $C_{2-6}$ alkynyl; $C_{6-10}$aryl; wherein said $C_{1-6}$alkyl, $C_{3-8}$cycloalkyl, $C_{2-6}$alkenyl, $C_{2-6}$alkynyl, $C_{6-10}$aryl, can be unsubstituted or substituted with Z;
$R^6$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-8}$cycloalkyl; $C_{2-6}$ alkenyl; $C_{2-6}$ alkynyl; $C_{6-10}$aryl; wherein said $C_{1-6}$alkyl, $C_{3-8}$cycloalkyl, $C_{2-6}$ alkenyl, $C_{2-6}$alkynyl, $C_{6-10}$aryl, can be unsubstituted or substituted with Z;
$R^2$ is selected from hydrogen; $C_{1-6}$alkyl; $C_{3-6}$ cycloalkyl; $C_{1-6}$alkenyl; and $C_{1-6}$ alkynyl;
$R^5$ is selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$ alkyl; $C_{3-8}$cycloalkyl; $C_{2-6}$ alkenyl; $C_{2-6}$alkynyl; $C_{6-10}$aryl; wherein said $C_{1-6}$alkyl, $C_{3-8}$cycloalkyl, $C_{2-6}$ alkenyl, $C_{2-6}$alkynyl, $C_{6-10}$aryl, can be unsubstituted or substituted with Z;

n is 1 or 2, preferably n is 1;
B is selected from $C_{3-8}$cycloalkyl; $C_{5-8}$cycloalkenyl; $C_{6-10}$aryl; or heterocycle; preferably B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;
m is selected from 0, 1, 2, 3,
$R^8$ is independently selected from hydrogen; halogen; $C_{1-6}$ alkyl; $C_{3-8}$cycloalkyl; $C_{2-6}$alkenyl; $C_{2-6}$alkynyl; —OH; —$OR^{10}$; —SH; —$SR^{10}$; —S(O)$R^{11}$; —S(O)$_2$$R^{11}$; —SO$_2$$NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}$C(O)$R^{10}$; —$NR^{10}$S(O)$_2$$R^{10}$; —$NR^{10}$C(O)$NR^{12}R^{13}$; —$NR^{12}R^{13}$; -cyano; —COOH; —$COOR^{10}$; —C(O)$NR^{12}R^{13}$; —C(O)$R^{11}$; wherein said $C_{1-6}$alkyl, $C_{3-8}$cycloalkyl, $C_{2-6}$alkenyl and $C_{2-6}$alkynyl optionally includes one or more heteroatoms, said heteroatoms being selected from the atoms O, S and N; and wherein said $C_{1-6}$alkyl, $C_{3-8}$cycloalkyl, $C_{2-6}$alkenyl and $C_{2-6}$alkynyl can be unsubstituted or substituted with Z;
each Z is independently selected from halogen; —OH; —$OR^{10}$; —SH; —$SR^{10}$; —S(O)$R^{11}$; —S(O)$_2R^{11}$; trifluoromethyl; trifluoromethoxy; nitro; —NHC(O)$R^{10}$; —NHS(O)$_2R^{10}$; —NHC(O)$NR^{12}R^{13}$; —$NR^{10}$C(O)$R^{10}$; —$NR^{12}R^{13}$; -cyano; —COOH; —$COOR^{10}$;
each $Z^1$ is independently selected from hydrogen; alkyl; or Z;
each $R^{10}$ is independently selected from $C_{1-6}$alkyl; $C_{3-8}$cycloalkyl; $C_{2-6}$ alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene or heterocycle-$C_{2-6}$ alkynylene; wherein said $C_{1-6}$alkyl, $C_{3-8}$cycloalkyl, $C_{2-6}$ alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$ alkynylene, heterocycle-$C_{1-6}$alkylene, heterocycle-$C_{2-6}C_{2-6}$alkenylene or heterocycle-$C_{2-6}$ alkynylene optionally include one or more heteroatoms in the $C_{1-6}$alkyl(ene), $C_{3-8}$cycloalkyl(ene), $C_{2-6}$alkenyl (ene) or $C_{2-6}$alkynyl(ene) moiety, said heteroatom selected from O, S and N; wherein a carbon atom or heteroatom of said $C_{1-6}$ alkyl, $C_{3-8}$cycloalkyl, $C_{2-6}$alkenyl, $C_{2-6}$ alkynyl, $C_{6-10}$ aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}$ alkenylene or heterocycle-$C_{2-6}$ alkynylene, can be oxidized to form a C=O, C=S, N=O, N=S, S=O or $S(O)_2$;

each $R^{101}$ is independently selected from hydrogen and $R^{10}$;

$R^{11}$ is independently selected from hydroxyl; $C_{1-6}$alkyl, $C_{3-8}$cycloalkyl, $C_{2-6}$ alkenyl, $C_{2-6}$ alkynyl, $C_{6-10}$ aryl, heterocycle, $C_{6-10}$ aryl$C_{1-6}$ alkylene, $C_{6-10}$aryl$C_{2-6}$ alkenylene, $C_{6-10}$aryl$C_{2-6}$ alkynylene, heterocycle-$C_{1-6}$alkylene, heterocycle-$C_{2-6}$$C_{2-6}$alkenylene or heterocycle-$C_{2-6}$alkynylene and wherein said $C_{1-6}$alkyl, $C_{3-8}$cycloalkyl, $C_{2-6}$alkenyl, $C_{2-6}$ alkynyl, $C_{6-10}$aryl, heterocycle, $C_{6-10}$aryl$C_{1-6}$alkylene, $C_{6-10}$aryl$C_{2-6}$ alkenylene, $C_{6-10}$aryl$C_{2-6}$alkynylene, heterocycle-$C_{1-6}$alkylene, heterocycle-$C_{2-6}$$C_{2-6}$ alkenylene or heterocycle-$C_{2-6}$alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; and wherein a carbon atom or heteroatom of said $C_{1-6}$alkyl, $C_{3-8}$cycloalkyl, $C_{2-6}$ alkenyl, $C_{2-6}$alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}$ $C_{2-6}$ alkenylene or heterocycle-$C_{2-6}$ alkynylene can be oxidized to form a C=O, C=S, N=O, N=S, S=O or $S(O)_2$;

each $R^{12}$ and $R^{13}$ is independently selected from hydrogen; $C_{1-6}$alkyl, $C_{3-8}$cycloalkyl, $C_{2-6}$alkenyl, $C_{2-6}$alkynyl, $C_{6-10}$aryl, heterocycle, $C_{6-10}$aryl$C_{1-6}$alkylene, $C_{6-10}$aryl$C_{2-6}$ alkenylene, $C_{6-10}$aryl$C_{2-6}$ alkynylene, heterocycle-$C_{1-6}$alkylene, heterocycle-$C_{2-6}$$C_{2-6}$alkenylene or heterocycle-$C_{2-6}$alkynylene; and wherein said $C_{1-6}$alkyl, $C_{3-8}$cycloalkyl, $C_{2-6}$ alkenyl, $C_{2-6}$ alkynyl, $C_{6-10}$aryl, heterocycle, $C_{6-10}$aryl$C_{1-6}$alkylene, $C_{6-10}$aryl$C_{2-6}$alkenylene, $C_{6-10}$aryl$C_{2-6}$alkynylene, heterocycle-$C_{1-6}$alkylene, heterocycle-$C_{2-6}$$C_{2-6}$alkenylene or heterocycle-$C_{2-6}$ alkynylene optionally include one or more heteroatoms in the $C_{1-6}$alkyl(ene), $C_{3-8}$cycloalkyl(ene), $C_{2-6}$alkenyl(ene) or $C_{2-6}$alkynyl(ene) moiety, said heteroatom selected from O, S and N; and wherein a carbon atom or heteroatom of said $C_{1-6}$alkyl, $C_{3-8}$cycloalkyl, $C_{2-6}$ alkenyl, $C_{2-6}$ alkynyl, $C_{6-10}$aryl, heterocycle, $C_{6-10}$aryl$C_{1-6}$alkylene, $C_{6-10}$aryl$C_{2-6}$ alkenylene, $C_{6-10}$aryl$C_{2-6}$alkynylene, heterocycle-$C_{1-6}$alkylene, heterocycle-$C_{2-6}$$C_{2-6}$alkenylene or heterocycle-$C_{2-6}$ alkynylene can be oxidized to form a C=O, C=S, N=O, N=S, S=O or $S(O)_2$; and wherein $R^{12}$ and $R^{13}$ can be taken together in order to form a (5-, 6-, or 7-membered) heterocycle which can be unsubstituted or substituted;

L is independently selected from —O—; —NH—; —$NR^{10}$—; $C_{1-6}$alkylene; $C_{1-6}$alkenylene; $C_{1-6}$alkynylene;

X, Y, T, W and V form with the dotted lines one of the cycles having one of the structural formula (Ia), (IIa), (IIIa), (IVa), (Va), (VIa), (VIIa), (VIIIa), (IXa), or more particularly form with the dotted lines one of the cycles having one of the structural formula (Ia) or (IIa), or (IIIa), wherein the left side of the formula (Ia), (IIa), (IIIa), (IVa), (Va), (VIa), (VIIa), (VIIIa), (IXa), is attached to Q and the right side thereof is attached to L.

In an embodiment, the present invention encompasses compounds of formula (A1) or any subgroup thereof wherein, $R^1$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$ cycloalkyl, or $C_{6-10}$aryl, can be unsubstituted or substituted with Z;

$R^3$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^4$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^6$ is selected from hydrogen; halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$cycloalkyl, or $C_{6-10}$aryl, can be unsubstituted or substituted with Z;

$R^2$ is selected from hydrogen or $C_{1-6}$alkyl;

$R^5$ is selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl; wherein said $C_{1-6}$alkyl, $C_{3-6}$ cycloalkyl, or $C_{6-10}$aryl, can be unsubstituted or substituted with Z;

n is 1;

B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;

m is 0, 1, or 2;

$R^8$ is independently selected from hydrogen; halogen; $C_{1-6}$alkyl; $C_{3-6}$cycloalkyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)$ $R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; wherein said $C_{1-6}$alkyl or $C_{3-6}$cycloalkyl can be unsubstituted or substituted with Z;

each Z is independently selected from halogen; —OH; —$OR^{10}$; —SH; —$SR^{10}$; —$S(O)R^{11}$; —$S(O)_2R^{11}$; trifluoromethyl; trifluoromethoxy; nitro; —$NHC(O)R^{10}$; —$NR^{10}C(O)R^{10}$; —$NR^{12}R^{13}$; -cyano; —COOH; —$COOR^{10}$;

each $Z^1$ is independently selected from hydrogen; alkyl; or Z; preferably each $Z^1$ is independently selected from hydrogen; $C_{1-6}$alkyl; $C_{3-6}$cycloalkyl; or Z; preferably each $Z^1$ is independently selected from hydrogen; $C_{1-6}$alkyl; or Z; preferably each $Z^1$ is independently selected from hydrogen; or Z;

each $R^{10}$ is independently selected from $C_{1-6}$alkyl; $C_{3-6}$cycloalkyl; $C_{6-10}$aryl; heterocycle; $C_{6-10}$aryl$C_{1-6}$alkylene; heterocycle-$C_{1-6}$alkylene;

each $R^{101}$ is independently selected from hydrogen and $R^{10}$;

$R^{11}$ is independently selected from hydroxyl; $C_{1-6}$alkyl, $C_{3-6}$cycloalkyl, $C_{6-10}$aryl, heterocycle, $C_{6-10}$aryl$C_{1-6}$alkylene, heterocycle-$C_{1-6}$alkylene;

each $R^{12}$ and $R^{13}$ is independently selected from hydrogen; $C_{1-6}$alkyl, $C_{3-6}$cycloalkyl, $C_{6-10}$aryl, heterocycle, $C_{6-10}$aryl$C_{1-6}$alkylene, heterocycle-$C_{1-6}$alkylene;

L is independently selected from —O—; —NH—; —$NR^{10}$—; $C_{1-6}$alkylene; and X, Y, T, W and V form with the dotted lines one of the cycles having one of the structural formula (Ia), (IIa), (IIIa), (IVa), (Va), (VIa), (VIIa), (VIIIa), (IXa), wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L.

60. The compound according to any one of statements 1 to 59 wherein, $R^1$ is selected from hydrogen; halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl;

$R^3$ is selected from hydrogen; halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl;

$R^4$ is selected from hydrogen; halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl;

$R^6$ is selected from hydrogen; halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl;

$R^2$ is hydrogen;

$R^5$ is selected from halogen; —OH; —$OR^{10}$; trifluoromethyl; trifluoromethoxy; nitro; —$NR^{12}R^{13}$; -cyano; —COOH; —$COOR^{10}$; $C_{1-6}$alkyl; $C_{3-6}$cycloalkyl; $C_{6-10}$aryl;

n is 1;

B is selected from $C_{3-6}$cycloalkyl; $C_{6-10}$aryl; or pyridyl, dihydroypyridyl, piperidyl, thiazolyl, tetrahydrothiophenyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, 4aH-carbazolyl, carbazolyl, B-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl;

m is 0, 1, or 2;

$R^8$ is independently selected from hydrogen; halogen; $C_{1-6}$alkyl; $C_{3-6}$ cycloalkyl; —OH; —$OR^{10}$; —SH; —$SR^{10}$; —$S(O)_2R^{11}$; trifluoromethyl; trifluoromethoxy; nitro; —$NHC(O)R^{10}$; —$NR^{10}C(O)R^{10}$; —$NR^{12}R^{13}$; -cyano; —COOH; —$COOR^{10}$; —$C(O)NR^{12}R^{13}$; wherein said $C_{1-6}$alkyl or $C_{3-6}$cycloalkyl can be unsubstituted or substituted with Z;

each Z is independently selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$;

each $Z^1$ is independently selected from hydrogen; alkyl; or Z; preferably each $Z^1$ is independently selected from hydrogen; $C_{1-6}$alkyl; $C_{3-6}$cycloalkyl; or Z; preferably each $Z^1$ is independently selected from hydrogen; $C_{1-6}$alkyl; or Z; preferably each $Z^1$ is independently selected from hydrogen; or Z;

each $R^{10}$ is independently selected from $C_{1-6}$alkyl; $C_{3-6}$ cycloalkyl; $C_{6-10}$aryl; or heterocycle;

each $R^{101}$ is independently selected from hydrogen and $R^{10}$;

$R^{11}$ is independently selected from hydroxyl; $C_{1-6}$alkyl, $C_{3-6}$cycloalkyl, $C_{6-10}$aryl, heterocycle, each $R^{12}$ and $R^{13}$ is independently selected from hydrogen; $C_{1-6}$alkyl, $C_{3-6}$cycloalkyl, $C_{6-10}$aryl, heterocycle, L is independently selected from —O—; or $C_{1-6}$alkylene; and X, Y, T, W and V form with the dotted lines one of the cycles having one of the structural formula (Ia), (IIa), (IIIa), (IVa), (Va), (VIa), (VIIa), (VIIIa), (IXa), wherein the left side of the formula (Ia), (IIa), (IIIa), (IVa), (Va), (VIa), (VIIa), (VIIIa), (IXa), is attached to Q and the right side thereof is attached to L.

61. The compound according to any one of statements 1 to 60 wherein, $R^1$ is selected from hydrogen; halogen; $C_{1-6}$alkyl; $R^3$ is selected from hydrogen; halogen; $C_{1-6}$alkyl; $R^4$ is selected from hydrogen; halogen; $C_{1-6}$alkyl; $R^6$ is selected from hydrogen; halogen; $C_{1-6}$alkyl; $R^2$ is hydrogen; $R^5$ is selected from halogen or $C_{1-6}$alkyl; n is 1; B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; m is 0, 1, or 2; R⁸ is independently selected from hydrogen; halogen; $C_{1-6}$alkyl; —OH; —OR¹⁰; —SH; trifluoromethyl; trifluoromethoxy; nitro; —NR¹²R¹³; -cyano; —COOH; —COOR¹⁶;
   each Z is independently selected from halogen; —OH; —OR¹⁰; trifluoromethyl; trifluoromethoxy; nitro; $NH_2$; -cyano; —COOH; or —$COO_{1-6}$alkyl;
   each Z¹ is independently selected from hydrogen; alkyl; or Z; preferably each Z¹ is independently selected from hydrogen; $C_{1-6}$alkyl; $C_{3-6}$cycloalkyl; or Z; preferably each Z¹ is independently selected from hydrogen; $C_{1-6}$alkyl; or Z; preferably each Z¹ is independently selected from hydrogen; or Z;
   each R¹⁰ is independently selected from $C_{1-6}$alkyl; or $C_{6-10}$aryl;
   each R¹⁰¹ is independently selected from hydrogen and R¹⁰;
   R¹¹ is independently selected from hydroxyl; $C_{1-6}$alkyl, or $C_{6-10}$aryl,
   each R¹² and R¹³ is independently selected from hydrogen; $C_{1-6}$alkyl, or $C_{6-10}$aryl,
   L is $C_{1-6}$alkylene; and X, Y, T, W and V form with the dotted lines one of the cycles having one of the structural formula (Ia), (IIa), (IIIa), (IVa), (Va), (VIa), (VIIa), (VIIIa), (IXa), preferably X, Y, T, W and V form with the dotted lines one of the cycles having one of the structural formula (Ia), (IIa), (IVa), (Va), preferably X, Y, T, W and V form with the dotted lines one of the cycles having one of the structural formula (Ia) or (IIa), wherein the left side of the formula (Ia), (IIa), (IIIa), (IVa), (Va), (VIa), (VIIa), (VIIIa), (IXa), is attached to Q and the right side thereof is attached to L.

62. The inhibitor for use according to any one of statements 1 to 61 wherein, R¹ is hydrogen; R³ is hydrogen; R⁴ is hydrogen; R⁶ is hydrogen; R² is hydrogen; R⁵ is selected from halogen or $C_{1-6}$alkyl; n is 1; B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; m is 0, 1, or 2; R⁸ is independently selected from hydrogen; halogen; $C_{1-6}$alkyl; —OH; —OR¹⁰; —SH; trifluoromethyl; trifluoromethoxy; nitro; —NR¹²R¹³; -cyano; —COOH; each Z is independently selected from halogen; —OH; —OR¹⁰; trifluoromethyl; trifluoromethoxy; nitro; $NH_2$; -cyano; —COOH; each Z¹ is independently selected from hydrogen; alkyl; or Z; preferably each Z¹ is independently selected from hydrogen; $C_{1-6}$alkyl; $C_{3-6}$ cycloalkyl; or Z; preferably each Z¹ is independently selected from hydrogen; $C_{1-6}$alkyl; or Z; preferably each Z¹ is independently selected from hydrogen, or Z; each R¹⁰ is $C_{1-6}$ alkyl; each R¹⁰¹ is independently selected from hydrogen and R¹⁰; R¹¹ is independently selected from hydroxyl or $C_{1-6}$alkyl, each R¹² and R¹³ is independently selected from hydrogen; or $C_{1-6}$alkyl, L is $C_{1-6}$alkylene; and X, Y, T, W and V form with the dotted lines one of the cycles having one of the structural formula (Ia), (IIa), (IIIa), (IVa), wherein the left side of the formula (Ia), (IIa), (IIIa), (IVa), is attached to Q and the right side thereof is attached to L.

63. The inhibitor for use according to any one of statements 1 to 62, wherein L is a single bond; and X, Y, T, W and V form with the dotted lines a cycle of formula (IIIa).

64. The compound according to any one of statements 1 to 63 having formula (I) or a tautomer thereof,

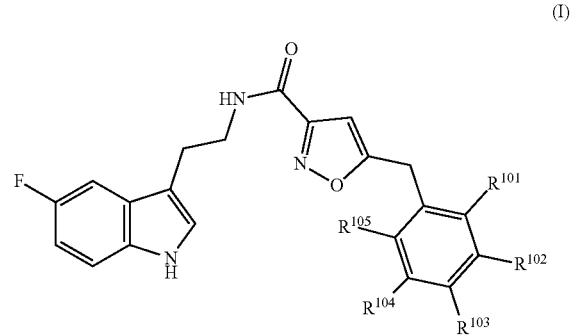

(I)

wherein,
   R¹⁰¹ is selected from the group consisting of hydrogen; F, Cl, and Br;
   R¹⁰² is selected from the group consisting of hydrogen, F, Cl, and Br;
   R¹⁰³ is selected from the group consisting of hydrogen, F, Cl, and Br;
   R¹⁰⁴ is selected from the group consisting of hydrogen, F, Cl, and Br;
   R¹⁰⁵ is selected from the group consisting of hydrogen, F, Cl, and Br;
   with the proviso that at least one of R¹⁰¹, R¹⁰², R¹⁰³, R¹⁰⁴ or R¹⁰⁵ is not hydrogen;
   with the proviso that said compound of formula (I) is not N-[2-(5-fluoro-1H-indol-3-yl)ethyl]-5-[(3-fluorophenyl)methyl]isoxazole-3-carboxamide,
or a solvate, a hydrate, a salt (in particular a pharmaceutically acceptable salt) or a prodrug thereof.

65. The inhibitor for use according to any one of statements 1 to 64, having structural formula (II), (III), (IV), (V) or (VI)

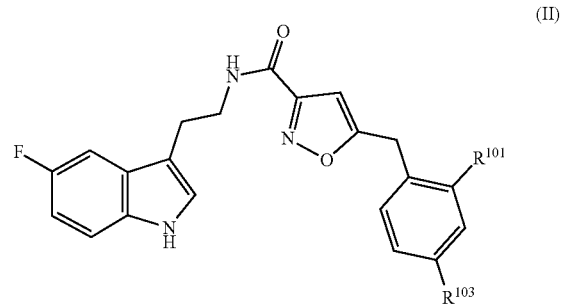

(II)

(III)

(IV)

(V)

(VI)

wherein $R^{101}$, $R^{102}$, $R^{103}$ and $R^{104}$ have the same meaning as defined in statement 64.

66. The inhibitor for use according to any one of statements 1 to 65, wherein $R^{102}$, $R^{103}$, $R^{104}$ and $R^{105}$ are hydrogen and wherein $R^{101}$ selected from the group consisting of F, Cl, and Br; preferably, $R^{101}$ is F or Cl, preferably $R^{101}$ is F.

67. The inhibitor for use according to any one of statements 1 to 65, wherein $R^{101}$, $R^{102}$, $R^{104}$ and $R^{105}$ are hydrogen and $R^{103}$ is selected from the group consisting of F, Cl, and Br, preferably, $R^{103}$ is F or Cl, preferably $R^{103}$ is F.

68. The inhibitor for use according to any one of statements 1 to 65, wherein $R^{102}$, $R^{104}$ and $R^{105}$ are hydrogen and $R^{101}$ and $R^{103}$ are each independently selected from hydrogen; F, Cl, Br; preferably $R^{101}$ and $R^{103}$ are each independently selected from the group consisting of hydrogen; and F.

69. The inhibitor for use according to statements 1 or 65 wherein $R^{103}$, $R^{104}$ and $R^{105}$ are hydrogen and $R^{101}$ and $R^{102}$ are each independently selected from hydrogen; F, Cl, and Br; preferably $R^{101}$ and $R^{102}$ are each independently selected from the group consisting of hydrogen; and F.

70. The inhibitor for use according to statements 1 or 65, wherein $R^{102}$, $R^{103}$ and $R^{105}$ are hydrogen and $R^{101}$ and $R^{104}$ are each independently selected from hydrogen; F, Cl, and Br; preferably $R^{101}$ and $R^{104}$ are each independently selected from the group consisting of hydrogen and F.

71. The inhibitor for use according to statements 1 or 65, wherein $R^{102}$, $R^{103}$ and $R^{105}$ are hydrogen and $R^{101}$ and $R^{105}$ are each independently selected from hydrogen; F, Cl, and Br; preferably $R^{101}$ and $R^{105}$ are each independently selected from the group consisting of hydrogen and F.

72. The inhibitor for use according to statements 1 or 65, wherein $R^{101}$, $R^{104}$ and $R^{105}$ are hydrogen and $R^{102}$ and $R^{103}$ are independently selected from hydrogen; F, Cl, or Br; preferably $R^{102}$ and $R^{103}$ are each independently selected from the group consisting of hydrogen and F.

73. The inhibitor for use according to statements 1 or 65, wherein $R^{101}$, $R^{103}$ and $R^{105}$ are hydrogen and $R^{102}$ and $R^{104}$ are independently selected from hydrogen; F, Cl, Br; preferably $R^{102}$ and $R^{104}$ are each independently selected from the group consisting of hydrogen and F.

74. The inhibitor for use according to statements 1 or 65, wherein $R^{101}$, $R^{103}$ and $R^{104}$ are hydrogen and $R^{102}$ and $R^{105}$ are independently selected from hydrogen; F, Cl, Br; preferably $R^{102}$ and $R^{105}$ are each independently selected from the group consisting of hydrogen and F.

75. An inhibitor of PDE6δ for use in the prevention and/or treatment of epilepsy, wherein said inhibitor is a compound according to formula (BB1), (BB1)

wherein,
each dotted line individually represents an optional double bond, wherein maximally two dotted lines selected from the five dotted lines are a double bond;
$E^1$ is independently selected from $CR^1$; and N;
$E^2$ is independently selected from $NR^2$; and O;
$E^3$ is independently selected from $CR^3$; and N;
$R^a$ is hydrogen or can be taken together with Rb to form a substituted or unsubstituted 4, 5, 6, 7 or 8 membered ring containing one N atom, preferably a piperidine ring;
$R^b$ is hydrogen or can be taken together with $R^a$ to form a substituted or unsubstituted 4, 5, 6, 7 or 8 membered ring containing one N atom, preferably a piperidine ring;
Q is independently selected from $NR^b$—C(O); C(O); and C(O)NH;
each $R^1$, $R^3$, $R^4$, $R^5$ and $R^6$ is independently selected from hydrogen; halogen; —OH; —$OR^{16}$; —SH; —$SR^{10}$; —$S(O)R^{11}$; —$S(O)_2R^{11}$; —$SO_2NR^{12}R^{13}$; trifluoromethyl; trifluoromethoxy; nitro; —NHC(O)$R^{10}$; —NHS(O)$_2R^{16}$; —NHC(O)$NR^{12}R^{13}$; —$NR^{10}$C(O)$R^{16}$; —$NR^{10}$S(O)$_2R^{10}$; —$NR^{10}$C(O)$NR^{12}R^{13}$; —$NR^{12}R^{13}$; -cyano; —COOH; —COO$R^{10}$; —C(O)$NR^{12}R^{13}$; —C(O)$R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

$R^2$ is selected from hydrogen; alkyl; alkenyl; and alkynyl;

n is selected from 0; 1 or 2;

each of X, Y, T, W and V is independently selected from C$Z^1$H—; —C$Z^1$—; —C—; —N—; $NR^{101}$; —O—; —S—; or —CO—; wherein at least one of X, Y, T; W or V is selected from C$Z^1$H— or —C$Z^1$— or C1-;

L is independently selected from being not present; —O—; —NH—; —$NR^{10}$—; $C_{1-6}$alkylene; $C_{1-6}$alkenylene; $C_{1-6}$alkynylene;

wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;

and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or S(O)$_2$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —O$R^{18}$; —SH; —S$R^{10}$; —S(O)$R^{11}$; —S(O)$_2R^{11}$; —SO$_2NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}$C(O)$R^{18}$; —$NR^{10}$S(O)$_2R^{10}$; —$NR^{10}$C(O)$NR^{12}R^{13}$; —$NR^{12}R^{13}$; -cyano; —COOH; —COO$R^{10}$; —C(O)$NR^{12}R^{13}$; —C(O)$R^{11}$;

wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with Z;

and wherein a carbon atom or heteroatom of said alkyl, alkenyl and alkynyl, can be oxidized to form a C=O, C=S, N=O, N=S, S=O or S(O)$_2$;

each Z is independently selected from halogen; —OH; —O$R^{10}$; —SH; —S$R^{10}$; —S(O)$R^{11}$; —S(O)$_2R^{11}$; —SO$_2NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}$C(O)$R^{10}$; —$NR^{10}$S(O)$_2R^{10}$; —$NR^{10}$C(O)$NR^{12}R^{13}$; —$NR^{12}R^{13}$; -cyano; —COOH; —COO$R^{10}$; —C(O)$NR^{12}R^{13}$; —C(O)$R^{11}$;

each $Z^1$ is independently selected from hydrogen; alkyl; and Z;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein $R^{12}$ and $R^{13}$ can be taken together in order to form a (5-, 6-, or 7-membered) heterocycle which can be unsubstituted or substituted;

and isomers (in particular stereoisomers, enantiomers or tautomers), solvates, hydrates, salts (in particular pharmaceutically acceptable salts) or prodrugs thereof.

76. The inhibitor for use according to statement 75 having a structure according to the formulae (BB2), (BB3), (BB4), (BB5), (BB6), or (BB7),

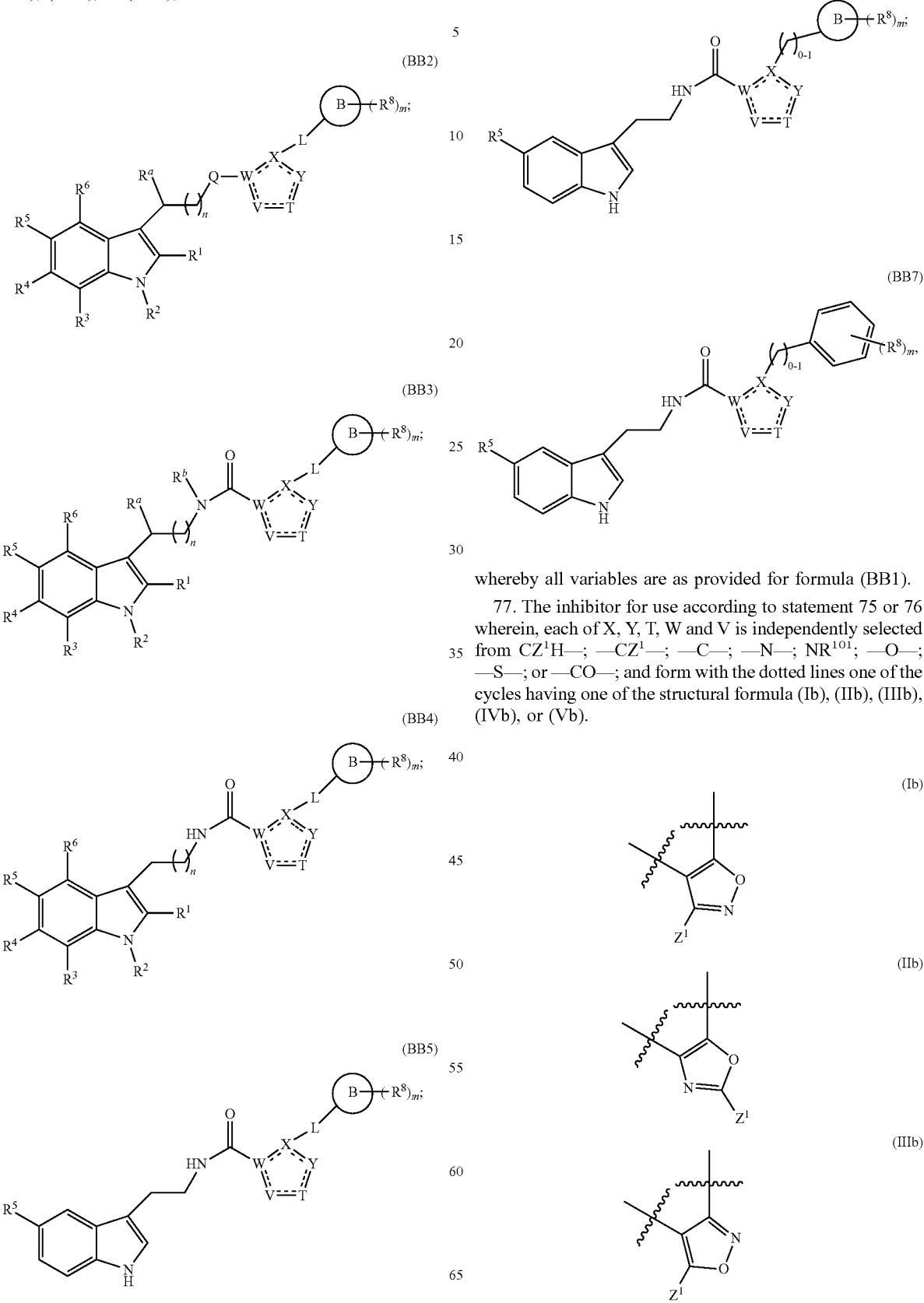

whereby all variables are as provided for formula (BB1).

77. The inhibitor for use according to statement 75 or 76 wherein, each of X, Y, T, W and V is independently selected from $CZ^1H-$; $-CZ^1-$; $-C-$; $-N-$; $NR^{101}$; $-O-$; $-S-$; or $-CO-$; and form with the dotted lines one of the cycles having one of the structural formula (Ib), (IIb), (IIIb), (IVb), or (Vb).

-continued

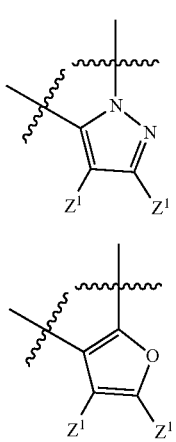

(IVb)

(Vb)

78. An inhibitor of PDE6δ for use in the prevention and/or treatment of epilepsy, wherein said inhibitor is a compound according to formula (CC1),

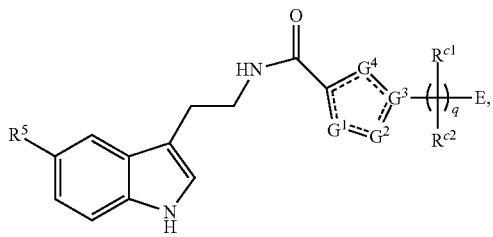

(CC1)

wherein,
each dotted line individually represents an optional double bond, wherein maximally two dotted lines selected from the five dotted lines are a double bond;
each of $G^1$, $G^2$, $G^3$ and $G^4$ is independently selected from N; $NR^{c3}$; O; $CHR^{c3}$; and $CR^{c3}$; wherein two of $G^1$, $G^2$, $G^3$ and $G^4$ are selected from N; $NR^{c3}$; and O; while the other two of $G^1$, $G^2$, $G^3$ and $G^4$ are selected from $CHR^{c3}$; and $CR^{c3}$;
each $R^{c3}$ is selected from hydrogen; and alkyl;
$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
q is selected from 0; 1; 2; or 3; preferably q is 0 or 1;
E is selected from hydrogen; halogen; —OH; —$OR^{10}$; —SH; —$SR^{10}$; trifluoromethoxy; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$;
each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
and wherein $R^{12}$ and $R^{13}$ can be taken together in order to form a (5-, 6-, or 7-membered) heterocycle which can be unsubstituted or substituted;
each of $R^{1c}$ and $R^{2c}$ is independently selected from hydrogen; halogen; alkyl; alkenyl or alkynyl;
each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;

and isomers (in particular stereoisomers, enantiomers or tautomers), solvates, hydrates, salts (in particular pharmaceutically acceptable salts) or prodrugs thereof.

79. The inhibitor for use according to statement 78, wherein each of $G^1$, $G^2$, $G^3$ and $G^4$ is independently selected from N; $NR^{c3}$; O; $CHR^{c3}$; and $CR^{c3}$; and form with the dotted lines one of the cycles having one of the structural formula (Ic), (IIc), (IIIc), (IVc), or (Vc):

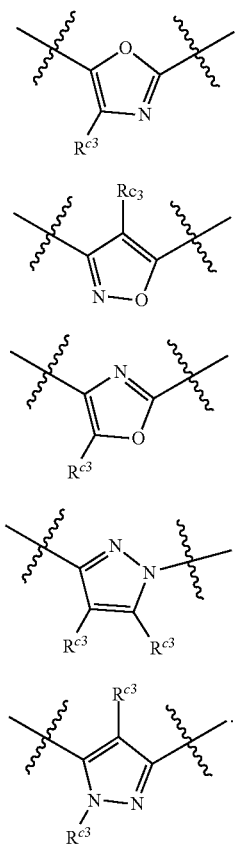

80. The inhibitor for use according to statements 78 or 79 having formula (CC2),

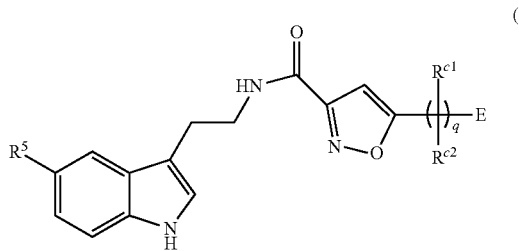

wherein,
R⁵ is independently selected from halogen; —OH; —OR¹⁰; —SH; —SR¹⁰; —S(O)R¹¹; —S(O)₂R¹¹; —SO₂NR¹²R¹³; trifluoromethyl; trifluoromethoxy; nitro; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³; -cyano; —COOH; —COOR¹⁰; —C(O)NR¹²R¹³; —C(O)R¹¹; alkyl; alkenyl; alkynyl; aryl; heterocycle; arylalkylene; arylalkenylene; arylalkynylene; heterocycle-alkylene; heterocycle-alkenylene; heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂;
q is selected from 0; 1; 2; or 3; preferably q is 0 or 1;
E is selected from hydrogen; halogen; —OH; —OR¹⁰; —SH; —SR¹⁰; trifluoromethoxy; —NHC(O)R¹⁰; —NHS(O)₂R¹⁰; —NHC(O)NR¹²R¹³; —NR¹⁰C(O)R¹⁰; —NR¹⁰S(O)₂R¹⁰; —NR¹⁰C(O)NR¹²R¹³; —NR¹²R¹³;
each R¹⁰ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂;
each R¹² and R¹³ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)₂;
and wherein R¹² and R¹³ can be taken together in order to form a (5-, 6-, or 7-membered) heterocycle which can be unsubstituted or substituted;
each of R¹ᶜ and R²ᶜ is independently selected from hydrogen; halogen; alkyl; alkenyl or alkynyl;
and isomers (in particular stereoisomers, enantiomers or tautomers), solvates, hydrates, salts (in particular pharmaceutically acceptable salts) or prodrugs thereof.

81. The inhibitor for use according to any one of statements 78 to 80, wherein E is selected from hydrogen; —OH;

—NR$^{12}$R$^{13}$ (preferably NH$_2$, NHMe, N(Me)$_2$, NHethyl or N(ethyl)$_2$); —O-alkyl; NHC(O)O-alkyl.

82. The inhibitor for use according to any one of statements 78 to 81, wherein each of R$^{1c}$ and R$^{2c}$ is independently selected from hydrogen; halogen; or alkyl; yet more particularly is hydrogen.

83. The inhibitor for use according to any one of statements 78 to 82, wherein R$^5$ is selected from halogen and alkyl (more preferably C$_{1-6}$ alkyl, yet more preferably methyl).

84. The inhibitor for use according to any one of statements 1 to 83, wherein the inhibitor is a compound of formula (AA1), (AA2), (AA3), (AA4), (A1), (A2), (A2'), (AB2), (AB2'), (A3), (A4), (A4'), (A4"), (AB3), (AB4), (AB4'), (AB4"), (BB1), (BB2), (BB3), (BB4), (BB5), (BB6), (BB7), (CC1) or (CC2).

85. The inhibitor for use according to any one of statements 1 to 84, selected from the group consisting of:

5-[(2,4-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(4-fluorophenyl)methyl]isoxazole-3-carboxamide;
5-[(2,3-difluorophenyl)methyl]-N-[2-(5-fluoro-1H-indol-3-yl)ethyl]isoxazole-3-carboxamide;
5-[(2,5-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(2-fluorophenyl)methyl]isoxazole-3-carboxamide;
5-[(3,4-difluorophenyl)methyl]-N-[2-(5-fluoro-1H-indol-3-yl)ethyl]isoxazole-3-carboxamide;
5-[(3,5-difluorophenyl)methyl]-N-[2-(5-fluoro-1H-indol-3-yl)ethyl]isoxazole-3-carboxamide,
N-(2-(5-chloro-1H-indol-3-yl)ethyl)-5-(3-methoxybenzyl)isoxazole-3-carboxamide;
N-(2-(5-chloro-1H-indol-3-yl)ethyl)-5-cyclopentylisoxazole-3-carboxamide;
N-(2-(5-chloro-1H-indol-3-yl)ethyl)-5-(3-cyanobenzyp-isoxazole-3-carboxamide;
N-(2-(5-chloro-1H-indol-3-yl)ethyl)-5-(4-cyanobenzyp-isoxazole-3-carboxamide;
N-(2-(5-chloro-1H-indol-3-yl)ethyl)-5-(2,5-difluorobenzypisoxazole-3-carboxamide;
N-(2-(5-chloro-1H-indol-3-yl)ethyl)-5-cyclopropylisoxazole-3-carboxamide;
5-benzyl-N-(2-(5-chloro-1H-indol-3-yl)ethyl)isoxazole-3-carboxamide;
N-(2-(5-chloro-1H-indol-3-yl)ethyl)-5-(2-methoxybenzyl)isoxazole-3-carboxamide;
N-(2-(5-chloro-1H-indol-3-yl)ethyl)-5-(4-(trifluoromethyl)benzypisoxazole-3-carboxamide;
N-(2-(5-chloro-1H-indol-3-yl)ethyl)-5-(4-methoxybenzyl)isoxazole-3-carboxamide;
N-(2-(5-chloro-1H-indol-3-yl)ethyl)-5-(furan-2-yl)isoxazole-3-carboxamide;
N-(2-(5-chloro-1H-indol-3-yl)ethyl)-5-(4-methylbenzyl)isoxazole-3-carboxamide;
N-(2-(5-chloro-1H-indol-3-yl)ethyl)-5-cyclohexylisoxazole-3-carboxamide;
5-(3-fluorobenzyl)-N-(2-(5-methyl-1H-indol-3-yl)ethyl)isoxazole-3-carboxamide;
N-(2-(5-chloro-1H-indol-3-yl)ethyl)-1-methyl-5-(thiophen-2-yl)-1H-pyrazole-3-carboxamide;
N-(2-(5-chloro-1H-indol-3-yl)ethyl)-5-(thiophen-2-yl)isoxazole-3-carboxamide;
N-(2-(5-chloro-1H-indol-3-yl)ethyl)-5-(furan-2-ylmethyl)isoxazole-3-carboxamide;
N-(2-(5-chloro-1H-indol-3-yl)ethyl)-5-(furan-2-yl)-1-methyl-1H-pyrazole-3-carboxamide;
N-(2-(5-chloro-1H-indol-3-yl)ethyl)-5-(3-methylbenzyl)isoxazole-3-carboxamide;
N-(2-(5-chloro-1H-indol-3-yl)ethyl)-5-(2-fluoro-3-methoxybenzyl)isoxazole-3-carboxamide;
N-(2-(5-chloro-1H-indol-3-yl)ethyl)-5-(furan-3-ylmethyl)isoxazole-3-carboxamide;
N-(2-(5-chloro-1H-indol-3-yl)ethyl)-5-(3-fluorobenzyl)isoxazole-3-carboxamide;
N-(2-(1H-indol-3-yl)ethyl)-4-methyl-2-p-tolylthiazole-5-carboxamide;
N-(2-(5-chloro-1H-indol-3-yl)ethyl)-5-(thiophen-3-ylmethyl)isoxazole-3-carboxamide;
N-(2-(5-chloro-1H-indol-3-yl)ethyl)-1-methyl-5-phenyl-1H-pyrazole-3-carboxamide;
N-(2-(5-chloro-1H-indol-3-yl)ethyl)-5-(thiophen-2-ylmethyl)isoxazole-3-carboxamide;
N-(2-(5-fluoro-1H-indol-3-yl)ethyl)-5-(3-fluorobenzyl)isoxazole-3-carboxamide;
tert-butyl 3-(2-(5-chloro-1H-indol-3-yl)ethylcarbamoyl)isoxazol-5-ylcarbamate;
N-(2-(5-chloro-1H-indol-3-yl)ethyl)-5-(3-(trifluoromethyl)benzyisoxazole-3-carboxamide;
N-(2-(1H-indol-3-yl)ethyl)-5-(3-fluorobenzyl)isoxazole-3-carboxamide;
N-(2-(5-methoxy-1H-indol-3-yl)ethyl)-4-methyl-2-p-tolylthiazole-5-carboxamide;
N-(2-(1H-indol-3-yl)ethyl)-4-methyl-2-(2-propylpyridin-4-yl)thiazole-5-carboxamide;
N-((5-chloro-1H-indol-3-yl)methyl)-5-(3-fluorobenzyl)isoxazole-3-carboxamide;
N-(3-(5-chloro-1H-indol-3-yl)propyl)-5-(3-fluorobenzyl)isoxazole-3-carboxamide;
N-(2-(5-chloro-1H-indol-3-yl)ethyl)-5-phenylisoxazole-3-carboxamide;
N-(2-(5-fluoro-1H-indol-3-yl)ethyl)-4-methyl-2-p-tolylthiazole-5-carboxamide;
N-(2-(5-chloro-1H-indol-3-yl)ethyl)-5-(2,3-dihydrobenzo[b][1,4]dioxin-5-yl)isoxazole-3-carboxamide;
N-(2-(1H-indol-3-yl)ethyl)-4-methyl-2-(phenethylamino)thiazole-5-carboxamide;
N-(2-(5-chloro-1H-indol-3-yl)ethyl)-1-(4-ethylphenyl)-2-oxopyrrolidine-3-carboxamide;
N-(2-(5-chloro-1H-indol-3-yl)ethyl)-5-(pyridin-4-ylmethyl)isoxazole-3-carboxamide;
5-((1H-pyrazol-1-yl)methyl)-N-(2-(5-chloro-1H-indol-3-yl)ethyl)isoxazole-3-carboxamide;
5-benzyl-N-(2-(5-chloro-1H-indol-3-yl)ethyl)-4,5-dihydroisoxazole-3-carboxamide;
N-(2-(5-chloro-1H-indol-3-yl)ethyl)-1-cyclohexyl-1H-1,2,3-triazole-4-carboxamide;
N-(2-(5-chloro-1H-indol-3-yl)ethyl)-4-methyl-2-p-tolylthiazole-5-carboxamide;
N-(2-(5-chloro-1H-indol-3-yl)ethyl)-4-methyl-2-phenylthiazole-5-carboxamide;
N-(2-(6-fluoro-1H-indol-3-yl)ethyl)-5-(3-fluorobenzyl)isoxazole-3-carboxamide;
1-(4-ethylphenyl)-N-(2-(5-methyl-1H-indol-3-yl)ethyl)-2-oxopyrrolidine-3-carboxamide;
N-(2-(5-chloro-1H-indol-3-yl)ethyl)-5-(4-methoxyphenyl)isoxazole-3-carboxamide;
N-(2-(5-chloro-1H-indol-3-yl)ethyl)-3-phenyl-4,5-dihydroisoxazole-5-carboxamide;
N-(2-(5-chloro-1-methyl-1H-indol-3-yl)ethyl)-5-(3-fluorobenzyl)isoxazole-3-carboxamide;

N-(2-(5-chloro-1H-indol-3-yl)ethyl)-5-phenyl-1,3,4-oxadiazole-2-carboxamide;
N-(2-(5-chloro-1H-indol-3-yl)ethyl)-5-phenyloxazole-2-carboxamide;
1-benzyl-N-(2-(5-chloro-1H-indol-3-yl)ethyl)-1H-1,2,3-triazole-4-carboxamide;
N-(2-(5-chloro-1H-indol-3-yl)ethyl)-5-phenyl-4,5-dihydroisoxazole-3-carboxamide;
N-(2-(5-chloro-1H-indol-3-yl)ethyl)-5-(4-chlorophenyl)isoxazole-3-carboxamide;
N-(2-(5-chloro-1H-indol-3-yl)ethyl)-5-p-tolylisoxazole-3-carboxamide;
(R)—N-(2-(5-chloro-1H-indol-3-yl)ethyl)-4-cyclohexyl-4,5-dihydrooxazole-2-carboxamide;
(S)—N-(2-(5-chloro-1H-indol-3-yl)ethyl)-4-cyclohexyl-4,5-dihydrooxazole-2-carboxamide;
5-benzyl-N-(2-(5-chloro-1H-indol-3-yl)ethyl)-1,3,4-oxadiazole-2-carboxamide;
N-(2-(5-chloro-1H-indol-3-yl)ethyl)-5-(pyrrolidin-1-ylmethyl)isoxazole-3-carboxamide;
N-(2-(5-chloro-1H-indol-3-yl)ethyl)-5-methyl-2-phenyloxazole-4-carboxamide;
N-(2-(5-chloro-1H-indol-3-yl)ethyl)-3-phenylpyrrolidine-1-carboxamide;
N-(2-(5-chloro-1H-indol-3-yl)ethyl)-2-oxo-1-phenylpyrrolidine-3-carboxamide;
N-(2-(5-chloro-1H-indol-3-yl)ethyl)-1-(3-fluorophenyl)-2-oxopyrrolidine-3-carboxamide;
N-(2-(5-chloro-1H-indol-3-yl)ethyl)-5-((ethylamino)methyl)isoxazole-3-carboxamide;
N-(2-(5-chloro-1H-indol-3-yl)ethyl)-2-phenylthiazole-4-carboxamide;
N-(2-(5-chloro-1H-indol-3-yl)ethyl)-5-(4-chlorophenyl)-2-(trifluoromethyl)furan-3-carboxamide 3-benzyl-N-(2-(5-chloro-1H-indol-3-yl)ethyl)imidazolidine-1-carboxamide;
N-(2-(5-chloro-1H-indol-3-yl)ethyl)-1-(4-methoxyphenyl)-2-oxopyrrolidine-3-carboxamide;
N-(2-(5-chloro-1H-indol-3-yl)ethyl)-1-(4-isopropylphenyl)-2-oxopyrrolidine-3-carboxamide;
N-(2-(1H-indol-3-yl)ethyl)-1-cyclopropyl-2,5-dimethyl-1H-pyrrole-3-carboxamide;
N-(2-(5-chloro-1H-indol-3-yl)ethyl)-4-methyl-2-(pyrazin-2-yl)thiazole-5-carboxamide;
5-(3-fluorobenzyl)-N-(2-((6-methoxy-1H-indol-3-yl)ethyl)isoxazole-3-carboxamide;
3-benzyl-N-(2-(5-chloro-1H-indol-3-yl)ethyl)pyrrolidine-1-carboxamide;
N-(2-(5-chloro-1H-indol-3-yl)ethyl)-1-cyclohexyl-2-oxopyrrolidine-3-carboxamide;
N-(2-(5-chloro-1H-indol-3-yl)ethyl)-5-cyclohexyl-1,3,4-oxadiazole-2-carboxamide;
N-(2-(5-chloro-1H-indol-3-yl)ethyl)-1-(4-fluorophenyl)-2-oxopyrrolidine-3-carboxamide;
N-(2-(5-chloro-1H-indol-3-yl)ethyl)-1-(2-fluorophenyl)-2-oxopyrrolidine-3-carboxamide;
(S)-4-benzyl-N-(2-(5-chloro-1H-indol-3-yl)ethyl)-4,5-dihydrooxazole-2-carboxamide;
(R)-4-benzyl-N-(2-(5-chloro-1H-indol-3-yl)ethyl)-4,5-dihydrooxazole-2-carboxamide;
N-(2-(5-chloro-1H-indol-3-yl)ethyl)-1-(3-ethylphenyl)-2-oxopyrrolidine-3-carboxamide;
N-(2-(5-chloro-1H-indol-3-yl)ethyl)-4-phenyl-4,5-dihydrooxazole-2-carboxamide;
N-(2-(5-chloro-1H-indol-3-yl)ethyl)-5-oxo-1-phenylpyrrolidine-3-carboxamide;
N-(2-(5-chloro-1H-indol-3-yl)ethyl)-5-(4-chlorophenyl)-2-methylfuran-3-carboxamide;
N-(2-(1H-indol-3-yl)ethyl)-1-(furan-2-ylmethyl)-5-oxopyrrolidine-3-carboxamide;
N-(2-(1H-indol-3-yl)ethyl)-1-(2,3-dihydrobenzo[b][1,4]dioxin-6-yl)-5-oxopyrrolidine-3-carboxamide;
N-(2-(1H-indol-3-yl)ethyl)-1-(naphthalen-1-yl)-5-oxopyrrolidine-3-carboxamide;
N-(2-(1H-indol-3-yl)ethyl)-1-(2-chlorobenzyl)-5-oxopyrrolidine-3-carboxamide;
N-(2-(1H-indol-3-yl)ethyl)-1-(4-(N,N-diethylsulfamoyl)phenyl)-5-oxopyrrolidine-3-carboxamide;
N-(2-(1H-indol-3-yl)ethyl)-5-oxo-1-phenethylpyrrolidine-3-carboxamide;
N-(2-(1H-indol-3-yl)ethyl)-1-benzyl-5-oxopyrrolidine-3-carboxamide;
N-(2-(5-chloro-1H-indol-3-yl)ethyl)-5-methyl-2-phenyl-2H-1,2,3-triazole-4-carboxamide;
5-amino-N-(2-(5-chloro-1H-indol-3-yl)ethyl)isoxazole-3-carboxamide;
N-(2-(5-chloro-1H-indol-3-yl)ethyl)-5-cyclohexyl-4,5-dihydroisoxazole-3-carboxamide;
1-benzyl-N-(2-(5-chloro-1H-indol-3-yl)ethyl)-2-oxopyrrolidine-3-carboxamide;
(S)-1-benzyl-N-(2-(5-chloro-1H-indol-3-yl)ethyl)pyrrolidine-3-carboxamide;
(R)-1-benzyl-N-(2-(5-chloro-1H-indol-3-yl)ethyl)pyrrolidine-3-carboxamide;
N-(2-(5-chloro-1H-indol-3-yl)ethyl)-1-cyclohexyl-5-oxopyrrolidine-3-carboxamide;
5-(3-fluorobenzyl)-N-(2-(5-methoxy-1H-indol-3-yl)ethyl)isoxazole-3-carboxamide;
N-(2-(5-chloro-1H-indol-3-yl)ethyl)-3-phenylisoxazole-5-carboxamide;
N-(2-(5-chloro-1H-indol-3-yl)ethyl)-1-phenylpyrrolidine-3-carboxamide;
N-(2-(benzofuran-3-yl)ethyl)-5-(3-fluorobenzyl)isoxazole-3-carboxamide;
N-(2-(5-chloro-1H-indol-3-yl)ethyl)-1-(4-cyanophenyl)-2-oxopyrrolidine-3-carboxamide;
N-(2-(5-chloro-1H-indol-3-yl)ethyl)-5-(2,5-difluorobenzyl)-1,2,4-oxadiazole-3-carboxamide;
N-(2-(5-chloro-1H-indol-3-yl)ethyl)-5-(2,3-difluorobenzyl)-1,2,4-oxadiazole-3-carboxamide;
N-(2-(5-chloro-1H-indol-3-yl)ethyl)-5-(3,4-difluorobenzyl)-1,2,4-oxadiazole-3-carboxamide;
N-(2-(5-chloro-2-methyl-1H-indol-3-yl)ethyl)-5-(2,5-difluorobenzyl)isoxazole-3-carboxamide;
N-(2-(5-methoxy-1H-indol-3-yl)ethyl)-5-methyl-3-phenylisoxazole-4-carboxamide;
N-(2-(1H-indol-3-yl)ethyl)-2-(p-tolylamino)thiazole-4-carboxamide;
N-(2-(5-chloro-1H-indol-3-yl)ethyl)-5-methyl-3-phenylisoxazole-4-carboxamide;
N-(2-(5-chloro-1H-indol-3-yl)ethyl)-4-methyloxazole-5-carboxamide;
N-(2-(5-chloro-1H-indol-3-yl)ethyl)-5-phenyloxazole-4-carboxamide;
N-(2-(5-chloro-1H-indol-3-yl)ethyl)-5-methylisoxazole-3-carboxamide;
N-(2-(5-chloro-1H-indol-3-yl)ethyl)-3-methyl-5-phenylisoxazole-4-carboxamide;
N-(2-(5-chloro-1H-indol-3-yl)ethyl)-2,5-dimethyloxazole-4-carboxamide;
N-(2-(5-chloro-1H-indol-3-yl)ethyl)-1-phenyl-1H-pyrazole-5-carboxamide;

N-(2-(5-chloro-1H-indol-3-yl)ethyl)-1-methyl-1H-pyrazole-3-carboxamide;
N-(2-(5-chloro-1H-indol-3-yl)ethyl)-1-methyl-1H-pyrazole-5-carboxamide;
1-benzyl-3-tert-butyl-N-(2-(5-chloro-1H-indol-3-yl)ethyl)-1H-pyrazole-5-carboxamide;
N-(2-(5-chloro-1H-indol-3-yl)ethyl)-5-(hydroxymethyl)isoxazole-3-carboxamide;
N-(2-(5-chloro-1H-indol-3-yl)ethyl)-5-methyl-2-phenylfuran-3-carboxamide;
N-(2-(5-chloro-1H-indol-3-yl)ethyl)-5-(ethoxymethyl)isoxazole-3-carboxamide;
N-(2-(5-chloro-1H-indol-3-yl)ethyl)-5-(dimethylamino)isoxazole-3-carboxamide;
N-(2-(5-chloro-1H-indol-3-yl)ethyl)-5-((diethylamino)methyl)isoxazole-3-carboxamide;
1-(3-benzylimidazolidin-1-yl)-3-(5-chloro-1H-indol-3-yl)propan-1-one;
N-(2-(5-chloro-1H-pyrrolo[2,3-b]pyridin-3-yl)ethyl)-5-(2,5-difluorobenzoyl)isoxazole-3-carboxamide;
N-(2-(5-chloro-1H-pyrrolo[2,3-b]pyridin-3-yl)ethyl)-5-(2,5-difluorobenzypisoxazole-3-carboxamide;
N-(2-(5-chloro-1H-indol-3-yl)ethyl)-5-(3,4-difluorobenzypisoxazole-3-carboxamide;
N-(2-(5-chloro-1H-indol-3-yl)ethyl)-5-(2,3-difluorobenzypisoxazole-3-carboxamide;
N-(2-(5-chloro-1H-indol-3-yl)ethyl)-5-(3,5-difluorobenzypisoxazole-3-carboxamide;
N-(2-(5-chloro-1H-indol-3-yl)ethyl)-2-oxo-1-(4-(trifluoromethyl)phenyl)pyrrolidine-3-carboxamide;
N-(2-(5-chloro-1H-indol-3-yl)ethyl)-2-oxo-1-p-tolylpyrrolidine-3-carboxamide;
1-(4-acetylphenyl)-N-(2-(5-chloro-1H-indol-3-yl)ethyl)-2-oxopyrrolidine-3-carboxamide;
5-(2,5-difluorobenzyl)-N-(2-(5-(trifluoromethyl)-1H-indol-3-yl)ethyl)isoxazole-3-carboxamide;
N-(2-(6-chloro-5-methyl-1H-indol-3-yl)ethyl)-5-(2,5-difluorobenzyl)isoxazole-3-carboxamide;
N-(2-(5-cyano-1H-indol-3-yl)ethyl)-5-(2,5-difluorobenzyl)isoxazole-3-carboxamide;
(4-(1H-indol-3-yl)piperidin-1-yl)(5-(2,5-difluorobenzyl)isoxazol-3-yl)methanone;
(4-(5-chloro-1H-indol-3-yl)piperidin-1-yl)(5-(2,5-difluorobenzyl)isoxazol-3-yl)methanone;
5-(2,5-difluorobenzyl)-N-(2-(5-phenyl-1H-indol-3-yl)ethyl)isoxazole-3-carboxamide;
N-(2-(5-chloro-7-fluoro-1H-indol-3-yl)ethyl)-5-(2,5-difluorobenzypisoxazole-3-carboxamide;
N-(2-(5-chloro-1H-indol-3-yl)ethyl)-1-(4-chloro-3-fluorophenyl)-2-oxopyrrolidine-3-carboxamide;
N-(2-(5-chloro-1H-indol-3-yl)ethyl)-1-(3,4-dimethylphenyl)-2-oxopyrrolidine-3-carboxamide;
N-(2-(5-chloro-1H-indol-3-yl)ethyl)-1-(3,5-difluorophenyl)-2-oxopyrrolidine-3-carboxamide;
N-(2-(5-chloro-1H-indol-3-yl)ethyl)-1-(2,3-dihydro-1H-inden-5-yl)-2-oxopyrrolidine-3-carboxamide;
N-(2-(5-chloro-1H-indol-3-yl)ethyl)-1-(1,3-dihydroisobenzofuran-5-yl)-2-oxopyrrolidine-3-carboxamide;
N-(2-(5-chloro-1H-indol-3-yl)ethyl)-1-(3-fluoro-4-methoxyphenyl)-2-oxopyrrolidine-3-carboxamide;
N-(2-(5-chloro-1H-indol-3-yl)ethyl)-1-(3,4-difluorophenyl)-2-oxopyrrolidine-3-carboxamide;
N-(2-(5-chloro-1H-indol-3-yl)ethyl)-1-cyclopropyl-2-oxopyrrolidine-3-carboxamide;
N-(2-(5-chloro-1H-indol-3-yl)ethyl)-1-(3-fluoro-4-(trifluoromethyl)phenyl)-2-oxopyrrolidine-3-carboxamide;
N-(2-(5-chloro-1H-indol-3-yl)ethyl)-1-(2,6-difluorophenyl)-2-oxopyrrolidine-3-carboxamide
N-(2-(5-chloro-1H-indol-3-yl)ethyl)-1-(3-fluoro-4-methylphenyl)-2-oxopyrrolidine-3-carboxamide;
N-(2-(5-chloro-1H-indol-3-yl)ethyl)-1-(4-chlorophenyl)-2-oxopyrrolidine-3-carboxamide;
N-(2-(5-chloro-1H-indol-3-yl)ethyl)-1-(3-chlorophenyl)-2-oxopyrrolidine-3-carboxamide;
1-(3-(1H-pyrrol-1-yl)phenyl)-N-(2-(5-chloro-1H-indol-3-yl)ethyl)-2-oxopyrrolidine-3-carboxamide;
N-(2-(5-chloro-1H-indol-3-yl)ethyl)-2-oxo-1-(1-phenylethyl)pyrrolidine-3-carboxamide;
N-(2-(5-chloro-1H-indol-3-yl)ethyl)-1-(2-ethylphenyl)-2-oxopyrrolidine-3-carboxamide;
N-(2-(5-chloro-1H-indol-3-yl)ethyl)-2-oxo-1-o-tolylpyrrolidine-3-carboxamide;
N-(2-(5-chloro-1H-indol-3-yl)ethyl)-2-oxo-1-m-tolylpyrrolidine-3-carboxamide;
N-(2-(5-chloro-1H-indol-3-yl)ethyl)-1-(1-methyl-1H-pyrazol-3-yl)-2-oxopyrrolidine-3-carboxamide;
N-(2-(5-chloro-1H-indol-3-yl)ethyl)-1-(2-chlorophenyl)-2-oxopyrrolidine-3-carboxamide;
N-(2-(5-chloro-1H-indol-3-yl)ethyl)-1-(3-methoxyphenyl)-2-oxopyrrolidine-3-carboxamide;
N-(2-(5-chloro-1H-indol-3-yl)ethyl)-1-(2-methoxyphenyl)-2-oxopyrrolidine-3-carboxamide;
N-(2-(5-chloro-1H-indol-3-yl)ethyl)-1-(cyclohexylmethyl)-2-oxopyrrolidine-3-carboxamide;
N-(2-(5-chloro-1H-indol-3-yl)ethyl)-1-p-tolylpyrrolidine-3-carboxamide;
N-(2-(1H-indazol-3-yl)ethyl)-5-(2,5-difluorobenzyl)isoxazole-3-carboxamide;
N-(2-(5-chloro-1H-indol-3-yl)ethyl)-1-(1-methyl-1H-indol-5-yl)-2-oxopyrrolidine-3-carboxamide;
5-benzyl-N-(2-(5-chloro-1H-indol-3-yl)ethyl)-1,2,4-oxadiazole-3-carboxamide;
N-(2-(5-chloro-1H-indol-3-yl)ethyl)-5-(3-fluorobenzyl)-1,2,4-oxadiazole-3-carboxamide;
N-(2-(5-chloro-1H-indol-3-yl)ethyl)-5-(2-fluorobenzyl)-1,2,4-oxadiazole-3-carboxamide;
N-(2-(5-chloro-1H-indol-3-yl)ethyl)-5-(4-fluorobenzyl)-1,2,4-oxadiazole-3-carboxamide;
N-(2-(5-chloro-1H-indol-3-yl)ethyl)-5-(4-chlorobenzyl)-1,2,4-oxadiazole-3-carboxamide;
N-(2-(5-chloro-1H-indol-3-yl)ethyl)-5-(4-methoxybenzyl)-1,2,4-oxadiazole-3-carboxamide;
N-(2-(5-chloro-1H-indol-3-yl)ethyl)-5-(3,4-dichlorobenzyl)-1,2,4-oxadiazole-3-carboxamide;
N-(2-(5-chloro-1H-indol-3-yl)ethyl)-5-(4-chloro-3-fluorobenzyl)-1,2,4-oxadiazole-3-carboxamide;
5-(4-tert-butylbenzyl)-N-(2-(5-chloro-1H-indol-3-yl)ethyl)-1,2,4-oxadiazole-3-carboxamide;
N-(2-(5-chloro-1H-indol-3-yl)ethyl)-5-(3-methoxybenzyl)-1,2,4-oxadiazole-3-carboxamide;
N-(2-(5-chloro-1H-indol-3-yl)ethyl)-5-(3,4-dimethoxybenzyl)-1,2,4-oxadiazole-3-carboxamide;
N-(2-(5-chloro-1H-indol-3-yl)ethyl)-5-(2,5-dimethoxybenzyl)-1,2,4-oxadiazole-3-carboxamide;
N-(2-(5-chloro-1H-indol-3-yl)ethyl)-5-(thiophen-2-ylmethyl)-1,2,4-oxadiazole-3-carboxamide;
N-(2-(5-chloro-1H-indol-3-yl)ethyl)-5-(4-methylbenzyl)-1,2,4-oxadiazole-3-carboxamide;
N-(2-(5-chloro-1H-indol-3-yl)ethyl)-5-(3,5-difluorobenzyl)-1,2,4-oxadiazole-3-carboxamide;
N-(2-(5-chloro-1H-indol-3-yl)ethyl)-5-(2-methoxybenzyl)-1,2,4-oxadiazole-3-carboxamide;

N-(2-(5-chloro-1H-indol-3-yl)ethyl)-5-(3-methylbenzyl)-1,2,4-oxadiazole-3-carboxamide;
N-(2-(5-chloro-1H-indol-3-yl)ethyl)-5-(4-(trifluoromethoxy)benzyl)-1,2,4-oxadiazole-3-carboxamide;
N-(2-(5-chloro-1H-indol-3-yl)ethyl)-5-(3-(trifluoromethyl)benzyl)-1,2,4-oxadiazole-3-carboxamide;
N-(2-(5-chloro-1H-indol-3-yl)ethyl)-5-(4-(trifluoromethyl)benzyl)-1,2,4-oxadiazole-3-carboxamide;
N-(2-(5-chloro-1H-indol-3-yl)ethyl)-5-(2,6-difluorobenzyl)-1,2,4-oxadiazole-3-carboxamide;
N-(2-(5-chloro-1H-indol-3-yl)ethyl)-5-(2,4-difluorobenzyl)-1,2,4-oxadiazole-3-carboxamide;
N-(2-(5-chloro-1H-indol-3-yl)ethyl)-5-(3-chlorobenzyl)-1,2,4-oxadiazole-3-carboxamide;
N-(2-(5-chloro-1H-indol-3-yl)ethyl)-5-(2-chlorobenzyl)-1,2,4-oxadiazole-3-carboxamide;
N-(2-(5-chloro-1H-indol-3-yl)ethyl)-5-(2-methylbenzyl)-1,2,4-oxadiazole-3-carboxamide;
N-(2-(5-chloro-1H-indol-3-yl)ethyl)-5-(thiophen-3-ylmethyl)-1,2,4-oxadiazole-3-carboxamide;
N-(2-(5-chloro-1H-indol-3-yl)ethyl)-5-(2,5-difluorobenzoyl)isoxazole-3-carboxamide;
N-(2-(5-chloro-1H-indol-3-yl)ethyl)-5-(hydroxy(phenyl)methyl)isoxazole-3-carboxamide;
N-(2-(5-chloro-1H-indol-3-yl)ethyl)oxazole-5-carboxamide;
N-(2-(5-chloro-1H-indol-3-yl)ethyl)-4-methyl-2-phenyloxazole-5-carboxamide;
N-(2-(5-chloro-1H-indol-3-yl)ethyl)-2-phenyloxazole-5-carboxamide;
N-(2-(5-chloro-1H-indol-3-yl)ethyl)-4-phenylisoxazole-3-carboxamide;
N-(2-(5-chloro-1H-indol-3-yl)ethyl)-5-phenyl-1,2,4-oxadiazole-3-carboxamide;
N-(2-(5-chloro-1H-indol-3-yl)ethyl)-5-(2,5-difluorophenyl)-1,2,4-oxadiazole-3-carboxamide;
N-(2-(5-chloro-1H-indol-3-yl)ethyl)-5-((5-methyl-2-phenyloxazol-4-yl)methyl)-1,2,4-oxadiazole-3-carboxamide;
N-(2-(5-chloro-1H-indol-3-yl)ethyl)-5-(2-fluoro-3-(trifluoromethyl)benzyl)-1,2,4-oxadiazole-3-carboxamide;
N-(2-(5-chloro-1H-indol-3-yl)ethyl)-5-(2-fluoro-5-(trifluoromethyl)benzyl)-1,2,4-oxadiazole-3-carboxamide;
N-(2-(5-chloro-1H-indol-3-yl)ethyl)-5-(4-fluoro-2-(trifluoromethyl)benzyl)-1,2,4-oxadiazole-3-carboxamide;
N-(2-(5-chloro-1H-indol-3-yl)ethyl)-5-(2,3,4-trifluorobenzyl)-1,2,4-oxadiazole-3-carboxamide;
N-(2-(5-chloro-1H-indol-3-yl)ethyl)-5-(2,4,6-trifluorobenzyl)-1,2,4-oxadiazole-3-carboxamide;
N-(2-(5-chloro-1H-indol-3-yl)ethyl)-5-((2,5-difluorophenyl)difluoromethyl)isoxazole-3-carboxamide;
N-(2-(5-chloro-1H-indol-3-yl)ethyl)-5-((2,5-difluorophenyl)fluoromethyl)isoxazole-3-carboxamide;
5-benzyl-N-(2-(5-chloro-1H-indol-3-yl)ethyl)-1,2,4-thiadiazole-3-carboxamide;
5-benzyl-N-(2-(5-chloro-1H-indol-3-yl)ethyl)isothiazole-3-carboxamide;
N-(2-(5-bromo-1H-indol-3-yl)ethyl)-5-(2,5-difluorobenzyl)isoxazole-3-carboxamide;
N-(2-(5-chloro-1H-indol-3-yl)ethyl)-1-phenyl-1H-1,2,3-triazole-4-carboxamide;
N-(2-(5-chloro-1H-indol-3-yl)ethyl)-2-oxo-1-(4-(trifluoromethoxy)phenyl)pyrrolidine-3-carboxamide;
N-(2-(5-chloro-1H-indol-3-yl)ethyl)-5-((2,5-difluorophenyl)(hydroxy)methyl)isoxazole-3-carboxamide; and
N-(2-(5-chloro-1H-indol-3-yl)ethyl)-5-(ethoxymethyl)-4,5-dihydroisoxazole-3-carboxamide.

86. The inhibitor for use according to any one of statements 1 to 85, wherein the epilepsy is selected from the group consisting of refractory epilepsy, West syndrome, Doose syndrome, benign rolandic epilepsy, Rasmussens's syndrome, Lennox-Gastaut syndrome, West syndrome, Sturge-Weber syndrome, juvenile myoclonic epilepsy, childhood absence epilepsy, idiopathic localization-related epilepsies, temporal lobe epilepsy, partial seizures, simple partial seizures, tonic seizures, tonic-clonic seizures, clonic seizures, myoclonic seizures, absence seizures and atonic seizures; preferably refractory epilepsy.

87. Use of the inhibitor according to any one of statements 1 to 85 for the manufacture of a medicament for the prevention and/or treatment of epilepsy.

88. The inhibitor for use according to any one of statements 1 to 85, wherein said inhibitor is contained within a pharmaceutical composition in a therapeutically effective amount.

89. A method of prevention and/or treatment of epilepsy, comprising administering an effective amount of an inhibitor according to any one of statements 1 to 85, or a pharmaceutical composition according to statement to a subject in need thereof.

90. The use according to statement 87 or the method according to statement 89, wherein the epilepsy is selected from the group consisting of refractory epilepsy, West syndrome, Doose syndrome, benign rolandic epilepsy, Rasmussens's syndrome, Lennox-Gastaut syndrome, West syndrome, Sturge-Weber syndrome, juvenile myoclonic epilepsy, childhood absence epilepsy, idiopathic localization-related epilepsies, temporal lobe epilepsy, partial seizures, simple partial seizures, tonic seizures, tonic-clonic seizures, clonic seizures, myoclonic seizures, absence seizures and atonic seizures; preferably refractory epilepsy.

91. An inhibitor of PDE6δ for use in the prevention and/or treatment of a neurodegenerative disorder, wherein said inhibitor is not a compound of formula (AA1), (BB1) or (CC1) or a stereoisomer, enantiomer, tautomer, solvate, hydrate, salt or prodrug thereof,

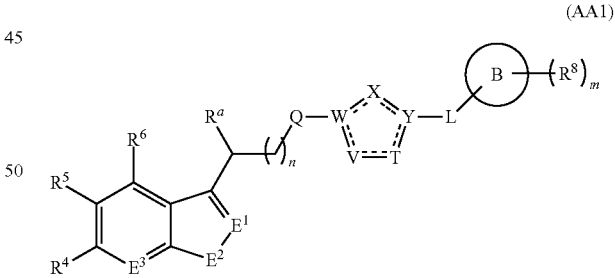

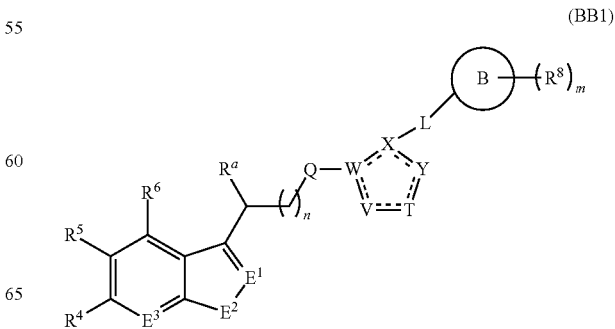

-continued

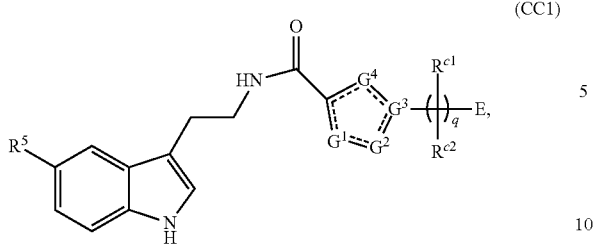
(CC1)

wherein for formula (AA1),
- each dotted line individually represents an optional double bond, wherein maximally two dotted lines selected from the five dotted lines are a double bond;
- $E^1$ is independently selected from $CR^1$; and N;
- $E^2$ is independently selected from $NR^2$; and O;
- $E^3$ is independently selected from $CR^3$; and N;
- Q is independently selected from $NR^b$—C(O); and C(O)NH;
- $R^a$ is hydrogen or can be taken together with $R^b$ to form a substituted or unsubstituted 4, 5, 6, 7 or 8 membered ring containing one N atom;
- $R^b$ is hydrogen or can be taken together with $R^a$ to form a substituted or unsubstituted 4, 5, 6, 7 or 8 membered ring containing one N atom;
- each $R^1$, $R^3$, $R^4$, and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; or heterocycle-alkynylene;
  - and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
  - and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
  - and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
- $R^2$ is selected from hydrogen; alkyl; alkenyl; and alkynyl;
- $R^5$ is selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; or heterocycle-alkynylene;
  - and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
  - and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
  - and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
- n is selected from 0; 1 or 2;
- L is independently selected from being not present; —O—; —NH—; —$NR^{10}$—; $C_{1-6}$alkylene; $C_{1-6}$alkenylene; or $C_{1-6}$alkynylene;
  - wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
  - and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or $S(O)_2$;
- B represents a cyclic structure selected from cycloalkyl; cycloalkenyl; cycloalkynyl; aryl; and heterocycle;
- m is selected from 0; 1; 2; 3; 4 and 5;
- $R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; or —$C(O)R^{11}$;
  - wherein said alkyl, alkenyl and alkynyl optionally includes one or more heteroatoms, said heteroatoms being selected from the atoms O, S and N;
  - and wherein said alkyl, alkenyl and alkynyl can be unsubstituted or substituted with Z;
  - and wherein a carbon atom or heteroatom of said alkyl, alkenyl and alkynyl, can be oxidized to form a C=O, C=S, N=O, N=S, S=O or $S(O)_2$;
- each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; or —$C(O)R^{11}$;
- each $Z^1$ is independently selected from hydrogen; alkyl; and Z;

each R¹⁰ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
  and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)₂;
each R¹⁰¹ is independently selected from hydrogen and R¹⁰;
each R¹¹ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
  and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)₂;
each R¹² and R¹³ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
  and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)₂;
  and wherein R¹² and R¹³ can be taken together in order to form a (5-, 6-, or 7-membered) heterocycle which can be unsubstituted or substituted;
and each of X, Y, T, W and V is independently selected from CZ¹H—; —CZ¹—; —C—; —N—; NR¹⁰¹; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa)

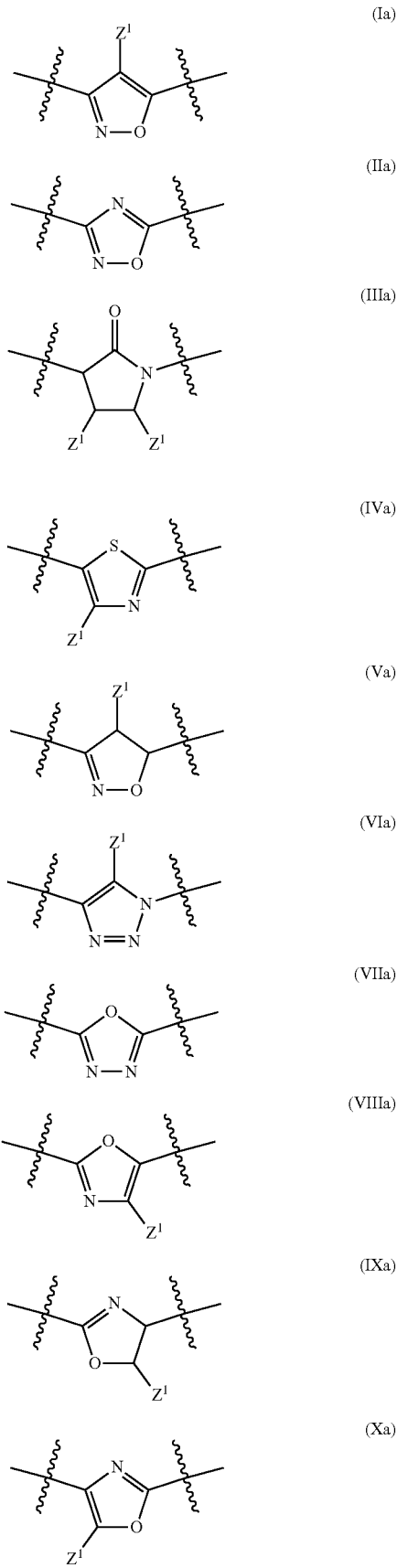

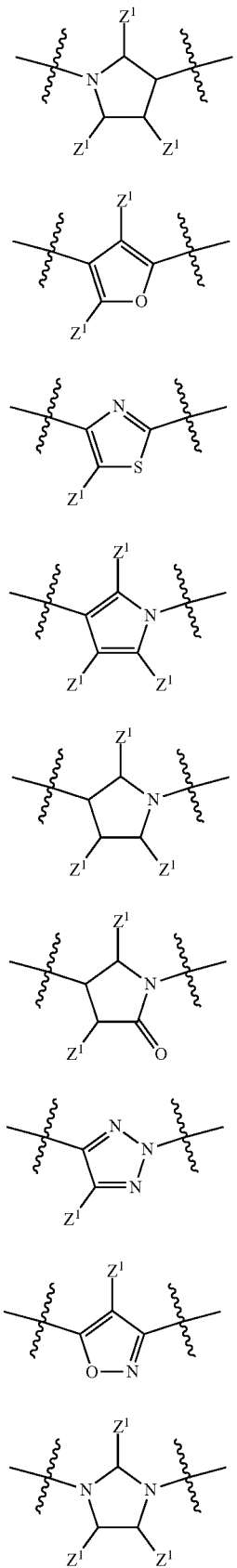
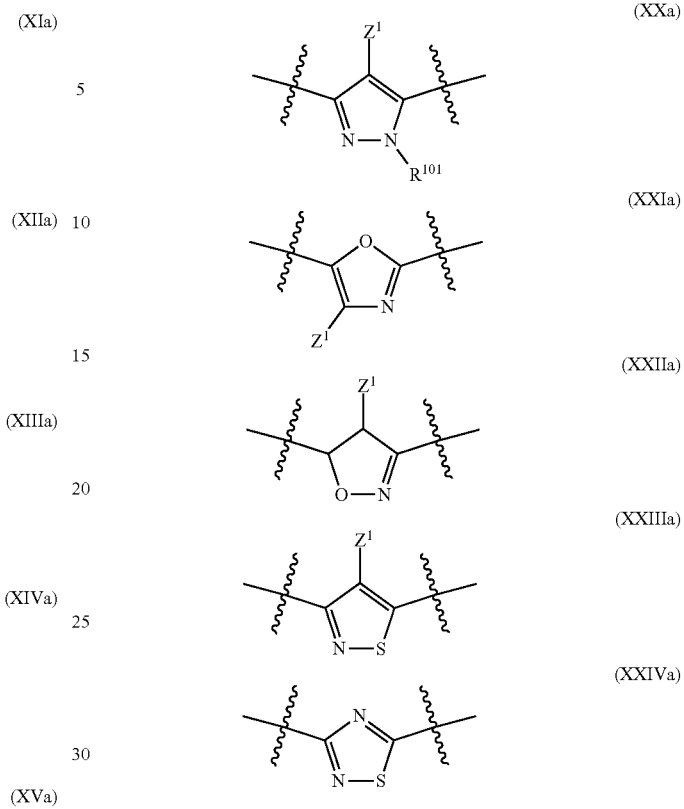

wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L;

wherein for (BB1)

$E^1$ is independently selected from $CR^1$; and N;

$E^2$ is independently selected from $NR^2$; and O;

$E^3$ is independently selected from $CR^3$; and N;

$R^a$ is hydrogen or can be taken together with $R^b$ to form a substituted or unsubstituted 4, 5, 6, 7 or 8 membered ring containing one N atom, preferably a piperidine ring;

$R^b$ is hydrogen or can be taken together with $R^a$ to form a substituted or unsubstituted 4, 5, 6, 7 or 8 membered ring containing one N atom, preferably a piperidine ring;

Q is independently selected from $NR^b$—C(O); C(O); and C(O)NH;

each $R^1$, $R^3$, $R^4$, $R^5$ and $R^6$ is independently selected from hydrogen; halogen; —OH; —$OR^{16}$; —SH; —$SR^{10}$; —$S(O)R^{11}$; —$S(O)_2R^{11}$; —$SO_2NR^{12}R^{13}$; trifluoromethyl; trifluoromethoxy; nitro; —NHC(O)$R^{10}$; —NHS(O)$_2R^{10}$; —NHC(O)$NR^{12}R^{13}$; —$NR^{10}$C(O)$R^{10}$; —$NR^{10}$S(O)$_2R^{10}$; —$NR^{10}$C(O)$NR^{12}R^{13}$; —$NR^{12}R^{13}$; -cyano; —COOH; —$COOR^{10}$; —C(O)$NR^{12}R^{13}$; —C(O)$R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

$R^2$ is selected from hydrogen; alkyl; alkenyl; and alkynyl;
n is selected from 0; 1 or 2;
each of X, Y, T, W and V is independently selected from $CZ^1H$—; —$CZ^1$—; —C—; —N—; $NR^{101}$; —O—; —S—; or —CO—; wherein at least one of X, Y, T; W or V is selected from $CZ^1H$— or —$CZ^1$— or C1-;
L is independently selected from being not present; —O—; —NH—; —$NR^{10}$—; $C_{1-6}$alkylene; $C_{1-6}$alkenylene; $C_{1-6}$alkynylene;
  wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, can be unsubstituted or substituted;
  and wherein a carbon atom or heteroatom of said $C_{1-6}$alkylene, $C_{1-6}$alkenylene or $C_{1-6}$alkynylene, can be oxidized to form a C=O, C=S, N=O, N=S, S=O or $S(O)_2$;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —$OR^{18}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{18}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
  wherein said alkyl, alkenyl and alkynyl optionally includes one or more heteroatoms, said heteroatoms being selected from the atoms O, S and N;
  and wherein said alkyl, alkenyl and alkynyl can be unsubstituted or substituted with Z;
  and wherein a carbon atom or heteroatom of said alkyl, alkenyl and alkynyl, can be oxidized to form a C=O, C=S, N=O, N=S, S=O or $S(O)_2$;
each Z is independently selected from halogen; —OH; —$OR^{18}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{18}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$;
each $Z^1$ is independently selected from hydrogen; alkyl; and Z;
each $R^{10}$ is selected from alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
  and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
each $R^{101}$ is independently selected from hydrogen and $R^{10}$;
each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
  and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;
  and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;
  and wherein a carbon atom or heteroatom of said alkyl, alkenyl, alkynyl, aryl, heterocycle, arylalkylene, arylalkynylene, heterocycle-alkylene, heterocycle-alkenylene or heterocycle-alkynylene, can be oxidized to form a C=O, C=S, N=O, N=S, S=O or $S(O)_2$;
  and wherein $R^{12}$ and $R^{13}$ can be taken together in order to form a (5-, 6-, or 7-membered) heterocycle which can be unsubstituted or substituted;

wherein for formula (CC1),
each of $G^1$, $G^2$, $G^3$ and $G^4$ is independently selected from N; $NR^{c3}$; O; $CHR^{c3}$; and $CR^{c3}$; wherein two of $G^1$, $G^2$, $G^3$ and $G^4$ are selected from N; $NR^{c3}$; and O; while the other two of $G^1$, $G^2$, $G^3$ and $G^4$ are selected from $CHR^{c3}$; and $CR^{c3}$;
each $R^{c3}$ is selected from hydrogen; and alkyl;
$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

q is selected from 0; 1; 2; or 3; preferably q is 0 or 1;

E is selected from hydrogen; halogen; —OH; —$OR^{10}$; —SH; —$SR^{10}$; trifluoromethoxy; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene or heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (5-, 6-, or 7-membered) heterocycle which can be unsubstituted or substituted;

each of $R^{1c}$ and $R^{2c}$ is independently selected from hydrogen; halogen; alkyl; alkenyl or alkynyl;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$.

92. An inhibitor of PDE6δ for use in the prevention and/or treatment of a neurodegenerative disorder, wherein said inhibitor is a compound having formula (I) or a tautomer thereof, (I)

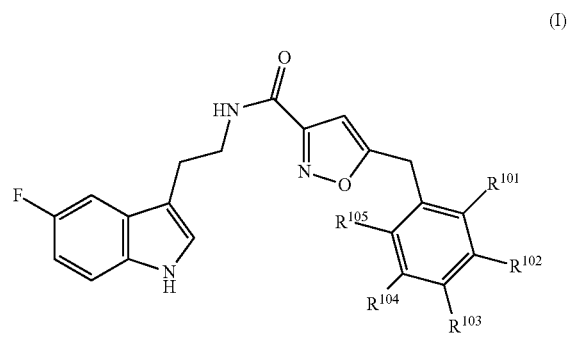

wherein, $R^{101}$ is selected from the group consisting of hydrogen; F, Cl, and Br;

$R^{102}$ is selected from the group consisting of hydrogen, F, Cl, and Br;

$R^{103}$ is selected from the group consisting of hydrogen, F, Cl, and Br;

$R^{104}$ is selected from the group consisting of hydrogen, F, Cl, and Br;

$R^{105}$ is selected from the group consisting of hydrogen, F, Cl, and Br;

with the proviso that at least one of $R^{101}$, $R^{102}$, $R^{103}$, $R^{104}$ or $R^{105}$ is not hydrogen;

with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt (in particular a pharmaceutically acceptable salt) or a prodrug thereof.

93. The inhibitor for use according to statement 92, having structural formula (II), (III), (IV), (V) or (VI)

(II)

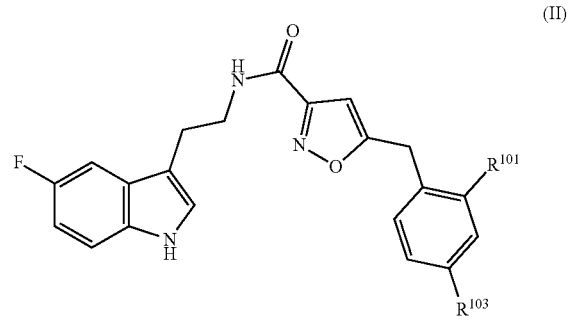

-continued

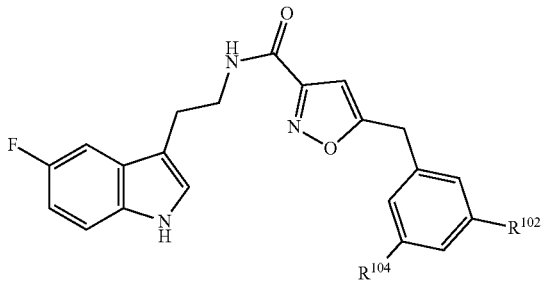
(III)

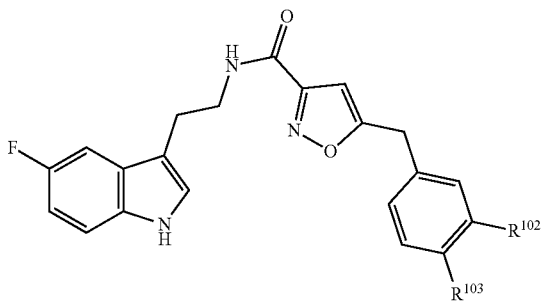
(IV)

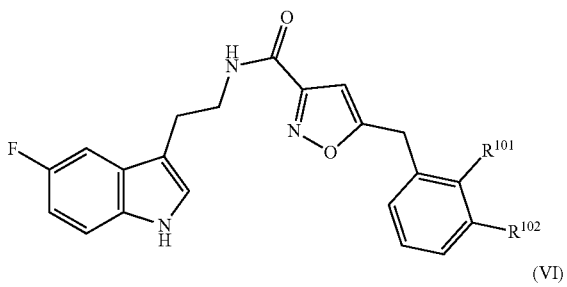
(V)

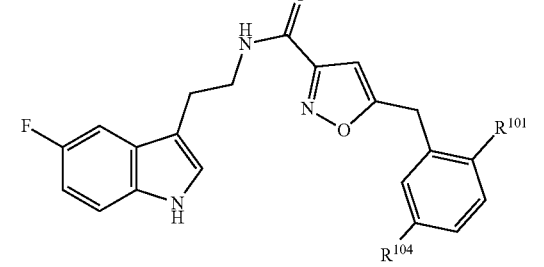
(VI)

wherein $R^{101}$, $R^{102}$, $R^{103}$ and $R^{104}$ have the same meaning as defined in statement 92.

94. The inhibitor for use according to statements 92 or 93, wherein $R^{102}$, $R^{103}$, $R^{104}$ and $R^{105}$ are hydrogen and wherein $R^{101}$ selected from the group consisting of F, Cl, and Br; preferably, $R^{101}$ is F or Cl, preferably $R^{101}$ is F.

95. The inhibitor for use according to statements 92 or 93, wherein $R^{101}$, $R^{102}$, $R^{104}$ and $R^{105}$ are hydrogen and $R^{103}$ is selected from the group consisting of F, Cl, and Br, preferably, $R^{103}$ is F or Cl, preferably $R^{103}$ is F.

96. The inhibitor for use according to statements 92 or 93, wherein $R^{102}$, $R^{104}$ and $R^{105}$ are hydrogen and $R^{101}$ and $R^{103}$ are each independently selected from hydrogen; F, Cl, Br; preferably $R^{101}$ and $R^{103}$ are each independently selected from the group consisting of hydrogen; and F.

97 The inhibitor for use according to statements 92 or 93, wherein $R^{103}$, $R^{104}$ and $R^{105}$ are hydrogen and $R^{101}$ and $R^{102}$ are each independently selected from hydrogen; F, Cl, and Br; preferably $R^{101}$ and $R^{102}$ are each independently selected from the group consisting of hydrogen; and F.

98. The inhibitor for use according to statements 92 or 93, wherein $R^{102}$, $R^{103}$ and $R^{105}$ are hydrogen and $R^{101}$ and $R^{104}$ are each independently selected from hydrogen; F, Cl, and Br; preferably $R^{101}$ and $R^{104}$ are each independently selected from the group consisting of hydrogen and F.

99. The inhibitor for use according to statements 92 or 93, wherein $R^{102}$, $R^{103}$ and $R^{105}$ are hydrogen and $R^{101}$ and $R^{105}$ are each independently selected from hydrogen; F, Cl, and Br; preferably $R^{101}$ and $R^{105}$ are each independently selected from the group consisting of hydrogen and F.

100. The inhibitor for use according to statements 92 or 93, wherein $R^{101}$, $R^{104}$ and $R^{105}$ are hydrogen and $R^{102}$ and $R^{103}$ are independently selected from hydrogen; F, Cl, or Br; preferably $R^{102}$ and $R^{103}$ are each independently selected from the group consisting of hydrogen and F.

101. The inhibitor for use according to statements 92 or 93, wherein $R^{101}$, $R^{103}$ and $R^{105}$ are hydrogen and $R^{102}$ and $R^{104}$ are independently selected from hydrogen; F, Cl, Br; preferably $R^{102}$ and $R^{104}$ are each independently selected from the group consisting of hydrogen and F.

102. The inhibitor for use according to statements 92 or 93, wherein $R^{101}$, $R^{103}$ and $R^{104}$ are hydrogen and $R^{102}$ and $R^{105}$ are independently selected from hydrogen; F, Cl, Br; preferably $R^{102}$ and $R^{105}$ are each independently selected from the group consisting of hydrogen and F.

103. The inhibitor for use according to any one of statements 92 to 102, wherein said inhibitor is a compound of formula (I) selected from the group consisting of:
5-[(2,4-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(4-fluorophenyl)methyl]isoxazole-3-carboxamide;
5-[(2,3-difluorophenyl)methyl]-N-[2-(5-fluoro-1H-indol-3-yl)ethyl]isoxazole-3-carboxamide;
5-[(2,5-difluorophenyl)methyl]-N-[2-(5-fluoro-1H-indol-3-yl)ethyl]isoxazole-3-carboxamide;
N-[2-(5-fluoro-1H-indol-3-yl)ethyl]-5-[(2-fluorophenyl)methyl]isoxazole-3-carboxamide;
5-[(3,4-difluorophenyl)methyl]-N-[2-(5-fluoro-1H-indol-3-yl)ethyl]isoxazole-3-carboxamide; and
5-[(3,5-difluorophenyl)methyl]-N-[2-(5-fluoro-1H-indol-3-yl)ethyl]isoxazole-3-carboxamide.

104. The inhibitor for use according to any one of statements 91 to 103, wherein the neurodegenerative disease is selected from the group consisting of of Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, and Creutzfeld-Jacob's disease; preferably Alzheimer's disease.

105. Use of the inhibitor according to any one of statements 91 to 103 for the manufacture of a medicament for the prevention and/or treatment of a neurodegenerative disease, preferably the neurodegenerative disease is selected from the group consisting of Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, and Creutzfeld-Jacob's disease; preferably Alzheimer's disease.

107. The inhibitor for use according to any one of statements 91 to 103, wherein said inhibitor is contained within a pharmaceutical composition in a therapeutically effective amount.

108. A method of prevention and/or treatment of neurodegenerative diseases, comprising administering an effective amount of an inhibitor according to any one of statements 91 to 103, or a pharmaceutical composition according to statement 107 to a subject in need thereof.

109. The method according to statement 108, wherein the neurodegenerative disease is selected from the group consisting of of Parkinson's disease, Alzheimer's disease, diffuse Lewy body disease, amyotrophic lateral sclerosis, Niemann-Pick disease, Hallervorden-Spatz syndrome, Down syndrome, neuroaxonal dystrophy, multiple system atrophy, Huntington's disease, frontotemporal lobar degeneration (FTLD), multiple system atrophy, cystic fibrosis, and Creutzfeld-Jacob's disease; preferably Alzheimer's disease.

The compounds as described herein can be prepared while using a series of chemical reactions well known to those skilled in the art, altogether making up the process for preparing said compounds and exemplified further. In particular, the compounds of the present invention can be prepared according to the general procedures described in patent application WO 2010142801.

EXAMPLES

The following examples are provided for the purpose of illustrating the present invention and by no means should be interpreted to limit the scope of the present invention.

Part A represents the preparation of the compounds which are inhibitor of PDE6δ as described herein (intermediates and final compounds) whereas Part B represents the pharmacological examples.

Exemplary compounds of the present invention are shown in Table 1.

TABLE 1

| Compound | Structure |
|---|---|
| 1 | 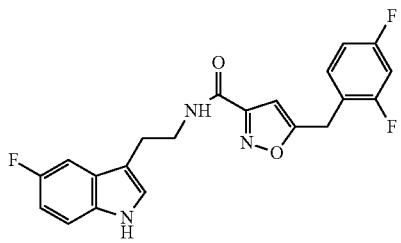 [SMILES: O=C(NCCc1c[nH]c2ccc(F)cc12)c1cc(Cc2ccc(F)cc2F)on1] |
| 2 | 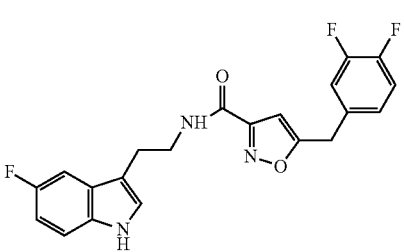 [SMILES: O=C(NCCc1c[nH]c2ccc(F)cc12)c1cc(Cc2ccc(F)c(F)c2)on1] |
| 3 | 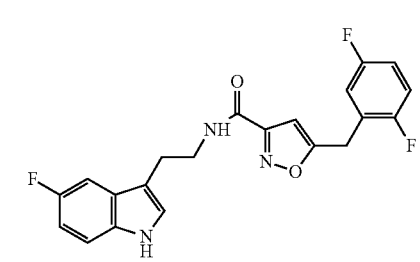 [SMILES: O=C(NCCc1c[nH]c2ccc(F)cc12)c1cc(Cc2cc(F)ccc2F)on1] |
| 4 | 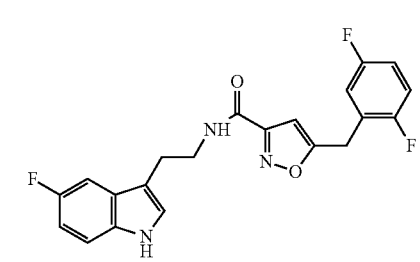 [SMILES: O=C(NCCc1c[nH]c2ccc(F)cc12)c1cc(Cc2cc(F)ccc2F)on1] |
| 5 | 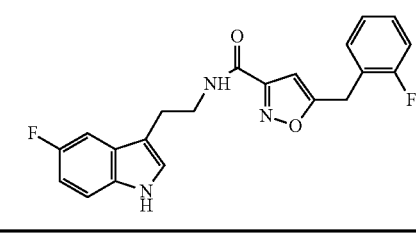 |
| 6 | 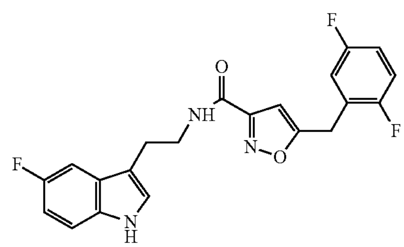 |
| 7 | 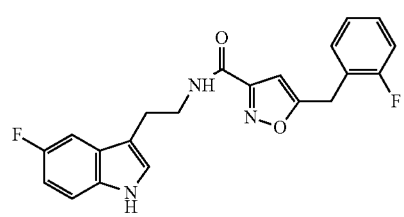 [SMILES: O=C(NCCc1c[nH]c2ccc(F)cc12)c1cc(Cc2ccccc2F)on1] |

For exemplary purposes, the synthesis of compounds in Table 1 is described herein. The compounds were prepared following two different synthetic pathways, illustrated in Scheme 1 and Scheme 2, shown below.

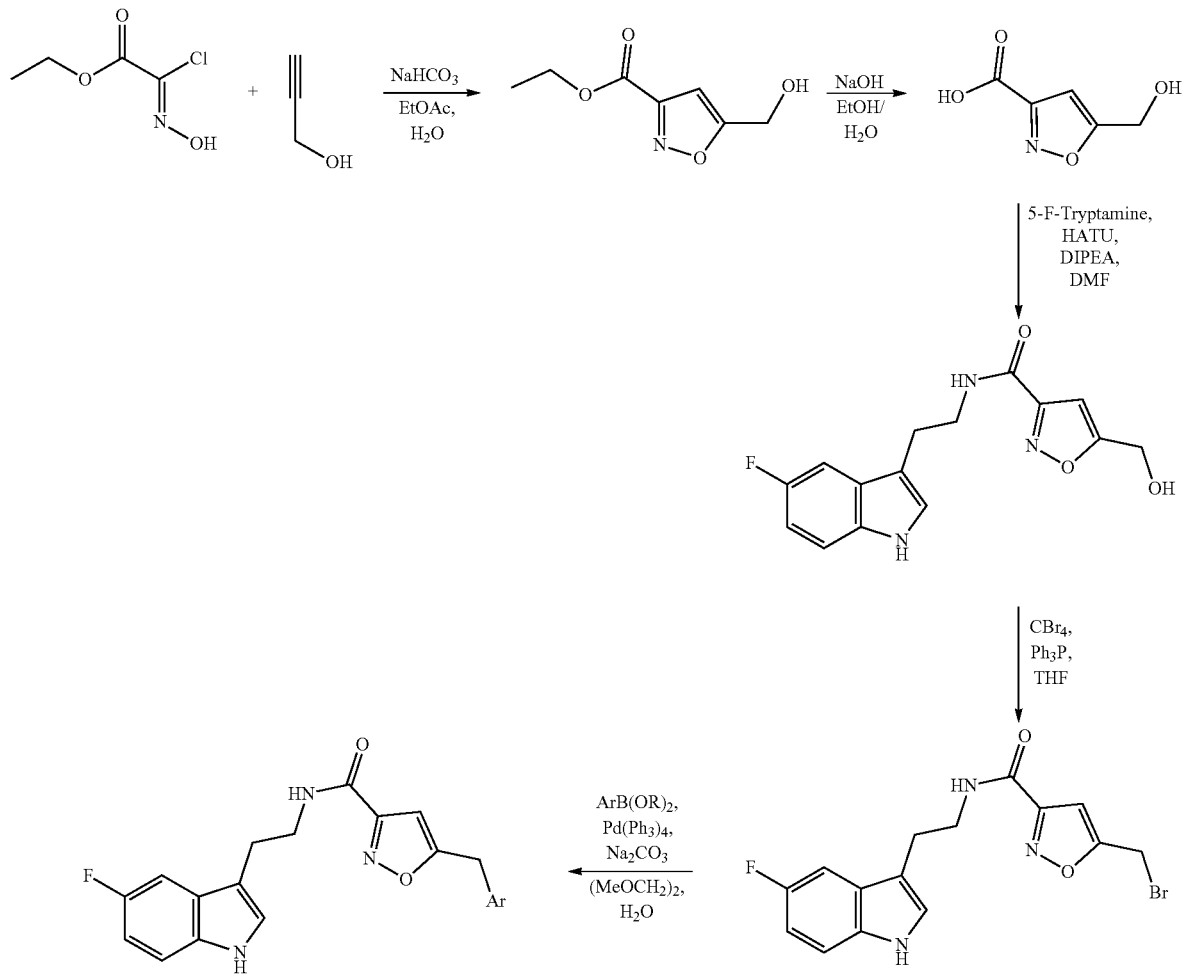
Scheme 1
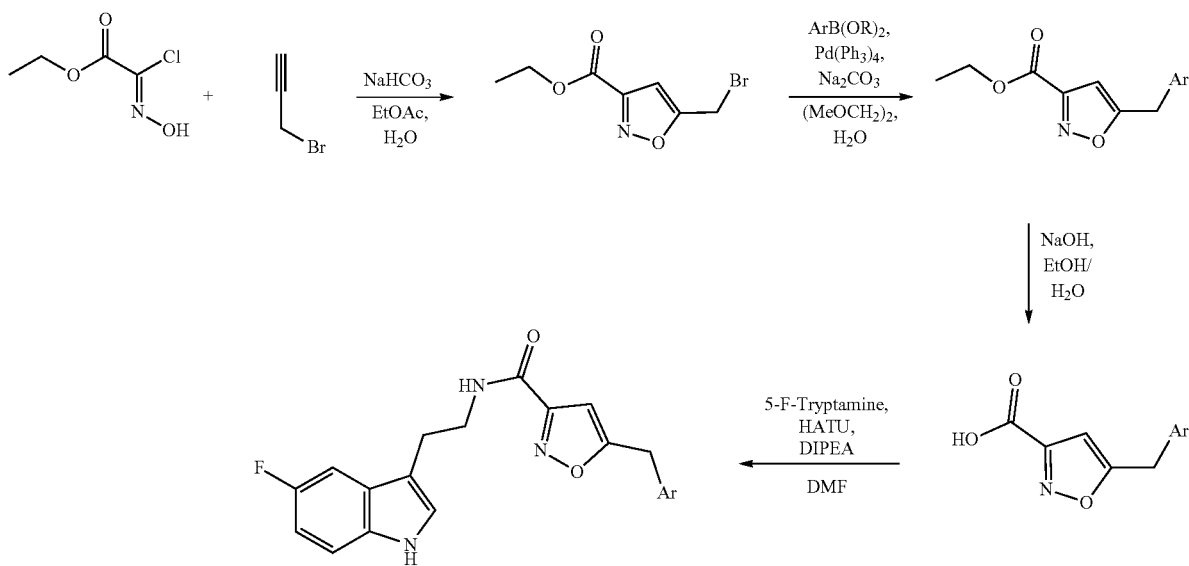
Scheme 2.

A solution of ethyl 2-chloro-2-(hydroxyimino)acetate (37.6 g, 240.66 mmol) in 200 mL of ethyl acetate was added dropwise at room temperature to a mixture of 3-bromoprop-1-yne (91 mL; 845 mmol), sodium bicarbonate (71.48 g; 842 mmol), ethyl acetate (1200 mL), and water (12 mL) and the mixture was stirred at room temperature for 108 hours. The solid was filtered off and the filtrate was washed twice with water, dried over magnesium sulfate and concentrated under reduced pressure. The residue was purified by flash chromatography on silica gel using a gradient of ethyl acetate (5-40%) in heptane to give 46.1 g (82%) of ethyl 5-(bromomethyl)isoxazole-3-carboxylate as a white solid. $^1$H NMR (CHLOROFORM-d) δ: 6.74 (s, 1H), 4.50 (s, 2H), 4.45 (q, 2H), 1.42 (t, 3H).

Intermediate II—Preparation of Ethyl 5-(2,5-difluorobenzyl)isoxazole-3-carboxylate Twenty-five microwave vials were individually charged with ethyl 5-(bromomethyl)isoxazole-3-carboxylate (1.2 g; 5.13 mmol), 2,5-difluorophenylboronic acid (0.928 g; 5.64 mmol), tetrakis(triphenylphosphine)palladium(0) (0.297 g; 0.256 mmol), sodium carbonate (1.09 g; 10.25 mmol) and a mixture of water (2 mL) and 1,2-dimethoxyethane (8 mL) was added. The vials were sealed and heated at 130° C. in a microwave oven for 20 min. The content of the twenty-five vials was combined, diluted with ethyl acetate, and washed with water. The organic layer was concentrated under reduced pressure and the residue was purified by flash chromatography on silica gel using a gradient of ethyl acetate (5-40%) in heptane to give 18.47 g (54%) of ethyl 5-(2,5-difluorobenzyl)isoxazole-3-carboxylate as a yellow oil. $^1$H NMR (CHLOROFORM-d) δ: 6.90-7.12 (m, 3H), 6.42 (s, 1H), 4.42 (q, 2H), 4.15 (s, 2H), 1.40 (t, 3H). ESI/APCI(+): 268 (M+H), 290 (M+Na).

Intermediate III—Preparation of 5-(2,5-difluorobenzyl)isoxazole-3-carboxylic Acid A solution of sodium hydroxide 1M (206 mL; 206 mmol) was added to a solution of ethyl 5-(2,5-difluorobenzyl) isoxazole-3-carboxylate (18.30 g; 68.48 mmol) in ethanol (20 mL). The mixture was stirred at room temperature for 2 hours. The solution was acidified to pH 1 by addition of a solution of hydrochloric acid 12N. The precipitate was collected by filtration and dried under reduced pressure to give 14.60 g (89%) of 5-(2,5-difluorobenzyl)isoxazole-3-carboxylic acid as a white solid. $^1$H NMR (DMSO-d$_6$) δ: 7.17-7.34 (m, 3H), 6.59 (s, 1H), 4.27 (s, 2H).

Intermediate IV—Preparation of Ethyl 5-(hydroxymethyl)isoxazole-3-carboxylate

Propargyl alcohol (11.42 mL; 191.36 mmol) was added to a mixture of ethyl 2-chloro-2-(hydroxyimino)acetate (14.50 g; 95.68 mmol) and sodium hydrogen carbonate (16.08 g; 191.36 mmol) in ethyl acetate (400 mL) and water (40 mL) and stirred at room temperature for 24 hours. The two phases were separated and the organic layer was concentrated under reduced pressure. The crude mixture was purified by flash chromatography on silica (eluent 1 to 10% ethyl acetate in dichloromethane) to yield 8.67 g (53%) of ethyl 5-(hydroxymethyl)isoxazole-3-carboxylate as an oil.

Intermediate V—Preparation of 5-(hydroxymethyl)isoxazole-3-carboxylic Acid

A solution of sodium hydroxide in water (2M; 50 mL) was added to a mixture of ethyl 5-(hydroxymethyl)isoxazole-3-carboxylate (8.67 g; 50.66 mmol) in ethanol (30 mL) and stirred vigorously for 2 hours. The solution was concentrated under reduced pressure, diluted in water and extracted with dichloromethane. The aqueous layer was acidified to pH 1 with hydrochloric acid 6N and extracted several times with ethyl acetate. The organic layer was dried and concentrated under reduced pressure to yield 5.43 g (75%) of 5-(hydroxymethyl)isoxazole-3-carboxylic acid as a white solid.

Intermediate VI Preparation of N-(2-(5-fluoro-1H-indol-3-yl)ethyl)-5-(hydroxymethyl) isoxazole-3-carboxamide N,N diisopropylethylamine (10.75 mL; 58.23 mmol) was added to mixture of 2-(5-fluoro-1H-indol-3-yl)ethanamine hydrochloride (5.00 g; 23.29 mmol), O-(7-azabenzotriazol-1-yl)-N,N,N',N'-tetramethyluronium hexafluorophosphate (8.86 g; 23.29 mmol) and 5-(hydroxymethyl)isoxazole-3-carboxylic acid (3.67 g; 25.62 mmol) in dry DMF (40 mL) and stirred at room temperature overnight. The reaction mixture was concentrated under reduced pressure and diluted in ethyl acetate, washed subsequently with an aqueous solution of potassium hydrogensulfate (1M) and an aqueous solution of sodium carbonate (1M). The organic layer was dried with magnesium sulfate and concentrated under reduced pressure. The crude residue was purified by flash column chromatography on silica (eluent methanol 0 to 10% in dichloromethane) to yield 5.26 g (74%) of N-(2-(5-fluoro-1H-indol-3-yl)ethyl)-5-(hydroxymethyl)isoxazole-3-carboxamide as a sticky yellowish solid.

Intermediate VII Preparation of 5-(bromomethyl)-N-(2-(5-fluoro-1H-indol-3-yl)ethyl)isoxazole-3-carboxamide A solution of N-(2-(5-fluoro-1H-indol-3-yl)ethyl)-5-(hydroxymethyl)isoxazole-3-carboxamide (5.30 g; 17.48 mmol) in THF (10 mL) was added to a solution of perbromomethane (8.69 g; 26.21 mmol) and triphenylphosphine (6.88 g; 26.21 mmol) in THF (60 mL). The resulting solution was stirred at room temperature for 2.5 hours. The solid was filtered off and the solution was concentrated under reduced pressure. The residue was purified by flash column chromatography on silica (eluent ethyl acetate 15 to 100% in heptane) to yield 2.64 g (41%) 5-(bromomethyl)-N-(2-(5-fluoro-1H-indol-3-yl)ethyl)isoxazole-3-carboxamide as a white solid. ESI/APCI(+): 366, 368 (M+H). ESI/APCI(−): 366, 364 (M−H).

Part A: Preparation of Novel Inhibitors of PDE6δ

Example 1—Preparation of 5-(2,5-difluorobenzyl)-N-(2-(5-fluoro-1H-indol-3-yl)ethyl)isoxazole-3-carboxamide N-Ethyldiisopropylamine (25.65 mL; 148.37 mmol) was added to a stirred mixture of 2-(5-fluoro-1H-indol-3-yl)ethan-1-amine hydrochloride (13.00 g; 59.35 mmol), 5-(2,5-difluorobenzyl)isoxazole-3-carboxylic acid (14.19 g; 59.35 mmol), and O-(7-azabenzotriazol-1-yl)-N,N,N',N'-tetramethyluronium hexafluorophosphate (22.57 g; 59.35 mmol.) in dry DMF (90 mL). The mixture was stirred at room temperature for 60 hours and then was concentrated under reduced pressure. The residue was dissolved in ethyl acetate and the solution was washed with water and brine, dried over magnesium sulfate, filtered, and concentrated under reduced pressure. The residue was purified by flash chromatography on silica gel using a gradient of ethyl acetate (1-10%) in dichloromethane to give 20.02 g of a yellowish solid which was recrystallized in a mixture of dichloromethane and n-heptane to yield 19.06 g (80%) of 5-(2,5-difluorobenzyl)-N-(2-(5-fluoro-1H-indol-3-yl)ethyl) isoxazole-3-carboxamide as a white solid.

or 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (2,5-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.038 g (23%) 5-(2,5-difluorobenzyl)-N-(2-(5-fluoro-1H-indol-3-yl)ethyl)isoxazole-3-carboxamide as a white solid.

$^1$H NMR (DMSO-d$_6$) δ: 10.92 (br. s., 1H), 8.82 (t, 1H), 7.1-7.38 (m, 6H), 6.90 (td, 1H), 6.53 (s, 1H), 4.26 (s, 2H), 3.48 (q, 2H), 2.88 (t, 2H). ESI/APCI(+): 400 (M+H). ESI/APCI(−): 398 (M−H).

Example 2—Preparation of 5-(2,4-difluorobenzyl)-N-(2-(5-fluoro-1H-indol-3-yl)ethyl)isoxazole-3-carboxamide 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (2,4-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.0462 g (28%) of 5-(2,4-difluorobenzyl)-N-(2-(5-fluoro-1H-indol-3-yl)ethyl) isoxazole-3-carboxamide as a white solid. $^1$H NMR (300 MHz, DMSO-d$_6$): δ 10.92 (br. s., 1H); 8.82 (t, 1H); 7.39-7.57 (m, 1H); 7.21-7.36 (m, 4H); 7.11 (td, 1H); 6.90 (td, 1H); 6.50 (s, 1H); 4.24 (s, 2H); 3.49 (q, 2H); 2.89 (t, 2H). ESI/APCI(+): 400 (M+H). ESI/APCI(−): 398 (M−H).

Example 3—Preparation of 5-(3,4-difluorobenzyl)-N-(2-(5-fluoro-1H-indol-3-yl)ethyl)isoxazole-3-carboxamide 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (3,4-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.065 g (40%) 5-(3,4-difluorobenzyl)-N-(2-(5-fluoro-1H-indol-3-yl)ethyl)isoxazole-3-carboxamide as a pale yellow solid. $^1$H NMR (300 MHz, DMSO-d$_6$) δ ppm 10.92 (br. s., 1H); 8.81 (t, 1H) 7.36-7.49 (m, 2H); 7.28-7.35 (m, 2H); 7.25 (d, 1H); 7.12-7.21 (m, 1H); 6.90 (td, 1H); 6.54 (s, 1H); 4.23 (s, 2H); 3.48 (q, 2H); 2.89 (t, 2H). ESI/APCI(+): 400 (M+H). ESI/APCI(−): 398 (M−H).

Example 4—Preparation of 5-(3,5-difluorobenzyl)-N-(2-(5-fluoro-1H-indol-3-yl)ethyl)isoxazole-3-carboxamide 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (3,5-difluorophenyl)boronic acid (0.068 g; 0.430 mmol), sodium carbonate (0.086 g; 0.430 mmol), Tetrakis(triphenylphosphine)palladium(0) (0.024 g; 0.020 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.068 g (41%) of 5-(3,5-difluorobenzyl)-N-(2-(5-fluoro-1H-indol-3-yl)ethyl)isoxazole-3-carboxamide as a white solid. $^1$H NMR (300 MHz, DMSO-d$_6$) δ ppm 10.93 (br. s, 1H.); 8.83 (t, 1H); 7.03-7.42 (m, 6H); 6.91 (td, 6H); 6.59 (s, 1H); 4.27 (s, 2H); 3.50 (q, 2H); 2.90 (t, 2H). ESI/APCI(+): 400 (M+H). ESI/APCI(−): 398 (M−H).

Example 5—Preparation of N-(2-(5-fluoro-1H-indol-3-yl)ethyl)-5-(4-fluorobenzyl)isoxazole-3-carboxamide 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (4-fluorophenyl)boronic acid (0.086 g; 0.430 mmol), N,N diisopropylethylamine (0.151 mL; 0.819 mmol), [1,1'-Bis (diphenylphosphino)ferrocene]dichloropalladium(11) (0.033 g; 0.040 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.088 g (57%) N-(2-(5-fluoro-1H-indol-3-yl)ethyl)-5-(4-fluorobenzyl)isoxazole-3-carboxamide as a white solid. $^1$H NMR (300 MHz, DMSO-d$_6$) δ ppm 10.92 (br. s., 1H,); 8.80 (t, 1H); 7.11-7.42 (m; 7H); 6.81-6.99 (m, 1H); 6.51 (s, 1H); 4.21 (s, 2H); 3.48 (q, 2H); 2.88 (t, 2H). ESI/APCI(+): 382 (M+H).
ESI/APCI(−): 380 (M−H).

Example 6—Preparation of 5-(2,3-difluorobenzyl)-N-(2-(5-fluoro-1H-indol-3-yl)ethyl)isoxazole-3-carboxamide 5-(bromomethyl)-N-(2-(5-fluoro-1H-indol-3-yl)ethyl) isoxazole-3-carboxamide (0.200 g; 0.546 mmol) was dissolved in DME (3 mL) and water (1 mL) with (2,3-difluorophenyl)boronic acid (0.129 g; 0.819 mmol), N,N diisopropylethylamine (0.201 mL; 1.09 mmol), Bis(diphenylphosphino)ferrocene]dichloropalladium(11) (0.045 g; 0.056 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 20 to 100% in heptane) to yield 0.015 g (7%) 5-(2,3-difluorobenzyl)-N-(2-(5-fluoro-1H-indol-3-yl)ethyl)isoxazole-3-carboxamide as a white solid. $^1$H NMR (300 MHz, DMSO-d$_6$) δ ppm 10.85-11.04 (m, 1H); 8.82 (t, 1H); 7.45-7.30 (1H, m); 7.28-7.36 (m, 2H); 7.17-7.27 (m, 3H); 6.90 (td, 1H); 6.55 (s; 1H); 4.33 (s; 2H); 3.48 (d, 2H); 2.88 (t, 2H).

ESI/APCI(+): 400 (M+H). ESI/APCI(−): 398 (M−H).

Example 7—Preparation of N-(2-(5-fluoro-1H-indol-3-yl)ethyl)-5-(2-fluorobenzyl)isoxazole-3-carboxamide 5-(bromomethyl)-N-(2-(5-fluoro-1H-indol-3-yl)ethyl) isoxazole-3-carboxamide (0.150 g; 0.409 mmol) was dissolved in DME (3 mL) and water (1 mL) with (2-fluorophenyl)boronic acid (0.086 g; 0.430 mmol), N,N diisopropylethylamine (0.151 mL; 0.819 mmol), Bis(diphenylphosphino)ferrocene]dichloropalladium(II) (0.033 g; 0.040 mmol) and heated overnight at 90° C. After cooling to RT, the reaction mixture was diluted with water and ethyl acetate, the organic layer was dried with magnesium sulfate and concentrated under reduced pressure. The crude mixture was purified by flash column chromatography on silica (eluent ethyl acetate 0 to 10% in dichloromethane) to yield 0.068 g (44%) N-(2-(5-fluoro-1H-indol-3-yl)ethyl)-5-(2-fluorobenzyl)isoxazole-3-carboxamide as a white solid. $^1$H NMR (300 MHz, DMSO-d$_6$) δ ppm 10.93 (br. s., 1H); 8.66-8.96 (m, 1H); 7.13-7.52 (m, 7H); 6.79-7.00 (m, 1H); 6.51 (s, 1H); 4.26 (s, 2H); 3.49 (q, 2H); 2.89 (t, 2H). ESI/APCI(+): 382 (M+H).

ESI/APCI(−): 380 (M−H).

Part B: Pharmacological Examples

Example 8—Demonstration of Direct and Specific Interaction of Compounds with PDE6δ

Surface plasmon resonance was used to assess direct interaction with PDE6δ and the compounds (FIG. 9). When the chip with immobilized compound was incubated with recombinant PDE6δ an increase of response units was observed indicating a direct interaction with MFC-42826 (fusion compound between Compound A and methotrexate):

When the chip is incubated with PDE6δ in the presence of unconjugated Compound A or exemplary Compound 6 (FIG. 9A, B) the response units were decreased. This competition of the signals with the unconjugated compounds indicates specific binding of the compounds on PDE6δ. Atorvastatin, an established PDE6δ binder (Chidley C. et al., 2011, Nat Chem Biol, 7(6), pp. 375-83.) also competed for the MFC-42826 interaction with PDE6δ (FIG. 9C).

Detailed Methods

Set-up: Biacore T100 apparatus. Incubation buffer: 10 mM HEPES pH 7.4, 150 mM NaCl, 0.05% Tween 20, 1 mM DTT, 8 μM NADPH, 1% DMSO, 50 μL/min, temperature 25° C. Covalent immobilization of His-DHFR via primary amines on a S-CM5 sensor chip. Compound A was coupled to methotrexate (herein referred to as MFC-42826, FIG. 10A). MFC-42826 was immobilised on DHFR coated chips and incubated with recombinant PDE6δ. Competitions were done with 20 μM compound.

Example 9—PDE6δ Mediates Toxicity and is Required for Lowering Toxicity in the TAU-Toxicity Model In the TAU-toxicity model genetic silencing of the gene encoding PDE6δ results in lowered toxicity compared to non-silenced controls (FIG. 10A). Incubating the non-silenced cells with exemplary Compound 6 reduced toxicity (see example 19). In PDE6δ silenced cells the toxicity was lowered and the effect of the compound on lowering toxicity was strongly reduced and did not reach levels below the maximum compound effect in the non-silenced cells. These data indicate that the compound lowers PDE6δ-dependent toxicity. Hence, the reducing effect of the compound on toxicity requires the presence of its binding target PDE6δ.

Deltarasin (Zimmerman et al., 2013, Nature, 497(7451), pp. 638-42.) binds PDE6δ in the prenyl binding pocket. Incubation cell the TAU-toxicity model with deltarasin lowered toxicity whereas in silenced the modulation (lowering) of the deltarasin on neurotoxicity was strongly reduced (FIG. 10B) demonstrating the reducing effect of deltarasin on toxicity requires the presence of its binding target PDE6δ.

Example 10—RAP1A GTPase Interacts with PDE6δ and this Interaction is Abrogated by an Exemplary Compound PDE6δ together with associated proteins was precipitated from a cellular extract either in the presence or absence of Compound A:

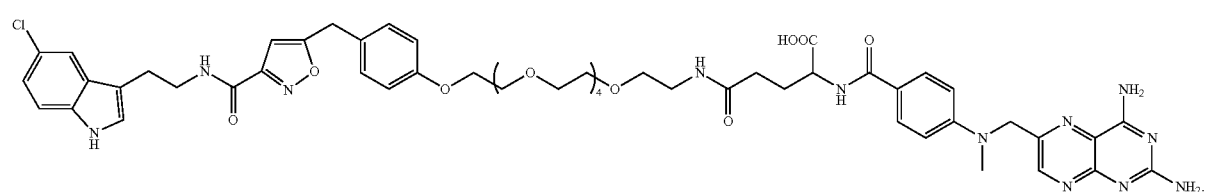

MFC-42826

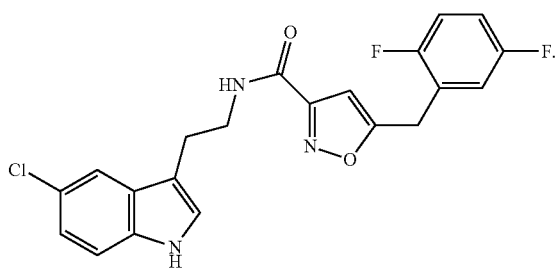 [SMILES: O=C(NCCc1c[nH]c2ccc(Cl)cc12)c1cc(Cc2cc(F)ccc2F)on1]

Using mass spectrometry based techniques interacting proteins were quantitatively identified in function of compound presence (FIG. 11).

In the absence of Compound A a host of interacting proteins were identified including known interactors such as Arl3 and RPGR. Also small GTpases RAP1A and Rab28 were identified but the interaction of only RAP1A was specifically reduced when cells were incubated with compound (FIG. 9). These data reveal the compound specifically disrupts or competes for RAP1A binding on PDE6δ. This effect is highly specific since a non-prenylated interactor of PDE6δ such as Arl3 which bind PDE6δ via different mechanisms is not impacted.

Detailed Methods

The cDNA encoding human PDE6δ was fused with a STREP-HA tag encoding DNA sequence and expressed in HEK293 cells using a standard expression vector. The bait sequence was verified by sequencing. For constitutive overexpression, the expression vector containing the gene encoding the bait PDE6δ-STREP/HA was transfected into HEK293 cells and selected for stable integration. Bait expression and solubility was monitored by immunoblotting using anti-HA antibodies. Protein extracts were prepared (n=3) from DMSO (black bars) and compound treated cells (grey bars) and the fusion protein was pulled-down with streptactin resin. Signals were background corrected and normalised to the DMSO control.

Affinity purification and mass spectrometrical analysis of PDE6δ-strep-HA expressed in HEK293 cells was performed with three biological replicates for label free quantitative mass spectrometrical analysis. The samples were analyzed on a Thermo LTQ Orbitrap XL spectrometer using a C18 column, ESI and a 60 min gradient. The signals' intenstity are provided as 2 Log values and correlates to the concentration of the detected mass (number/amount of peptide). The variation within the biological replicates for control, vehicle-treated PDE6δ pulldown, compound treated PDE6δ pulldown and compound treated PDE6δ pulldown was below 10%.

Example 11—Silencing RAP1A Lowers Toxicity and Abrogates Compound Modulation in the TAU-Toxicity Model In the TAU-toxicity model genetic silencing of the gene encoding RAP1A results in lowered toxicity compared to non-silenced controls (FIG. 12). Incubating in the non-silenced cells with exemplary Compound 6 reduced toxicity (see example 19). In silenced cells the compound effect on reducing neurotoxicity was strongly reduced. These data demonstrate the reducing effect of the compound on toxicity requires the presence of RAP1A.

Example 12—Method of Screening Compounds for Binding into PDE6δ Prenyl Binding Site In order to determine whether or not a compound is an inhibitor of PDE6δ, the binding of compounds to PDE6δ is tested using Surface Plasmon Resonance whereby competition for the interaction of PDE6δ with immobilized MFC-42826 is determined.

In order to ensure that this ability to bind to PDE6δ is indicative of PDE6δ inhibition, a secondary screening can be performed (before or after the SPR assay, which provides a functional readout, such as the TAU-toxicity assay as described in Example 16. In an exemplary screening run, compounds were tested in the TAU-toxicity assay, and those compounds with a half-maximal concentration of <20 μM to lower toxicity in the assay were retained and tested for binding to the PDE6δ prenyl binding site as described in Example 8 which describes the method of competing binding to the PDE6δ prenyl binding site using PDE6δ prenyl-binding compounds such as Compound 6, atorvastatine or deltarasin Example 13—in Silico Docking Illustrates High Affinity Binding of Compounds into PDE6δ Prenyl Binding Site In order to confirm the compounds bind with high affinity in the prenyl-binding pocket of PDE6δ in-silico docking and calculation of the predicted Gibbs binding energy of binding of compounds in the pocket was performed (FIG. 13, Table 2). This analysis revealed that Compounds 1-7, Compound A:

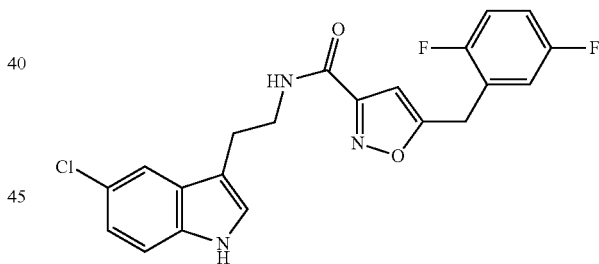

and
Compound B:

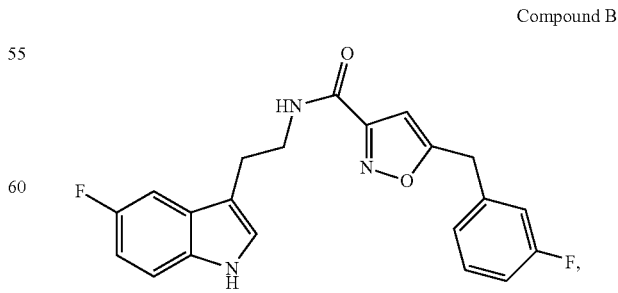

Compound B bind with a Gibbs energy value of less than −10 kcal/mol which indicates high affinity binding. Using the docking protocol, deltarasin, a known PDE6δ inhibitor, is predicted to bind with high affinity the PDE6δ prenyl-binding pocket consistent with published experimental binding and co-crystallisation data (Zimmerman et al., 2013, Nature, 497 (7451), pp. 638-42.).

TABLE 2

| Compound | Gibbs energy ΔG (kcal/mol) |
| --- | --- |
| Compound A | −10.5 |
| Compound 6 | −10.6 |
| Compound 5 | −10.7 |
| Compound B | −10.4 |
| Compound 4 | −10.4 |
| Compound 1 | −10.6 |
| Compound 2 | −10.6 |
| Compound 3 | −10.3 |
| Compound 7 | −10.3 |
| Deltarasin (control) | −12.5 |

Example 14—Testing of Compounds in the Kainite Epilepsy Model

Compounds were tested in the rat kainite epilepsy model.
Pharmacological evaluation of the anti-epilepsy activity of compounds is performed in a kainic acid (KA) mouse model (Gröticke et al., 2008, Experimental Neurology, 213, pp. 71-83; Dietrich et al., August 2016, Conf Proc IEEE Eng Med Biol Soc., pp. 4005-4008). This model shows recurrent seizures after an initial KA-induced status epilepticus (SE) and a latent epileptogenic phase of 2-to-3 weeks.

KA is injected into the CA1 area of the dorsal hippocampus followed by a surgical ipsilateral implantation of bipolar electrodes for EEG recording. Based on the occurrence of a nonconvulsive SE induced by KA mice are selected for enrolment into the study. A once or twice-a-week 1 hr video-EEG monitoring is used to record the hippocampal discharges (HPD) over time. Severity of behavioural (convulsive) seizures are rated according to Racine (Racine R J, 1972, Electroencephalogr Clin Neurophysiol., 38(1):1-12).

Daily subcutaneous administration of compound (25 mg/kg) or vehicle treatment starts before or after the initial kainate induced SE. Compound treated mice show a decrease of more than 20% in kainate induced HPD and/or spontaneous seizures compared to vehicle treated mice.

Example 15—Construction of a TAU Gene Over-Expressing Cell Line

A TAU expression plasmid was constructed by subcloning the cDNA of human TAU-P301L (encoding for TAU with proline 301 substituted by a leucine residue) into mammalian expression vector pcDNA3.1 resulting in plasmid pcDNA3.1-TAU P301L. Plasmids pcDNA3.1 and pcDNA3.1-TAU P301L were transfected to human neuroblastoma cells (BM17; ATCC No. CRL-2267) and independent clonal lines with the plasmids stably integrated into the genome were selected. These resulted in cell lines named M17-3.1 and M17-TAU(P301L) (transfected with pcDNA3.1 and pcDNA3.1-TAU P301L, respectively). Expression of the TAU P301L genes in the cell lines was confirmed by Western analysis.

Example 16—Use of P301L TAU Expressing Cells as a Model of Neuronal Degeneration The expression of TAU P301L in M17-TAU(P301L) cells was found to confer increased toxicity relative to control cells expressing wild type TAU (M17-TAUwt).

In degenerated or dead cells lactate dehydrogenase (LDH) leaks out of the cells into the extracellular environment due to a loss of plasma-membrane integrity. This principle was used to determine cytotoxicity by quantifying the level of leaked LDH into the growth medium relative to the sum of total LDH activity from living cells and dead cells.

The detailed method for determining cytotoxicity was as follows: From appropriate precultures of M17-3.1 and M17-TAU(P301L) cells were seeded at 2500 cells/cm2 in Optimem Reduced Serum without phenol red (Gibco, Cat. 31985-047) supplemented with 1% fetal calf serum, 1 mM sodium pyruvate, 1× non-essential amino acids, 500 μg/ml G418 0.5×antibiotic/antimycotic. After 3 hours of incubation at 37° C./5% CO2 1 volume of Optimem Reduced Serum (same as described above; except without fetal calf serum) supplemented with 2.5 μM all-trans retinoic acid (ATRA) was added. The cells were further incubated for 7 days. Subsequently, LDH activity was determined using Promega Cytotox 96 Non-Radioactive cytotoxicity assay, (Cat. G1780) according the supplier's instructions.

Figure 1:
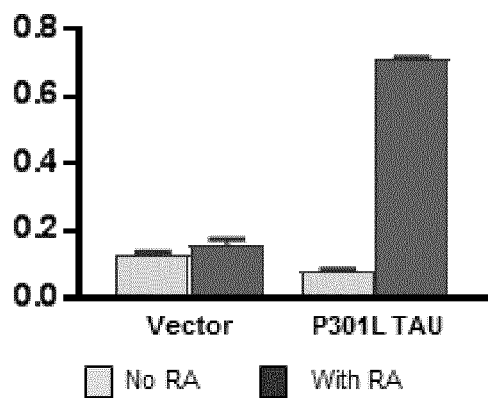
FIG. 1 Section A represents a graph plotting the percentage of LDH leaked into the medium by each of M17-TAU P301L cells (P301L TAU), and M17-3.1 cells (vector) in the presence and absence of all-trans retinoic acid (RA). Section B represents a graph plotting the relative levels of cytosolic calcium in the M17-TAU P301L cells in the presence and absence of retinoic acid (RA). **** indicate p<0.0001.
Figure 1:
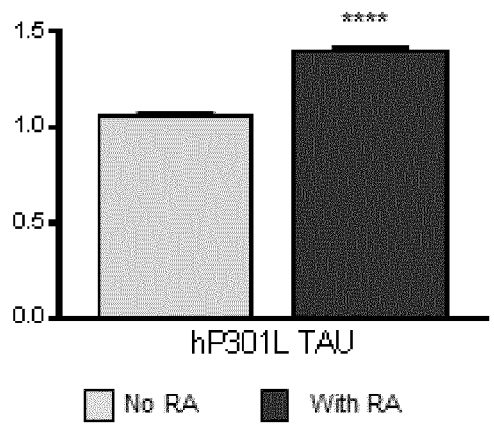

FIG. 1A shows that M17-TAU P301L cells, but not M17-3.1 cells display a relatively high level of LDH leaked into the medium demonstrating a TAU P301 dependent toxicity.

Example 17—Use of P301L TAU Expressing Cells as a Model of Calcium Dyshomeostasis Cystosic calcium was measured by loading the cells with a medium containing Fura-2 AM (Sigma-Aldrich), a cell permeable fluorescent probe for $Ca^{2+}$. Fura-2-AM was dissolved in DMSO plus 20% Pluronic Acid (F-127) (Invitrogen) in a 1:1 ratio and diluted in medium to a final concentration of 0.5 μM. To this loading medium probenecid (Sigma-Aldrich) was added to a final concentration of 2.5 mM. Then, culture medium was replaced by loading medium and after incubation for 1 hour at 37° C. cells were washed twice and replaced with HBSS (Gibco) supplemented with 0.2% FBS and 0.02M HEPES. Next, changes in cytosolic calcium were measured using a FlexStation 3 microplate reader (Molecular Devices) and quantified ratiometric, by calculating changes in the amount of cytosolic $Ca^{2+}$ bound Fura-2 (fluorescence intensity at 340 nm) relative to the amount of $Ca^{2+}$ unbound Fura-2 (fluorescence intensity at 380 nm). Data was processed in SoftMax Pro 5.4.6 software (Molecular Devices).

FIG. 1B shows that in P301L TAU expressing cells in which toxicity was induced by ATRA according the method of Example 16 displayed in increased levels of cytosolic calcium.

Example 18—the P301L TAU Expressing Cells can be Used in the Screening of Compounds for the Treatment of Alzheimer's Disease and Epilepsy The cell line model of TAU-induced cytotoxicity allows identification of compounds which can be used in animal and human patients for the treatment of Alzheimer's disease. This correlation is demonstrated by the following experimental example (Figure. 2) in which addition of Methylthioninium chloride, which is a potential disease-modifying therapy for Alzheimer's disease, lowered TAU-induced neuronal cell toxicity using the assay described in example 16.

Figure 2:
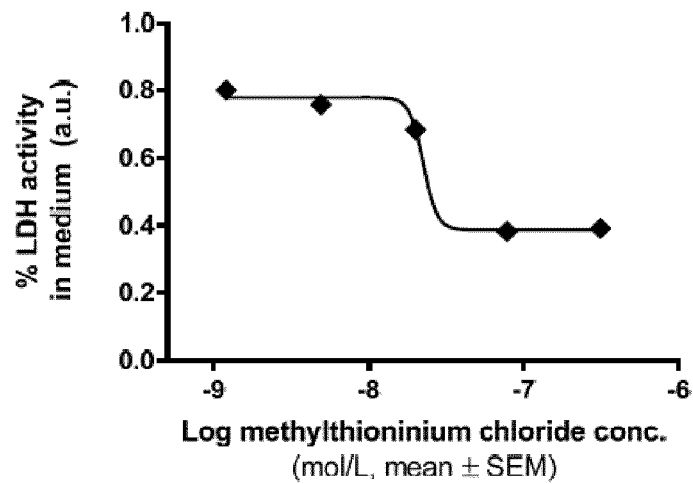
FIG. 2 represents a graph plotting the percentage of LDH activity leaked into the medium by M17-TAU P301L cells in the presence of RA as a function of the concentration of methylthioninium chloride (A) or of isradepine (B) added to the cells.
Figure 2:
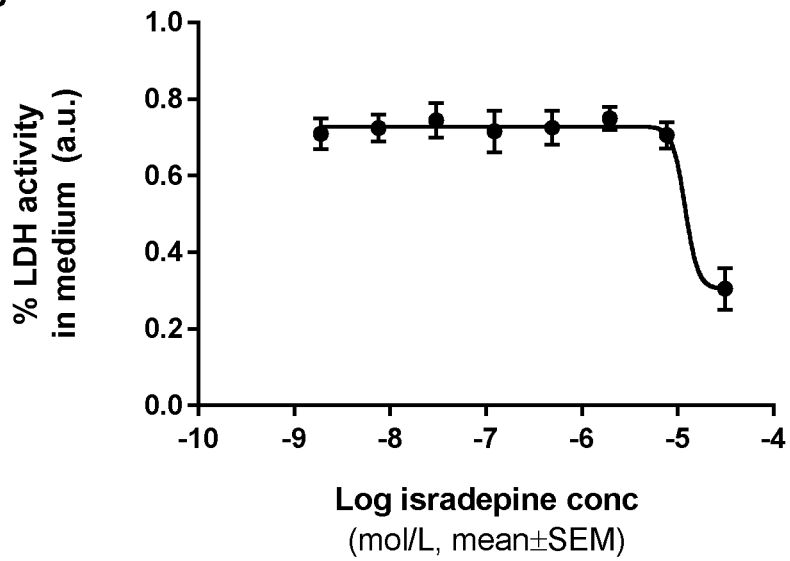

The present inventors have additionally found that the cell line model of TAU-induced cytotoxicity allows identification of compounds which can be used for the treatment or prevention of epilepsy. Isradepine is a voltage-gated calcium channel (VGCC) inhibitor. VGCCs are a well-established target for treating epilepsy and iradepine is active in models of epilepsy. FIG. 2 shows that isradepine lowered toxicity in the model described in example 16.

Example 19—Use of the TAU Expressing Cells in the Screening of Exemplary Compounds of this Invention The M17-TAU P301L cell line made it possible to assess the ability of novel compounds to inhibit PDE6δ and counteract TAU cytotoxicity. Active inhibitors of TAU cytotoxicity were found to inhibit LDH leakage of M17-TAU P301L cells treated as described in example 16. Efficacy (potency) of the compounds was determined by testing compounds at different concentrations ranging from non-effective (thus at a relatively low concentration) to an effective concentration for their ability to reduce LDH activity of retinoic acid incubated M17-TAU P301L cells. These measurements were used to calculate $EC_{50}$ values.

Exemplary compounds of the present invention are shown in Table 3, with their chemical structure and their $EC_{50}$ value (expressed in μg/ml) as determined from example 19 in the TAU-induced toxicity experiment.

TABLE 3

| Compound | Structure | $EC_{50}$ (μg/ml) |
|---|---|---|
| 1 | 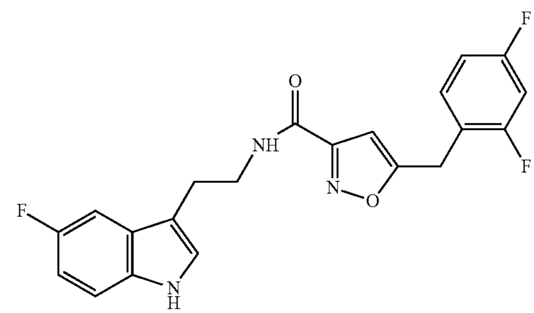 [SMILES: O=C(NCCc1c[nH]c2ccc(F)cc12)c1cc(Cc2ccc(F)cc2F)on1] | 0.0020 |
| 2 | 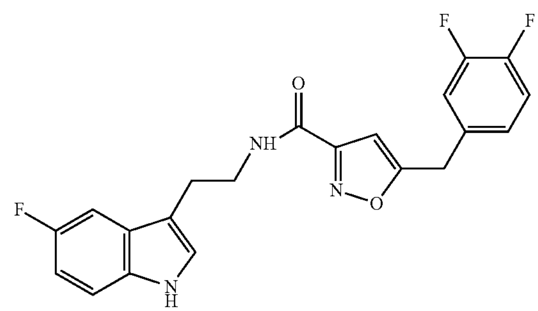 [SMILES: O=C(NCCc1c[nH]c2ccc(F)cc12)c1cc(Cc2ccc(F)c(F)c2)on1] | 0.0020 |
| 3 | 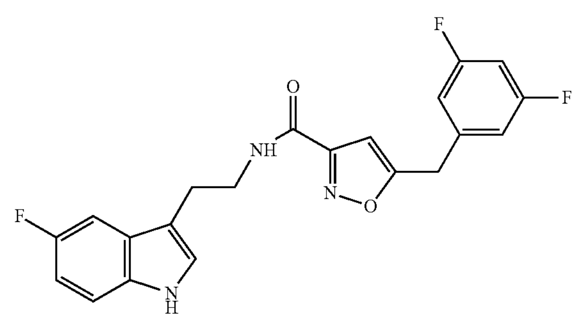 [SMILES: O=C(NCCc1c[nH]c2ccc(F)cc12)c1cc(Cc2cc(F)cc(F)c2)on1] | 0.0021 |
| 4 | 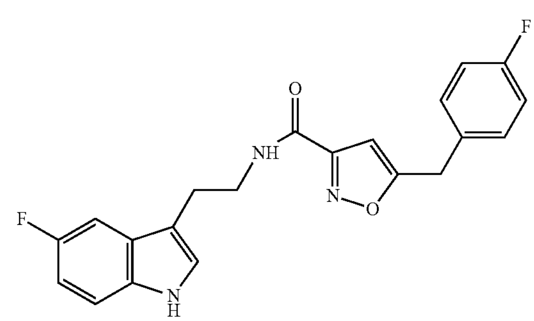 [SMILES: O=C(NCCc1c[nH]c2ccc(F)cc12)c1cc(Cc2ccc(F)cc2)on1] | 0.0022 |

TABLE 3-continued

| Compound | Structure | EC$_{50}$ (µg/ml) |
|---|---|---|
| 5 | 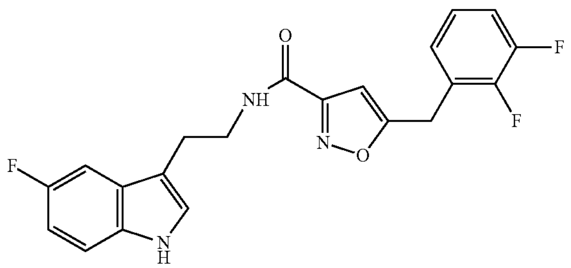 [SMILES: O=C(NCCc1c[nH]c2ccc(F)cc12)c1cc(Cc2cccc(F)c2F)on1] | 0.0028 |
| 6 | 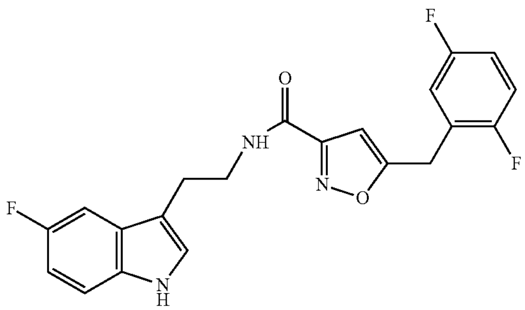 [SMILES: O=C(NCCc1c[nH]c2ccc(F)cc12)c1cc(Cc2cc(F)ccc2F)on1] | 0.0034 |
| 7 | 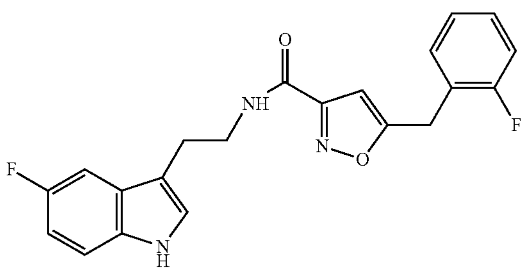 [SMILES: O=C(NCCc1c[nH]c2ccc(F)cc12)c1cc(Cc2ccccc2F)on1] | 0.0043 |

Figure 3:
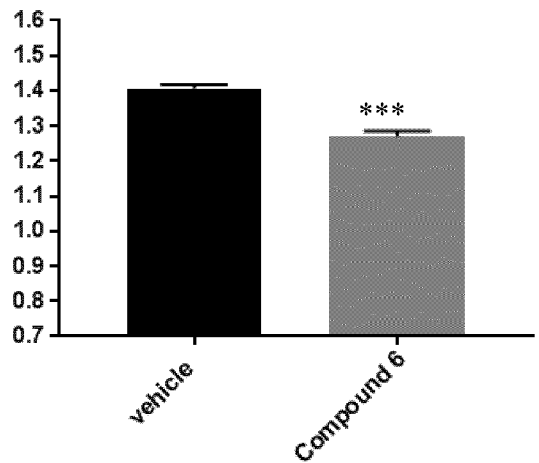
FIG. 3 represents a graph plotting the relative levels of cytosolic calcium in M17-TAU P301L cells, after being challenged with retinoic acid, in the presence of vehicle or exemplary Compound 6 at 625 nM. *** indicate p<0.001.

In addition compounds were tested to lower the elevated cytosolic calcium levels. In the presence of the compounds these cytosolic calcium levels were decreased. FIG. 3 shows the compounds mitigate the calcium dyshomeostasis under conditions of toxicity in the M17-TAU P301 L cell line model of example 16.

Example 20—Ex-Vivo Inhibition of Oligomeric Amyloid Beta Toxicity

Figure 4:
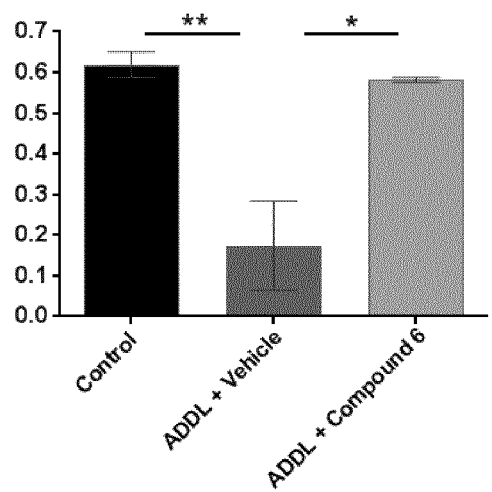
FIG. 4 represents a graph plotting relative number of viable primary neurons after being challenged with amyloid-derived diffusible ligands (ADDLs), in the presence of vehicle or exemplary Compound 6. * indicates p<0.05 and ** indicate p<0.01.

An exemplary compound of this invention was tested for its ability to inhibit toxicity elicited by oligomeric amyloid beta (Aβo). Neurons from rat embryos were harvested and cultured using standard methods (such as used in Schlager et al., 2014. Cell reports, 8(5), pp. 1248-56.). Differentiated neurons were challenged with Aβo and viability was quantified. Aβo treatment led to severely reduced neuronal viability, whereas viability was strongly rescued in Aβo treated neurons in the presence of 100 ng/mL Compound 6 (FIG. 4). These results demonstrate that examplary Compound 6 strongly mitigates Aβo instigated neuronal cell death.

Detailed Methods:

At day in-vitro 19 days after isolation primary hippocampal neurons were transfected with Marcks-GFP in order to visualize the neurons with fluorescence microscopy.

Preparation of ADDL's to Generate Aβo:

ADDL (Abeta-derived diffusible ligands) preparation (representing Aβo) was done according to Klein (Klein, 2002. Neurochemistry international, 41(5), pp. 345-52.). Abeta 1-42 was purchased from AnaSpec Inc. and dissolved in HFIP to homogenize the peptide. HFIP was then evaporated in a speedvac and Abeta film was dried at −20° C. overnight over desiccant. Abeta film was then resolubilised in 100% DMSO and further diluted (1/25) in Ham's F12 medium. Blanks were prepared by adding equal amounts of DMSO to Ham's F12 medium. Abeta and Blank solutions were incubated overnight at 4° C.

The solution was centrifuged at 14.000×g for 10 min at 4° C. and supernatants were transferred to fresh tubes and protein concentration determined by NanoDrop®.

Cell Treatment:

At day in-vitro 21 primary rat hippocampal neurons were treated with equal volume of Blank/ADDL solution amounting to 0 and 1000 nM ADDL. Cultures were kept at 37° C. 5% CO2 for 24 h before PFA fixation. Viability was assessed using the Live-Dead assay from Thermo Fisher Catalog number: L3224.

Fixation:

Neurons were fixed in 4% PFA/Sucrose for 10 min at RT. Cells were permeabilized using a buffer containing 0.1% Triton-X/0.1% NaCit/PBS. After washing, the coverslips containing neurons were inverted onto a drop of mounting medium (H1000, Vector Laboratories) (w/o DAPI), dried at RT and sealed off.

Example 21—Ex-Vivo Inhibition of VGCC Activity

Figure 5:
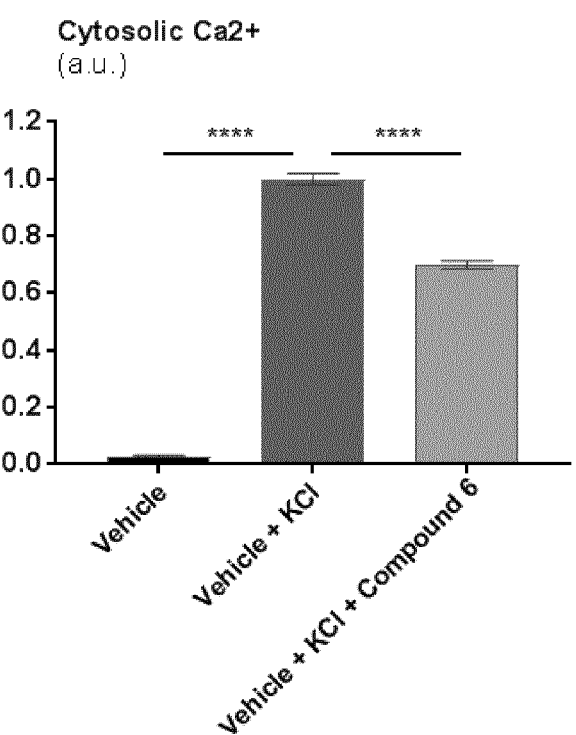
FIG. 5 represents a graph plotting cytosolic $Ca^{2+}$ levels in primary neurons after depolarization with 45 mM KCl of in the presence of vehicle or 1.5 µM of exemplary Compound 6. **** indicate p<0.0001.

Examplary compound 6 was tested for its ability to inhibit VGCC activity in primary neurons. Neurons from mouse embryos were harvested and cultured using standard methods (such as used in Schlager et al., 2014. Cell reports, 8(5), pp. 1248-56). To stimulate VGCC activity, neurons were depolarized using 45 mM KCl and incubated with vehicle or 1.5 µM of compound. Calcium influx was measured using fluorescent cytosolic $Ca^{2+}$ detection reagent Fura2. FIG. 5 shows that in compound treated neurons the $Ca^{2+}$ influx upon KCl depolarisation was significantly reduced indicating that the compound inhibits VGCC activity.

Detailed Methods:

Changes in cytosolic $Ca^{2+}$ concentrations were measured after loading the cells with Fura-2 AM (Sigma-Aldrich), a cell permeable fluorescent probe for $Ca^{2+}$. Briefly, Fura-2-AM was dissolved in DMSO plus 20% Pluronic Acid (F-127) (Invitrogen) in a 1:1 ratio and diluted in medium to a final concentration of 0.5 µM. Probenecid (Sigma-Aldrich) was added to this loading medium at a final concentration of 2.5 mM. Then, culture medium was replaced by loading medium and after incubation for 1 hour at 37° C. cells were washed twice and replaced with HBSS (Gibco) supplemented with 0.2% FBS and 0.02M HEPES. Next, changes in cytosolic calcium were measured using a FlexStation 3 microplate reader (Molecular Devices) and quantified ratiometric, by calculating changes in the amount of cytosolic $Ca^{2+}$ bound Fura-2 (fluorescence intensity at 340 nm) relative to the amount of $Ca^{2+}$ unbound Fura-2 (fluorescence intensity at 380 nm). Data was processed in SoftMax Pro 5.4.6 software (Molecular Devices).

Example 22—In Vivo Inhibition of TAU-Instigated Pathologies

Transgenic human 5-month old APP*PS1 mice (The Journal of Neuroscience, Sep. 1, 2000, 20(17):6452-6458) were treated daily subcutaneously with 20 mg/kg Compound 6 or for two weeks with Compound A:

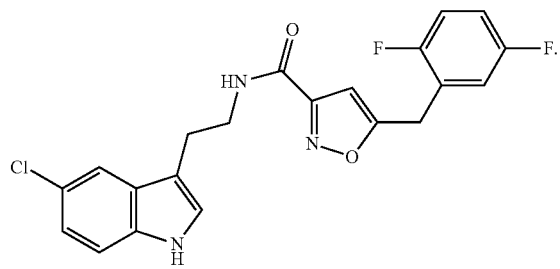 [SMILES: O=C(NCCc1c[nH]c2ccc(Cl)cc12)c1cc(Cc2cc(F)ccc2F)on1]

Figure 6:
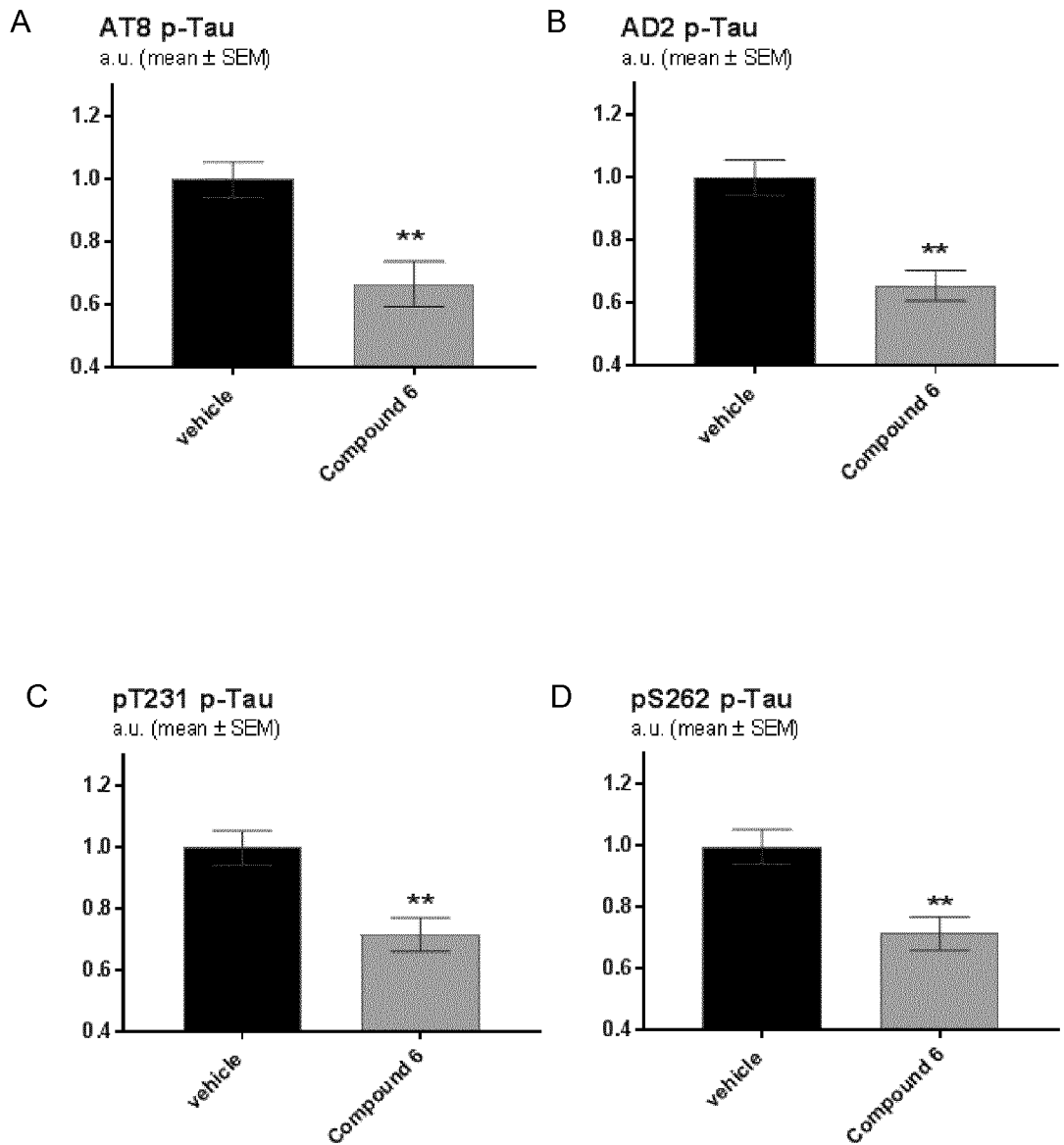
FIG. 6 represents graphs plotting quantifications of pathologically phosphorylated TAU species determined by Western blots of brain extracts from transgenic APP mice treated with vehicle or with exemplary Compound 6. The graphs depict the mean normalized TAU signals±SEM. ** indicate p<0.01 relative to vehicle treated animals. The TAU signals were obtained by using antibodies directed against.

At the end of the treatment period, mice were sacrificed and the corresponding brains were used for biochemical analysis. Western analysis of brain extracts using phospho-TAU specific antibodies showed that compared to vehicle treated mice, Compound 6 effectively reduced TAU phosphorylation, demonstrating an in-vivo lowering effect of pathological TAU species in brain by Compound 6 (FIG. 6).

Example 23—In-Vivo Effects on Cognition in a Mouse Model of Alzheimer's Disease Transgenic human 4-month old APP mice (THE JOURNAL OF BIOLOGICAL CHEMISTRY Vol. 274, No. 10, Issue of March 5, pp. 6483-6492, 1999) were treated subcutaneously, daily for 8 weeks with examplary Compound 6 at 20 mg/kg (FIG. 7). Cognition was assessed using the Morris Water Maze test. During the training phase, which evaluates the learning performance, the mice had over time a reduced search path compared to vehicle treated mice (FIG. 7, Section A). After the learning phase a probe test was conducted in which the platform was removed from the water bath to evaluate the spatial memory of the location of the platform. This test revealed (FIG. 7, Section B) a higher annulus crossing index score (which represents the number of swims over the platform site in the target area adjusted for swims over corresponding areas in other quadrants) than vehicle treated animals.

Both indices indicate that compound treated mice have improved cognitive performance almost identical to wild type controls compared to vehicle treated mice.

Example 24—Normalization of Neuronal Hyperactivation Ex-Vivo in a Mouse Model of Alzheimer's Disease Brain slices from wild type and tgAPP mice were incubated with DMSO or Compound 6. Neurons were stimulated with increasing currents and the frequency of action potentials was measured.

In tgAPP mice the frequency of action potentials at higher stimuli was higher compared to wild type mice suggesting an impaired spike frequency adaptation in tgAPP mice. Incubation of the slices of tgAPP mice with exemplary Compound 6 significantly lowered the frequency towards wild type level (FIG. 8) indicating a spike frequency adaptation mechanism is restored by the compound and so reducing the neuronal hyperactivity in tgAPP mice at high stimulation.

Acute Brain Slices:

Acute sagittal brain slices from WT or hAPP mice were prepared by decapitation of the mice after isoflurane anaesthesia. Brains were removed quickly and immersed during 3-4 min in ice-cold freshly prepared cutting artificial cerebrospinal fluid (cutting aCSF) containing (in mM) 214 sucrose, 2.5 KCl, 2 CaCl2, 2 MgSO4, 1.25 NaH2PO2, 26 NaHCO3 and 10 glucose and oxygenated with 95% O2/5% CO2. Sagittal 350 µm slices were generated using a vibratome (VT 1000S; Leica Microsystems) and were incubated in standard carboxygenated aCSF (in mM: 125 NaCl, 2.5 KCl, 2 CaCl2), 2 MgSO4, 1.25 NaH2PO2, 26 $NaHCO_3$ and 10 glucose, osmolarity 305 mOsm) at 34° C. during 20 min. The incubation continued at room temperature (RT) for another hour before each slice was transferred to a submerged recording chamber and perfused continuously with carboxygenated aCSF.

Patch Clamp Recording of CA1 Single Action Potential (sAP) and Firing Rate:

Somatic or dendritic (>200 µm from the soma) current-clamp recordings were performed at RT (24 to 28° C.) and slices were continuously perfused with carboxygenated standard aCSF, supplemented with control or test article REM0043039 at 2 µM. For whole-cell recordings, patch pipettes were filled with a solution containing (in mM) 140 K-gluconate, 5 NaCl, 2 MgCl2, 10 HEPES, 0.5 EGTA, 2 MgATP, 0.4 NaGTP, osmolarity 305, pH adjusted to 7.25 with KOH. The soma or dendrite of large CA1 pyramidal neurons were identified and patch-clamped after visual approach of the recording pipette using a combination of infrared light and differential interference contrast (DIC) optics. Patch electrodes had a resistance of around 5 and 14

MC when filled for somatic and dendritic recording, respectively. Recordings were terminated when the series resistances exceeded 40 MO. Signals were digitized and low-pass filtered at 10 kHz. The signal was amplified with an Axopatch 200B amplifier, digitized by a Digidata 155 interface and sampled with Clampex 10 (Molecular Devices, CA).

A single spike was elicited by injecting a 2 ms depolarizing current pulse (35 pA) and action potential (AP) parameters were at baseline and after 25 min vehicle or compound perfusion.

Dendritic firing rate of CA1 cells was recorded in response to hyperpolarizing and depolarizing steps (−0.4 to +0.45 nA, steps of 0.05 nA) after a 1 hr perfusion with vehicle or compound at 2 µM. The mean number of action potentials (firing rate) was plotted in function of current step intensity.

Example 25—Compound Increases Afterhyperpolarization of Action Potentials

RAP1A controls the A-type potassium currents required for neuronal repolarization. Improving the A-type potassium current has therapeutic potential for treating epilepsy as it reduced excitability of neurons.

Action potentials (AP) after electrical stimulation of mouse brain slices were analysed (FIG. 14). The afterhyperpolarization of AP's of slices incubated with Compound 6 was increased indicating that the compound facilitates neuronal repolarization to a resting state.

The experiment was performed as described in Example 24.

Example 26—Testing of Novel Inhibitors of PDE6δ in the Calcium Dyshomeostasis Model of TAU.P301L Overexpressing Cells Compounds 1-7 were tested to lower the elevated cytosolic Ca' levels in the cell model of calcium dyshomeostasis (FIG. 1B) as described in Example 17. Efficacy (potency) of the compounds was determined by testing compounds at different concentrations, ranging from non-effective to effective concentrations, for their ability to reduce the level of cytosolic $Ca^{2+}$ bound Fura-2 (fluorescence intensity at 340 nm) relative to the amount of $Ca^{2+}$ unbound Fura-2 (fluorescence intensity at 380 nm).

Potencies of compounds of the present invention are shown in Table 4

TABLE 4

| Compound | Structure | $EC_{50}$ of lowering cytosolic $Ca^{2+}$ (µg/ml) |
|---|---|---|
| 1 | 5-fluoroindole-3-ethyl-NH-C(O)-isoxazole-5-CH2-(2,4-difluorophenyl) | 0.0010 |
| 2 | 5-fluoroindole-3-ethyl-NH-C(O)-isoxazole-5-CH2-(3,4-difluorophenyl) | 0.0014 |
| 3 | 5-fluoroindole-3-ethyl-NH-C(O)-isoxazole-5-CH2-(3,5-difluorophenyl) | 0.0024 |

TABLE 4-continued

| Compound | Structure | EC$_{50}$ of lowering cytosolic Ca$^{2+}$ (µg/ml) |
|---|---|---|
| 4 | (5-fluoroindol-3-yl)ethyl amide of 5-(4-fluorobenzyl)isoxazole-3-carboxamide | 0.0035 |
| 5 | (5-fluoroindol-3-yl)ethyl amide of 5-(2,3-difluorobenzyl)isoxazole-3-carboxamide | 0.0071 |
| 6 | (5-fluoroindol-3-yl)ethyl amide of 5-(2,5-difluorobenzyl)isoxazole-3-carboxamide | 0.0024 |
| 7 | (5-fluoroindol-3-yl)ethyl amide of 5-(2-fluorobenzyl)isoxazole-3-carboxamide | 0.0047 |

Example 27—Testing of the Novel Inhibitors of PDE6δ in the Ex-Vivo Model of KCL-Induced Calcium Influx for the Treatment of Epilepsy and Other Neurodegenerative Diseases Involving Calcium Dyshomeostasis Compounds 1-7 were tested at 10 µM for their ability to inhibit Ca$^{2+}$ influx in primary neurons (FIG. 5) as described in Example 21 (Table 5). Primary neurons treated with vehicle in which no compound was dissolved was used as a no-effect control. The percentage (%) inhibition of Ca$^{2+}$ influx relative to vehicle treated neurons was calculated.

TABLE 5

| Compound | % inhibition of cytosolic Ca$^{2+}$ influx |
|---|---|
| 1 | 43 |
| 2 | 48 |
| 3 | 42 |
| 4 | 39 |
| 5 | 42 |
| 6 | 43 |
| 7 | 56 |

The invention claimed is:
1. A method for treating epilepsy in a subject suffering from epilepsy comprising, administering to said subject in need thereof, a therapeutically effective amount of an inhibitor of PDE6δ, wherein said inhibitor of PDE6δ is a compound of formula (AA1); wherein the compound of formula (AA1) has the following structure:

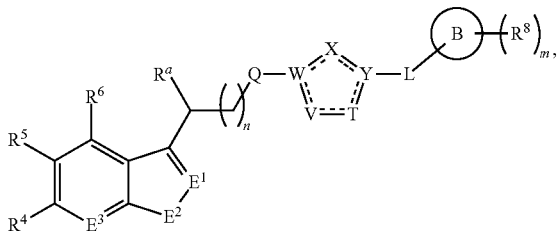

wherein, each dotted line individually represents an optional double bond, wherein maximally two dotted lines selected from the five dotted lines are a double bond;
$E^1$ is independently selected from $CR^1$ and N;
$E^2$ is independently selected from $NR^2$ and O;
$E^3$ is independently selected from $CR^3$ and N;
$R^a$ is hydrogen and $R^b$ is hydrogen; or $R^a$ and $R^b$ are taken together to form a substituted or unsubstituted 4, 5, 6, 7 or 8 membered ring containing one N atom;
Q is independently selected from $NR^b$—C(O); C(O); and C(O) NH;
each $R^1$, $R^3$, $R^4$, $R^5$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; $NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;
wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with Z;
wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or $S(O)_2$;
$R^2$ is selected from hydrogen; alkyl; alkenyl; and alkynyl;
n is selected from 0; 1 and 2;
L is independently selected from being not present; —O—; —NH—; —$NR^{10}$—; $C_{1-6}$alkylene; $C_{1-6}$alkenylene; and $C_{1-6}$alkynylene;
wherein each of said $C_{1-6}$alkylene, $C_{1-6}$alkenylene or $C_{1-6}$alkynylene optionally includes one or more heteroatoms, said heteroatoms being selected from the heteroatoms consisting of O, S and N, and wherein each of said $C_{1-6}$alkylene, $C_{1-6}$alkenylene or $C_{1-6}$alkynylene, is unsubstituted or substituted;
wherein a carbon atom or heteroatom of said $C_{1-6}$alkylene, $C_{1-6}$alkenylene or $C_{1-6}$alkynylene, can be oxidized to form a C═O, C═S, N═O, N═S, S—O or $S(O)_2$;
B represents a cyclic structure selected from cycloalkyl; cycloalkenyl; cycloalkynyl; aryl; and heterocycle;
m is selected from 0; 1; 2; 3; 4 and 5;
$R^8$ is independently selected from hydrogen; halogen; alkyl; alkenyl; alkynyl; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;
wherein said alkyl, alkenyl and alkynyl optionally includes one or more heteroatoms, said heteroatoms being selected from the atoms O, S and N;
wherein said alkyl, alkenyl and alkynyl can be unsubstituted or substituted with Z;
wherein a carbon atom or heteroatom of said alkyl, alkenyl and alkynyl, can be oxidized to form a C═O, C═S, N═O, N═S, S═O or $S(O)_2$;
each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; $NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;
each $Z^1$ is independently selected from hydrogen; alkyl; and Z;
each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;
wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl (ene), alkenyl (ene) or alkynyl (ene) moiety, said heteroatom selected from O, S and N;
wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or $S(O)_2$;
each $R^{101}$ is independently selected from hydrogen and $R^{10}$; each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;
wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl (ene), alkenyl (ene) and alkynyl (ene) moiety, said heteroatom selected from O, S and N;
wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or $S(O)_2$;
each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl (ene), alkenyl (ene) or alkynyl (ene) moiety, said heteroatom selected from O, S and N;

wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C═O, C═S, N═O, N═S, S═O or S(O)$_2$;

wherein $R^{12}$ and $R^{13}$ can be taken together in order to form a (5-, 6-, or 7-membered) heterocycle which can be unsubstituted or substituted and each of X, Y, T, W and V is independently selected from —CZ$^1$H—; —CZ$^1$—; —C—; —N—; NR$^{101}$; —O—; —S—; or —CO—; and form with the dotted lines one of the cycles having one of the structural formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa) or (XXIVa)

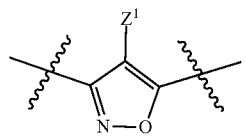
(Ia)

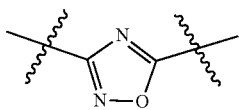
(IIa)

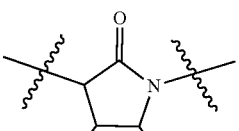
(IIIa)

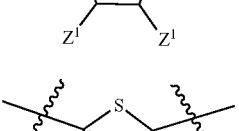
(IVa)

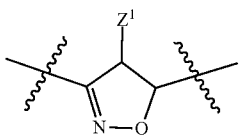
(Va)

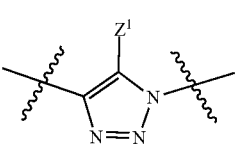
(VIa)

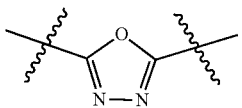
(VIIa)

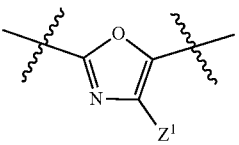
(VIIIa)

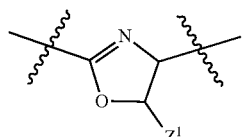
(IXa)

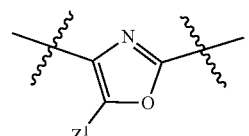
(Xa)

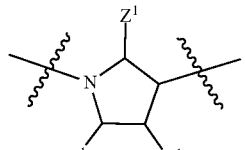
(XIa)

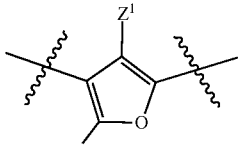
(XIIa)

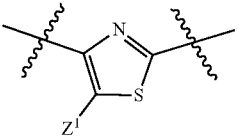
(XIIIa)

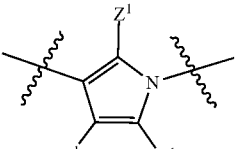
(XIVa)

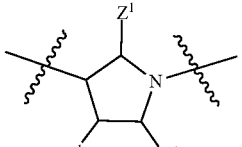
(XVa)

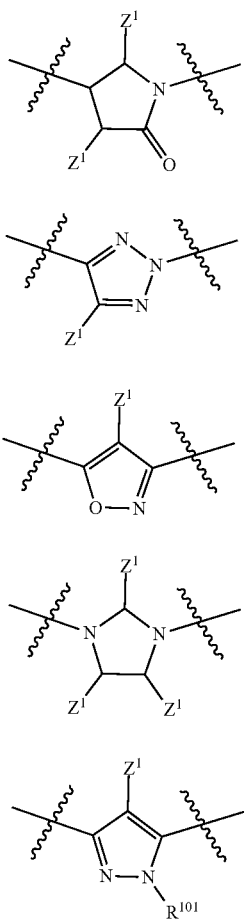

(XVIa)

(XVIIa)

(XVIIIa)

(XIXa)

(XXa)

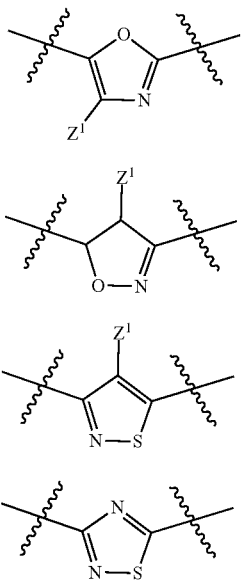

(XXIa)

(XXIIa)

(XXIIIa)

(XXIVa)

wherein the left side of the formula (Ia), (IIa), (IIIa), (IVa), (Va), (VIa), (VIIa), (VIIIa), (IXa), (Xa), (XIa), (XIIa), (XIIIa), (XIVa), (XVa), (XVIa), (XVIIa), (XVIIIa), (XIXa), (XXa), (XXIa), (XXIIa), (XXIIIa), (XXIVa) is attached to Q and the right side thereof is attached to L; and enantiomers, tautomers, solvates, hydrates, salts or prodrugs thereof.

2. A method for treating epilepsy in a subject suffering from epilepsy comprising, administering to said subject in need thereof, a therapeutically effective amount of an inhibitor of PDE6δ, wherein said inhibitor of PDE6δ is a compound selected from the group consisting of:

| Compound code | STRUCTURE |
|---|---|
| D1 | 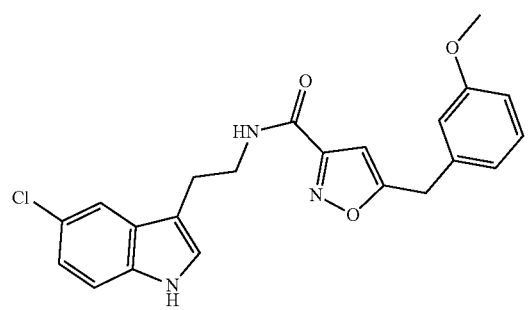 [SMILES: COc1cccc(Cc2cc(C(=O)NCCc3c[nH]c4ccc(Cl)cc34)no2)c1] |
| D2 | 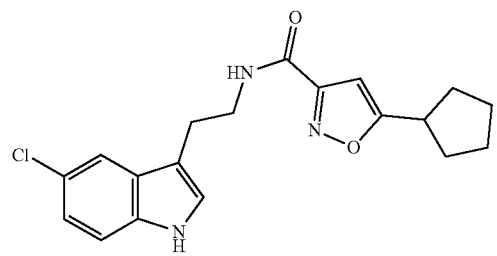 [SMILES: O=C(NCCc1c[nH]c2ccc(Cl)cc12)c1cc(C2CCCC2)on1] |

-continued
| Compound code | STRUCTURE |
|---|---|
| D3 | 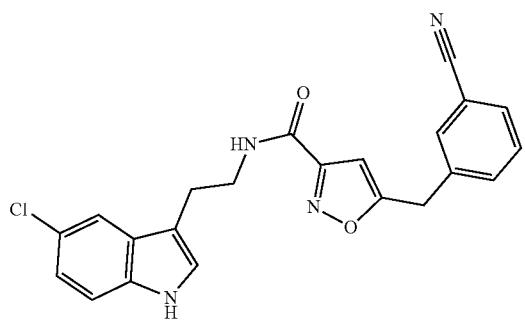 [SMILES: N#Cc1cccc(Cc2cc(C(=O)NCCc3c[nH]c4ccc(Cl)cc34)no2)c1] |
| D4 | 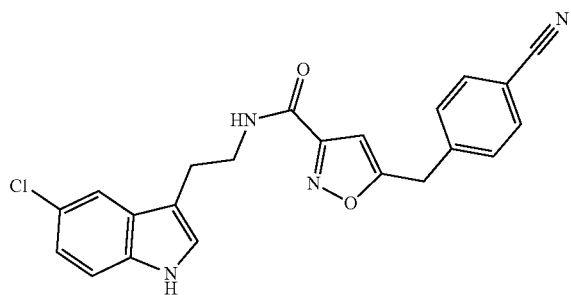 [SMILES: N#Cc1ccc(Cc2cc(C(=O)NCCc3c[nH]c4ccc(Cl)cc34)no2)cc1] |
| D5 | 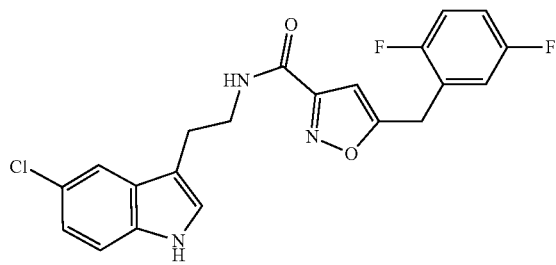 [SMILES: O=C(NCCc1c[nH]c2ccc(Cl)cc12)c1cc(Cc2cc(F)ccc2F)on1] |
| D6 | 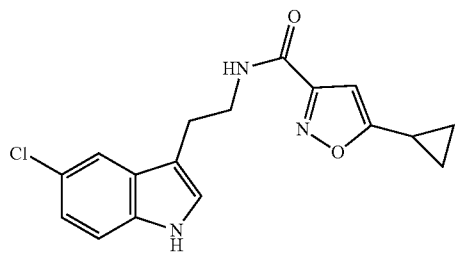 [SMILES: O=C(NCCc1c[nH]c2ccc(Cl)cc12)c1cc(C2CC2)on1] |
| D7 | 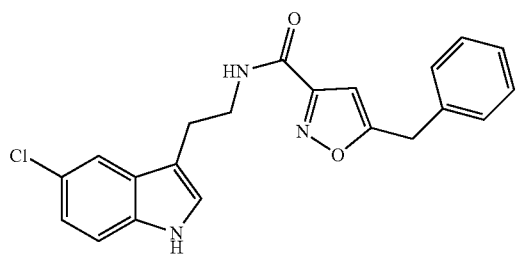 [SMILES: O=C(NCCc1c[nH]c2ccc(Cl)cc12)c1cc(Cc2ccccc2)on1] |

-continued
| Compound code | STRUCTURE |
|---|---|
| D8 | 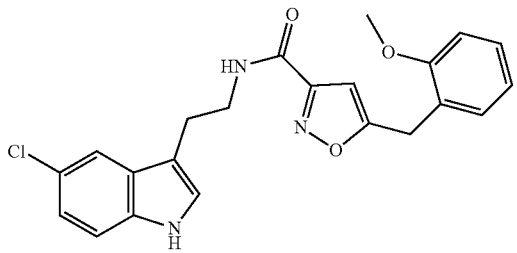 [SMILES: COc1ccccc1Cc1cc(C(=O)NCCc2c[nH]c3ccc(Cl)cc23)no1] |
| D9 | 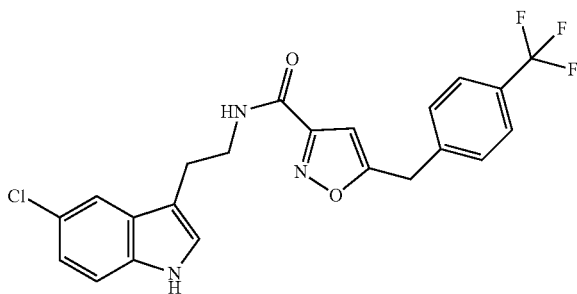 [SMILES: O=C(NCCc1c[nH]c2ccc(Cl)cc12)c1cc(Cc2ccc(C(F)(F)F)cc2)on1] |
| D10 | 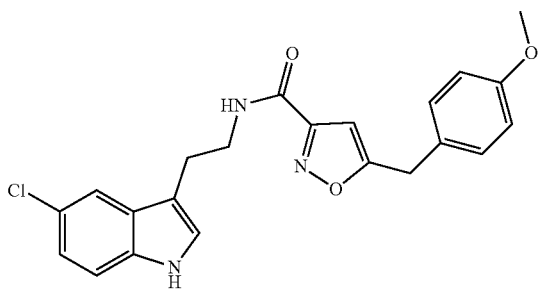 [SMILES: COc1ccc(Cc2cc(C(=O)NCCc3c[nH]c4ccc(Cl)cc34)no2)cc1] |
| D11 | 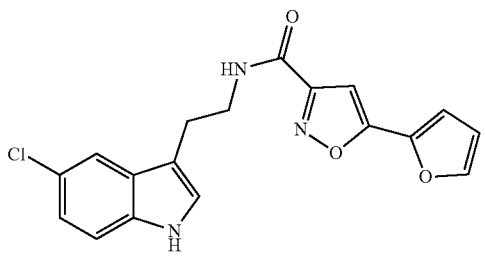 [SMILES: O=C(NCCc1c[nH]c2ccc(Cl)cc12)c1cc(-c2ccco2)on1] |
| D12 | 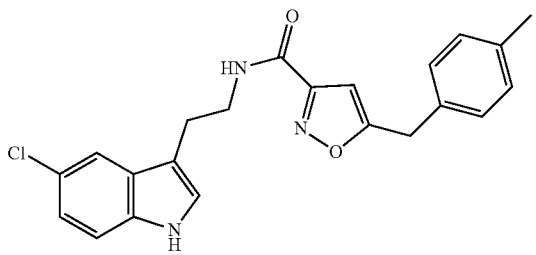 [SMILES: Cc1ccc(Cc2cc(C(=O)NCCc3c[nH]c4ccc(Cl)cc34)no2)cc1] |

-continued

| Compound code | STRUCTURE |
|---|---|
| D13 | 5-chloro-tryptamine linked via amide to isoxazole-3-carboxamide with 5-cyclohexyl substituent |
| D14 | 5-methyl-tryptamine linked via amide to isoxazole-3-carboxamide with 5-(3-fluorobenzyl) substituent |
| D15 | 5-chloro-tryptamine linked via amide to 1-methyl-pyrazole-3-carboxamide with 5-(2-thienyl) substituent |
| D16 | 5-chloro-tryptamine linked via amide to isoxazole-3-carboxamide with 5-(2-thienyl) substituent |
| D17 | 5-chloro-tryptamine linked via amide to isoxazole-3-carboxamide with 5-(2-furylmethyl) substituent |
| D19 | 5-chloro-tryptamine linked via amide to 1-methyl-pyrazole-3-carboxamide with 5-(2-furyl) substituent |

-continued
| Compound code | STRUCTURE |
|---|---|
| D20 | 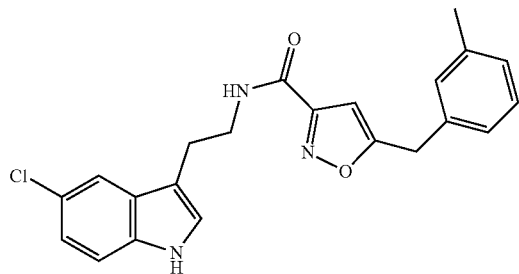 [SMILES: Cc1cccc(Cc2cc(C(=O)NCCc3c[nH]c4ccc(Cl)cc34)no2)c1] |
| D21 | 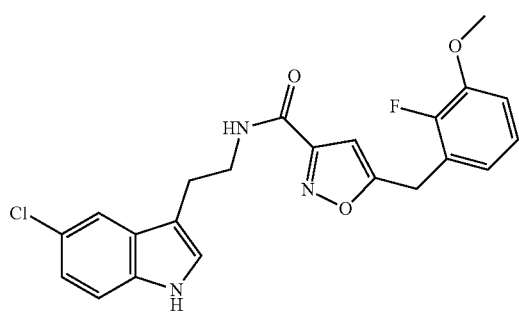 [SMILES: COc1cccc(Cc2cc(C(=O)NCCc3c[nH]c4ccc(Cl)cc34)no2)c1F] |
| D22 | 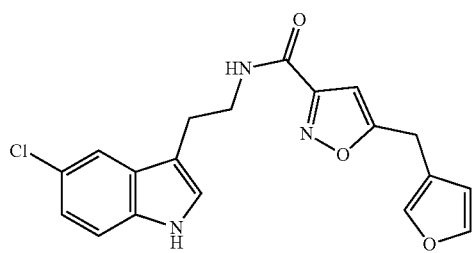 [SMILES: O=C(NCCc1c[nH]c2ccc(Cl)cc12)c1cc(Cc2ccoc2)on1] |
| D23 | 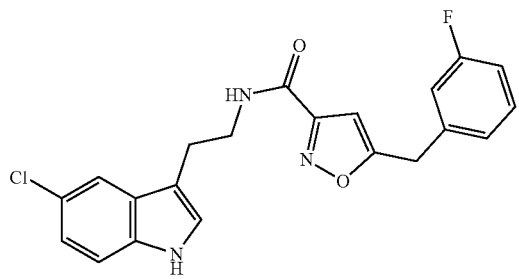 [SMILES: O=C(NCCc1c[nH]c2ccc(Cl)cc12)c1cc(Cc2cccc(F)c2)on1] |
| D24 | 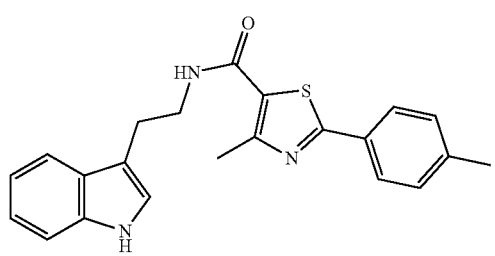 [SMILES: Cc1ccc(-c2nc(C)c(C(=O)NCCc3c[nH]c4ccccc34)s2)cc1] |

-continued
| Compound code | STRUCTURE |
|---|---|
| D25 | 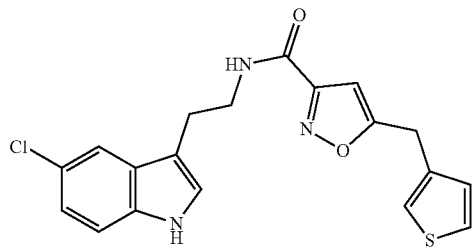 |
| D26 | 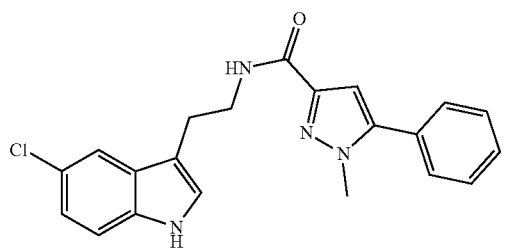 [SMILES: Cn1nc(C(=O)NCCc2c[nH]c3ccc(Cl)cc23)cc1-c1ccccc1] |
| D27 | 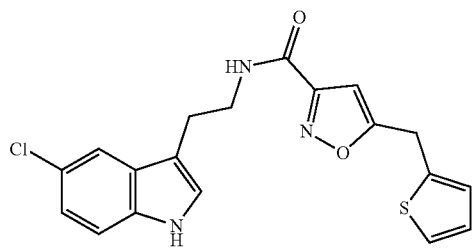 [SMILES: O=C(NCCc1c[nH]c2ccc(Cl)cc12)c1cc(Cc2cccs2)on1] |
| D28 | 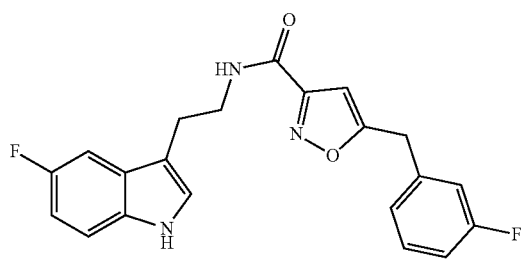 [SMILES: O=C(NCCc1c[nH]c2ccc(F)cc12)c1cc(Cc2cccc(F)c2)on1] |
| D29 | 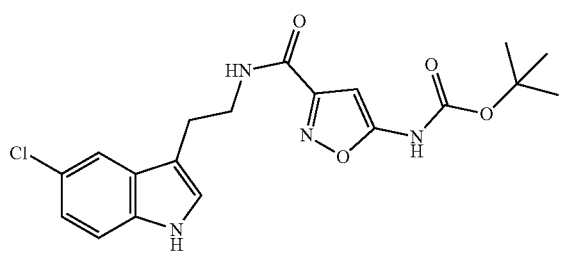 [SMILES: CC(C)(C)OC(=O)Nc1cc(C(=O)NCCc2c[nH]c3ccc(Cl)cc23)no1] |

-continued
| Compound code | STRUCTURE |
|---|---|
D30
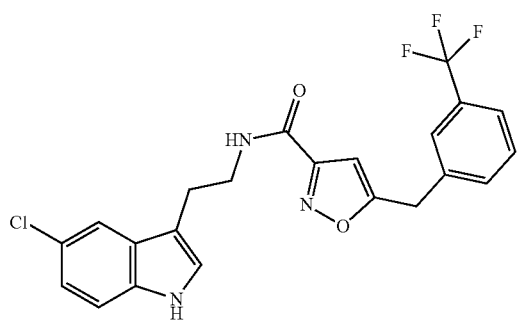 [SMILES: O=C(NCCc1c[nH]c2ccc(Cl)cc12)c1cc(Cc2cccc(C(F)(F)F)c2)on1]
D31
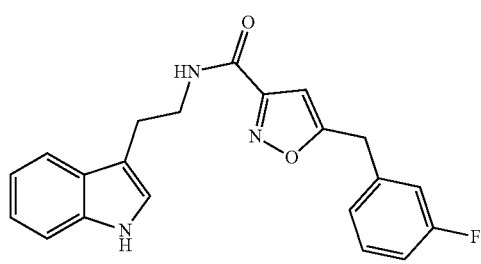 [SMILES: O=C(NCCc1c[nH]c2ccccc12)c1cc(Cc2cccc(F)c2)on1]
D32
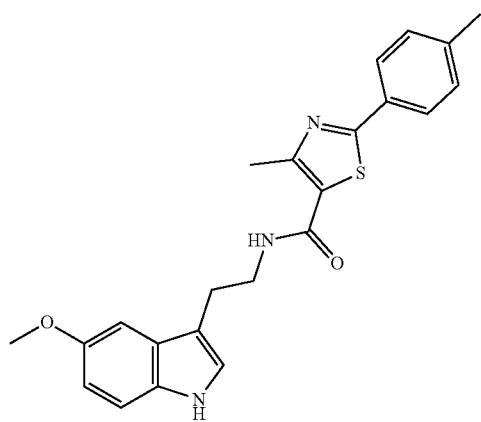
D33
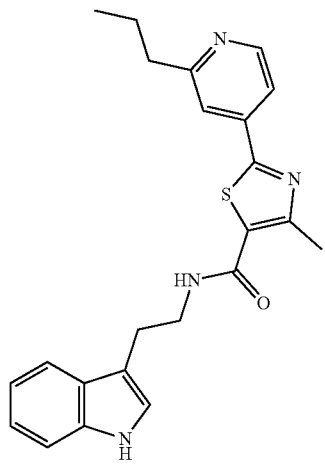 [SMILES: CCCc1cc(-c2nc(C)c(C(=O)NCCc3c[nH]c4ccccc34)s2)ccn1]

-continued
| Compound code | STRUCTURE |
|---|---|
| D34 | 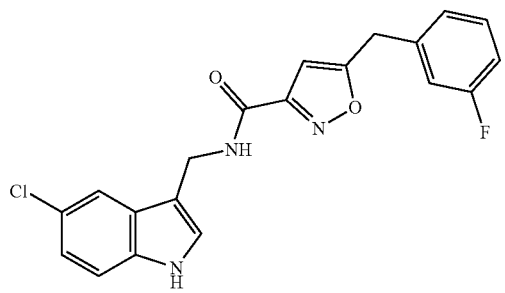 [SMILES: O=C(NCc1c[nH]c2ccc(Cl)cc12)c1cc(Cc2cccc(F)c2)on1] |
| D35 | 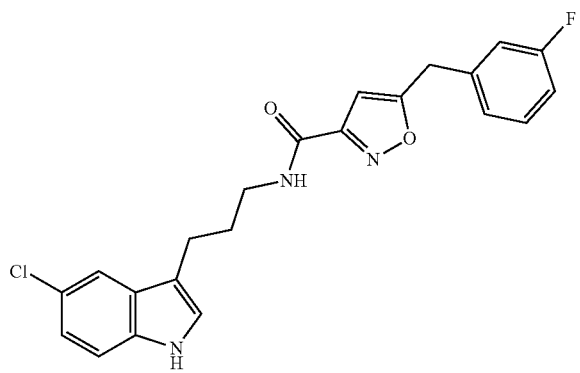 [SMILES: O=C(NCCCc1c[nH]c2ccc(Cl)cc12)c1cc(Cc2cccc(F)c2)on1] |
| D36 | 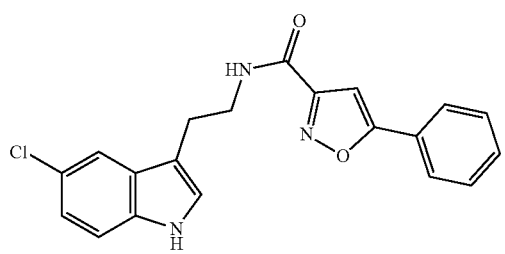 [SMILES: O=C(NCCc1c[nH]c2ccc(Cl)cc12)c1cc(-c2ccccc2)on1] |
| D37 | 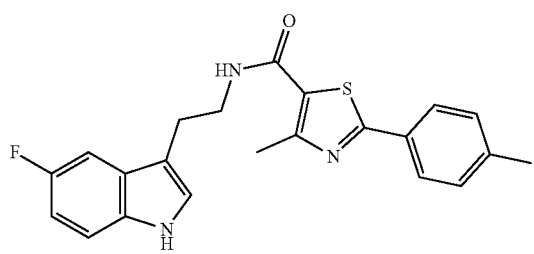 [SMILES: Cc1ccc(-c2nc(C)c(C(=O)NCCc3c[nH]c4ccc(F)cc34)s2)cc1] |
| D38 | 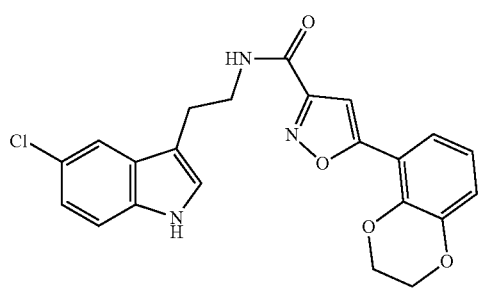 [SMILES: O=C(NCCc1c[nH]c2ccc(Cl)cc12)c1cc(-c2cccc3c2OCCO3)on1] |

| Compound code | STRUCTURE |
|---|---|
| D39 | 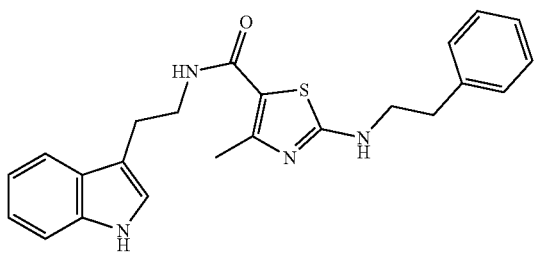 [SMILES: Cc1nc(NCCc2ccccc2)sc1C(=O)NCCc1c[nH]c2ccccc12] |
| D40 | 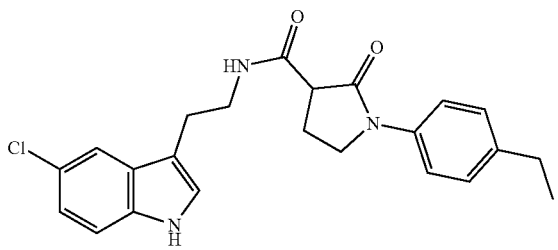 [SMILES: CCc1ccc(N2CCC(C(=O)NCCc3c[nH]c4ccc(Cl)cc34)C2=O)cc1] |
| D41 | 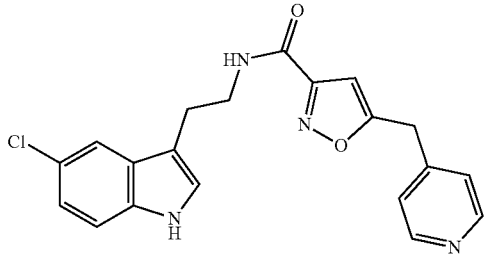 [SMILES: O=C(NCCc1c[nH]c2ccc(Cl)cc12)c1cc(Cc2ccncc2)on1] |
| D42 | 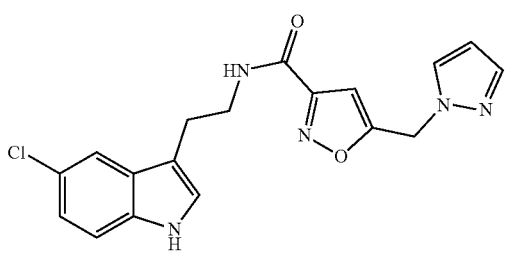 [SMILES: O=C(NCCc1c[nH]c2ccc(Cl)cc12)c1cc(Cn2cccn2)on1] |
| D43 | 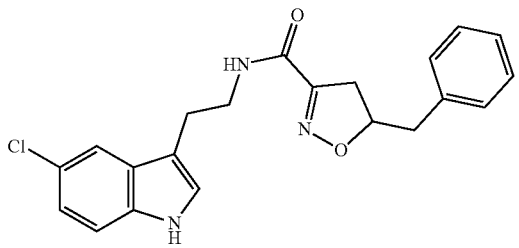 [SMILES: O=C(NCCc1c[nH]c2ccc(Cl)cc12)C1=NOC(Cc2ccccc2)C1] |
| D44 | 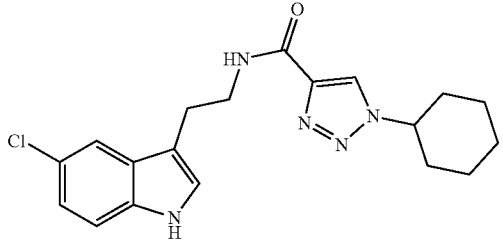 [SMILES: O=C(NCCc1c[nH]c2ccc(Cl)cc12)c1cn(C2CCCCC2)nn1] |

| Compound code | STRUCTURE |
|---|---|
| D45 | 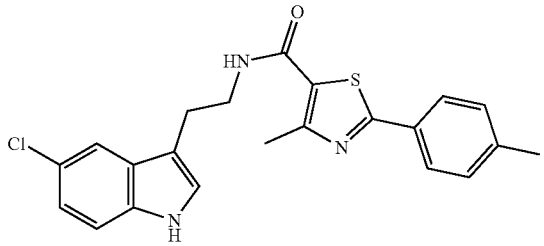 [SMILES: Cc1ccc(-c2nc(C)c(C(=O)NCCc3c[nH]c4ccc(Cl)cc34)s2)cc1] |
| D46 | 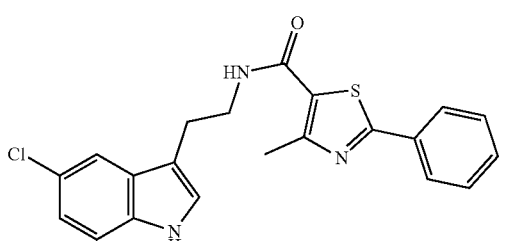 |
| D47 | 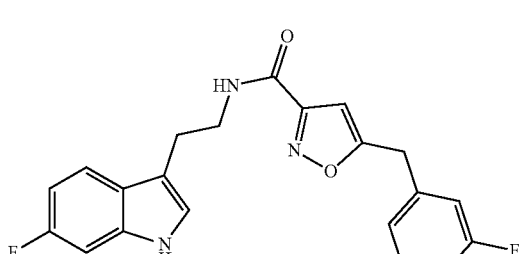 |
| D48 | 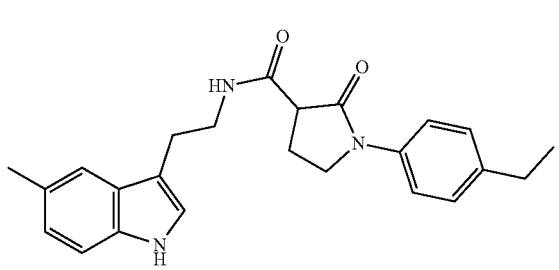 [SMILES: CCc1ccc(N2CCC(C(=O)NCCc3c[nH]c4ccc(C)cc34)C2=O)cc1] |
| D49 | 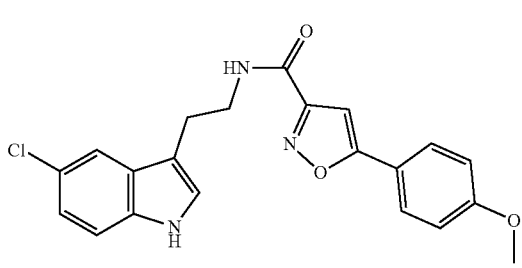 [SMILES: COc1ccc(-c2cc(C(=O)NCCc3c[nH]c4ccc(Cl)cc34)no2)cc1] |
| D50 | 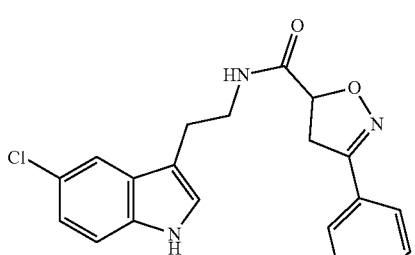 |

-continued

| Compound code | STRUCTURE |
|---|---|
| D51 | (5-chloro-1-methyl-1H-indol-3-yl)ethyl 5-(3-fluorobenzyl)isoxazole-3-carboxamide |
| D52 | N-(2-(5-chloro-1H-indol-3-yl)ethyl)-5-phenyl-1,3,4-oxadiazole-2-carboxamide |
| D53 | N-(2-(5-chloro-1H-indol-3-yl)ethyl)-5-phenyloxazole-2-carboxamide |
| D54 | N-(2-(5-chloro-1H-indol-3-yl)ethyl)-1-benzyl-1H-1,2,3-triazole-4-carboxamide |
| D55 | N-(2-(5-chloro-1H-indol-3-yl)ethyl)-5-phenyl-4,5-dihydroisoxazole-3-carboxamide |
| D56 | N-(2-(5-chloro-1H-indol-3-yl)ethyl)-5-(4-chlorophenyl)isoxazole-3-carboxamide |

-continued
| Compound code | STRUCTURE |
|---|---|
| D57 | 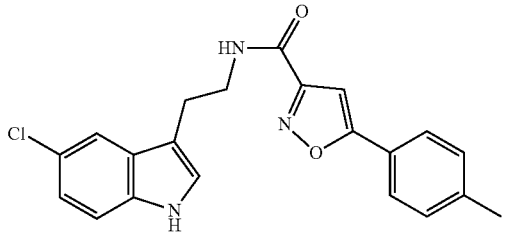 [SMILES: Cc1ccc(-c2cc(C(=O)NCCc3c[nH]c4ccc(Cl)cc34)no2)cc1] |
| D58 | 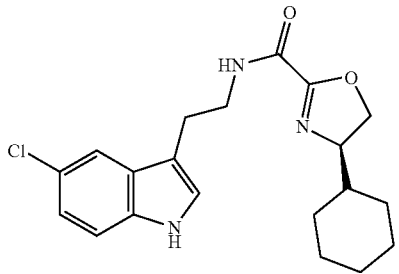 [SMILES: O=C(NCCc1c[nH]c2ccc(Cl)cc12)C1=N[C@H](C2CCCCC2)CO1] |
| D59 | 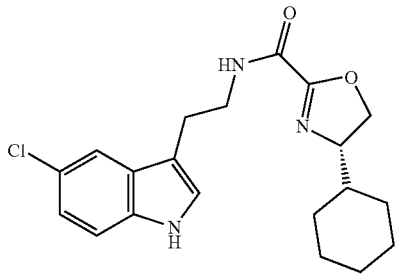 [SMILES: O=C(NCCc1c[nH]c2ccc(Cl)cc12)C1=N[C@@H](C2CCCCC2)CO1] |
| D60 | 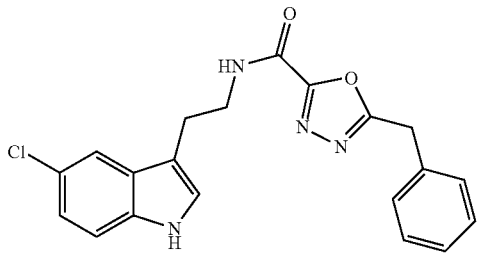 [SMILES: O=C(NCCc1c[nH]c2ccc(Cl)cc12)c1nnc(Cc2ccccc2)o1] |
| D61 | 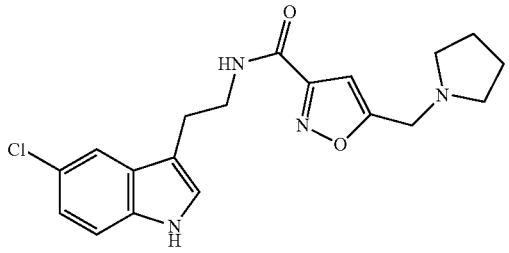 [SMILES: O=C(NCCc1c[nH]c2ccc(Cl)cc12)c1cc(CN2CCCC2)on1] |
| D62 | 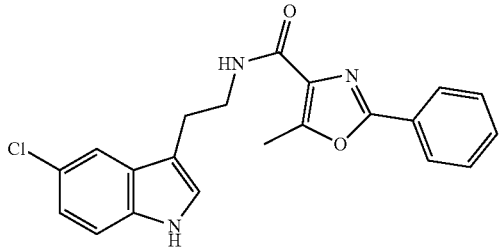 [SMILES: Cc1oc(-c2ccccc2)nc1C(=O)NCCc1c[nH]c2ccc(Cl)cc12] |

-continued
| Compound code | STRUCTURE |
|---|---|
| D63 | 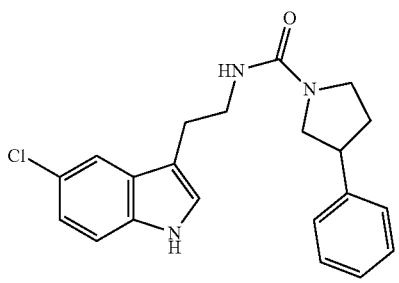 [SMILES: O=C(NCCc1c[nH]c2ccc(Cl)cc12)N1CCC(c2ccccc2)C1] |
| D64 | 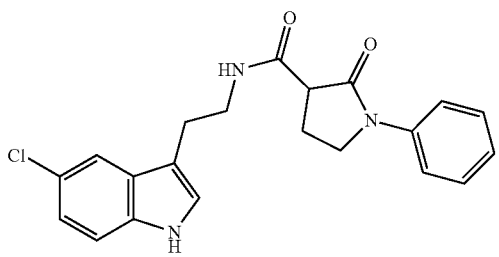 [SMILES: O=C(NCCc1c[nH]c2ccc(Cl)cc12)C1CCN(c2ccccc2)C1=O] |
| D65 | 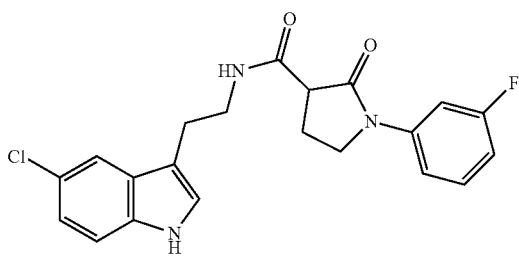 [SMILES: O=C(NCCc1c[nH]c2ccc(Cl)cc12)C1CCN(c2cccc(F)c2)C1=O] |
| D66 | 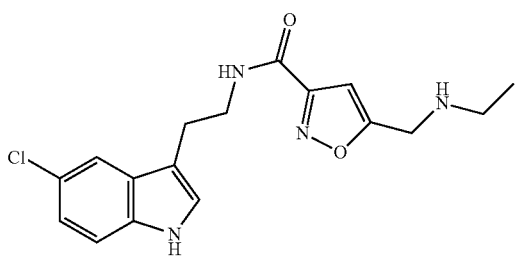 [SMILES: CCNCc1cc(C(=O)NCCc2c[nH]c3ccc(Cl)cc23)no1] |
| D67 | 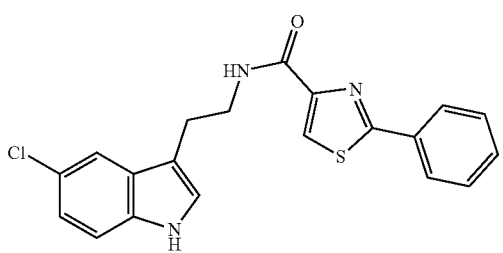 [SMILES: O=C(NCCc1c[nH]c2ccc(Cl)cc12)c1csc(-c2ccccc2)n1] |

-continued
| Compound code | STRUCTURE |
|---|---|
| D68 | 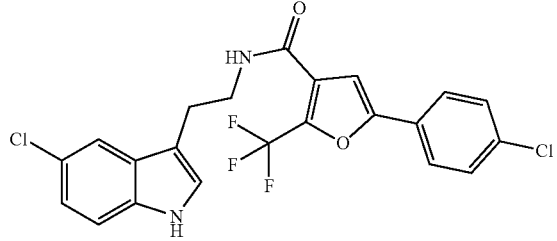 [SMILES: O=C(NCCc1c[nH]c2ccc(Cl)cc12)c1cc(-c2ccc(Cl)cc2)oc1C(F)(F)F] |
| D69 | 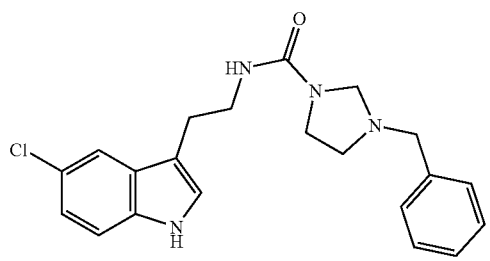 [SMILES: O=C(NCCc1c[nH]c2ccc(Cl)cc12)N1CCN(Cc2ccccc2)C1] |
| D70 | 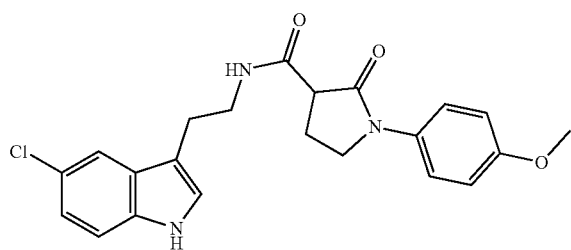 [SMILES: COc1ccc(N2CCC(C(=O)NCCc3c[nH]c4ccc(Cl)cc34)C2=O)cc1] |
| D71 | 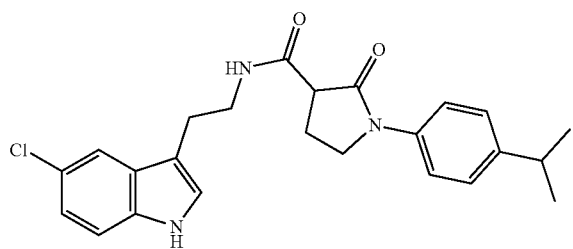 [SMILES: CC(C)c1ccc(N2CCC(C(=O)NCCc3c[nH]c4ccc(Cl)cc34)C2=O)cc1] |
| D72 | 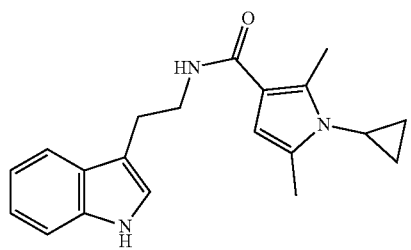 [SMILES: Cc1cc(C(=O)NCCc2c[nH]c3ccccc23)c(C)n1C1CC1] |
| D73 | 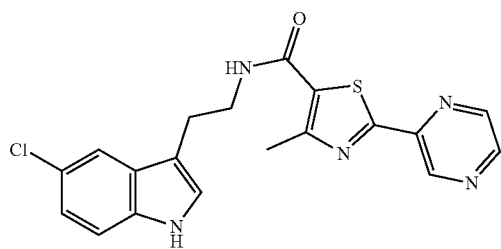 [SMILES: Cc1nc(-c2cnccn2)sc1C(=O)NCCc1c[nH]c2ccc(Cl)cc12] |

-continued
| Compound code | STRUCTURE |
|---|---|
| D74 | 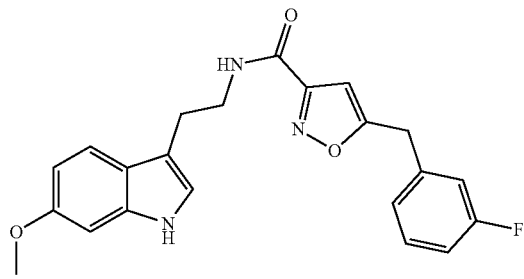 [SMILES: COc1ccc2c(CCNC(=O)c3cc(Cc4cccc(F)c4)on3)c[nH]c2c1] |
| D75 | 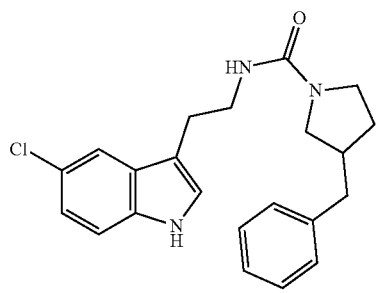 [SMILES: O=C(NCCc1c[nH]c2ccc(Cl)cc12)N1CCC(Cc2ccccc2)C1] |
| D76 | 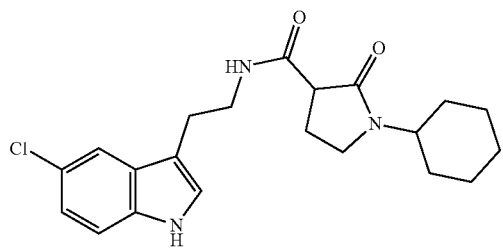 [SMILES: O=C(NCCc1c[nH]c2ccc(Cl)cc12)C1CCN(C2CCCCC2)C1=O] |
| D77 | 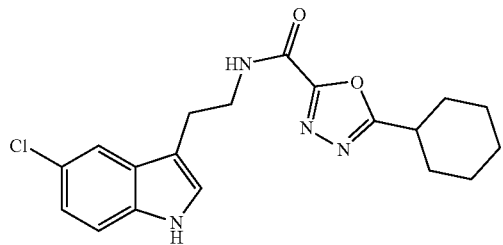 [SMILES: O=C(NCCc1c[nH]c2ccc(Cl)cc12)c1nnc(C2CCCCC2)o1] |
| D78 | 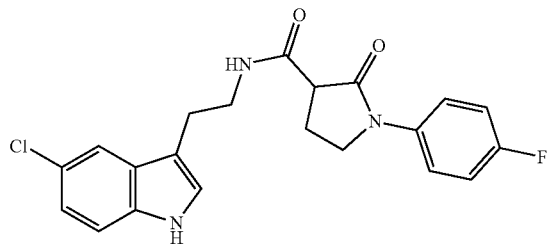 [SMILES: O=C(NCCc1c[nH]c2ccc(Cl)cc12)C1CCN(c2ccc(F)cc2)C1=O] |

-continued
| Compound code | STRUCTURE |
|---|---|
| D79 | 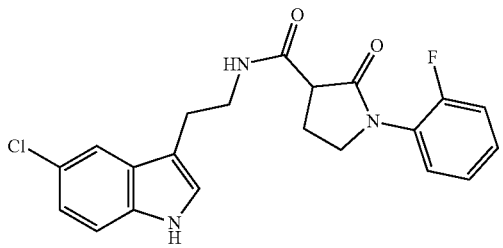 [SMILES: O=C(NCCc1c[nH]c2ccc(Cl)cc12)C1CCN(c2ccccc2F)C1=O] |
| D80 | 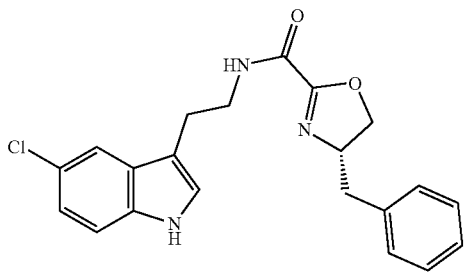 [SMILES: O=C(NCCc1c[nH]c2ccc(Cl)cc12)C1=N[C@@H](Cc2ccccc2)CO1] |
| D81 | 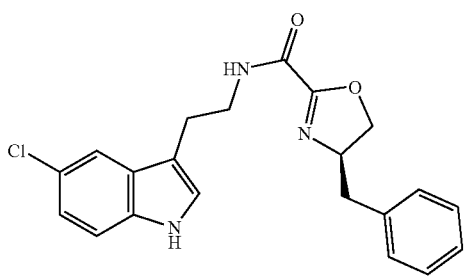 [SMILES: O=C(NCCc1c[nH]c2ccc(Cl)cc12)C1=N[C@H](Cc2ccccc2)CO1] |
| D82 | 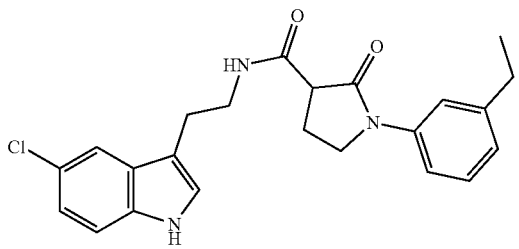 [SMILES: CCc1cccc(N2CCC(C(=O)NCCc3c[nH]c4ccc(Cl)cc34)C2=O)c1] |
| D83 | 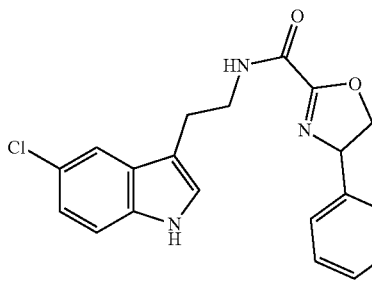 |

-continued
| Compound code | STRUCTURE |
|---|---|
| D84 | 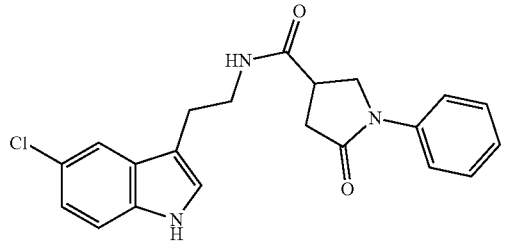 [SMILES: O=C(NCCc1c[nH]c2ccc(Cl)cc12)C1CC(=O)N(c2ccccc2)C1] |
| D85 | 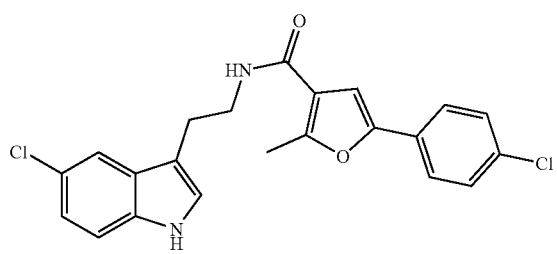 [SMILES: Cc1oc(-c2ccc(Cl)cc2)cc1C(=O)NCCc1c[nH]c2ccc(Cl)cc12] |
| D86 | 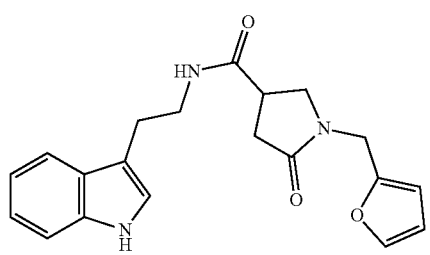 [SMILES: O=C(NCCc1c[nH]c2ccccc12)C1CC(=O)N(Cc2ccco2)C1] |
| D87 | 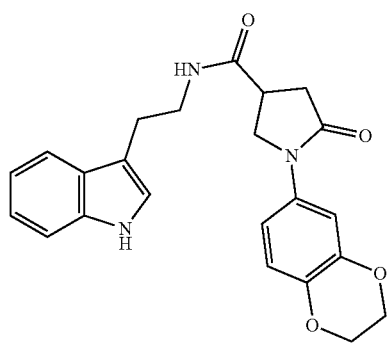 [SMILES: O=C(NCCc1c[nH]c2ccccc12)C1CC(=O)N(c2ccc3c(c2)OCCO3)C1] |
| D88 | 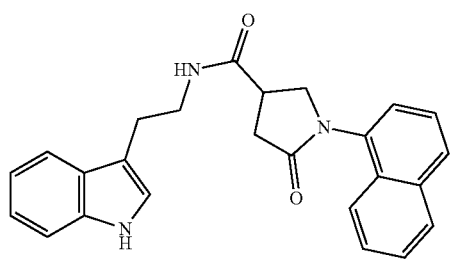 [SMILES: O=C(NCCc1c[nH]c2ccccc12)C1CC(=O)N(c2cccc3ccccc23)C1] |

| Compound code | STRUCTURE |
|---|---|
| D89 | ![structure] |
| D90 | ![structure] |
| D91 | ![structure] |
| D92 | ![structure] |
| D93 | ![structure] |
| D94 | ![structure] |

-continued
| Compound code | STRUCTURE |
|---|---|
| D95 | 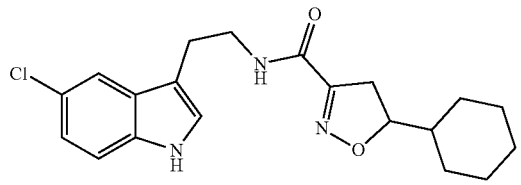 [SMILES: O=C(NCCc1c[nH]c2ccc(Cl)cc12)C1=NOC(C2CCCCC2)C1] |
| D96 | 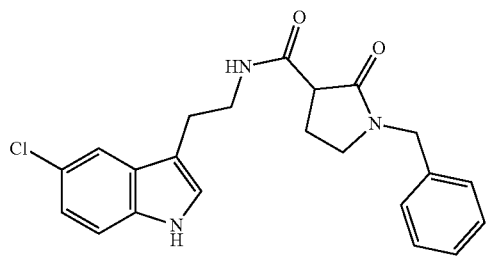 [SMILES: O=C(NCCc1c[nH]c2ccc(Cl)cc12)C1CCN(Cc2ccccc2)C1=O] |
| D97 | 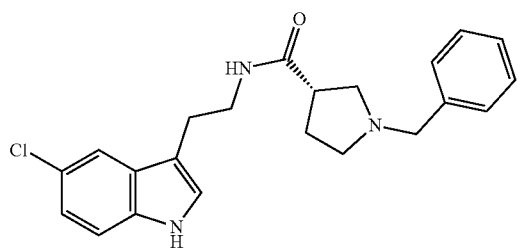 [SMILES: O=C(NCCc1c[nH]c2ccc(Cl)cc12)[C@H]1CCN(Cc2ccccc2)C1] |
| D98 | 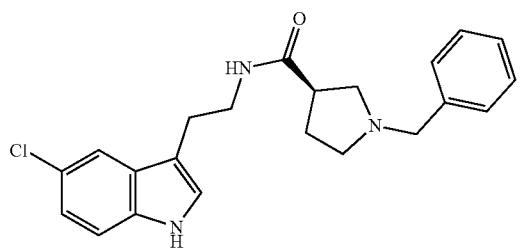 [SMILES: O=C(NCCc1c[nH]c2ccc(Cl)cc12)[C@@H]1CCN(Cc2ccccc2)C1] |
| D99 | 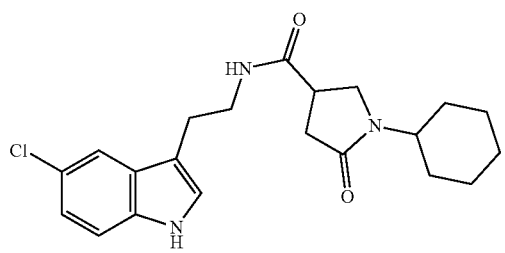 [SMILES: O=C(NCCc1c[nH]c2ccc(Cl)cc12)C1CC(=O)N(C2CCCCC2)C1] |
| D100 | 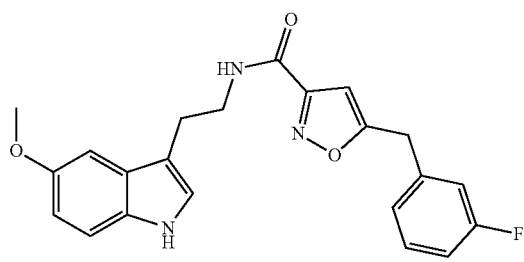 [SMILES: COc1ccc2[nH]cc(CCNC(=O)c3cc(Cc4cccc(F)c4)on3)c2c1] |

-continued
| Compound code | STRUCTURE |
|---|---|
| D101 | 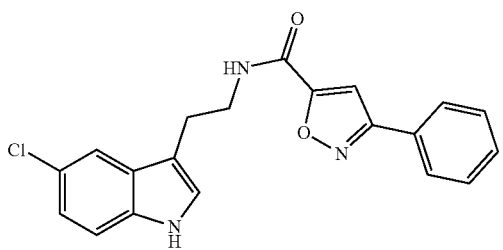 [SMILES: O=C(NCCc1c[nH]c2ccc(Cl)cc12)c1cc(-c2ccccc2)no1] |
| D102 | 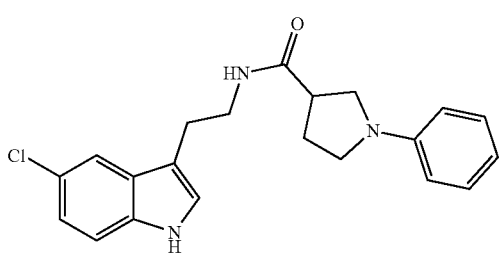 [SMILES: O=C(NCCc1c[nH]c2ccc(Cl)cc12)C1CCN(c2ccccc2)C1] |
| D103 | 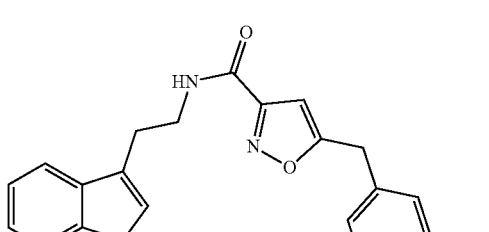 |
| D104 | 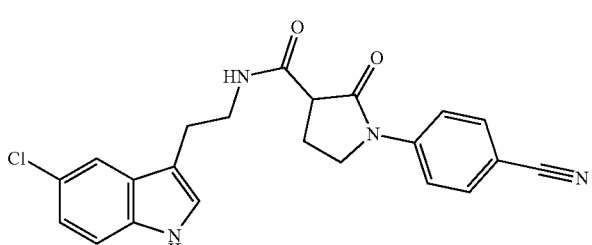 |
| D105 | 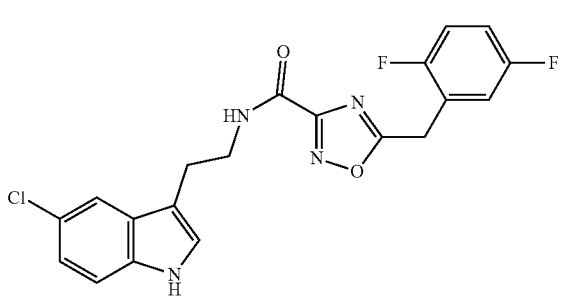 [SMILES: O=C(NCCc1c[nH]c2ccc(Cl)cc12)c1noc(Cc2cc(F)ccc2F)n1] |

-continued
| Compound code | STRUCTURE |
|---|---|
| D106 | 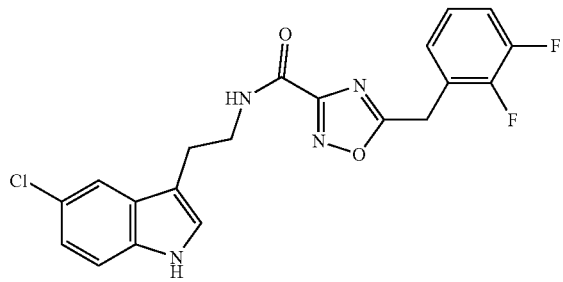 [SMILES: O=C(NCCc1c[nH]c2ccc(Cl)cc12)c1noc(Cc2cccc(F)c2F)n1] |
| D107 | 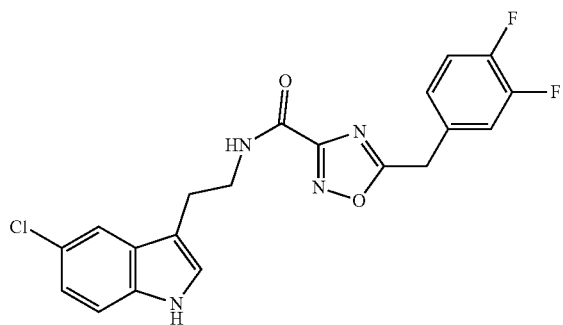 [SMILES: O=C(NCCc1c[nH]c2ccc(Cl)cc12)c1noc(Cc2ccc(F)c(F)c2)n1] |
| D108 | 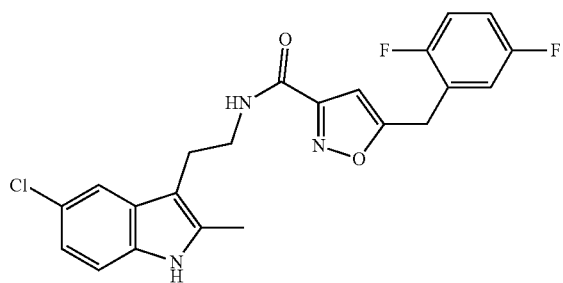 [SMILES: Cc1[nH]c2ccc(Cl)cc2c1CCNC(=O)c1cc(Cc2cc(F)ccc2F)on1] |
| D109 | 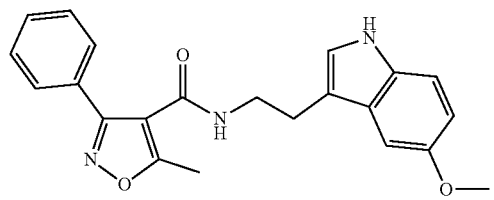 [SMILES: COc1ccc2[nH]cc(CCNC(=O)c3c(-c4ccccc4)noc3C)c2c1] |
| D110 | 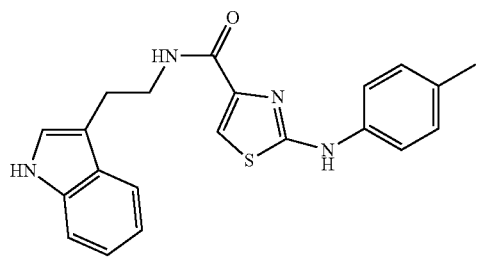 [SMILES: Cc1ccc(Nc2nc(C(=O)NCCc3c[nH]c4ccccc34)cs2)cc1] |

-continued
| Compound code | STRUCTURE |
|---|---|
| D111 | 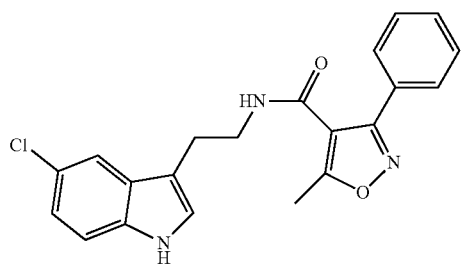 [SMILES: Cc1onc(-c2ccccc2)c1C(=O)NCCc1c[nH]c2ccc(Cl)cc12] |
| D112 | 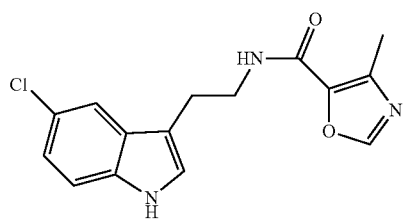 [SMILES: Cc1ncoc1C(=O)NCCc1c[nH]c2ccc(Cl)cc12] |
| D113 | 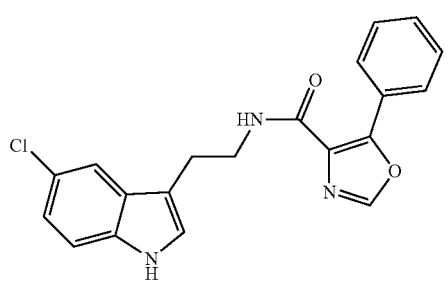 [SMILES: O=C(NCCc1c[nH]c2ccc(Cl)cc12)c1ncoc1-c1ccccc1] |
| D114 | 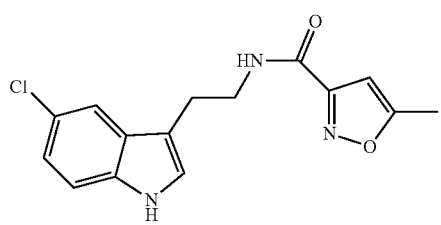 [SMILES: Cc1cc(C(=O)NCCc2c[nH]c3ccc(Cl)cc23)no1] |
| D115 | 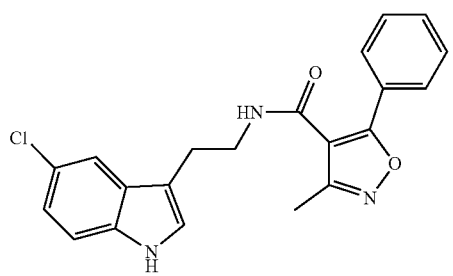 [SMILES: Cc1noc(-c2ccccc2)c1C(=O)NCCc1c[nH]c2ccc(Cl)cc12] |
| D116 | 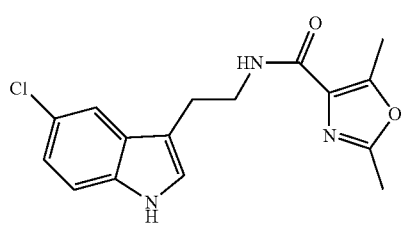 [SMILES: Cc1nc(C(=O)NCCc2c[nH]c3ccc(Cl)cc23)c(C)o1] |

-continued
| Compound code | STRUCTURE |
|---|---|
| D117 | 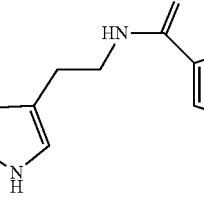 |
| D118 | 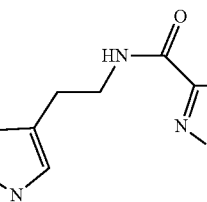 |
| D119 | 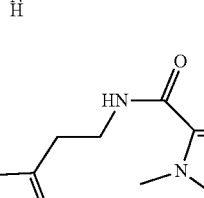 |
| D120 | 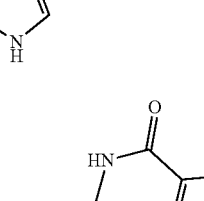 |
| D121 | 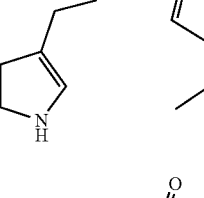 |
| D122 | 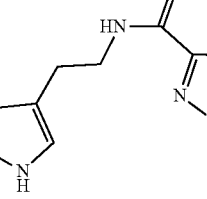 |

-continued
| Compound code | STRUCTURE |
|---|---|
| D123 | 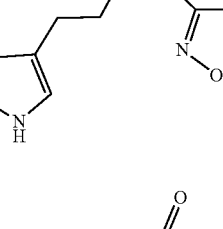 |
| D124 | 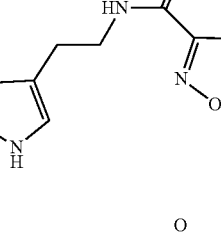 |
| D125 | 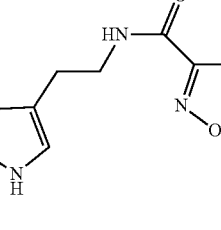 |
| D126 | 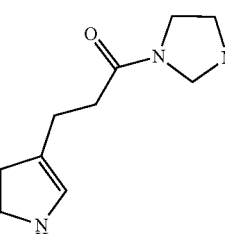 |
| D127 | 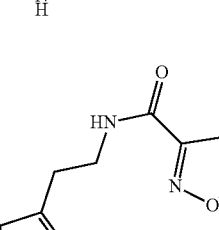 |
| D128 | 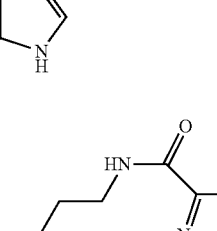 |

-continued

| Compound code | STRUCTURE |
|---|---|
| D129 | 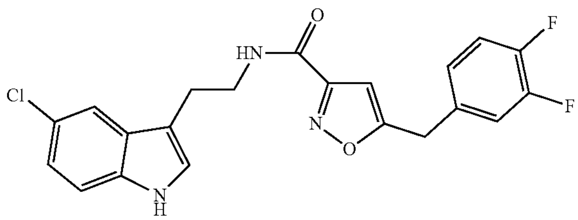 [SMILES: O=C(NCCc1c[nH]c2ccc(Cl)cc12)c1cc(Cc2ccc(F)c(F)c2)on1] |
| D130 | 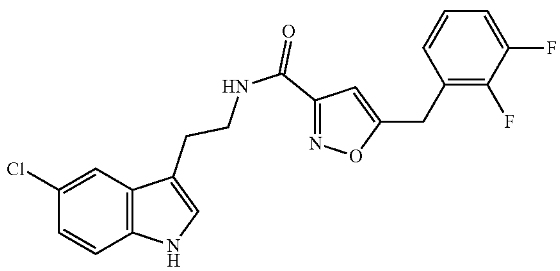 [SMILES: O=C(NCCc1c[nH]c2ccc(Cl)cc12)c1cc(Cc2cccc(F)c2F)on1] |
| D131 | 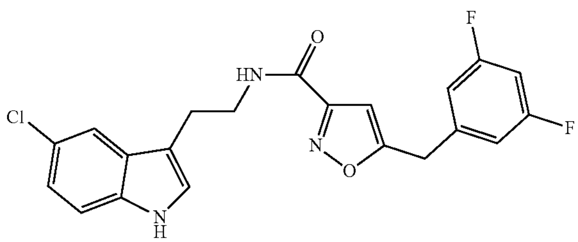 [SMILES: O=C(NCCc1c[nH]c2ccc(Cl)cc12)c1cc(Cc2cc(F)cc(F)c2)on1] |
| D132 | 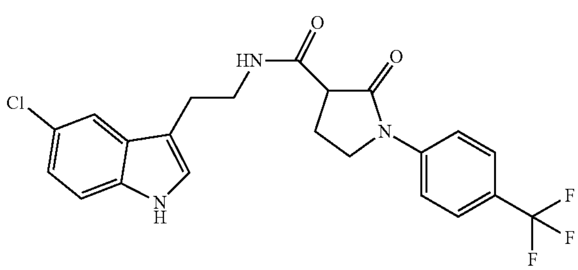 [SMILES: O=C(NCCc1c[nH]c2ccc(Cl)cc12)C1CCN(c2ccc(C(F)(F)F)cc2)C1=O] |
| D133 | 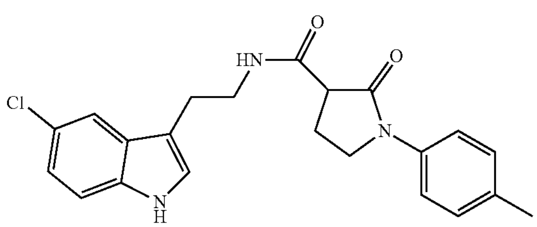 [SMILES: Cc1ccc(N2CCC(C(=O)NCCc3c[nH]c4ccc(Cl)cc34)C2=O)cc1] |
| D134 | 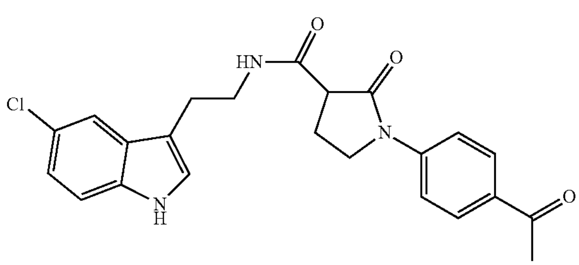 [SMILES: CC(=O)c1ccc(N2CCC(C(=O)NCCc3c[nH]c4ccc(Cl)cc34)C2=O)cc1] |

| Compound code | STRUCTURE |
|---|---|
| D135 | 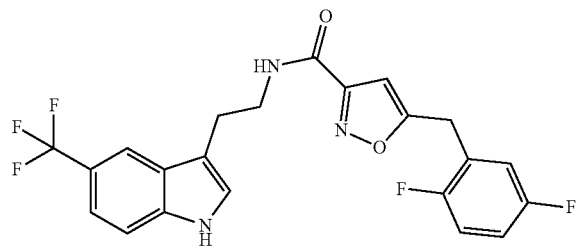 [SMILES: O=C(NCCc1c[nH]c2ccc(C(F)(F)F)cc12)c1cc(Cc2cc(F)ccc2F)on1] |
| D136 | 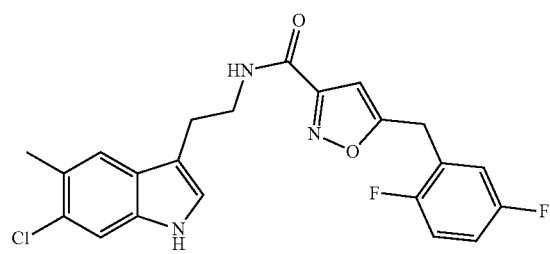 [SMILES: Cc1cc2c(CCNC(=O)c3cc(Cc4cc(F)ccc4F)on3)c[nH]c2cc1Cl] |
| D137 | 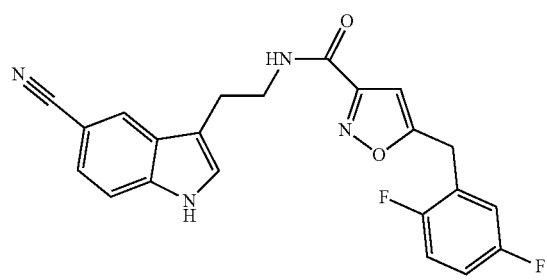 [SMILES: N#Cc1ccc2[nH]cc(CCNC(=O)c3cc(Cc4cc(F)ccc4F)on3)c2c1] |
| D138 | 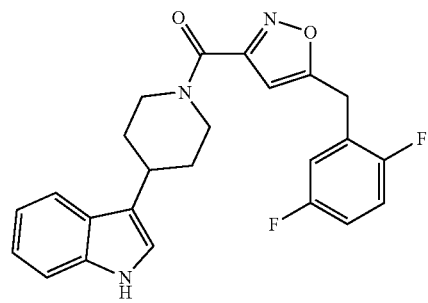 [SMILES: O=C(c1cc(Cc2cc(F)ccc2F)on1)N1CCC(c2c[nH]c3ccccc23)CC1] |
| D139 | 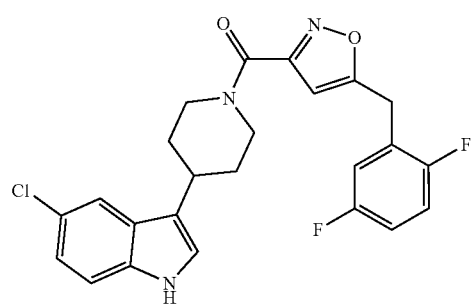 [SMILES: O=C(c1cc(Cc2cc(F)ccc2F)on1)N1CCC(c2c[nH]c3ccc(Cl)cc23)CC1] |

-continued
| Compound code | STRUCTURE |
|---|---|
| D140 | 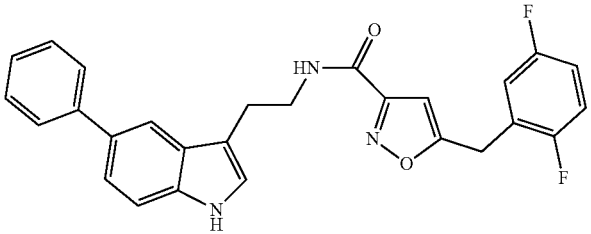 [SMILES: O=C(NCCc1c[nH]c2ccc(-c3ccccc3)cc12)c1cc(Cc2cc(F)ccc2F)on1] |
| D141 | 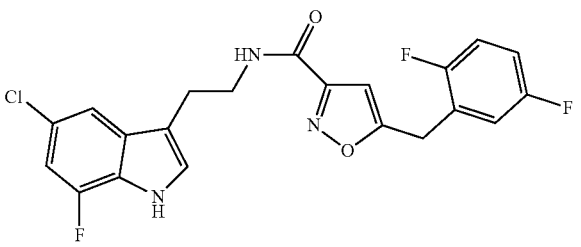 [SMILES: O=C(NCCc1c[nH]c2c(F)cc(Cl)cc12)c1cc(Cc2cc(F)ccc2F)on1] |
| D142 | 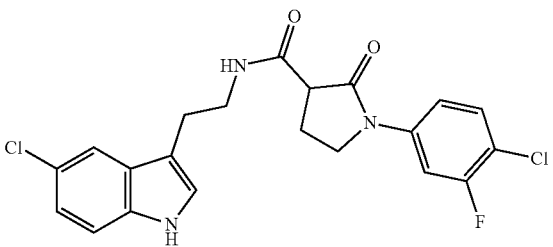 [SMILES: O=C(NCCc1c[nH]c2ccc(Cl)cc12)C1CCN(c2ccc(Cl)c(F)c2)C1=O] |
| D143 | 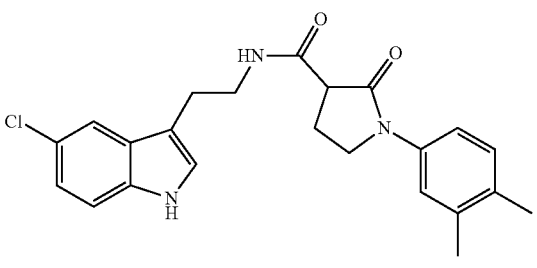 [SMILES: Cc1ccc(N2CCC(C(=O)NCCc3c[nH]c4ccc(Cl)cc34)C2=O)cc1C] |
| D144 | 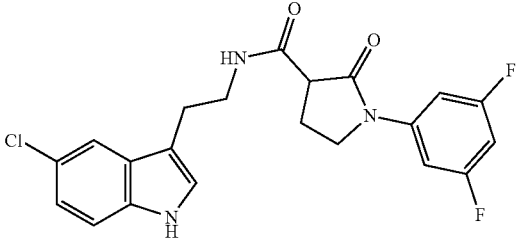 [SMILES: O=C(NCCc1c[nH]c2ccc(Cl)cc12)C1CCN(c2cc(F)cc(F)c2)C1=O] |
| D145 | 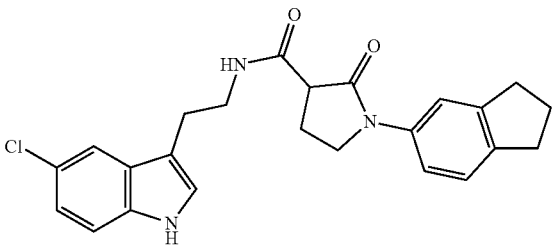 [SMILES: O=C(NCCc1c[nH]c2ccc(Cl)cc12)C1CCN(c2ccc3c(c2)CCC3)C1=O] |

-continued
| Compound code | STRUCTURE |
|---|---|
| D146 | 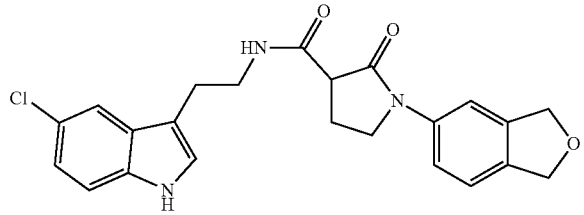 [SMILES: O=C(NCCc1c[nH]c2ccc(Cl)cc12)C1CCN(c2ccc3c(c2)COC3)C1=O] |
| D147 | 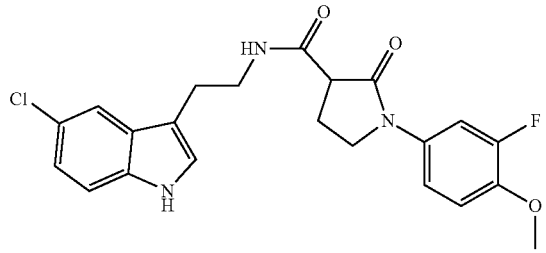 [SMILES: COc1ccc(N2CCC(C(=O)NCCc3c[nH]c4ccc(Cl)cc34)C2=O)cc1F] |
| D148 | 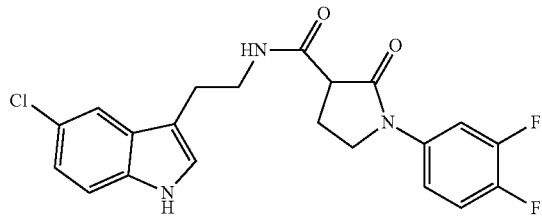 [SMILES: O=C(NCCc1c[nH]c2ccc(Cl)cc12)C1CCN(c2ccc(F)c(F)c2)C1=O] |
| D149 | 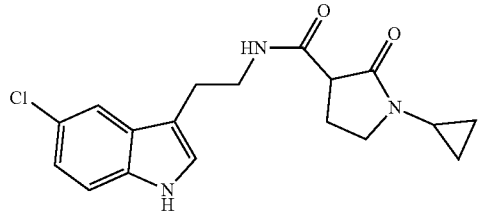 [SMILES: O=C(NCCc1c[nH]c2ccc(Cl)cc12)C1CCN(C2CC2)C1=O] |
| D150 | 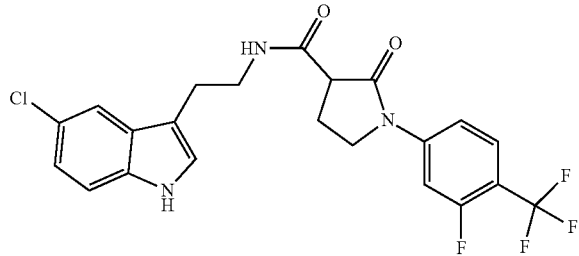 [SMILES: O=C(NCCc1c[nH]c2ccc(Cl)cc12)C1CCN(c2ccc(C(F)(F)F)c(F)c2)C1=O] |
| D151 | 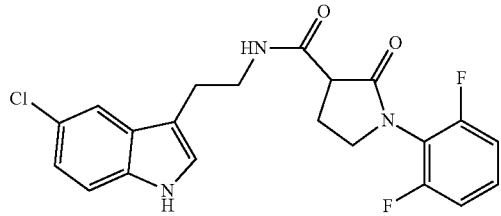 [SMILES: O=C(NCCc1c[nH]c2ccc(Cl)cc12)C1CCN(c2c(F)cccc2F)C1=O] |

-continued
| Compound code | STRUCTURE |
|---|---|
| D152 | 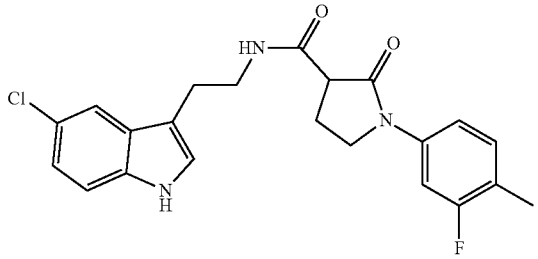 [SMILES: Cc1ccc(N2CCC(C(=O)NCCc3c[nH]c4ccc(Cl)cc34)C2=O)cc1F] |
| D153 | 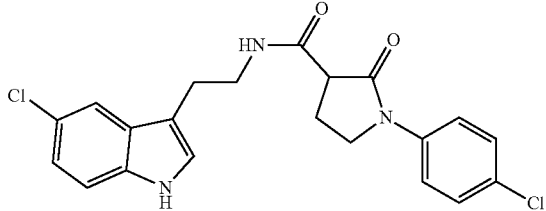 [SMILES: O=C(NCCc1c[nH]c2ccc(Cl)cc12)C1CCN(c2ccc(Cl)cc2)C1=O] |
| D154 | 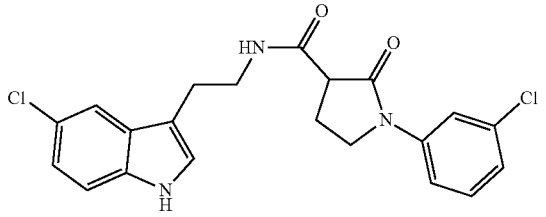 [SMILES: O=C(NCCc1c[nH]c2ccc(Cl)cc12)C1CCN(c2cccc(Cl)c2)C1=O] |
| D155 | 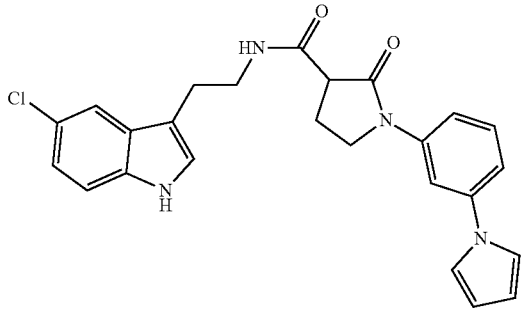 [SMILES: O=C(NCCc1c[nH]c2ccc(Cl)cc12)C1CCN(c2cccc(-n3cccc3)c2)C1=O] |
| D156 | 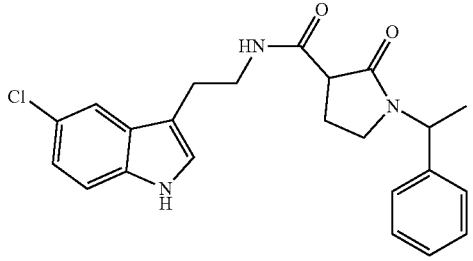 [SMILES: CC(c1ccccc1)N1CCC(C(=O)NCCc2c[nH]c3ccc(Cl)cc23)C1=O] |
| D157 | 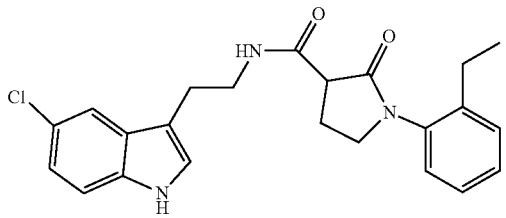 [SMILES: CCc1ccccc1N1CCC(C(=O)NCCc2c[nH]c3ccc(Cl)cc23)C1=O] |

| Compound code | STRUCTURE |
|---|---|
| D158 | 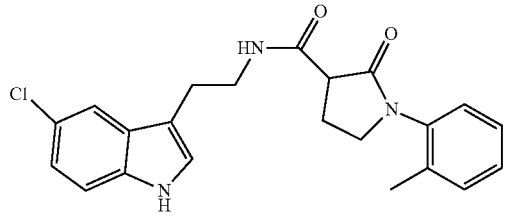 [SMILES: Cc1ccccc1N1CCC(C(=O)NCCc2c[nH]c3ccc(Cl)cc23)C1=O] |
| D159 | 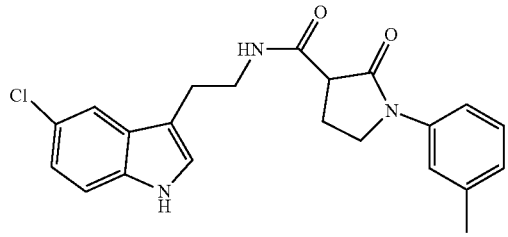 [SMILES: Cc1cccc(N2CCC(C(=O)NCCc3c[nH]c4ccc(Cl)cc34)C2=O)c1] |
| D160 | 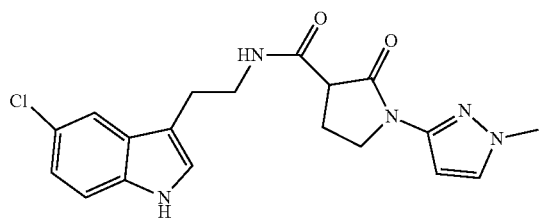 [SMILES: Cn1ccc(N2CCC(C(=O)NCCc3c[nH]c4ccc(Cl)cc34)C2=O)n1] |
| D161 | 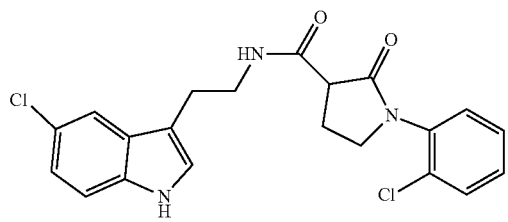 [SMILES: O=C(NCCc1c[nH]c2ccc(Cl)cc12)C1CCN(c2ccccc2Cl)C1=O] |
| D162 | 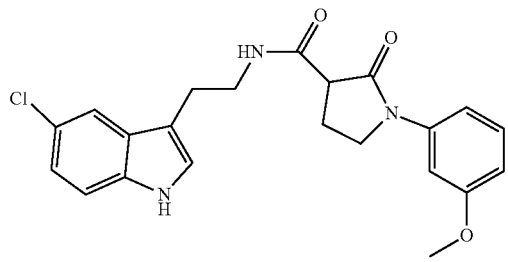 [SMILES: COc1cccc(N2CCC(C(=O)NCCc3c[nH]c4ccc(Cl)cc34)C2=O)c1] |
| D163 | 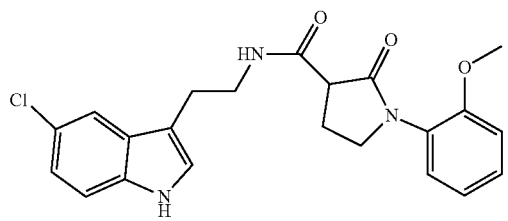 [SMILES: COc1ccccc1N1CCC(C(=O)NCCc2c[nH]c3ccc(Cl)cc23)C1=O] |

-continued
| Compound code | STRUCTURE |
|---|---|
| D164 | 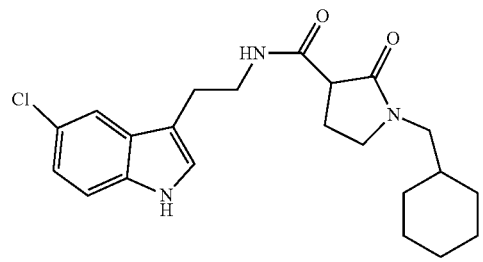 [SMILES: O=C(NCCc1c[nH]c2ccc(Cl)cc12)C1CCN(CC2CCCCC2)C1=O] |
| D165 | 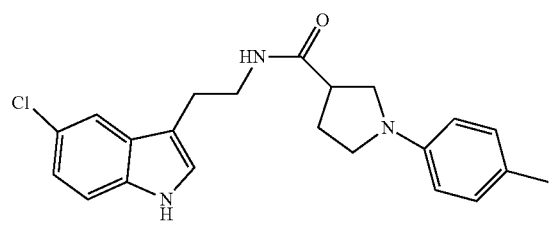 [SMILES: Cc1ccc(N2CCC(C(=O)NCCc3c[nH]c4ccc(Cl)cc34)C2)cc1] |
| D166 | 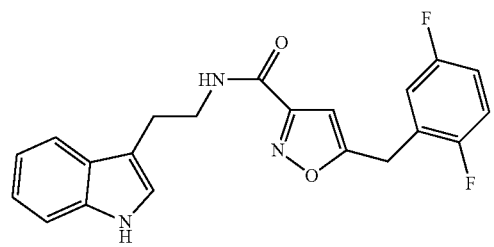 [SMILES: O=C(NCCc1c[nH]c2ccccc12)c1cc(Cc2cc(F)ccc2F)on1] |
| D167 | 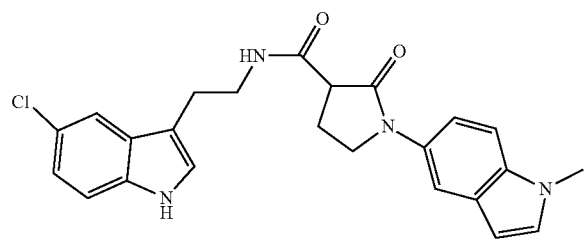 [SMILES: Cn1ccc2cc(N3CCC(C(=O)NCCc4c[nH]c5ccc(Cl)cc45)C3=O)ccc21] |
| D168 | 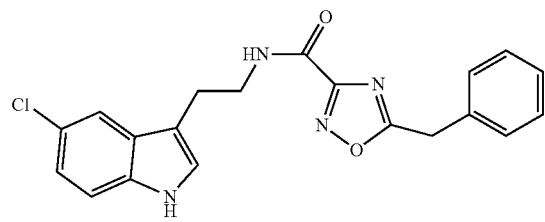 [SMILES: O=C(NCCc1c[nH]c2ccc(Cl)cc12)c1noc(Cc2ccccc2)n1] |
| D169 | 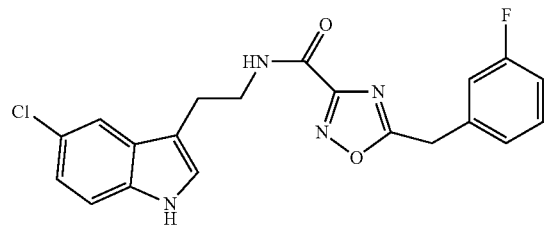 [SMILES: O=C(NCCc1c[nH]c2ccc(Cl)cc12)c1noc(Cc2cccc(F)c2)n1] |

-continued

| Compound code | STRUCTURE |
|---|---|
| D170 | 5-chloro-tryptamine-N-C(=O)-[1,2,4-oxadiazole]-CH2-(2-fluorophenyl) |
| D171 | 5-chloro-tryptamine-N-C(=O)-[1,2,4-oxadiazole]-CH2-(4-fluorophenyl) |
| D172 | 5-chloro-tryptamine-N-C(=O)-[1,2,4-oxadiazole]-CH2-(4-chlorophenyl) |
| D173 | 5-chloro-tryptamine-N-C(=O)-[1,2,4-oxadiazole]-CH2-(4-methoxyphenyl) |
| D174 | 5-chloro-tryptamine-N-C(=O)-[1,2,4-oxadiazole]-CH2-(3,4-dichlorophenyl) |
| D175 | 5-chloro-tryptamine-N-C(=O)-[1,2,4-oxadiazole]-CH2-(4-chloro-3-fluorophenyl) |

-continued
| Compound code | STRUCTURE |
|---|---|
| D176 | 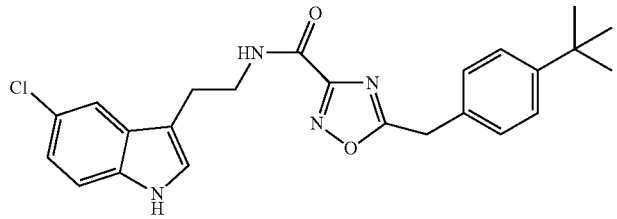 [SMILES: CC(C)(C)c1ccc(Cc2nc(C(=O)NCCc3c[nH]c4ccc(Cl)cc34)no2)cc1] |
| D177 | 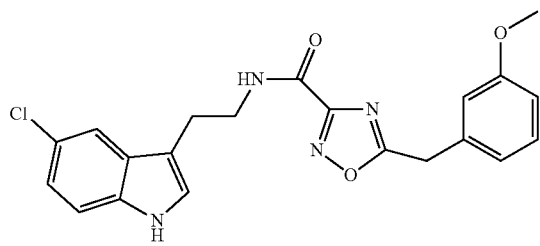 [SMILES: COc1cccc(Cc2nc(C(=O)NCCc3c[nH]c4ccc(Cl)cc34)no2)c1] |
| D178 | 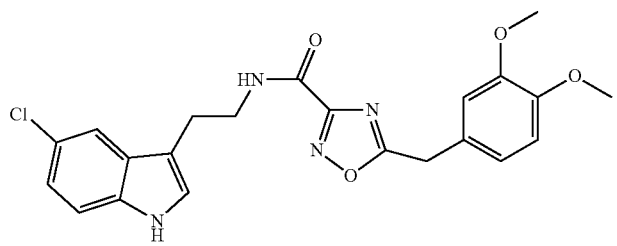 [SMILES: COc1ccc(Cc2nc(C(=O)NCCc3c[nH]c4ccc(Cl)cc34)no2)cc1OC] |
| D179 | 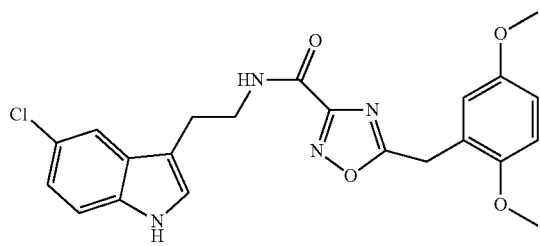 [SMILES: COc1ccc(OC)c(Cc2nc(C(=O)NCCc3c[nH]c4ccc(Cl)cc34)no2)c1] |
| D180 | 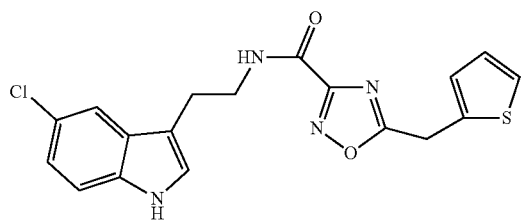 [SMILES: O=C(NCCc1c[nH]c2ccc(Cl)cc12)c1noc(Cc2cccs2)n1] |
| D181 | 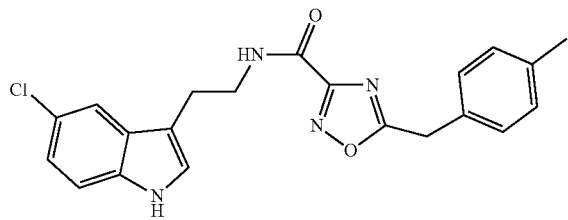 [SMILES: Cc1ccc(Cc2nc(C(=O)NCCc3c[nH]c4ccc(Cl)cc34)no2)cc1] |

-continued
| Compound code | STRUCTURE |
|---|---|
| D182 | 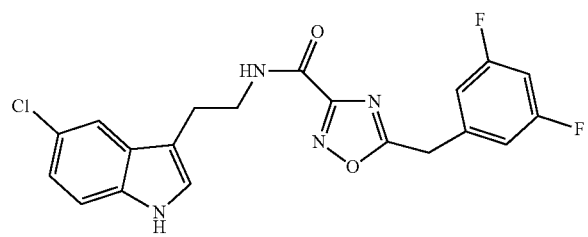 [SMILES: O=C(NCCc1c[nH]c2ccc(Cl)cc12)c1noc(Cc2cc(F)cc(F)c2)n1] |
| D183 | 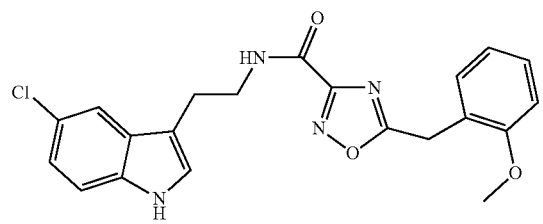 [SMILES: COc1ccccc1Cc1nc(C(=O)NCCc2c[nH]c3ccc(Cl)cc23)no1] |
| D184 | 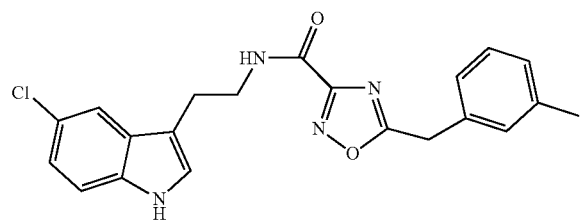 [SMILES: Cc1cccc(Cc2nc(C(=O)NCCc3c[nH]c4ccc(Cl)cc34)no2)c1] |
| D185 | 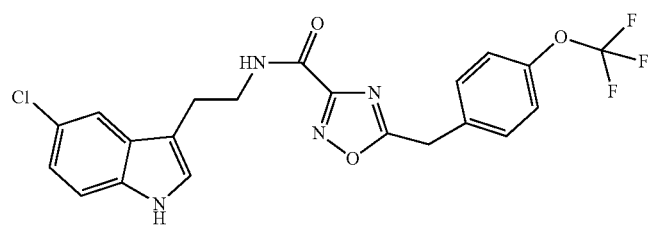 [SMILES: O=C(NCCc1c[nH]c2ccc(Cl)cc12)c1noc(Cc2ccc(OC(F)(F)F)cc2)n1] |
| D186 | 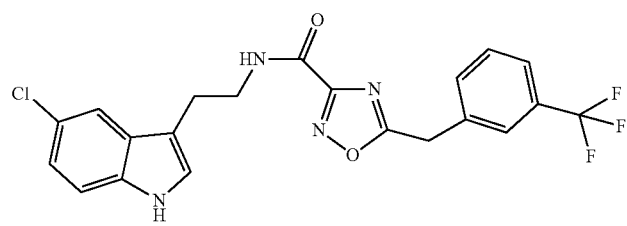 [SMILES: O=C(NCCc1c[nH]c2ccc(Cl)cc12)c1noc(Cc2cccc(C(F)(F)F)c2)n1] |
| D187 | 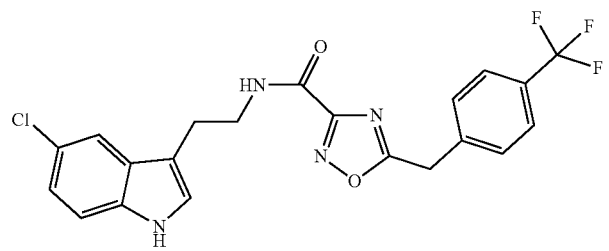 [SMILES: O=C(NCCc1c[nH]c2ccc(Cl)cc12)c1noc(Cc2ccc(C(F)(F)F)cc2)n1] |

| Compound code | STRUCTURE |
|---|---|
| D188 | 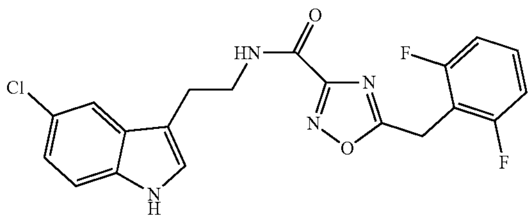 [SMILES: O=C(NCCc1c[nH]c2ccc(Cl)cc12)c1noc(Cc2c(F)cccc2F)n1] |
| D189 | 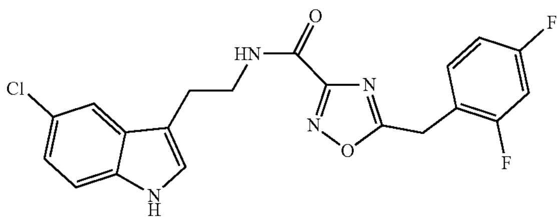 [SMILES: O=C(NCCc1c[nH]c2ccc(Cl)cc12)c1noc(Cc2ccc(F)cc2F)n1] |
| D190 | 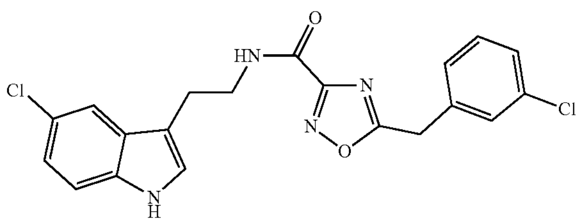 [SMILES: O=C(NCCc1c[nH]c2ccc(Cl)cc12)c1noc(Cc2cccc(Cl)c2)n1] |
| D191 | 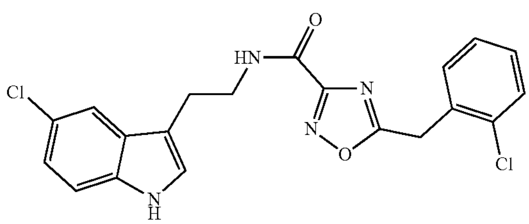 [SMILES: O=C(NCCc1c[nH]c2ccc(Cl)cc12)c1noc(Cc2ccccc2Cl)n1] |
| D192 | 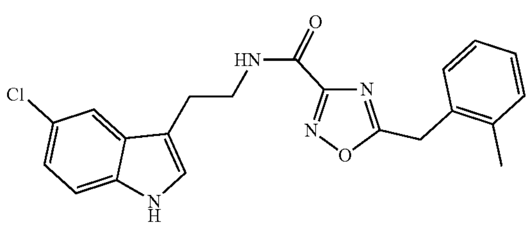 [SMILES: Cc1ccccc1Cc1nc(C(=O)NCCc2c[nH]c3ccc(Cl)cc23)no1] |
| D193 | 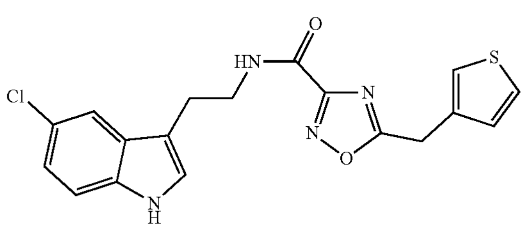 [SMILES: O=C(NCCc1c[nH]c2ccc(Cl)cc12)c1noc(Cc2ccsc2)n1] |
| D194 | 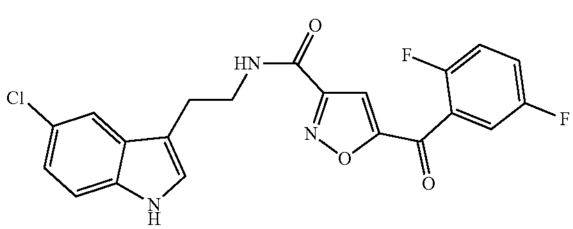 [SMILES: O=C(NCCc1c[nH]c2ccc(Cl)cc12)c1cc(C(=O)c2cc(F)ccc2F)on1] |

-continued

| Compound code | STRUCTURE |
|---|---|
| D195 | 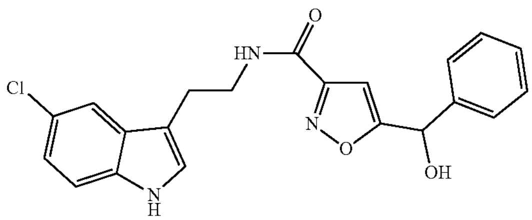 [SMILES: O=C(NCCc1c[nH]c2ccc(Cl)cc12)c1cc(C(O)c2ccccc2)on1] |
| D196 | 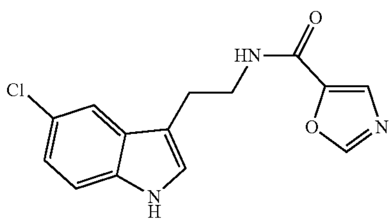 [SMILES: O=C(NCCc1c[nH]c2ccc(Cl)cc12)c1cnco1] |
| D197 | 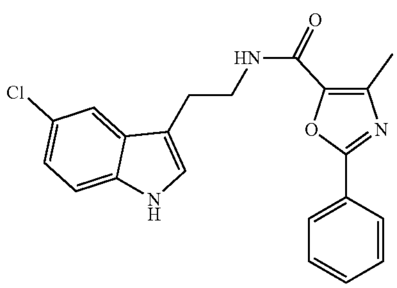 [SMILES: Cc1nc(-c2ccccc2)oc1C(=O)NCCc1c[nH]c2ccc(Cl)cc12] |
| D198 | 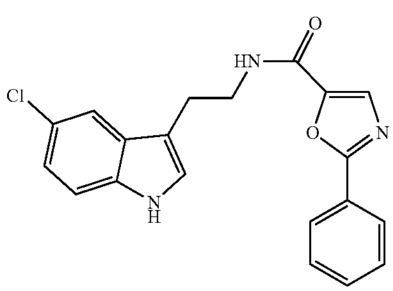 [SMILES: O=C(NCCc1c[nH]c2ccc(Cl)cc12)c1cnc(-c2ccccc2)o1] |
| D199 | 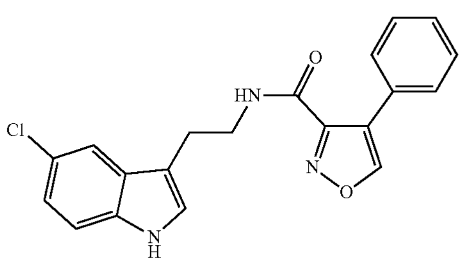 [SMILES: O=C(NCCc1c[nH]c2ccc(Cl)cc12)c1nocc1-c1ccccc1] |
| D200 | 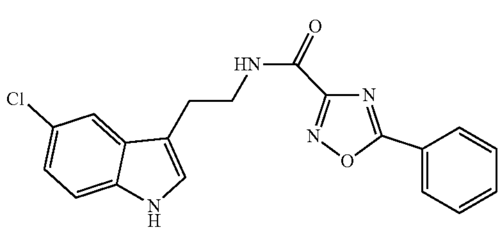 [SMILES: O=C(NCCc1c[nH]c2ccc(Cl)cc12)c1noc(-c2ccccc2)n1] |

-continued

| Compound code | STRUCTURE |
|---|---|
| D201 | 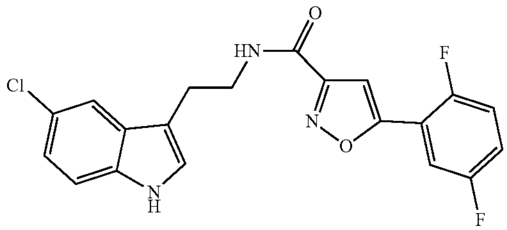 [SMILES: O=C(NCCc1c[nH]c2ccc(Cl)cc12)c1cc(-c2cc(F)ccc2F)on1] |
| D202 | 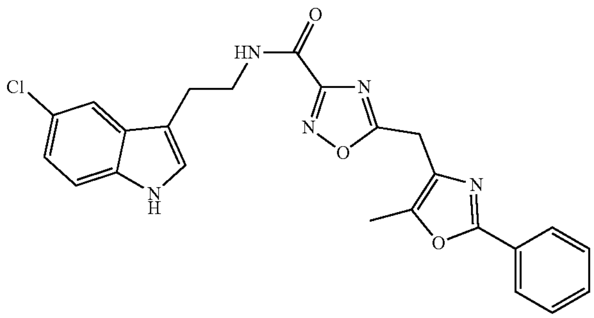 [SMILES: Cc1oc(-c2ccccc2)nc1Cc1nc(C(=O)NCCc2c[nH]c3ccc(Cl)cc23)no1] |
| D203 | 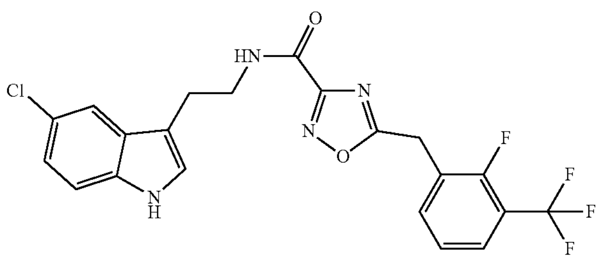 [SMILES: O=C(NCCc1c[nH]c2ccc(Cl)cc12)c1noc(Cc2cccc(C(F)(F)F)c2F)n1] |
| D204 | 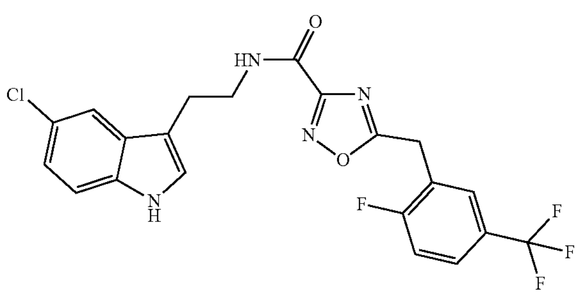 [SMILES: O=C(NCCc1c[nH]c2ccc(Cl)cc12)c1noc(Cc2cc(C(F)(F)F)ccc2F)n1] |
| D205 | 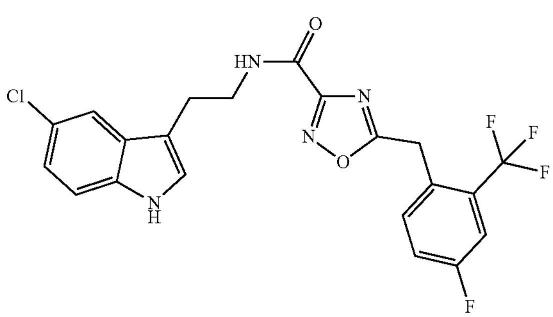 [SMILES: O=C(NCCc1c[nH]c2ccc(Cl)cc12)c1noc(Cc2ccc(F)cc2C(F)(F)F)n1] |

-continued
| Compound code | STRUCTURE |
|---|---|
| D206 | 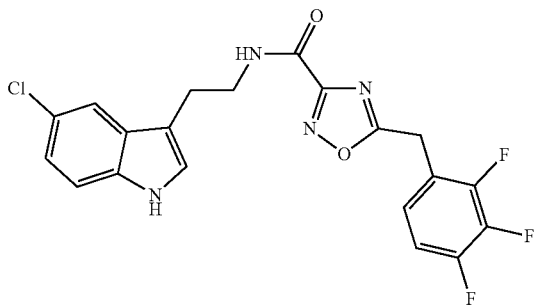 [SMILES: O=C(NCCc1c[nH]c2ccc(Cl)cc12)c1noc(Cc2ccc(F)c(F)c2F)n1] |
| D207 | 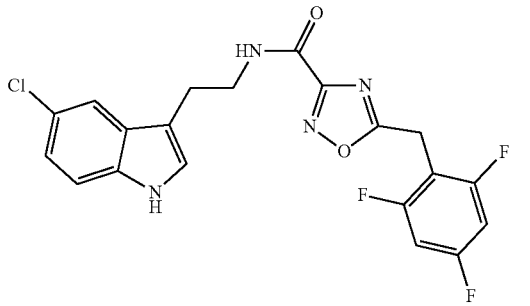 [SMILES: O=C(NCCc1c[nH]c2ccc(Cl)cc12)c1noc(Cc2c(F)cc(F)cc2F)n1] |
| D208 | 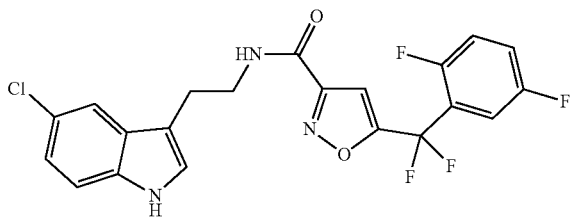 [SMILES: O=C(NCCc1c[nH]c2ccc(Cl)cc12)c1cc(C(F)(F)c2cc(F)ccc2F)on1] |
| D209 | 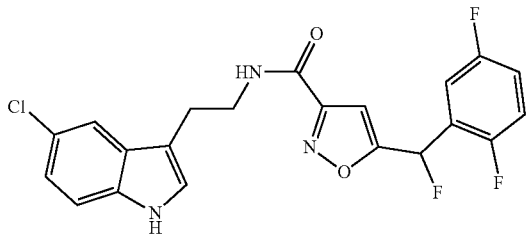 [SMILES: O=C(NCCc1c[nH]c2ccc(Cl)cc12)c1cc(C(F)c2cc(F)ccc2F)on1] |
| D210 | 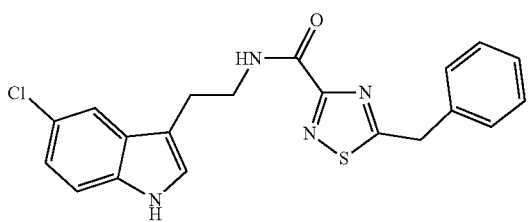 [SMILES: O=C(NCCc1c[nH]c2ccc(Cl)cc12)c1nsc(Cc2ccccc2)n1] |
| D211 | 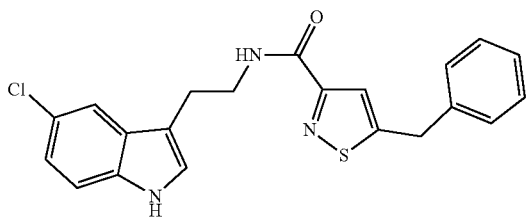 [SMILES: O=C(NCCc1c[nH]c2ccc(Cl)cc12)c1cc(Cc2ccccc2)sn1] |

| Compound code | STRUCTURE |
|---|---|
| D212 | 5-bromoindole-ethyl-NHC(O)-isoxazole-CHF-(2,5-difluorophenyl) |
| D213 | 5-chloroindole-ethyl-NHC(O)-(1-phenyl-1,2,3-triazol-4-yl) |
| D214 | 5-chloroindole-ethyl-NHC(O)-(2-oxo-1-(4-trifluoromethoxyphenyl)pyrrolidin-3-yl) |
| D215 | 5-chloroindole-ethyl-NHC(O)-isoxazole-CH(OH)-(2,5-difluorophenyl) |
| D216 | 5-chloroindole-ethyl-NHC(O)-(5-(ethoxymethyl)-4,5-dihydroisoxazol-3-yl) | and enantiomers, tautomers, solvates, hydrates, salts or prodrugs of any of the foregoing.

3. The method of claim 1, wherein said compound is a compound of formula (I), or a tautomer thereof,

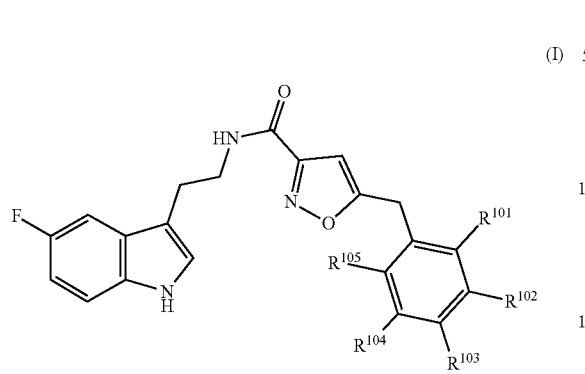
(I)

wherein:
- $R^{101}$ is selected from the group consisting of hydrogen; F, Cl and Br;
- $R^{102}$ is selected from the group consisting of hydrogen, F, Cl and Br;
- $R^{103}$ is selected from the group consisting of hydrogen, F, Cl, and Br;
- $R^{104}$ is selected from the group consisting of hydrogen, F, Cl and Br;
- $R^{105}$ is selected from the group consisting of hydrogen, F, Cl and Br;

with the proviso that at least one of $R^{101}$, $R^{102}$, $R^{103}$, $R^{104}$ or $R^{105}$ is not hydrogen; and with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt or a prodrug thereof.

4. The method of claim 3, wherein said compound of formula (I) is a compound of any one of formula (II), (III), (IV), (V) or (VI)

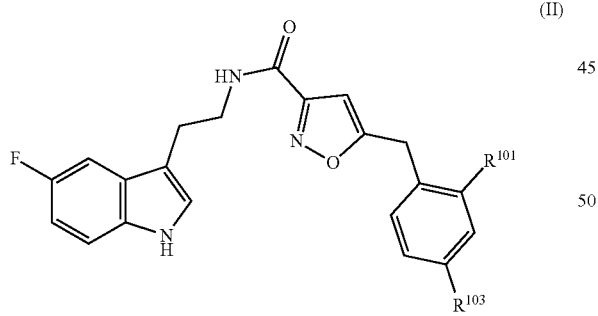
(II)

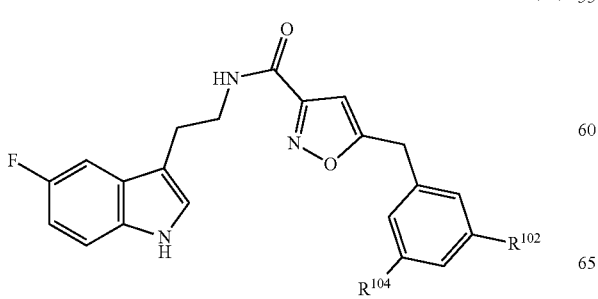
(III)

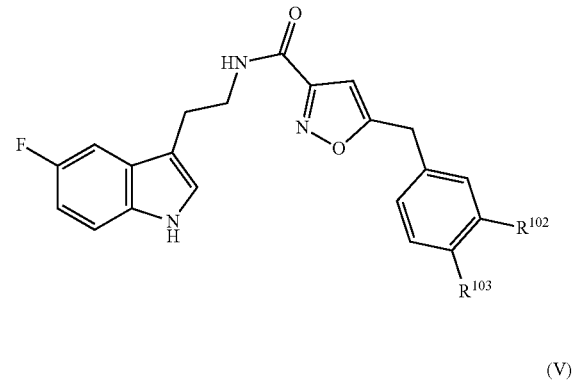
(IV)

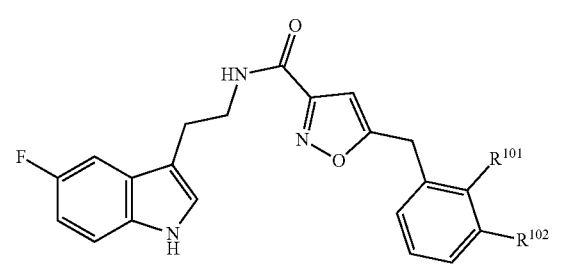
(V)

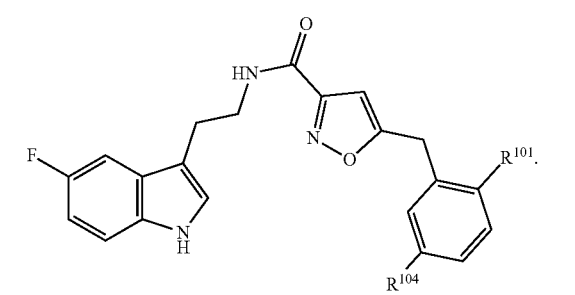
(VI)

5. The method of claim 3, wherein said compound of formula (I) is selected from the group consisting of:

- 5-[(2,4-difluorophenyl)methyl]-N-[2-(5-fluoro-1H-indol-3-yl)ethyl]isoxazole-3-carboxamide;
- N-[2-(5-fluoro-1H-indol-3-yl)ethyl]-5-[(4-fluorophenyl)methyl]isoxazole-3-carboxamide;
- 5-[(2,3-difluorophenyl)methyl]-N-[2-(5-fluoro-1H-indol-3-yl)ethyl]isoxazole-3-carboxamide;
- 5-[(2,5-difluorophenyl)methyl]-N-[2-(5-fluoro-1H-indol-3-yl)ethyl]isoxazole-3-carboxamide;
- N-[2-(5-fluoro-1H-indol-3-yl)ethyl]-5-[(2-fluorophenyl)methyl]isoxazole-3-carboxamide;
- 5-[(3,4-difluorophenyl)methyl]-N-[2-(5-fluoro-1H-indol-3-yl)ethyl]isoxazole-3-carboxamide; and
- 5-[(3,5-difluorophenyl)methyl]-N-[2-(5-fluoro-1H-indol-3-yl)ethyl]isoxazole-3-carboxamide.

6. A method of treating of Alzheimer's disease in a subject suffering from Alzheimer's disease, wherein said method comprises, administering to said subject a therapeutically effective amount of an inhibitor of PDE6δ, wherein said inhibitor is a compound of formula (I) or a tautomer thereof, (I)

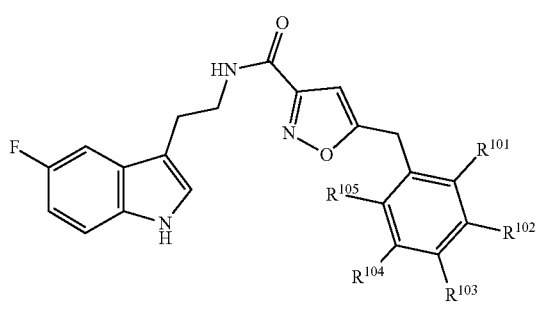

wherein:
- $R^{101}$ is selected from the group consisting of hydrogen; F, Cl and Br;
- $R^{102}$ is selected from the group consisting of hydrogen, F, Cl and Br;
- $R^{103}$ is selected from the group consisting of hydrogen, F, Cl and Br;
- $R^{104}$ is selected from the group consisting of hydrogen, F, Cl and Br;
- $R^{105}$ is selected from the group consisting of hydrogen, F, Cl and Br;

with the proviso that at least one of $R^{101}$, $R^{102}$, $R^{103}$, $R^{104}$ or $R^{105}$ is not hydrogen; and with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt or a prodrug thereof.

7. The method of claim 6, wherein said compound of formula (I) is a compound of any one of formula (II), (III), (IV), (V) or (VI)

(II)

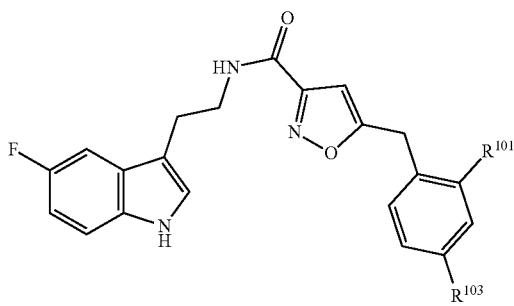

(III)

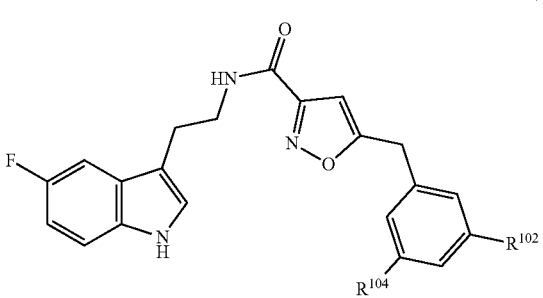

(IV)

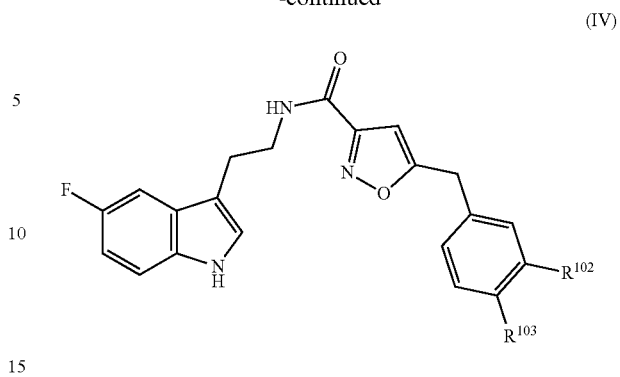

(V)

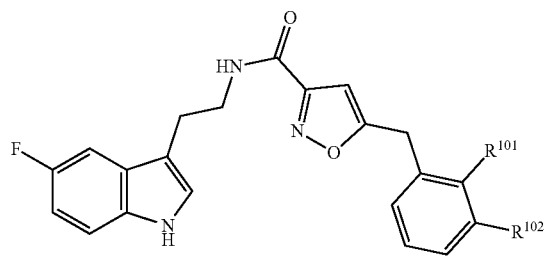

(VI)

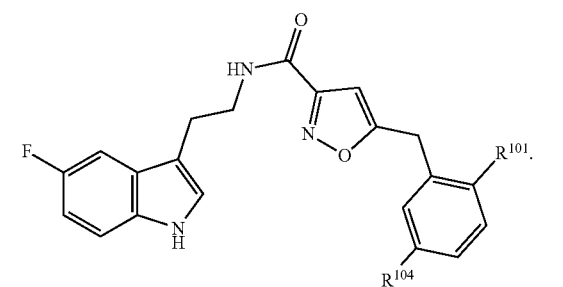

8. The method of claim 6, wherein said compound of formula (I) is selected from the group consisting of:
- 5-[(2,4-difluorophenyl)methyl]-N-[2-(5-fluoro-1H-indol-3-yl)ethyl]isoxazole-3-carboxamide;
- N-[2-(5-fluoro-1H-indol-3-yl)ethyl]-5-[(4-fluorophenyl)methyl]isoxazole-3-carboxamide;
- 5-[(2,3-difluorophenyl)methyl]-N-[2-(5-fluoro-1H-indol-3-yl)ethyl]isoxazole-3-carboxamide;
- 5-[(2,5-difluorophenyl)methyl]-N-[2-(5-fluoro-1H-indol-3-yl)ethyl]isoxazole-3-carboxamide;
- N-[2-(5-fluoro-1H-indol-3-yl)ethyl]-5-[(2-fluorophenyl)methyl]isoxazole-3-carboxamide;
- 5-[(3,4-difluorophenyl)methyl]-N-[2-(5-fluoro-1H-indol-3-yl)ethyl]isoxazole-3-carboxamide; and
- 5-[(3,5-difluorophenyl)methyl]-N-[2-(5-fluoro-1H-indol-3-yl)ethyl]isoxazole-3-carboxamide.

9. The method of claim 6, wherein said inhibitor is contained within a pharmaceutical composition in a therapeutically effective amount.

10. The method of claim 6, wherein said inhibitor is a compound of formula (I) or a tautomer thereof,

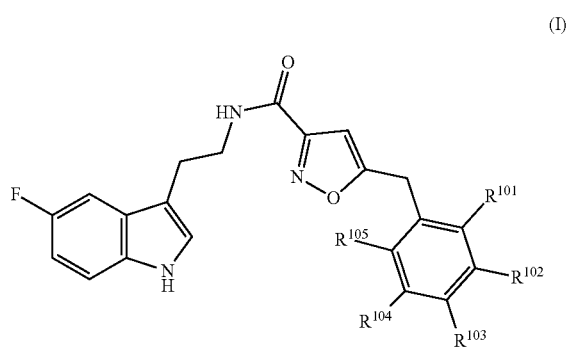

(I)

wherein:
- $R^{101}$ is selected from the group consisting of hydrogen, and F;
- $R^{102}$ is selected from the group consisting of hydrogen, and F;
- $R^{103}$ is selected from the group consisting of hydrogen, and F;
- $R^{104}$ is selected from the group consisting of hydrogen, and F;
- $R^{105}$ is selected from the group consisting of hydrogen, and F;

with the proviso that at least one of $R^{101}$, $R^{102}$, $R^{103}$, $R^{104}$ or $R^{105}$ is not hydrogen; and with the proviso that said compound of formula (I) is not N-[2-(5-fluoro-1H-indol-3-yl)ethyl]-5-[(3-fluorophenyl)methyl]isoxazole-3-carboxamide, or a solvate, a hydrate, a salt or a prodrug thereof.

* * * * *